(12) United States Patent
Isshiki et al.

(10) Patent No.: US 8,084,645 B2
(45) Date of Patent: Dec. 27, 2011

(54) 4-PHENYLAMINO-BENZALDOXIME DERIVATIVES AND USES THEREOF AS MITOGEN-ACTIVATED PROTEIN KINASE KINASE (MEK) INHIBITORS

(75) Inventors: Yoshiaki Isshiki, Kanagawa (JP); Yasunori Kohchi, Kanagawa (JP); Kazuo Hattori, Kanagawa (JP); Nobuo Shimma, Kanagawa (JP); Masanori Miwa, Kanagawa (JP); Naohito Inagaki, Kanagawa (JP); Hitoshi Iikura, Kanagawa (JP); Yasuaki Matsubara, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 710 days.

(21) Appl. No.: 10/572,255

(22) PCT Filed: Sep. 16, 2004

(86) PCT No.: PCT/JP2004/013501
§ 371 (c)(1),
(2), (4) Date: Jan. 16, 2007

(87) PCT Pub. No.: WO2005/028426
PCT Pub. Date: Mar. 31, 2005

(65) Prior Publication Data
US 2007/0105859 A1   May 10, 2007

(30) Foreign Application Priority Data

Sep. 19, 2003 (JP) ................. 2003-329181
Dec. 22, 2003 (JP) ................. 2003-424668
Aug. 11, 2004 (JP) ................. 2004-234332

(51) Int. Cl.
*C07C 239/00* (2006.01)
*C07C 259/00* (2006.01)
*C07C 229/00* (2006.01)
*C07D 265/00* (2006.01)
*A01N 37/18* (2006.01)
*A61K 31/16* (2006.01)

(52) U.S. Cl. .......... 564/253; 564/300; 514/619; 544/63; 562/454

(58) Field of Classification Search .................. None
See application file for complete search history.

(56) References Cited

U.S. PATENT DOCUMENTS

| | | | |
|---|---|---|---|
| 2,967,187 A | 1/1961 | Serres, Jr. et al. |
| 3,725,417 A | 4/1973 | Holland |
| 3,821,237 A | 6/1974 | Malen et al. |
| 4,001,420 A | 1/1977 | Malen et al. |
| 4,469,885 A | 9/1984 | Mueller et al. |
| 4,501,895 A | 2/1985 | Mueller et al. |
| 6,440,966 B1 | 8/2002 | Barrett et al. |
| 6,750,217 B2 | 6/2004 | Barrett et al. |
| 7,001,905 B2 | 2/2006 | Biwersi et al. |
| 7,538,120 B2 | 5/2009 | Koch et al. |
| 2003/0092748 A1 | 5/2003 | Barrett et al. |
| 2003/0225076 A1* | 12/2003 | Biwersi et al. ............ 514/230.5 |
| 2009/0233915 A1 | 9/2009 | Isshiki et al. |
| 2010/0197676 A1 | 8/2010 | Isshiki et al. |

FOREIGN PATENT DOCUMENTS

| | | |
|---|---|---|
| EP | 1 262 176 | 12/2002 |
| EP | 1 144 385 | 8/2005 |
| EP | 1 674 452 | 6/2006 |
| EP | 1780197 | 5/2007 |
| JP | 46-015935 | 4/1971 |
| JP | 48-61448 | 8/1973 |
| JP | 59-210046 | 11/1984 |
| JP | 2002-534491 | 10/2002 |
| JP | 2002-534510 | 10/2002 |
| JP | 2002-332247 | 11/2002 |
| JP | 2003-527379 | 9/2003 |
| JP | 2007-504241 | 3/2007 |
| WO | WO 99/01426 | 1/1999 |
| WO | WO 00/35436 | 6/2000 |
| WO | WO 00/41994 | 7/2000 |
| WO | WO 01/68619 | 9/2001 |
| WO | WO02/06213 * | 1/2002 |
| WO | WO 03/051877 | 6/2003 |

(Continued)

OTHER PUBLICATIONS

Watson et al. J. Med. Chem. 2003, 46(15) 3181-3184.*
C. Garcia-Echeverria and W. R. Sellers Oncogene (2008) 27, 5511-5526.*
Shioi, T et al. Mol. Cell Biol. Apr. 2002; 22(8): 2799-809.*
Patani et al. Chem. Rev. 1996, 96, 3147-3176.*
Chardonnens et al., "256. Fluorènacènes et fluorènaphènes. Synthèses dans la série des indéno-fluorènes VIII.) Méthyl-3-, diméthyl-1,4-, diméthyl-1,3- et triméthyl-1,3,4-*cis*-fluorènacène," *Helv. Chim. Acta,* 41:2436-2440 (1958).

(Continued)

*Primary Examiner* — Daniel Sullivan
*Assistant Examiner* — Clinton Brooks
(74) *Attorney, Agent, or Firm* — Fish & Richardson P.C.

(57) ABSTRACT

A compound of the present invention, or a pharmaceutically acceptable salt thereof is indicated by formula (1) below:

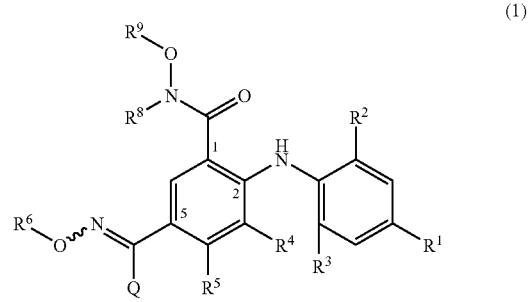

(1)

wherein, $R^1$, $R^2$, $R^3$, $R^4$, $R^5$, $R^6$, $Q$, $R^8$, and $R^9$ have the same meanings as $R^1$, $R^2$, $R^3$, $R^4$, $R^5$, $R^6$, $Q$, $R^8$, and $R^9$ in the specification.

34 Claims, No Drawings

FOREIGN PATENT DOCUMENTS

| | | |
|---|---|---|
| WO | WO 2005/028426 | 3/2005 |
| WO | WO 2006/011466 | 2/2006 |

OTHER PUBLICATIONS

Heintz et al., "Electrosynthesis of aryl-carboxylic acids from chlorobenzene derivatives and carbon dioxide," *Tetrahedron*, 44:1631-1636 (1988).

LoRusso et al., "A phase 1 clinical and pharmacokinetic evaluation of the oral MEK inhibitor, CI-1040, administered for 21 consecutive days, repeated every 4 weeks in patients with advanced cancer," *American Society of Clinical Oncology Annual Meeting*, Abstract No. 321, 2 pages (2002).

Mitchell et al., "Pharmacokinetics (PK) and pharmacodynamics (PD) of the oral MEK inhibitor, CI-1040, following multiple dose administration to patients with advanced cancer," *American Society of Clinical Oncology Annual Meeting*, Abstract No. 320, 2 pages (2002).

Ozaki et al., "Studies on 4(1*H*)-Quinazolinones. 5. Synthesis and Antiinflammatory Activity of 4(1*H*)-Quinazolinone Derivatives," *J. Med. Chem.*, 28:568-576 (1985).

Japanese Patent Office, International Search Report for App. Ser. No. PCT/JP2005/013620, dated Nov. 22, 2005, 3 pages.

Japanese Patent Office, International Preliminary Report on Patentability for App. Ser. No. PCT/JP2005/013620, 6 pages.

Japanese Patent Office, International Search Report for App. Ser. No. PCT/JP2004/013501, mailed Dec. 28, 2004, 4 pages.

Japanese Patent Office, International Preliminary Report on Patentability for App. Ser. No. PCT/JP2004/013501, 6 pages.

European Search Report for App. Ser. No. EP 04 77 3160, dated Sep. 4, 2007 (2 pages).

Patani et al., "Bioisosterism: A Rational Approach in Drug Design," *Chem. Rev.*, 96:3147-3176 (1996).

USPTO Restriction Requirement in U.S. Appl. No. 11/658,533, mailed Oct. 28, 2009, 9 pages.

Fish & Richardson P.C., Third Preliminary Amendment and Response to Restriction Requirement dated Oct. 28, 2009 in U.S. Appl. No. 11/658,533, filed Dec. 28, 2009, 27 pages.

USPTO Notice of Allowance in U.S. Appl. No. 11/658,533, Jan. 28, 2010, 18 pages.

\* cited by examiner

4-PHENYLAMINO-BENZALDOXIME DERIVATIVES AND USES THEREOF AS MITOGEN-ACTIVATED PROTEIN KINASE KINASE (MEK) INHIBITORS

CROSS-REFERENCE TO RELATED APPLICATIONS

This application is the National Stage of International Application No. PCT/JP2004/013501, filed on Sep. 16, 2004, which claims the benefit of Japanese Patent Applications Serial No. 2003/329181, filed on Sep. 19, 2003, Serial No. 2003/424668, filed on Dec. 22, 2003, and Serial No. 2004/234332, filed on Aug. 11, 2004. The contents of all of the foregoing applications are hereby incorporated by reference in their entireties.

TECHNICAL FIELD

The present invention relates to novel 4-phenylamino-benzaldoxime derivatives, pharmaceutically acceptable salts thereof, synthetic intermediates of the aforementioned compounds, methods of producing the compounds by using the intermediates, and pharmaceutical compositions comprising the compounds or pharmaceutically acceptable salts thereof.

Compounds of the present invention can be mitogen-activated protein kinase (MEK) inhibitors. The compounds are useful for treating proliferative diseases such as cancers, psoriasis, restenosis, autoimmune diseases, and atherosclerosis, and for treating sequalae of heart failure, xenograft rejection, osteoarthrosis, chronic rheumatoid arthritis, asthma, cystic fibrosis, hepatomegaly, cardiac hypertrophy Alzheimer's disease, diabetes, septic shock, and HIV infection.

BACKGROUND ART

Cell survival is regulated by various extracellular signals such as growth factors, cytokines, and extracellular matrices (ECMs) through cell surface receptors.

Two major signal transduction pathways regulate this signal transduction process from the cell surface in to the cell nucleus. One of these is the Ras signal transduction pathway, and the other is the Phosphatidylinositol 3 kinase (PI3K) pathway. The PI3K pathway is activated by cell surface receptors, or indirectly activated by Ras. The present invention focuses on the Ras signal transduction pathway.

The mitogen-activated protein kinase (MAPK) cascade composed by three kinases, specifically Raf, MEK (MAPK kinase or extracellular stimulus regulated kinase (ERK) kinase), and ERK, is a key module for the Ras signal transduction pathway. This cascade is initiated by the activation of Ras, and plays an important role in adjusting cell proliferation, differentiation, and transformation in response to extracellular signals (Non-Patent Documents 1 to 7).

Ras activation is regulated by the interplay between GTP exchange factors (GEFs) and GTPase activating proteins (GAPs) (Non-Patent Document 8). GEFs activate Ras through Ras-GTP complex formation, and GAPs inactivate Ras through Ras-GDP complex formation. Ras is activated by the action of extracellular signals, such as growth factors, on cell surface receptors, or by mutation of Ras itself. Mutations of Ras have been observed in many human cancer cells. Ras is known to be constitutively activated (GTP complex) by mutation to play an important role in human cancer cell proliferation.

Activated Ras interacts with Raf-1, which is a serine-threonine protein kinase, and activates Raf-1 (Non-Patent Documents 9 and 10).

Activated Raf-1 then phosphorylates and activates MEK1 and MEK2. This phosphorylation takes place at two MEK serine residues (Ser218 and Ser222) (Non-Patent Documents 11 to 15).

MEK is a dual specificity kinase, and the activated MEK phosphorylates ERK1 and ERK2 at the tyrosine (185) and threonine (183) residues (Non-Patent Documents 16 and 17).

Phosphorylation of ERKs by MEK not only activates ERKs but also translocates them to the nucleus.

Consequently, the activated ERKs (MAPK) activate various substrates in the cytoplasm and nucleus, such as transcription factors, and cause cellular changes (proliferation, differentiation, and transformation) in response to extracellular signals.

MEK has high substrate specificity, and no substrates other than ERK1 and ERK2 have been found to be phosphorylated by MEK (Non-Patent Document 18).

These unique MEK characteristics, such as high substrate specificity (ERK1 and 2 are the only substrates) and dual specificity (phosphorylates tyrosine and threonine), are not so commonly observed in other kinases, indicating that MEK has a central role in integrating signals into the MAPK pathway.

Constitutive activation of the MEK/MAPK pathway has been shown to be related to a relatively wide variety of neoplastic phenotypes of cancer cells (Non-Patent Documents 19 to 21).

Furthermore, constitutive activation of MEK is known to result in cell alteration (transformation) (canceration) (Non-Patent Documents 22 and 23).

In addition, studies using MEK inhibitors (such as PD98059) have shown that inhibition of MEK not only impairs proliferation of cells, but also has an impact on (interferes with) various cellular phenomena comprising differentiation of cells, apoptosis, and angiogenesis (Non-Patent Documents 24 to 31).

Thus MEK, which is one of the major mediators of the MAPK cascade, may be a potential target for therapeutic agents for treating diseases caused by abnormal cell proliferation.

To date, many compounds for MEK inhibition have been reported (Patent Documents 1 to 31). However, some of these compounds have problems with solubility or metabolic stability. Other compounds have problems with PK difference. For example, compound CI-1040 (Patent Document 6, Example 95), shown below, has been reported to be a MEK inhibitor. However, the results of its phase I clinical trials, which were reported at the 2002 American Society of Clinical Oncology Annual Meeting (Non-Patent Document 32), indicate problems of quick in vivo inactivation by hydrolysis, high lipid solubility and low water solubility, and large differences in pharmacokinetic parameters between patients.

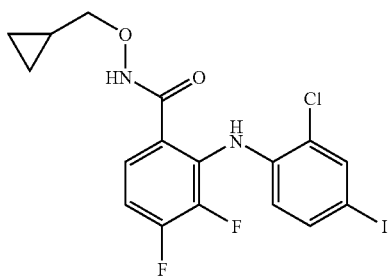

Patent Document 1: U.S. Pat. No. 6,251,943
Patent Document 2: U.S. Pat. No. 6,310,060
Patent Document 3: U.S. Pat. No. 6,506,798
Patent Document 4: International Publication WO98/37881
Patent Document 5: International Publication WO99/01421
Patent Document 6: International Publication WO99/01426
Patent Document 7: International Publication WO00/35435
Patent Document 8: International Publication WO00/35436
Patent Document 9: International Publication WO00/37141
Patent Document 10: International Publication WO00/40235
Patent Document 11: International Publication WO00/40237
Patent Document 12: International Publication WO00/41505
Patent Document 13: International Publication WO00/41994
Patent Document 14: International Publication WO00/42002
Patent Document 15: International Publication WO00/42003
Patent Document 16: International Publication WO00/42022
Patent Document 17: International Publication WO00/42029
Patent Document 18: International Publication WO00/64856
Patent Document 19: International Publication WO01/05390
Patent Document 20: International Publication WO01/05391
Patent Document 21: International Publication WO01/05392
Patent Document 22: International Publication WO01/05393
Patent Document 23: International Publication WO01/68619
Patent Document 24: International Publication WO02/06213
Patent Document 25: International Publication WO02/18319
Patent Document 26: International Publication WO03/062189
Patent Document-27: International Publication WO03/062191
Patent Document 28: International Publication WO03/077855
Patent Document 29: International Publication WO03/077914
Patent Document 30: International Publication WO03/056789
Patent Document 31: Japanese Patent Application Kokai Publication No. (JP-A) 2001-55376 (unexamined, published Japanese patent application)
Non-Patent Document 1: Person, G. F. Robinson, T. Beers Gibson, B. Xu, M. Karandikar, K. Berman, and M. H. Cobb. Endocrine Rev., 22, 153-183 (2001)
Non-Patent Document 2: Bryan A. Ballif and John Blenis, Cell Growth & Differentiation, 12, 397-408 (2001)
Non-Patent Document 3: Cobb M H, Prog. Biophys. Mol. Biol., 71 479-500 (1999)
Non-Patent Document 4: Lewis T S, Shapiro P S and Ahn N G. Adv. Cancer Res., 74 49-139 (1998)
Non-Patent Document 5: Kolch W, Biochem. J., 351, 289-305 (2000)
Non-Patent Document 6: Judith S Sebolt-Leopold, Oncogene, 19, 6594-6599 (2000)
Non-Patent Document 7: Roman Herrera and Judith S. Sebolt-Leopold, Trends in Molecular Medicine, 8, S27-S31 (2002)
Non-Patent Document 8: Giorgio Scita, Pierluigi Tenca, Emanuela Frittoli Arianna Tocchetti, Metello Innocenti, Giuseppina Giardina and Pier Paolo Di Fiore, EMBO Journal. 19, 2393-2398 (2000)
Non-Patent Document 9: Daum G. Eisenmann-Tappe I, Fries H W, Troppmair J and Rapp U R, Trends Biochem. Sci., 19, 474-480 (1994)
Non-Patent Document 10: Stokoe D, Macdonald S G, Cadwallader K, Symons M and Hacock J F, Science, 264, 1463-1467 (1994)
Non-Patent Document 11: Dent P, Haser W, Haystead T A, Vincent L A, Roberts T M and Sturgill T W, Science, 257, 1404-1407 (1992)
Non-Patent Document 12: Crews C M, Alessandrini A and Erikson R L, Science, 258, 478-480 (1992)
Non-Patent Document 13: Her J H, Lakhani S, Zu K, Vila J, Dent P, Sturgill T W and Weber M J, Biochem. J., 296, 25-31 (1993)
Non-Patent Document 14: Alessi, D. R., Y. Saito, D. G. Campgell, P. Cohen, G. Sithanandam, U. Rapp, A. Ashworth, C. J. Marshall, and S. Cowley. Trends Biochem. Sci. 21 373-372 (1994)
Non-Patent Document 15: Zheng, C. F., and K. L. Guan. J. Biol. Chem. 268, 23933-23939 (1993)
Non-Patent Document 16: Anderson N G, Maller J L, Tonks N K and Sturgill T W, Nature, 343, 651-653 (1990)
Non-Patent Document 17: Seger R and Krebs E G, FASEG J, 9 716-735 (1995)
Non-Patent Document 18: Seger R, Ahn N G, Posada J, Munar E S, Jensen A M, Cooper J A, Cobb M H and Kregs E G, J. Biol. Chem., 267, 14373-14381 (1992)
Non-Patent Document 19: Hoshino, Chatani Y, Yamori T, Tsuruo T, Oka H, Yoshida O, Sshimada Y, Ari-I S, Wada H, Fujimoot J, Kohno M, oncogene, 18, 813 (1999)
Non-Patent Document 20: Kim S C, Hahn J S, Min Y H, Yoo N C, Ko Y W, Lee W J, Blood, 93, 3893 (1999)
Non-Patent Document 21: Morgan M A, Dolp O, Reuter C W, Blood, 97, 1823 (2001)
Non-Patent Document 22: Cowley S, Paterson H, Kemp P and Marshall C J, Cell, 77, 841-852 (1994)
Non-Patent Document 23: Mansour S J, Matten W T, Hermann A S, Candia J M, Rong S, Fukasawa K, Vande Woude G F and Ahn N G, Science, 265, 966-970 (1994)
Non-Patent Document 24: Dudley D T, Pang L, Decker S J, Bridges A J and Saltiel A R, Proc. Natl. Acad. Sci. USA, 92, 7686-7689 (1995)
Non-Patent Document 25: Alessi D R, Cuenda A, Cohen P, Dudley D T and Saltiel A R, J. Biol. Chem., 270, 27489-27494 (1995)
Non-Patent Document 26: Pages G, Lenorman D, L'Allemain G, Chambard J C, Meloche S and Puyssegur J, Proc. Natl. Acad. Sci. USA., 90, 8319-8323 (1993)
Non-Patent Document 27: Pang L, Sawada T, Decker S J and Saltiel A R., J. Biol. Chem., 270, 13585-13588 (1995)
Non-Patent Document 28: Finalay D, Healy V, Furlong F, O'Connell F C, Keon N K and Martin F, Cell Death Differ. 7, 303-313 (2000)
Non-Patent Document 29: Holmstrom T H, Tran S E, Johnson V L, Ahn N G, Chow S C and Eriksson J E, Mol. Cell. Biol., 19, 5991-6002 (1999)
Non-Patent Document 30: Elliceiri B P, Klemke R, Stromblad S and Cherexh D A, J. Cell Biol., 141, 1255-1263 (1998)
Non-Patent Document 31: Milanini J, Vinals F, Pouyssegur J and Pages G, J. Biol. Chem., 273, 18165-18172 (1998)

Non-Patent Document 32: 2002 American Society of Clinical Oncology Annual Meeting (May 18-21, 2002) Abstract Nos. 320 and 321

DISCLOSURE OF THE INVENTION

The present inventors made every effort to develop compounds having excellent MEK inhibitory effects, and found that 2-phenylamino-benzaldoxime derivatives with a unique structure comprise an excellent MEK inhibitory effect, have excellent stability in vivo and solubility in water, and are useful as highly safe preventive or therapeutic agents (particularly therapeutic agents) against proliferative diseases. The present invention was thus completed.

Specifically, compounds of the present invention show excellent stability in liver microsomes. In addition, they have high water solubility.

Furthermore, compounds of the present invention are expected to show higher Cmax values, AUC values, and longer half-lives than known compounds. Compared to CI-1040 or MEK inhibitors having similar physicochemical properties, compounds of the present invention show excellent in vivo absorbability, and are expected to show small differences in PK parameters between patients. In addition, since the active forms of these compounds maintain a high blood concentration for a long period of time, a sufficient amount of the active forms are exposed to the target molecule (i.e., MEK) compared to conventional compounds. Such effects may lead to enhanced efficacy and reduced strain on patients due to reduced administration frequency. Moreover, compounds of the present invention can be expected to inhibit angiogenesis and to become clinically effective therapeutic agents.

Specifically, the present invention relates to:

[1] a compound represented by formula (1), or a pharmaceutically acceptable salt thereof:

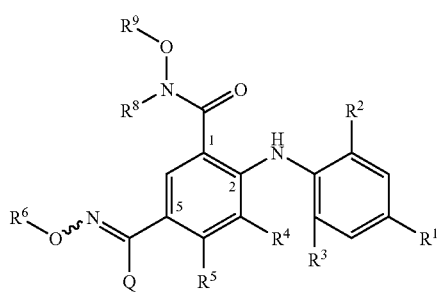

(1)

wherein, the wavy line ～ indicates that the compound can be either one of the stereoisomers, E-form or Z-form, depending on the manner of binding of $R^6O$— to —N, $R^1$ represents a hydrogen atom, a halogen atom, —S—$R^a$, —SO—$R^a$, —SO$_2$—$R^a$, —COO$R^a$, an alkyl group which may have 1 to 3 substituents selected from Group A indicated below, an alkenyl group which may have 1 to 3 substituents selected from Group A indicated below, or an alkynyl group which may have 1 to 3 substituents selected from Group A indicated below, $R^2$ and $R^3$ independently represent a hydrogen atom, a halogen atom, or an alkyl group which may have 1 to 3 substituents selected from Group A indicated below, $R^4$ and $R^5$ independently represent a hydrogen atom, a halogen atom, or a nitro group, $R^6$ and $R^9$ independently represent a hydrogen atom;

an alkyl group, an alkenyl group, or an alkynyl group, each of which may have 1 to 3 substituents selected from Group A indicated below; or a cycloalkyl group, an aryl group, a heteroaryl group, a heterocyclic group, a cycloalkylalkyl group, a cycloalkylalkenyl group, a cycloalkylalkynyl group, an arylalkyl group, an arylalkenyl group, an arylalkynyl group, a heteroarylalkyl group, a heteroarylalkenyl group, a heteroarylalkynyl group, a heterocyclic alkyl group, a heterocyclic alkenyl group, or a heterocyclic alkynyl group, each of which may have 1 to 3 substituents selected from Group B indicated below, Q represents —$NR^aR^b$ or a group represented by $R^7$, $R^7$ represents a hydrogen atom;

an alkyl group, an alkenyl group, or an alkynyl group, each of which may have 1 to 3 substituents selected from Group A indicated below; or a cycloalkyl group, a heterocyclic group, an aryl group, a heteroaryl group, an arylalkyl group, or a heterocyclic alkyl group, each of which may have 1 to 3 substituents selected from Group B indicated below, $R^8$ represents a hydrogen atom, or an alkyl group which may have 1 to 3 substituents selected from Group A indicated below, Group A: a halogen atom, a nitro group, —O—$R^a$, -(an alkylene group)-O$R^a$, —[O-(an alkylene group)]$_n$-O$R^a$, —$NR^aR^b$, —$NR^b$-(an alkylene group)-O$R^a$, —$NR^aSO_2R^b$, —C=N—O$R^a$, —CO$_2R^a$, —CON$R^aR^b$, —$NR^aOR^b$, —COR$^a$, —S$R^a$, —SO$_2R^a$, and —SO$_2NR^aR^b$, Group B: a halogen atom, a nitro group, —O—$R^a$, -(an alkylene group)-O$R^a$, —[O-(an alkylene group)]$_n$-O$R^a$, —$NR^aR^b$, —$NR^b$-(an alkylene group)-O$R^a$, —$NR^aSO_2R^b$, —C=N—O$R^a$, —CO$_2R^a$, —CON$R^aR^b$, —$NR^aCOR^b$, —COR$^a$, —S$R^a$, —SO$_2R^a$, —SO$_2NR^aR^b$, an oxo group, an alkyl group, an alkenyl group, an alkynyl group, an aryl group, and a heteroaryl group, and the above-mentioned $R^a$ and $R^b$ are identical to or different from each other and independently represent a hydrogen atom; an alkyl group that may be substituted with an OH group; an aryl group; or a heteroaryl group, and n=1 to 4;

[2] the compound of [1], or a pharmaceutically acceptable salt thereof, wherein $R^1$ is an iodine atom, a bromine atom, a vinyl group, or an ethynyl group;

[3] the compound of [1] or [2], or a pharmaceutically acceptable salt thereof, wherein $R^2$ is a hydrogen atom, a chlorine atom, a fluorine atom, a methyl group, or a hydroxymethyl group;

[4] the compound of any one of [1] to [3], or a pharmaceutically acceptable salt thereof, wherein $R^2$ is a chlorine atom or a fluorine atom;

[5] the compound of any one of [1] to [4], or a pharmaceutically acceptable salt thereof, wherein $R^3$ is a hydrogen atom, a chlorine atom, or a fluorine atom;

[6] the compound of any one of [1] to [5], or a pharmaceutically acceptable salt thereof, wherein $R^3$ is a hydrogen atom;

[7] the compound of any one of [1] to [6], or a pharmaceutically acceptable salt thereof, wherein $R^4$ is a hydrogen atom or a fluorine atom;

[8] the compound of any one of [1] to [7], or a pharmaceutically acceptable salt thereof, wherein $R^5$ is a fluorine atom;

[9] the compound of any one of [1] to [8], or a pharmaceutically acceptable salt thereof, wherein $R^6$ and $R^9$ independently represent a hydrogen atom;

an alkyl group, an alkenyl group, or an alkynyl group, each of which may have 1 to 3 substituents selected from Group C indicated below; or a cycloalkylalkyl group, an arylalkyl group, a heteroarylalkyl group, or a heterocyclic alkyl group, each of which may have 1 to 3 substituents selected from Group D indicated below, Group C: —O—$R^a$, —$NR^aR^b$, -(a C1-C4 alkylene group)-$OR^a$, —[O-(a C1-C4 alkylene group)]$_n$-$OR^a$, —$NR^b$-(a C1-C4 alkylene group)-$OR^a$, —$NR^aSO_2R^b$, —C=N—$OR^a$, —$CONR^aR^b$, —$NR^aCOR^b$, —$SR^a$, and —$SO_2R^a$, Group D: —O—$R^8$, -(a C1-C4 alkylene group)-$OR^a$, —[O-(a C1-C4 alkylene group)]$_n$-$OR^a$, —$NR^b$-(a C1-C4 alkylene group)-$OR^a$, —C=N—$OR^a$, —$CONR^aR^b$, —$NR^aCOR^b$, —$SR^a$, —$SO_2R^a$, an oxo group, and a C1-C4 alkyl group, provided that $R^a$ and $R^b$ are identical to or different from each other and independently represent a hydrogen atom; a C1-C4 alkyl group that may be substituted with an OH group; an aryl group; or a heteroaryl group, and n=1 to 4;

[10] the compound of any one of [1] to [9], or a pharmaceutically acceptable salt thereof, wherein $R^6$ is a hydrogen atom, a methyl group, an isopropyl group, a 2-hydroxyethyl group, a 2-hydroxypropyl group, a 3-hydroxypropyl group, a 2,3-dihydroxypropyl group, a 2-hydroxy-1-(hydroxymethyl)ethyl group, a 2-hydroxypropyl group, a 2-hydroxy-2-methylpropyl group, a 2-hydroxy-1-methylethyl group, a cyclopropylmethyl group, a cyclopentylmethyl group, a 2-(2-hydroxyethoxy)ethyl group, a 2-(2-hydroxyethylamino)ethyl group, a 2-(morpholin-4-yl)ethyl group, a 2-(4-methylpiperazin-1-yl)ethyl group, a 2-(4-hydroxypiperidin-1-yl)ethyl group, a 2-(hydroxyimino)ethyl group, a 2-(methoxyimino)ethyl group, a 2-methylcarbamoyl-ethyl group, a 2-propenyl group, a 2-propynyl group, a benzyl group, a pyridin-4-ylmethyl group, an oxazol-2-ylmethyl group, a 3-hydroxy-3-methylbutyl group, a 3-hydroxy-2,2-dimethyl-propyl group, a 1-hydroxymethyl-cyclopropyl-methyl group, a 4-hydroxybutyl group, a 3-methoxy-3-methylbutyl group, a 2-methoxyethyl group, a 2-methylsulfanylethyl group, a 2-methanesulfonylethyl group, a 2-aminoethyl group, a 2-methylaminoethyl group, a 2-dimethylaminoethyl group, a 2-(piperidin-1-yl)ethyl group, a 2-(pyrrolidin-1-yl)ethyl group, a 2-((S)-2-hydroxymethyl-pyrrolidin-1-yl)ethyl group, a 2-((R)-2-hydroxymethyl-pyrrolidin-1-yl)ethyl group, a methylcarbamoyl-methyl group, a 2-dimethylcarbamoyl-ethyl group, a 3-methylcarbamoyl-propyl group, a (2-hydroxyethylcarbamoyl)methyl group, a 2-acetylaminoethyl group, a 2-acetylmethylaminoethyl group, a 2-(2-oxo-pyrrolidin-1-yl)ethyl group, a 2-(2-oxoimidazolidin-1-yl)ethyl group, a 1H-imidazol-2-ylmethyl group, a 3H-imidazol-4-ylmethyl group, or a 2-methanesulfonylamino-ethyl group;

[11] the compound of any one of [1] to [10], or a pharmaceutically acceptable salt thereof, wherein $R^6$ is a hydrogen atom, a 2-hydroxyethyl group, a 3-hydroxypropyl group, a 3-hydroxy-3-methylbutyl group, a 3-hydroxy-2,2-dimethyl-propyl group, a 1-hydroxymethyl-cyclopropyl-methyl group, a 4-hydroxybutyl group, a 3-methoxy-3-methylbutyl group, a 2-methoxyethyl group, a 2,3-dihydroxypropyl group, a 2-hydroxy-1-(hydroxymethyl)ethyl group, a 2-hydroxypropyl group, a 2-hydroxy-2-methylpropyl group, a 2-hydroxy-1-methylethyl group, a 2-(2-hydroxyethoxy)ethyl group, a 2-methylsulfanylethyl group, or a 2-methanesulfonylethyl group;

[12] the compound of any one of [1] to [10], or a pharmaceutically acceptable salt thereof, wherein $R^6$ is a 2-aminoethyl group, a 2-methylaminoethyl group, a 2-dimethylaminoethyl group, a 2-(2-hydroxyethylamino)ethyl group, a 2-(morpholin-4-yl)ethyl group, a 2-(piperidin-1-yl)ethyl group, a 2-(4-methylpiperazin-1-yl)ethyl group, a 2-(4-hydroxypiperidin-1-yl)ethyl group, a 2-(pyrrolidin-1-yl)ethyl group, a 2-((S)-2-hydroxymethyl-pyrrolidin-1-yl)ethyl group, a 2-((R)-2-hydroxymethyl-pyrrolidin-1-yl)ethyl group, a 2-(hydroxyimino)ethyl group, a 2-(methoxyimino)ethyl group, a methylcarbamoyl-methyl group, a 2-methylcarbamoyl-ethyl group, a 2-dimethylcarbamoyl-ethyl group, a 3-methylcarbamoyl-propyl group, a (2-hydroxyethylcarbamoyl)methyl group, a 2-acetylaminoethyl group, a 2-acetylmethylaminoethyl group, a 2-(2-oxo-pyrrolidin-1-yl)ethyl group, a 2-(2-oxoimidazolidin-1-yl)ethyl group, a 1H-imidazol-2-ylmethyl group, a 3H-imidazol-4-ylmethyl group, a pyridin-4-ylmethyl group, an oxazol-2-ylmethyl group, or a 2-methanesulfonylamino-ethyl group;

[13] the compound of any one of [1] to [10], or a pharmaceutically acceptable salt thereof, wherein $R^6$ is a methyl group, an isopropyl group, a cyclopropylmethyl group, a cyclopentylmethyl group, a 2-propenyl group, a 2-propynyl group, or a benzyl group;

[14] the compound of any one of [1] to [13], or a pharmaceutically acceptable salt thereof, wherein $R^6$ is a hydrogen atom, a 2-hydroxyethyl group, a 2-hydroxypropyl group, a 2-hydroxy-2-methylpropyl group, a 2,3-dihydroxypropyl group, a 3-hydroxypropyl group, a 2-dimethylaminoethyl group, a 2-aminoethyl group, a 2-methylaminoethyl group, a 2-acetylaminoethyl group, a 2-acetylmethylaminoethyl group, a 2-(2-oxo-pyrrolidin-1-yl)ethyl group, a 2-(2-oxoimidazolidin-1-yl)ethyl group, a 1H-imidazol-2-ylmethyl group, a pyridin-4-ylmethyl group, a 3-hydroxy-2,2-dimethyl-propyl group, a 2-methylsulfanylethyl group, a 2-methanesulfonylethyl group, a methylcarbamoylmethyl group, a 2-methylcarbamoyl-ethyl group, a 2-dimethylcarbamoyl-ethyl group, a 3-methylcarbamoylpropyl group, a (2-hydroxyethylcarbamoyl)methyl group, or a 2-methanesulfonylamino-ethyl group;

[15] the compound of any one of [1] to [14], wherein Q is a hydrogen atom;

—$NR^aR^b$;

an alkyl group, an alkenyl group, or an alkynyl group, each of which may have 1 to 3 substituents selected from Group C indicated below; or a cycloalkylalkyl group, an arylalkyl group, a heteroarylalkyl group, or a heterocyclic alkyl group, each of which may have 1 to 3 substituents selected from Group D indicated below;

Group C: —O—$R^a$, —[O-(an alkylene group)]$_n$-$OR^a$, —$NR^b$-(an alkylene group)-$OR^a$, and —C=N—$OR^a$;

Group D: —O—$R^a$, —[O-(an alkylene group)]$_n$-$OR^a$, —$NR^b$-(an alkylene group)-$OR^a$, —C=N—$OR^a$, and an alkyl group;

provided that $R^a$ and $R^b$ are identical to or different from each other and independently represent a hydrogen atom, an alkyl group, an aryl group, or a heteroaryl group, and n=1 to 4;

[16] the compound of any one of [1] to [15], or a pharmaceutically acceptable salt thereof, wherein Q is a hydrogen atom, a methyl group, an isopropyl group, a 2-hydroxyethyl group, a 2,3-dihydroxypropyl group, a 2-(morpholin-4-yl)ethyl group, a 2-propenyl group, a benzyl group, an amino group, or a methylamino group;

[17] the compound of any one of [1] to [15], or a pharmaceutically acceptable salt thereof, wherein Q is —NR$^a$R$^b$;

[18] the compound of any one of [1] to [15], or a pharmaceutically acceptable salt thereof, wherein Q is an alkyl group;

[19] the compound of any one of [1] to [15], or a pharmaceutically acceptable salt thereof, wherein Q is a hydrogen atom;

[20] the compound of any one of [1] to [19], or a pharmaceutically acceptable salt thereof, wherein R$^8$ is a hydrogen atom or a methyl group;

[21] the compound of any one of [1] to [20], or a pharmaceutically acceptable salt thereof, wherein R$^8$ is a hydrogen atom;

[22] the compound of any one of [1] to [21], or a pharmaceutically acceptable salt thereof, wherein R$^9$ is a hydrogen atom, a methyl group, an isopropyl group, a 2-hydroxyethyl group, a 3-hydroxypropyl group, a 2,3-dihydroxypropyl group, a 2-hydroxy-1-(hydroxymethyl)ethyl group, a 2-hydroxypropyl group, a 2-hydroxy-2-methylpropyl group, a 2-hydroxy-1-methylethyl group, a cyclopropylmethyl group, a cyclopentylmethyl group, a 2-(2-hydroxyethoxy)ethyl group, a 2-(2-hydroxyethylamino)ethyl group, a 2-(morpholin-4-yl)ethyl group, a 2-(4-methylpiperazin-1-yl)ethyl group, a 2-(4-hydroxypiperidin-1-yl)ethyl group, a 2-(hydroxyimino)ethyl group, a 2-(methoxyimino)ethyl group, a 2-propenyl group, a 2-propynyl group, a benzyl group, a pyridylmethyl group, or an oxazol-2-ylmethyl group;

[23] the compound of any one of [1] to [21], or a pharmaceutically acceptable salt thereof, wherein R$^9$ is an alkyl group substituted with at least one hydroxyl group;

[24] the compound of any one of [1] to [22], or a pharmaceutically acceptable salt thereof, wherein R$^9$ is a 2-hydroxyethyl group, a 3-hydroxypropyl group, a 2,3-dihydroxypropyl group, a 2-hydroxy-1-(hydroxymethyl)ethyl group, a 2-hydroxypropyl group, a 2-hydroxy-2-methylpropyl group, or a 2-hydroxy-1-methylethyl group;

[25] the compound of any one of [1] to [22], or a pharmaceutically acceptable salt thereof, wherein R$^9$ is a 2-(2-hydroxyethylamino)ethyl group, a 2-(mopholin-4-yl)ethyl group, a 2-(4-methylpiperazin-1-yl)ethyl group, a 2-(4-hydroxypiperidin-1-yl)ethyl group, a 2-(hydroxyimino)ethyl group, a 2-(methoxyimino)ethyl group, a pyridylmethyl group, or an oxazol-2-ylmethyl group;

[26] the compound of any one of [1] to [22], or a pharmaceutically acceptable salt thereof, wherein R$^9$ is a methyl group, an isopropyl group, a cyclopropylmethyl group, a cyclopentylmethyl group, a 2-propenyl group, a 2-propynyl group, or a benzyl group;

[27] the compound of [1] or a pharmaceutically acceptable salt thereof, wherein R$^2$ is a fluorine atom, R$^3$ is a hydrogen atom, R$^4$ is a fluorine atom, and R$^5$ is a fluorine atom;

[28] the compound of any one of [1] to [27], or a pharmaceutically acceptable salt thereof, wherein in formula (1), R$^6$—O—N=C(Q)- is an E-form oxime represented by formula (a):

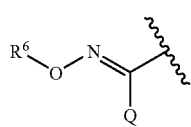

(a)

wherein, R$^6$ and Q have the same meaning as R$^6$ and Q of formula (1);

[29] the compound of any one of [1] to [27], or a pharmaceutically acceptable salt thereof, wherein in formula (1), R$^6$—O—N=C(Q)- is a Z-form oxime represented by formula (b):

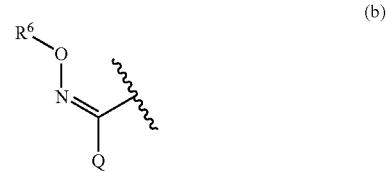

(b)

wherein, R$^6$ and Q have the same meaning as R$^6$ and Q of formula (1);

[30] the compound of [1] or a pharmaceutically acceptable salt thereof, wherein the compound of formula (1) is selected from the group consisting of:

(1): (E)-3,4-difluoro-2-(2-fluoro-4-iodo-phenylamino)-N-(2-hydroxy-ethoxy)-5-[(2-hydroxy-ethoxyimino)-methyl]-benzamide, (2): (E)-2-(4-ethynyl-2-fluorophenylamino)-3,4-difluoro-N-(2-hydroxy-ethoxy)-5-[(2-hydroxy-ethoxyimino)-methyl]-benzamide, (3): (E)-3,4-difluoro-2-(2-fluoro-4-vinyl-phenylamino)-N-(2-hydroxy-ethoxy)-5-[(2-hydroxy-ethoxyimino)-methyl]-benzamide, (4): (E)-3,4-difluoro-N-(2-hydroxy-ethoxy)-5-[(2-hydroxy-ethoxyimino)-methyl]-2-(4-iodo-phenylamino)-benzamide, (5): (E)-2-(2-chloro-4-iodo-phenylamino)-3,4-difluoro-N-(2-hydroxy-ethoxy)-5-[(2-hydroxy-ethoxyimino)-methyl]-benzamide, (6): (E)-3,4-difluoro-N-(2-hydroxy-ethoxy)-5-[(2-hydroxy-ethoxyimino)-methyl]-2-(4-iodo-2-methyl-phenylamino)-benzamide, (7): (E)-3,4-difluoro-N-(2-hydroxy-ethoxy)-5-[(2-hydroxy-ethoxyimino)-methyl]-2-(2-hydroxymethyl-4-iodo-phenylamino)-benzamide, (8): (E)-2-(2-chloro-6-fluoro-4-iodo-phenylamino)-3,4-difluoro-N-(2-hydroxy-ethoxy)-5-[(2-hydroxy-ethoxyimino)-methyl]-benzamide, (9): (E)-2-(2,6-difluoro-4-iodo-phenylamino)-3,4-difluoro-N-(2-hydroxy-ethoxy)-5-[(2-hydroxy-ethoxyimino)-methyl]-benzamide, (10): (E)-4-fluoro-2-(2-fluoro-4-iodo-phenylamino)-N-(2-hydroxy-ethoxy)-5-[(2-hydroxy-ethoxyimino)-methyl]-benzamide, (11): (E)-3,4-difluoro-2-(2-fluoro-4-iodo-phenylamino)-N-(2-hydroxy-ethoxy)-5-[(3-hydroxy-propoxyimino)-methyl]-benzamide, (12): (E)-5-[(2,3-dihydroxy-propoxyimino)-methyl]-3,4-difluoro-2-(2-fluoro-4-iodo-phenylamino)-N-(2-hydroxy-ethoxy)-benzamide, (13): (E)-3,4-difluoro-2-(2-fluoro-4-iodo-phenylamino)-N-(2-hydroxy-ethoxy)-5-[(2-hydroxy-1-hydroxymethyl-ethoxyimino)-methyl]-benzamide, (14): (E)-3,4-difluoro-2-(2-fluoro-4-iodo-phenylamino)-N-(2-hydroxy-ethoxy)-5-[(2-hydroxy-propoxyimino)-methyl]-benzamide, (15): (E)-3,4-difluoro-2-(2-fluoro-4-iodo-phenylamino)-N-(2-hydroxy-ethoxy)-5-[(2-hydroxy-2-methyl-propoxyimino)-methyl]-benzamide, (16): (E)-3,4-difluoro-2-(2-fluoro-4-iodo-phenylamino)-N-(2-hydroxy-ethoxy-5-[(2-hydroxy-1-methyl-ethoxyimino)-methyl]-benzamide, (17): (E)-3,4-difluoro-2-(2-fluoro-4-iodo-phenylamino)-N-(2-hydroxy-ethoxy)-5-{[(2-hydroxy-ethoxy)-ethoxyimino]-methyl}-benzamide,
(18): (E)-3,4-difluoro-2-(2-fluoro-4-iodo-phenylamino)-N-(2-hydroxy-ethoxy)-5-{[(2-hydroxy-ethylamino)-ethoxyimino]-methyl}-benzamide,
(19): (E)-3,4-difluoro-2-(2-fluoro-4-iodo-phenylamino)-N-(2-hydroxy-ethoxy)-5-[(2-morpholin-4-yl-ethoxyimino)-methyl]-benzamide,
(20): (E)-3,4-difluoro-2-(2-fluoro-4-iodo-phenylamino)-N-(2-hydroxy-ethoxy)-5-{[2-(4-hydroxy-piperidin-1-yl)-ethoxyimino]-methyl}-benzamide,
(21) (E)-3,4-difluoro-2-(2-fluoro-4-iodo-phenylamino)-N-(2-hydroxy-ethoxy)-5-{[2-(4-methyl-piperazin-1-yl)-ethoxyimino]-methyl}-benzamide,
(22): (E)-3,4-difluoro-2-(2-fluoro-4-iodo-phenylamino)-N-(2-hydroxy-ethoxy)-5-[(2-hydroxyimino-ethoxyimino)-methyl]-benzamide,
(23): (E)-3,4-difluoro-2-(2-fluoro-4-iodo-phenylamino)-N-(2-hydroxy-ethoxy)-5-[(2-methoxyimino-ethoxyimino)-methyl]-benzamide,
(24): (E)-3,4-difluoro-2-(2-fluoro-4-iodo-phenylamino)-N-(2-hydroxy-ethoxy)-5-(hydroxyimino-methyl)-benzamide,
(25): (E)-3,4-difluoro-2-(2-fluoro-4-iodo-phenylamino)-N-(2-hydroxy-ethoxy)-5-(methoxyimino-methyl)-benzamide,
(26): (E)-3,4-difluoro-2-(2-fluoro-4-iodo-phenylamino)-N-(2-hydroxy-ethoxy)-5-(isopropoxyimino-methyl)-benzamide,
(27): (E)-5-(cyclopropylmethoxyimino-methyl)-3,4-difluoro-2-(2-fluoro-4-iodo-phenylamino)-N-(2-hydroxy-ethoxy)-benzamide,
(28): (E)-5-(cyclopentylmethoxyimino-methyl)-3,4-difluoro-2-(2-fluoro-4-iodo-phenylamino)-N-(2-hydroxy-ethoxy)-benzamide,
(29): (E)-5-(allyloxyimino-methyl)-3,4-difluoro-2-(2-fluoro-4-iodo-phenylamino)-N-(2-hydroxy-ethoxy)-benzamide,
(30): (E)-3,4-difluoro-2-(2-fluoro-4-iodo-phenylamino)-N-(2-hydroxy-ethoxy)-5-(2-propynyloxyimino-methyl)-benzamide,
(31): (E)-5-(benzyloxyimino-methyl)-3,4-difluoro-2-(2-fluoro-4-iodo-phenylamino)-N-(2-hydroxy-ethoxy)-benzamide,
(32): (E)-3,4-difluoro-2-(2-fluoro-4-iodo-phenylamino)-N-(2-hydroxy-ethoxy)-5-[(pyridin-4-ylmethoxyimino)-methyl]-benzamide,
(33): (E)-3,4-difluoro-2-(2-fluoro-4-iodo-phenylamino)-N-(2-hydroxy-ethoxy)-5-[(oxazol-2-ylmethoxyimino)-methyl]-benzamide,
(34): (E)-3,4-difluoro-2-(2-fluoro-4-iodo-phenylamino)-N-(2-hydroxy-ethoxy)-5-[1-(2-hydroxy-ethoxyimino)-ethyl]-benzamide,
(35): (E)-3,4-difluoro-2-(2-fluoro-4-iodo-phenylamino)-N-(2-hydroxy-ethoxy)-5-[1-(2-hydroxy-ethoxyimino)-2-methyl-propyl]-benzamide,
(36): (E)-3,4-difluoro-2-(2-fluoro-4-iodo-phenylamino)-N-(2-hydroxy-ethoxy)-5-[1-(2-hydroxy-ethoxyimino)-3-butenyl]-benzamide,
(37): (E)-3,4-difluoro-2-(2-fluoro-4-iodo-phenylamino)-N-(2-hydroxy-ethoxy)-5-[1-(2-hydroxy-ethoxyimino)-2-phenylethyl]-benzamide,
(38): (E)-3,4-difluoro-2-(2-fluoro-4-iodo-phenylamino)-N-(2-hydroxy-ethoxy)-5-[3-hydroxy-1-(2-hydroxy-ethoxyimino)-propyl]-benzamide,
(39): (E)-5-[3,4-dihydroxy-1-(hydroxy-ethoxyimino)-butyl]-3,4-difluoro-2-(2-fluoro-4-iodo-phenylamino)-N-(2-hydroxy-ethoxy)-benzamide,
(40): (E)-3,4-difluoro-2-(2-fluoro-4-iodo-phenylamino)-N-(2-hydroxy-ethoxy)-5-[1-(2-hydroxy-ethoxyimino)-3-morpholin-4-yl-propyl]-benzamide,
(41): (E)-3,4-difluoro-2-(2-fluoro-4-iodo-phenylamino)-N-(2-hydroxy-ethoxy)-5-[N-(2-hydroxy-ethoxyimino)-carbamimidoyl]-benzamide,
(42): (E)-3,4-difluoro-2-(2-fluoro-4-iodo-phenylamino)-N-(2-hydroxy-ethoxy)-5-[N-(2-hydroxy-ethoxyimino)-N'-methyl-carbamimidoyl]-benzamide,
(43): (E)-3,4-difluoro-2-(2-fluoro-4-iodo-phenylamino)-N-(2-hydroxy-ethoxy)-5-[(2-hydroxy-ethoxyimino)-methyl]-N-methyl-benzamide,
(44): (E)-3,4-difluoro-2-(2-fluoro-4-iodo-phenylamino)-5-[(2-hydroxy-ethoxyimino)-methyl]-N-(3-hydroxy-propoxy)-benzamide,
(45): (E)-N-(2,3-dihydroxy-propoxy)-3,4-difluoro-2-(2-fluoro-4-iodo-phenylamino)-5-[(2-hydroxy-ethoxyimino)-methyl]-benzamide,
(46): (E)-3,4-difluoro-2-(2-fluoro-4-iodo-phenylamino)-5-[(2-hydroxy-ethoxyimino)-methyl]-N-(2-hydroxy-1-hydroxymethyl-ethoxy)-benzamide,
(47): (E)-3,4-difluoro-2-(2-fluoro-4-iodo-phenylamino)-5-[(2-hydroxy-ethoxyimino)-methyl]-N-(2-hydroxy-propoxy)-benzamide,
(48): (E)-3,4-difluoro-2-(2-fluoro-4-iodo-phenylamino)-5-[(2-hydroxy-ethoxyimino)-methyl]-N-(2-hydroxy-2-methyl-propoxy)-benzamide,
(49): (E)-3,4-difluoro-2-(2-fluoro-4-iodo-phenylamino)-5-[(2-hydroxy-ethoxyimino)-methyl]-N-(2-hydroxy-1-methyl-ethoxy)-benzamide,
(50): (E)-3,4-difluoro-2-(2-fluoro-4-iodo-phenylamino)-N-[(2-hydroxy-ethoxy)-ethoxy]-5-[(2-hydroxy-ethoxyimino)-methyl]-benzamide,
(51): (E)-3,4-difluoro-2-(2-fluoro-4-iodo-phenylamino)-5-[(2-hydroxy-ethoxyimino)-methyl]-N-[(2-hydroxy-ethylamino)-ethoxy]-benzamide,
(52): (E)-3,4-difluoro-2-(2-fluoro-4-iodo-phenylamino)-5-[(2-hydroxy-ethoxyimino)-methyl]-N-(2-morpholin-4-yl-ethoxy)-benzamide,
(53): (E)-3,4-difluoro-2-(2-fluoro-4-iodo-phenylamino)-5-[(2-hydroxy-ethoxyimino)-methyl]-N-[2-(4-hydroxy-piperidin-1-yl)-ethoxy]-benzamide,
(54): (E)-3,4-difluoro-2-(2-fluoro-4-iodo-phenylamino)-5-[(2-hydroxy-ethoxyimino)-methyl]-N-[2-(4-methyl-piperazin-1-yl)-ethoxy]-benzamide,
(55): (E)-3,4-difluoro-2-(2-fluoro-4-iodo-phenylamino)-5-[(2-hydroxy-ethoxyimino)-methyl]-N-(2-hydroxyimino-ethoxy)-benzamide,
(56): (E)-3,4-difluoro-2-(2-fluoro-4-iodo-phenylamino)-5-[(2-hydroxy-ethoxyimino)-methyl]-N-(2-methoxyimino-ethoxy)-benzamide,
(57): (E)-3,4-difluoro-2-(2-fluoro-4-iodo-phenylamino)-N-hydroxy-5-[(2-hydroxy-ethoxyimino)-methyl]-benzylamide,
(58): (E)-3,4-difluoro-2-(2-fluoro-4-iodo-phenylamino)-5-[(2-hydroxy-ethoxyimino)-methyl]-N-methoxy-benzamide,
(59): (E)-3,4-difluoro-2-(2-fluoro-4-iodo-phenylamino)-5-[(2-hydroxy-ethoxyimino)-methyl]-N-isopropoxy-benzamide,
(60): (E)-N-cyclopropylmethoxy-3,4-difluoro-2-(2-fluoro-4-iodo-phenylamino)-5-[(2-hydroxy-ethoxyimino)-methyl]-benzamide, (61): (E)-N-cyclopentylmethoxy-3,4-difluoro-2-(2-fluoro-4-iodo-phenylamino)-5-[(2-hydroxy-ethoxyimino)-methyl]-benzamide,
(62): (E)-N-allyloxy-3,4-difluoro-2-(2-fluoro-4-iodo-phenylamino)-5-[(2-hydroxy-ethoxyimino)-methyl]-benzamide,
(63): (E)-3,4-difluoro-2-(2-fluoro-4-iodo-phenylamino)-5-[(2-hydroxy-ethoxyimino)-methyl]-N-(2-propynyloxy)-benzamide,
(64): (E)-N-benzyloxy-3,4-difluoro-2-(2-fluoro-4-iodo-phenylamino)-5-[(2-hydroxy-ethoxyimino)-methyl]-benzamide,
(65): (E)-3,4-difluoro-2-(2-fluoro-4-iodo-phenylamino)-5-[(2-hydroxy-ethoxyimino)-methyl]-N-(pyridin-4-yl-methoxy)-benzamide,
(66): (E)-3,4-difluoro-2-(2-fluoro-4-iodo-phenylamino)-5-[(2-hydroxy-ethoxyimino)-methyl]-N-(oxazol-2-yl-methoxy)-benzamide,
(67): (E)-2-(4-ethynyl-2-fluoro-phenylamino)-3,4-difluoro-5-[(2-hydroxy-ethoxyimino)-methyl]-N-(3-hydroxy-propoxy)-benzamide,
(68): (E)-N-(2,3-dihydroxy-propoxy)-2-(4-ethynyl-2-fluoro-phenylamino)-5,4-difluoro-5-[(2-hydroxy-ethoxyimino)-methyl]-benzamide,
(69): (E)-2-(4-ethynyl-2-fluoro-phenylamino)-3,4-difluoro-5-[(2-hydroxy-ethoxyimino)-methyl]-N-(2-hydroxy-1-hydroxymethyl-ethoxy)-benzamide,
(70): (E)-2-(4-ethynyl-2-fluoro-phenylamino)-3,4-difluoro-N-(2-hydroxy-ethoxy)-5-[(3-hydroxy-propoxyimino)-methyl]-benzamide,
(71): (E)-5-[(2,3-dihydroxy-propoxyimino)-methyl]-2-(4-ethynyl-2-fluoro-phenylamino)-3,4-difluoro-N-(2-hydroxy-ethoxy)benzamide,
(72): (E)-2-(4-ethynyl-2-fluoro-phenylamino)-3,4-difluoro-N-(2-hydroxy-ethoxy)-5-[(2-hydroxy-1-hydroxymethyl-ethoxyimino)-methyl]-benzamide,
(73): (E)-2-(4-ethynyl-2-fluoro-phenylamino)-3,4-difluoro-N-(2-hydroxyethoxy)-5-[(2-hydroxy-2-methyl-propoxyimino)-methyl]-benzamide,
(74): (E)-3,4-difluoro-2-(2-fluoro-4-iodo-phenylamino)-N-(2-hydroxy-ethoxy)-5-[(2-methylcarbamoyl-ethoxyimino)-methyl]-benzamide,
(75): (E)-5-[(2-dimethylamino-ethoxyimino)-methyl]-3,4-difluoro-2-(2-fluoro-4-iodo-phenylamino)-N-(2-hydroxy-ethoxy)-benzamide,
(76): (E)-3,4-difluoro-2-(2-fluoro-4-iodo-phenylamino)-N-(2-hydroxy-ethoxy)-5-[(2-piperidin-1-yl-ethoxyimino)-methyl]-benzamide,
(77): (E)-3,4-difluoro-2-(2-fluoro-4-iodo-phenylamino)-N-(2-hydroxy-ethoxy)-5-[(3-methoxy-3-methyl-butoxyimino)-methyl]-benzamide,
(78): (E)-3,4-difluoro-2-(2-fluoro-4-iodo-phenylamino)-N-(2-hydroxy-ethoxy)-5-[(3-hydroxy-3-methy 1-butoxyimino)-methyl]-benzamide,
(79): (E)-3,4-difluoro-2-(2-fluoro-4-iodo-phenylamino)-5-[(3-hydroxy-2,2-dimethyl-propoxyimino)-methyl]-N-(2-hydroxy-ethoxy)-benzamide,
(80): (E)-3,4-difluoro-2-(2-fluoro-4-iodo-phenylamino)-N-(2-hydroxy-ethoxy)-5-[(1-hydroxymethyl-cyclopropylmethoxyimino)-methyl]-benzamide,
(81): (E)-3,4-difluoro-2-(2-fluoro-4-iodo-phenylamino)-5-[(4-hydroxy-butoxyimino)-methyl]-N-(2-hydroxy-ethoxy)-benzamide,
(82): (E)-3,4-difluoro-2-(2-fluoro-4-iodo-phenylamino)-N-(2-hydroxy-ethoxy)-5-[(2-methylsulfanyl-ethoxyimino)-methyl]benzamide,
(83): (E)-3,4-difluoro-2-(2-fluoro-4-iodo-phenylamino)-N-(2-hydroxy-ethoxy)-5-[(2-methanesulfonyl-ethoxyimino)-methyl]-benzamide,
(84): (E)-3,4-difluoro-2-(2-fluoro-4-iodo-phenylamino)-N-(2-hydroxy-ethoxy)-5-[methylcarbamoylmethoxyiminomethyl]-benzamide,
(85): (E)-3,4-difluoro-2-(2-fluoro-4-iodo-phenylamino)-N-(2-hydroxy-ethoxy)-5-{[(2-hydroxyethylcarbamoyl)-methoxyimino]-methyl}-benzamide,
(86): (E)-3,4-difluoro-2-(2-fluoro-4-iodo-phenylamino)-N-(2-hydroxy-ethoxy)-5-{[(3-methylcarbamoyl-propoxyimino)-methyl]-benzamide,
(87): (E)-3,4-difluoro-2-(2-fluoro-4-iodo-phenylamino)-N-(2-hydroxy-ethoxy)-5-[(2-methoxy-ethoxyimino)-methyl]-benzamide,
(88): (E)-3,4-difluoro-2-(2-fluoro-4-iodo-phenylamino)-N-(2-hydroxy-ethoxy)-5-[isopropoxyimino-methyl]-benzamide,
(89): (E)-3,4-difluoro-2-(2-fluoro-4-iodo-phenylamino)-N-(2-hydroxy-ethoxy)-5-[(3H-imidazol-4-ylmethoxyimino)-methyl]-benzamide,
(90): (E)-3,4-difluoro-2-(2-fluoro-4-iodo-phenylamino)-N-(2-hydroxy-ethoxy)-5-{[2-(2-oxo-pyrrolidin-1-yl)-ethoxyimino]-methyl}-benzamide,
(91): (E)-3,4-difluoro-2-(2-fluoro-4-iodo-phenylamino)-N-(2-hydroxy-ethoxy)-5-[(2-pyrrolidin-1-yl-ethoxyimino)-methyl]-benzamide,
(92): (E)-3,4-difluoro-2-(2-fluoro-4-iodo-phenylamino)-N-(2-hydroxy-ethoxy)-5-{[2-(2-oxo-imidazolidin-1-yl)-ethoxyimino]-methyl}-benzamide,
(93): (E)-3,4-difluoro-2-(2-fluoro-4-iodo-phenylamino)-N-(2-hydroxy-ethoxy)-5-{[2-((S)-hydroxymethyl-pyrrolidin-1-yl)ethoxyimino]-methyl-benzamide,
(94): (E)-5-[(2-amino-ethoxyimino)-methyl]-3,4-difluoro-2-(2-fluoro-4-iodo-phenylamino)-N-(2-hydroxy-ethoxy)-benzamide,
(95): (E)-{2-[2,3-difluoro-4-(2-fluoro-4-iodo-phenylamino)-5-(2-hydroxy-ethoxycarbamoyl)-benzylidene-aminooxy]-ethyl}-carbamic acid tert-butyl ester,
(96): (E)-5-[(2-acetylamino-ethoxyimino)-methyl]-3,4-difluoro-2-(2-fluoro-4-iodo-phenylamino)-N-(2-hydroxy-ethoxy)-benzamide,
(97): (E)-3,4-difluoro-2-(2-fluoro-4-iodo-phenylamino)-N-(2-hydroxy-ethoxy)-5-[(1H-imidazol-2-ylmethoxyimino)-methyl]-benzamide,
(98): (E)-3,4-difluoro-2-(2-fluoro-4-iodo-phenylamino)-N-(2-hydroxy-ethoxy)-5-[(2-methylamino-ethoxyimino)-methyl]-benzamide,
(99): (E)-5-{[2-(acetyl-methyl-amino)-ethoxyimino]-methyl}-3,4-difluoro-2-(2-fluoro-4-iodo-phenylamino)-N-(2-hydroxyethoxy)-benzamide,
(101): (E)-2-(4-ethynyl-2-fluoro-phenylamino)-3,4-difluoro-N-(2-hydroxy-ethoxy)-5-[(2-methylcarbamoyl-ethoxyimino)-methyl]-benzamide,
(102): (Z)-3,4-difluoro-2-(2-fluoro-4-iodo-phenylamino)-N-(2-hydroxy-ethoxy)-5-[(2-hydroxy-ethoxyimino)-methyl]-benzamide,
(103): (Z)-2-(4-ethynyl-2-fluoro-phenylamino)-3,4-difluoro-N-(2-hydroxy-ethoxy)-5-[(2-hydroxy-ethoxyimino)-methyl]-benzamide,
(104): (Z)-3,4-difluoro-2-(2-fluoro-4-iodo-phenylamino)-N-(2-hydroxy-ethoxy)-5-[(2-methanesulfonyl-ethoxyimino)-methyl]-benzamide,
(105): (dl)-(Z)-5-[(2,3-dihydroxy-propoxyimino)-methyl]-3,4-difluoro-2-(2-fluoro-4-iodo-phenylamino)-N-(2-hydroxy-ethoxy)-benzamide, (106): (Z)-5-[(2-acetylamino-ethoxyimino)-methyl]-3,4-difluoro-2-(2-fluoro-4-iodo-phenylamino)-N-(2-hydroxy-ethoxy)-benzamide,
(107): (Z)-3,4-difluoro-2-(2-fluoro-4-iodo-phenylamino)-N-(2-hydroxy-ethoxy)-5-[(2-methylcarbamoyl-ethoxy-imino)-methyl]-benzamide,
(108): (Z)-3,4-difluoro-2-(2-fluoro-4-iodo-phenylamino)-N-(2-hydroxy-ethoxy)-5-[(2-hydroxy-2-methyl-propoxy-imino)-methyl]-benzamide,
(109): (Z)-3,4-difluoro-2-(2-fluoro-4-iodo-phenylamino)-N-(2-hydroxy-ethoxy)-5-(methylcarbamoylmethoxyimino-methyl)benzamide,
(110): (Z)-3,4-difluoro-2-(2-fluoro-4-iodo-phenylamino)-N-(2-hydroxy-ethoxy)-5-{[(2-hydroxyethylcarbamoyl)-methoxyimino]-methyl}-benzamide,
(111): (Z)-3,4-difluoro-2-(2-fluoro-4-iodo-phenylamino)-N-(2-hydroxy-ethoxy)-5-{[(3-methylcarbamoyl-propoxy-imino)-methyl]-benzamide,
(112): dl-(Z)—N-(2,3-dihydroxy-propoxy)-3,4-difluoro-2-(2-fluoro-4-iodo-phenylamino)-5-[(2-hydroxy-ethoxy-imino)-methyl]-benzamide,
(113): (Z)-3,4-difluoro-2-(2-fluoro-4-iodo-phenylamino)-N-(2-hydroxy-ethoxy)-5-{[2-(2-oxo-imidazolidin-1-yl)-ethoxyimino]-methyl}-benzamide,
(114): (Z)-3,4-difluoro-2-(2-fluoro-4-iodo-phenylamino)-N-(2-hydroxy-ethoxy)-5-{[2-(2-oxo-pyrrolidin-1-yl)-ethoxyimino]-methyl}-benzamide,
(115): (E)-3,4-difluoro-2-(2-fluoro-4-iodo-phenylamino)-N-(2-hydroxy-ethoxy)-5-[(2-methanesulfonylamino-ethoxyimino)-methyl]-benzamide, and
(116): (E)-3,4-difluoro-2-(2-fluoro-4-iodo-phenylamino)-N-(2-hydroxy-ethoxy)-5-[dimethylcarbamoylethoxyimino-methyl]-benzamide;

[31] a synthetic intermediate (U) of the compound of [1] represented by formula (1), wherein the intermediate is represented by formula (2):

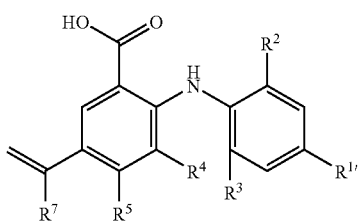

(2)

wherein, $R^{1'}$ represents a hydrogen atom, a halogen atom, —S—$R^a$, —SO—$R^a$, —SO$_2$—$R^a$, —COOR$^a$ an alkyl group which may have 1 to 3 substituents selected from Group A indicated below, an alkenyl group which may have 1 to 3 substituents selected from Group A indicated below, or an alkynyl group which may have 1 to 3 substituents selected from Group A indicated below;

$R^2$ and $R^3$ independently represent a hydrogen atom, a halogen atom, or an alkyl group which may have 1 to 3 substituents selected from Group A indicated below;

$R^4$ and $R^5$ independently represent a hydrogen atom, a halogen atom, or a nitro group;

$R^7$ represents a hydrogen atom;

an alkyl group, an alkenyl group, or an alkynyl group, each of which may have 1 to 3 substituents selected from Group A indicated below; or a cycloalkyl group, a heterocyclic group, an aryl group, a heteroaryl group, an arylalkyl group, or a heterocyclic alkyl group, each of which may have 1 to 3 substituents selected from Group B indicated below, Group A: a halogen atom, a nitro group, —O—$R^a$, -(an alkylene group)-OR$^a$, —[O-(an alkylene group)]$_n$-OR$^a$, —NR$^a$R$^b$, —NR$^b$-(an alkylene group)-OR$^a$, —NR$^a$SO$_2$R$^b$, —C=N—OR$^a$, —CO$_2$R$^a$, —CONR$^a$R$^b$, —NR$^a$COR$^b$, —COR$^a$, —SR$^a$, —SO$_2$R$^a$, and —SO$_2$NR$^a$R$^b$, Group B: a halogen atom, a nitro group, —O—$R^a$, -(an alkylene group)-OR$^a$, —[O-(an alkylene group)]$_n$-OR$^a$, —NR$^a$R$^b$, —NR$^b$-(an alkylene group)-OR$^a$, —NR$^a$SO$_2$R$^b$, —C=N—OR$^a$, —CO$_2$R$^a$, —CONR$^a$R$^b$, —NR$^a$COR$^a$, —COR$^a$, —SR$^a$, —SO$_2$R$^a$, —SO$_2$NR$^a$R$^b$, an oxo group, an alkyl group, an alkenyl group, an alkynyl group, an aryl group, and a heteroaryl group; and the above-mentioned $R^a$ and $R^b$ are identical to or different from each other and independently represent a hydrogen atom, an alkyl group that may be substituted with an OH group, an aryl group, or a heteroaryl group, and n=1 to 4;

[32] the synthetic intermediate (U) of [31], wherein $R^{1'}$ is an iodine atom, a bromine atom, a vinyl group, or an ethynyl group that may be protected with a protecting group;

$R^1$ is a chlorine atom or a fluorine atom;

$R^3$ is a hydrogen atom;

$R^4$ is a hydrogen atom or a fluorine atom;

$R^5$ is a fluorine atom; and $R^7$ is a hydrogen atom;

an alkyl group, an alkenyl group, or an alkynyl group, each of which may have 1 to 3 substituents selected from Group E indicated below; or a cycloalkylalkyl group, an arylalkyl group, a heteroarylalkyl group, or a heterocyclic alkyl group, each of which may have 1 to 3 substituents selected from Group F indicated below, Group E: —O—$R^a$-(a C1-C4 alkylene group)-OR$^a$, —[O-(a C1-C4 alkylene group)]$_n$-OR$^a$, —NR$^b$-(a C1-C4 alkylene group)-OR$^a$, —C=N—OR$^a$, —CONR$^a$R$^b$, —NR$^a$COR$^b$, —SR$^a$, and —SO$_2$R$^a$;

Group F: —O—$R^a$, -(a C1-C4 alkylene group)-OR$^a$, —[O-(a C1-C4 alkylene group)]$_n$-OR$^a$, —NR$^b$-(a C1-C4 alkylene group)-OR$^a$, —C=N—OR$^a$, —CONR$^a$R$^b$, —NR$^a$COR$^b$, —SR$^a$, —SO$_2$R$^a$, and a C1-C4 alkyl group;

provided that $R^a$ and $R^b$ are identical to or different from each other and independently represent a hydrogen atom; a C1-C4 alkyl group that may be substituted with an OH group; an aryl group; or heteroaryl group, and n=1 to 4;

[33] the synthetic intermediate (U) of [31] or [32], wherein the synthetic intermediate (U) is selected from the compounds represented by formulas (21) and (22):

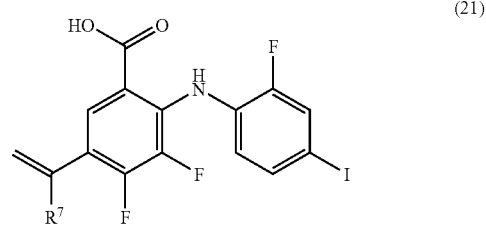

(21)

-continued

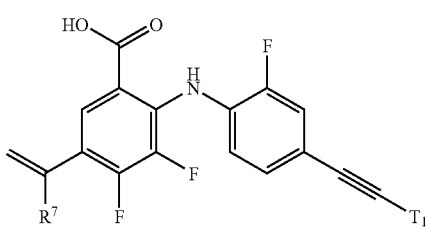

(22)

wherein, $T_1$ represents a hydrogen atom or a protecting group; and $R^7$ is a hydrogen atom;

an alkyl group, an alkenyl group, or an alkynyl group, each of which may have 1 to 3 substituents selected from Group E indicated below; or a cycloalkylalkyl group, an arylalkyl group, a heteroarylalkyl group, or a heterocyclic alkyl group, each of which may have 1 to 3 substituents selected from Group F indicated below, Group E: —O—$R^a$, -(a C1-C4 alkylene group)-$OR^a$, —[O-(a C1-C4 alkylene group)]$_n$-$OR^a$, —$NR^b$-(a C1-C4 alkylene group)-$OR^a$, —C=N—$OR^a$, —$CONR^aR^b$, —$NR^aCOR^b$, —$SR^a$, and —$SO_2R^a$ Group F: —O—$R^a$, -(a C1-C4 alkylene group)-$OR^a$, —[O-(a C1-C4 alkylene group)]$_n$-$OR^a$, —$NR^b$-(a C1-C4 alkylene group)-$OR^a$, —C=N—$OR^a$, —$CONR^aR^b$, —$NR^aCOR^b$, —$SR^a$, —$SO_2R^a$, and a C1-C4 alkyl group, provided that $R^a$ and $R^b$ are identical to or different from each other and independently represent a hydrogen atom; a C1-C4 alkyl group that may be substituted with an OH group; an aryl group; or a heteroaryl group, and n=1 to 4;

[34] a synthetic intermediate (V) of the compound of [1] represented by formula (1), wherein the intermediate is represented by formula (3):

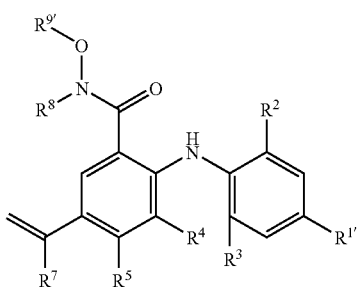

(3)

wherein, $R^{1'}$ represents a hydrogen atom, a halogen atom, —S—$R^a$, —SO—$R^a$, —$SO_2$—$R^a$, —$COOR^a$, an alkyl group which may have 1 to 3 substituents selected from Group A indicated below, an alkenyl group which may have 1 to 3 substituents selected from Group A indicated below, or an alkynyl group which may have 1 to 3 substituents selected from Group A indicated below and may be protected with a protecting group, $R^2$ and $R^3$ independently represent a hydrogen atom, a halogen atom, or an alkyl group which may have 1 to 3 substituents selected from Group A indicated below, $R^4$ and $R^5$ independently represent a hydrogen atom, a halogen atom, or a nitro group, $R^7$ represents a hydrogen atom;

an alkyl group, an alkenyl group, or an alkynyl group, each of which may have 1 to 3 substituents selected from Group A indicated below; or a cycloalkyl group, a heterocyclic group, an aryl group, a heteroaryl group, an arylalkyl group, or a heterocyclic alkyl group, each of which may have 1 to 3 substituents selected from Group B indicated below, $R^8$ represents a hydrogen atom, or an alkyl group which may have 1 to 3 substituents selected from Group A indicated below;

$R^{9'}$ represents a hydrogen atom;

an alkyl group, an alkenyl group, or an alkynyl group, each of which may have 1 to 3 substituents selected from Group A indicated below; or a cycloalkyl group, an aryl group, a heteroaryl group, a heterocyclic group, a cycloalkylalkyl group, a cycloalkylalkenyl group, a cycloalkylalkynyl group, an arylalkyl group, an arylalkenyl group, an arylalkynyl group, a heteroarylalkyl group, a heteroarylalkenyl group, a heteroarylalkynyl group, a heterocyclic alkyl group, a heterocyclic alkenyl group, or a heterocyclic alkynyl group, each of which may have 1 to 3 substituents selected from Group B indicated below, when $R^{9'}$ has a hydroxyl group, an amino group, or an alkylamino group, the hydroxyl group, amino group, or alkylamino group may be protected with a protecting group;

Group A: a halogen atom, a nitro group, —O—$R^a$, -(an alkylene group)-$OR^a$, —[O-(an alkylene group)]$_n$-$OR^a$, —$NR^aR^b$, —$NR^b$-(an alkylene group)-$OR^a$, —$NR^aSO_2R^b$, —C=N—$OR^a$, —$CO_2R^a$, —$CONR^aR^b$, —$NR^aCOR^b$, —$COR^a$, —$SR^a$, —$SO_2R^a$, and —$SO_2NR^aR^b$, Group B: a halogen atom, a nitro group, —O—$R^a$, -(an alkylene group)-$OR^a$, —[O-(an alkylene group)]$_n$-$OR^a$, —$NR^aR^b$, —$NR^b$-(an alkylene group)-$OR^a$, —$NR^aSO_2R^b$, —C=N—$OR^a$, —$CO_2R^a$, —$CONR^aR^b$, —$NR^aCOR^b$, —$COR^a$, —$SR^a$, —$SO_2R^a$, —$SO_2NR^aR^b$, an oxo group, an alkyl group, an alkenyl group, an alkyl group, an aryl group, and a heteroaryl group, and the above-mentioned $R^a$ and $R^b$ are identical to or different from each other and independently represent a hydrogen atom; an alkyl group that may be substituted with an OH group; an aryl group; or a heteroaryl group, and n=1 to 4;

[35] the synthetic intermediate (V) of [34], wherein $R^{1'}$ is an iodine atom, a bromine atom, a vinyl group, or an ethynyl group that may be protected with a protecting group;

$R^2$ is a chlorine atom or a fluorine atom;

$R^3$ is a hydrogen atom;

$R^4$ is a hydrogen atom or a fluorine atom;

$R^5$ is a fluorine atom;

$R^8$ is a hydrogen atom or a methyl group;

$R^7$ and $R^{9'}$ independently represent a hydrogen atom;

an alkyl group, an alkenyl group, or an alkynyl group, each of which may have 1 to 3 substituents selected from Group E indicated below; or a cycloalkylalkyl group, an arylalkyl group, a heteroarylalkyl group, or a heterocyclic alkyl group, each of which may have 1 to 3 substituents selected from Group F indicated below, and when $R^{9'}$ has a hydroxyl group, an amino group, or an alkylamino group, the hydroxyl group, amino group, or alkylamino group may be protected with a protecting group;

Group E: —O—$R^a$, -(a C1-C4 alkylene group)-$OR^a$, —[O-(a C1-C4 alkylene group)]$_n$-$OR^a$, —$NR^b$-(a C1-C4 alkylene group)-$OR^a$, —C=N—$OR^a$, —$CONR^aR^b$, —$NR^aCOR^b$, —$SR^a$, and —$SO_2R^a$, Group F: —O—$R^a$, -(a C1-C4 alkylene group)-$OR^a$, —[O-(a C1-C4 alkylene group)]$_n$-$OR^a$, —$NR^b$ (a C1-C4 alkylene group)-OR$^a$, —C=N—OR$^a$, —CONR$^a$R$^b$, —NR$^a$COR$^b$, —SR$^a$, —SO$_2$R$^a$, and a C1-C4 alkyl group, provided that R$^a$ and R$^b$ are identical to or different from each other and independently represent a hydrogen atom; a C1-C4 alkyl group that may be substituted with an OH group; an aryl group; or a heteroaryl group, and n=1 to 4;

[36] the compound of [34] or [35], wherein the synthetic intermediate (V) is selected from the compounds represented by formulas (31) and (32):

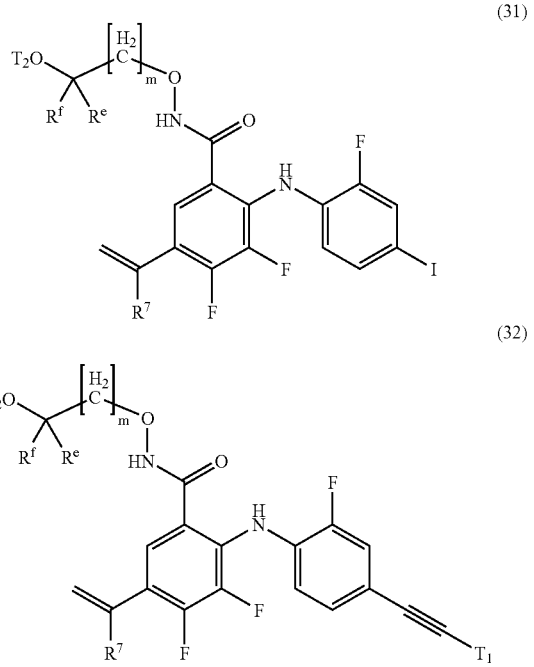

wherein, $T_1$ and $T_2$ independently represent a hydrogen atom or a protecting group; R$^e$ and R$^f$ independently represent a hydrogen atom, a C1-C4 alkyl group, an aryl group, or a heteroaryl group;

an arbitrary hydrogen atom in a repeating unit represented by above —[CH$_2$]m- (m is an integer from 1 to 4) may be replaced with a group represented by R$^c$; R$^c$ represents a C1-C4 alkyl group, an aryl group, or a heteroaryl group, R$^c$ may be substituted with a hydroxyl group that may be protected with a protecting group, and when two or more hydrogen atoms are each substituted with R$^c$, each R$^c$ may be identical to or different from each other; and R$^7$ represents a hydrogen atom, an alkyl group, an alkenyl group, or an alkynyl group, each of which may have 1 to 3 substituents selected from Group E indicated below; or a cycloalkylalkyl group, an arylalkyl group, a heteroarylalkyl group, or a heterocyclic alkyl group which may have 1 to 3 substituents selected from Group F indicated below, Group E: —O—R$^a$, -(a C1-C4 alkylene group)-OR$^a$, —[O-(a C1-C4 alkylene group)]$_n$-OR$^a$, —NR$^b$-(a C1-C4 alkylene group)-OR$^a$, —C=N—OR$^a$, —CONR$^a$R$^b$, —NR$^a$COR$^b$, —SR$^a$, and —SO$_2$R$^a$, Group F: —O—R$^a$, -(a C1-C4 alkylene group)-OR$^a$, —[O-(a C1-C4 alkylene group)]$_n$-OR$^a$, —NR$^b$-(a C1-C4 alkylene group)-OR$^a$, —C=N—OR$^a$, —CONR$^a$R$^b$, —NR$^a$COR$^b$, —SR$^a$, —SO$_2$R$^a$, and a C1-C4 alkyl group, provided that R$^a$ and R$^b$ are identical to or different from each other and independently represent a hydrogen atom; a C1-C4 alkyl group that may be substituted with an OH group; an aryl group; or a heteroaryl group, and n=1 to 4;

[37] a synthetic intermediate (W) of the compound of [1] represented by formula (1), wherein the intermediate is represented by formula (4):

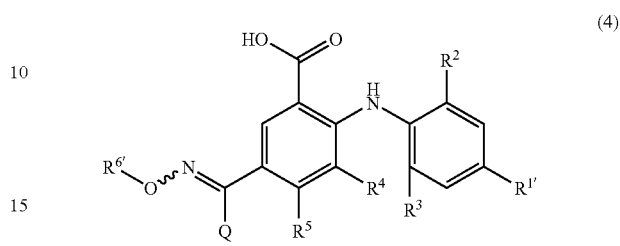

wherein, the wavy line ∿ indicates that the compound can be either one of the stereoisomers, E-form or Z-form, depending on the manner of binding of O— to —N, R$^{1'}$ represents a hydrogen atom, a halogen atom, —S—R$^a$, —SO—R$^a$, —SO$_2$—R$^a$, —COOR$^a$, an alkyl group which may have 1 to 3 substituents selected from Group A indicated below, an alkenyl group which may have 1 to 3 substituents selected from Group A indicated below, or an alkynyl group which may have 1 to 3 substituents selected from Group A indicated below and may be protected with a protecting group, R$^2$ and R$^3$ independently represent a hydrogen atom, a halogen atom, or an alkyl group which may have 1 to 3 substituents selected from Group A indicated below, R$^4$ and R$^5$ independently represent a hydrogen atom, a halogen atom, or a nitro group;

R$^{6'}$ represents a hydrogen atom;

an alkyl group, an alkenyl group, or an alkynyl group, each of which may have 1 to 3 substituents selected from Group A indicated below; or a cycloalkyl group, an aryl group, a heteroaryl group, a heterocyclic group, a cycloalkylalkyl group, a cycloalkylalkenyl group, a cycloalkylalkynyl group, an arylalkyl group, an arylalkenyl group, an arylalkynyl group, a heteroarylalkyl group, a heteroarylalkenyl group, a heteroarylalkynyl group, a heterocyclic alkyl group, a heterocyclic alkenyl group, or a heterocyclic alkynyl group, each of which may have 1 to 3 substituents selected from Group B indicated below, when R$^{6'}$ has a hydroxyl group, an amino group, or an alkylamino group, the hydroxyl group, amino group, or alkylamino group may be protected with a protecting group;

Q represents —NR$^a$R$^b$ or a group represented by R$^7$;

R$^7$ represents a hydrogen atom;

an alkyl group, an alkenyl group, or an alkynyl group, each of which may have 1 to 3 substituents selected from Group A indicated below, or a cycloalkyl group, a heterocyclic group, an aryl group, a heteroaryl group, an arylalkyl group, or a heterocyclic alkyl group, each of which may have 1 to 3 substituents selected from Group B indicated below, Group A: a halogen atom, a nitro group, —O—R$^a$, -(an alkylene group)-OR$^a$, —[O-(an alkylene group)]$_n$-OR$^a$, —NR$^a$R$^b$, —NR$^b$-(an alkylene group)-OR$^a$, —NR$^a$SO$_2$R$^b$, —C=N—OR$^a$, —CO$_2$R$^a$, —CONR$^a$R$^b$, —NR$^a$COR$^b$, —COR$^a$, —SR$^a$, —SO$_2$R$^a$, and —SO$_2$NR$^a$R$^b$, Group B: a halogen atom, a nitro group, —O—R$^a$, -(an alkylene group)-OR$^a$, —[O-(an alkylene group)]$_n$-OR$^a$, —NR$^a$R$^b$, —NR$^b$-(an alkylene group)-OR$^a$, —NR$^a$SO$_2$R$^b$, —C=N—OR$^a$, —CO$_2$R$^a$, —CONR$^a$R$^b$, —NR$^a$COR$^b$, —COR$^a$, —SR$^a$, —SO$_2$R$^a$, —SO$_2$NR$^a$R$^b$, an oxo group, an alkyl group, an alkenyl group, an alkynyl group, an aryl group, and a heteroaryl group; and the above-mentioned R$^a$ and R$^b$ are identical to or different from each other and independently represent a hydrogen atom; an alkyl group that may be substituted with an OH group; an aryl group; or a heteroaryl group, and n=1 to 4;

[38] the compound of [37], wherein R$^{1'}$ is an iodine atom, a bromine atom, a vinyl group, or an ethynyl group that may be protected with a protecting group;

R$^2$ is a chlorine atom or a fluorine atom;

R$^3$ is a hydrogen atom;

R$^4$ is a hydrogen atom or a fluorine atom;

R$^5$ is a fluorine atom;

R$^{6'}$ is a hydrogen atom;

an alkyl group, an alkenyl group, or an alkynyl group, each of which may have 1 to 3 substituents selected from Group E indicated below; or a cycloalkylalkyl group, arylalkyl group, a heteroarylalkyl group, or a heterocyclic alkyl group, each of which may have 1 to 3 substituents selected from Group F indicated below;

when R$^{6'}$ has a hydroxyl group, an amino group, or an alkylamino group, the hydroxyl group, amino group, or alkylamino group may be protected with a protecting group;

Q is a hydrogen atom;

—NR$^a$R$^b$;

an alkyl group, an alkenyl group, or an alkynyl group, each of which may have 1 to 3 substituents selected from Group E indicated below; or a cycloalkylalkyl group, an arylalkyl group, a heteroarylalkyl group, or a heterocyclic alkyl group, each of which may have 1 to 3 substituents selected from Group F indicated below;

Group E: —O—R$^a$, —NR$^a$R$^b$, -(a C1-C4 alkylene group)-OR$^a$, —[O-(a C1-C4 alkylene group)]$_n$-OR$^a$, —NR$^b$-(a C1-C4 alkylene group)-OR$^a$, —C=N—OR$^a$, —CONR$^a$R$^b$, —NR$^a$COR$^b$, —SR$^a$, and —SO$_2$R$^a$;

Group F: —O—R$^a$, -(a C1-C4 alkylene group)-OR$^a$, —[O-(a C1-C4 alkylene group)]$_n$-OR$^a$, —NR$^b$-(a C1-C4 alkylene group)-OR$^a$, —C=N—OR$^a$, —CONR$^a$R$^b$, —NR$^a$COR$^b$, —SR$^a$, —SO$_2$R$^a$, an oxo group, and a C1-C4 alkyl group, provided that R$^a$ and R$^b$ are identical to or different from each other and independently represent a hydrogen atom; a C1-C4 alkyl group that may have an OH group; an aryl group; or a heteroaryl group, and n=1 to 4;

[39] the compound of [37] or [38], wherein the synthetic intermediate (W) is selected from the compounds represented by formulas (41), (42), (63), and (64):

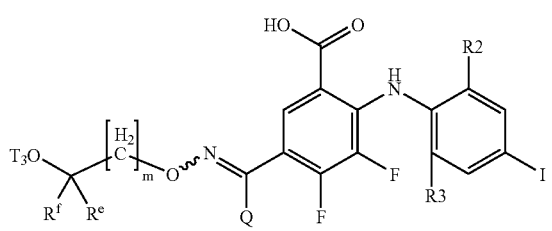
(41)

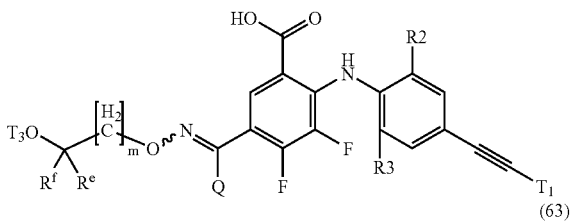
(42)

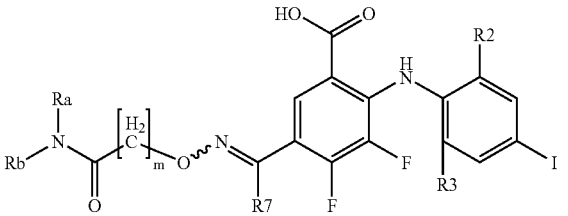
(63)

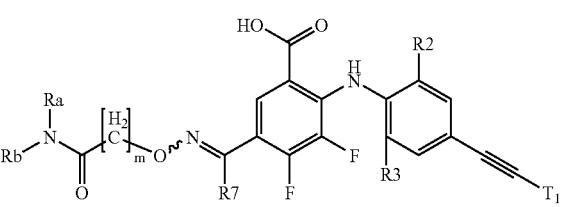
(64)

wherein, the wavy line ∿ indicates that the compound can be either one of the stereoisomers, E-form or Z-form, depending on the manner of binding of O— to —N, T$_1$ and T$_3$ independently represent a hydrogen atom or a protecting group;

R$^2$ and R$^3$ independently represent a hydrogen atom, a halogen atom, or an alkyl group which may have 1 to 3 substituents selected from Group A indicated below;

R$^7$ represents a hydrogen atom;

an alkyl group, an alkenyl group, or an alkynyl group, each of which may have 1 to 3 substituents selected from Group A indicated below; or a cycloalkyl group, a heterocyclic group, an aryl group, a heteroaryl group, an arylalkyl group, or a heterocyclic alkyl group, each of which may have 1 to 3 substituents selected from Group B indicated below, Group A: a halogen atom, a nitro group, —O—R$^a$, -(an alkylene group)-OR$^a$, —[O-(an alkylene group)]$_n$-OR$^a$, —NR$^a$R$^b$, —NR$^b$-(an alkylene group)-OR$^a$, —NR$^a$SO$_2$R$^b$, —C=N—OR$^a$, —CO$_2$R$^a$, —CONR$^a$R$^b$, —NR$^a$COR$^b$, —COR$^a$, —SR$^a$, —SO$_2$R$^a$, and —SO$_2$NR$^a$R$^b$, Group B: a halogen atom, a nitro group, —O—R$^a$, -(an alkylene group)-OR$^a$, —[O-(an alkylene group)]$_n$-OR$^a$, —NR$^a$R$^b$, —NR$^b$-(an alkylene group)-OR$^a$, —NR$^a$SO$_2$R$^b$, —C=N—OR$^a$, —CO$_2$R$^a$, —CONR$^a$R$^b$, —NR$^a$COR$^b$, —COR$^a$, —SR$^a$, —SO$_2$R$^a$, —SO$_2$NR$^a$R$^b$, an oxo group, an alkyl group, an alkenyl group, an alkyl group, an aryl group, and a heteroaryl group, and Q is a hydrogen atom; —NR$^a$R$^b$;

an alkyl group, an alkenyl group, or an alkynyl group, each of which may have 1 to 3 substituents selected from Group E indicated below; or a cycloalkylalkyl group, an arylalkyl group, a heteroarylalkyl group, or a heterocyclic alkyl group, each of which may have 1 to 3 substituents selected from Group F indicated below, Group E: —O—$R^a$, -(a C1-C4 alkylene group)-$OR^a$, —[O-(a C1-C4 alkylene group)]$_n$-$OR^a$, —$NR^b$-(a C1-C4 alkylene group)-$OR^a$, —C=N—$OR^a$, —$CONR^aR^b$, —$NR^aCOR^b$, —$SR^a$, and —$SO_2R^a$, Group F: —O—$R^a$, -(a C1-C4 alkylene group)-$OR^a$, —[O-(a C1-C4 alkylene group)]$_n$-$OR^a$, —$NR^b$-(a C1-C4 alkylene group)-$OR^a$, —C=N—$OR^a$, —$CONR^aR^b$, —$NR^aCOR^b$, —$SR^a$, —$SO_2R^a$, and a C1-C4 alkyl group, provided that $R^a$ and $R^b$ are identical to or different from each other and independently represent a hydrogen atom; a C1-C4 alkyl group that may be substituted with an OH group; an aryl group; or a heteroaryl group, and n=1 to 4; and $R^e$ and $R^f$ independently represent a hydrogen atom, a C1-C4 alkyl group, an aryl group, or a heteroaryl group;

an arbitrary hydrogen atom in a repeating unit represented by above —[$CH_2$]m- (m is an integer from 1 to 4) may be replaced with a group represented by $R^c$; $R^c$ represents a C1-C4 alkyl group, an aryl group, or a heteroaryl group, $R^c$ may be substituted with a hydroxyl group that may be protected with a protecting group, and when two or more hydrogen atoms are each substituted with $R^c$, each $R^c$ may be identical to or different from each other;

[40] a synthetic intermediate (X) of the compound of [1] represented by formula (1), wherein the intermediate is represented by formula (5):

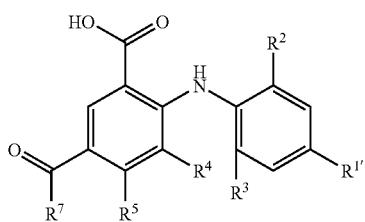

(5)

wherein, $R^{1'}$ represents a hydrogen atom, a halogen atom, —S—$R^a$, —SO—$R^a$, —$SO_2$—$R^a$, —$COOR^a$, an alkyl group which may have 1 to 3 substituents selected from Group A indicated below, an alkenyl group which may have 1 to 3 substituents selected from Group A indicated below, or an alkynyl group which may have 1 to 3 substituents selected from Group A indicated below and may be protected with a protecting group, $R^2$ and $R^3$ independently represent a hydrogen atom, a halogen atom, or an alkyl group which may have 1 to 3 substituents selected from Group A indicated below, $R^4$ and $R^5$ independently represent a hydrogen atom, a halogen atom, or a nitro group;

$R^7$ represents a hydrogen atom;

an alkyl group, an alkenyl group, or an alkynyl group, each of which may have 1 to 3 substituents selected from Group A indicated below; or a cycloalkyl group, a heterocyclic group, an aryl group, a heteroaryl group, an arylalkyl group, or a heterocyclic alkyl group, each of which may have 1 to 3 substituents selected from Group B indicated below, Group A: halogen atom, a nitro group, —O—$R^a$, -(an alkylene group)-$OR^a$, —[O-(an alkylene group)]$_n$-$OR^a$, —$NR^aR^b$, —$NR^b$-(an alkylene group)-$OR^a$, —$NR^aSO_2R^b$, —C=N—$OR^a$, —$CO_2R^a$, —$CONR^aR^b$, —$NR^aCOR^b$, —$COR^a$, —$SR^a$, —$SO_2R^a$, and —$SO_2NR^aR^b$, Group B: a halogen atom, a nitro group, —O—$R^a$, -(an alkylene group)-$OR^a$, —[O-(an alkylene group)]$_n$-$OR^8$, —$NR^aR^b$, —$NR^b$-(an alkylene group)-$OR^a$, —$NR^aSO_2R^b$, —C=N—$OR^a$, —$CO_2R^a$, —$CONR^aR^b$, —$NR^aCOR^b$, —$COR^a$, —$SR^a$, —$SO_2R^a$, —$SO_2NR^aR^b$, an oxo group, an alkyl group, an alkenyl group, an alkynyl group, an aryl group, and a heteroaryl group, and the above-mentioned $R^a$ and $R^b$ are identical to or different from each other and independently represent a hydrogen atom; an alkyl group that may have an OH group; an aryl group; or a heteroaryl group; and n=1 to 4;

[41] the compound of [40], wherein $R^{1'}$ is an iodine atom, a bromine atom, a vinyl group, or an ethynyl group that may be protected with a protecting group;

$R^2$ is a chlorine atom or a fluorine atom;

$R^3$ is a hydrogen atom;

$R^4$ is a hydrogen atom or a fluorine atom;

$R^5$ is a fluorine atom; and $R^7$ is a hydrogen atom, an alkyl group, an alkenyl group, or an alkynyl group, each of which may have 1 to 3 substituents selected from Group E indicated below, or a cycloalkylalkyl group, an arylalkyl group, a heteroarylalkyl group, or a heterocyclic alkyl group, each which may have 1 to 3 substituents selected from Group F indicated below;

Group E: —O—$R^a$, -(a C1-C4 alkylene group)-$OR^a$, —[O-(a C1-C4 alkylene group)]$_n$-$OR^a$, —$NR^b$-(a C1-C4 alkylene group)-$OR^a$, —C=N—$OR^a$, —$CONR^aR^b$, —$NR^aCOR^b$, —$SR^a$, and —$SO_2R^a$;

Group F: —O—$R^a$, -(a C1-C4 alkylene group)-$OR^a$, —[O-(a C1-C4 alkylene group)]$_n$-$OR^a$, —$NR^b$-(a C1-C4 alkylene group)-$OR^a$, —C=N—$OR^a$, —$CONR^aR^b$, —$NR^aCOR^b$, —$SR^a$, —$SO_2R^a$, and a C1-C4 alkyl group;

provided that $R^a$ and $R^b$ are identical to or different from each other and independently represent a hydrogen atom; a C1-C4 alkyl group that may have an OH group; an aryl group; or a heteroaryl group, and n=1 to 4;

[42] the compound of [40] or [41], wherein the synthetic intermediate (X) is selected from the compounds represented by formulas (51) and (52):

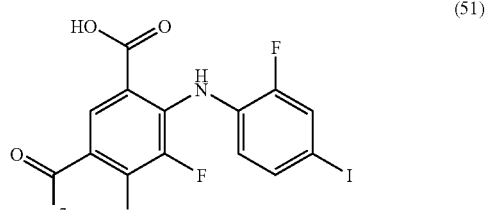

(51)

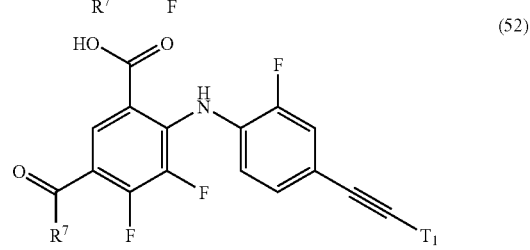

(52)

wherein, $T_1$ represents a hydrogen atom or a protecting group; and $R^7$ represents a hydrogen atom, an alkyl group, an alkenyl group, or an alkynyl group, each of which may have 1 to 3 substituents selected from Group E indicated below, or a cycloalkylalkyl group, an arylalkyl group, a heteroarylalkyl group, or a heterocyclic alkyl group, each which may have 1 to 3 substituents selected from Group F indicated below;

Group E: —O—$R^a$, -(a C1-C4 alkylene group)-$OR^a$, —[O-(a C1-C4 alkylene group)]$_n$-$OR^a$, —$NR^b$-(a C1-C4 alkylene group)-$OR^a$, —C=N—$OR^a$, —$CONR^aR^b$, —$NR^aCOR^b$, —$SR^a$, and —$SO_2R^a$;

Group F: —O—$R^a$, -(a C1-C4 alkylene group)-$OR^a$, —[O-(a C1-C4 alkylene group)]$_n$-$OR^a$, —$NR^b$-(a C1-C4 alkylene group)-$OR^a$, —C=N—$OR^a$, —$CONR^aR^b$, —$NR^aCOR^b$, —$SR^a$, —$SO_2R^a$, a C1-C4 alkyl group;

provided that $R^a$ and $R^b$ are identical to or different from each other and independently represent a hydrogen atom, a C1-C4 alkyl group that may have an OH group, an aryl group, or a heteroaryl group, and n=1 to 4;

[43] a synthetic intermediate (Y) of the compound of [1] represented by formula (1), wherein the intermediate is represented by formula (6):

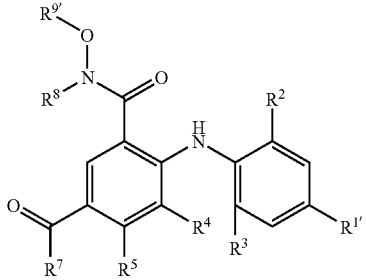

(6)

wherein, $R^{1'}$ represents a hydrogen atom, a halogen atom, —S—$R^a$, —SO—$R^a$, —$SO_2$—$R^a$, —$COOR^a$, an alkyl group which may have 1 to 3 substituents selected from Group A indicated below, an alkenyl group which may have 1 to 3 substituents selected from Group A indicated below, or an alkynyl group which may have 1 to 3 substituents selected from Group A indicated below and may be protected with a protecting group;

$R^2$ and $R^3$ independently represent a hydrogen atom; a halogen atom; or an alkyl group which may have 1 to 3 substituents selected from Group A indicated below;

$R^4$ and $R^5$ independently represent a hydrogen atom, a halogen atom, or a nitro group;

$R^7$ represents a hydrogen atom, an alkyl group, an alkenyl group, or an alkynyl group, each of which may have 1 to 3 substituents selected from Group A indicated below, or a cycloalkyl group, a heterocyclic group, an aryl group, a heteroaryl group, an arylalkyl group, or a heterocyclic alkyl group, each of which may have 1 to 3 substituents selected from Group B indicated below;

$R^8$ represents a hydrogen atom, or an alkyl group which may have 1 to 3 substituents selected from Group A indicated below;

$R^{9'}$ represents a hydrogen atom, an alkyl group, an alkenyl group, or an alkynyl group, each of which may have 1 to 3 substituents selected from Group A indicated below, or a cycloalkyl group, an aryl group, a heteroaryl group, a heterocyclic group, a cycloalkylalkyl group, a cycloalkylalkenyl group, a cycloalkylalkynyl group, an arylalkyl group, an arylalkenyl group, an arylalkynyl group, a heteroarylalkyl group, a heteroarylalkenyl group, a heteroarylalkynyl group, a heterocyclic alkyl group, a heterocyclic alkenyl group, or a heterocyclic alkynyl group, each of which may have 1 to 3 substituents selected from Group B indicated below;

when $R^{9'}$ has a hydroxyl group, an amino group, or an alkylamino group, the hydroxyl group, amino group, or alkylamino group may be protected with a protecting group;

Group A: a halogen atom, a nitro group, —O—$R^a$, -(an alkylene group)-$OR^a$, —[O-(an alkylene group)]$_n$-$OR^a$, —$NR^aR^b$, —$NR^b$-(an alkylene group)-$OR^a$, —$NR^aSO_2R^b$, —C=N—$OR^a$, —$CO_2R^a$, —$CONR^aR^b$, —$NR^aCOR^b$, —$COR^a$, —$SR^a$, —$SO_2R^a$, and —$SO_2NR^aR^b$;

Group B: a halogen atom, a nitro group, —O—$R^a$, -(an alkylene group)-$OR^a$, —[O-(an alkylene group)]$_n$-$OR^a$, —$NR^aR^b$, —$NR^b$-(an alkylene group)-$OR^a$, —$NR^aSO_2R^b$, —C=N—$OR^a$, —$CO_2R^a$, —$CONR^aR^b$, —$NR^aCOR^b$, —$COR^a$, —$SR^a$, —$SO_2R^a$, —$SO_2NR^aR^b$, an oxo group, an alkyl group, an alkenyl group, an alkynyl group, an aryl group, a heteroaryl group; and the above-mentioned $R^a$ and $R^b$ are identical to or different from each other and independently represent a hydrogen atom, an alkyl group that may have an OH group, an aryl group, or a heteroaryl group, and n=1 to 4;

[44] the compound according to [43], wherein $R^{1'}$ of the synthetic intermediate (Y) is an ethynyl group that may be protected with an iodine atom, a bromine atom, a vinyl group, or a protecting group;

$R^2$ is a chlorine atom or a fluorine atom;

$R^3$ is a hydrogen atom;

$R^4$ is a hydrogen atom or a fluorine atom;

$R^5$ is a fluorine atom;

$R^7$ is a hydrogen atom, an alkyl group, an alkenyl group, or an alkynyl group, each of which may have 1 to 3 substituents selected from Group E below, or a cycloalkylalkyl group, an arylalkyl group, a heteroarylalkyl group, or a heterocyclic alkyl group, each of which may have 1 to 3 substituents selected from Group F below;

$R^8$ is a hydrogen atom or a methyl group;

$R^{9'}$ is a hydrogen, an alkyl group, an alkenyl group, or an alkynyl group, each of which may have 1 to 3 substituents selected from Group E below, or a cycloalkylalkyl group, an arylalkyl group, a heteroarylalkyl group, or a heterocyclic alkyl group, each of which may have 1 to 3 substituents selected from Group F below;

when $R^{9'}$ has a hydroxyl group, an amino group, or an alkylamino group, the hydroxyl group, amino group, or alkylamino group may be protected with a protecting group;

Group E: —O—$R^a$, -(a C1-C4 alkylen)-$OR^a$, —[O-(a C1-C4 alkylene group)]$_n$-$OR^a$, —$NR^b$-(a C1-C4 alkylene group)-$OR^a$, —C=N—$OR^a$, —$CONR^aR^b$, —$NR^aCOR^b$, —$SR^a$, and —$SO_2R^a$;

Group F: —O—$R^a$, -(a C1-C4 alkylene group)-$OR^a$, —[O-(a C1-C4 alkylene group)]n-$OR^a$, —$NR^b$-(a C1-C4 alkylene group)-$OR^a$, —C=N—$OR^a$, —$CONR^aR^b$, —$NR^aCOR^b$, —$SR^a$, —$SO_2R^a$, and a C1-C4 alkyl group; and provided that $R^a$ and $R^b$ may be identical to or different, and represent
- a hydrogen atom,
- a C1-C4 alkyl group that may have an OH group,
- an aryl group, or
- a heteroaryl group, and n=1 to 4;

[45] the compound according to [43] or [44], wherein the synthetic intermediate (Y) is selected from formulae (61) and (62) below:

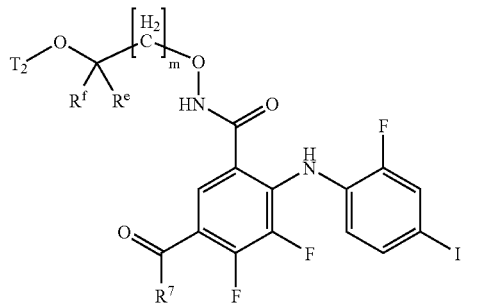

(61)

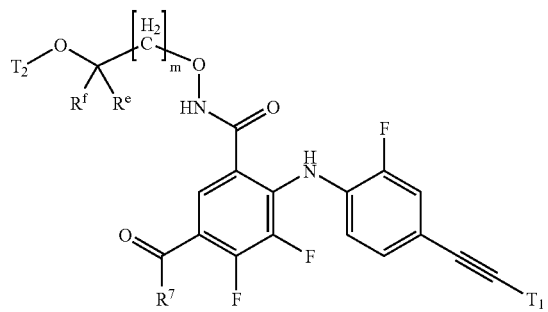

(62)

wherein, T1 and T2 each independently represent a hydrogen atom or a protecting group, $R^e$ and $R^f$ each independently represent a hydrogen atom, a C1-C4 alkyl group, an aryl group, or a heteroaryl group;

an arbitrary hydrogen atom in a repeating unit represented by above —[CH$_2$]m- (m is an integer from 1 to 4) may be replaced with a group represented by $R^c$; $R^c$ represents a C1-C4 alkyl group, an aryl group, or a heteroaryl group, $R^c$ may be substituted with a hydroxyl group that may be protected with a protecting group, and when two or more hydrogen atoms are each substituted with $R^c$, each $R^c$ may be identical to or different from each other; and $R^7$ is
- a hydrogen atom,
- an alkyl group, an alkenyl group, or an alkynyl group, each of which may have 1 to 3 substituents selected from Group E below, or
- a cycloalkylalkyl group, an arylalkyl group, a heteroarylalkyl group, or a heterocyclic alkyl group, each of which may have 1 to 3 substituents selected from Group F below;

Group E: —O—$R^a$, -(a C1-C4 alkylene group)-$OR^a$, —[O-(a C1-C4 alkylene group)]$_n$-$OR^a$, —$NR^b$-(a C1-C4 alkylene group)-$OR^a$, —C=N—$OR^a$, —$CONR^aR^b$, —$NR^aCOR^b$, —$SR^a$, and —$SO_2R^a$;

Group F: —O—$R^a$, -(a C1-C4 alkylene group)-$OR^a$, —[O-(a C1-C4 alkylene group)]$_n$-$OR^a$, —$NR^b$-(a C1-C4 alkylene group)-$OR^a$, —C=N—$OR^a$, —$CONR^aR^b$, —$NR^aCOR^b$, —$SR^a$, —$SO_2R^a$, and a C1-C4 alkyl group; and provided that $R^a$ and $R^b$ may be identical to or different, and represent
- a hydrogen atom,
- a C1-C4 alkyl group that may have an OH group,
- an aryl group, or
- a heteroaryl group, and n=1 to 4;

[46] a method for preparing a compound of formula (1):

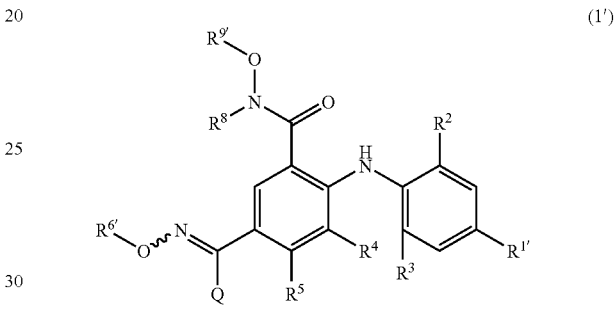

(1')

wherein, the wavy line ∿ indicates that the compound can be either one of the stereoisomers, E-form or Z-form, depending on the manner of binding of O— to —N, $R^1$ represents a hydrogen atom, a halogen atoms —S—$R^a$, —SO—$R^a$, —$SO_2$—$R^a$, —$COOR^a$, an alkyl group that may have 1 to 3 substituents selected from Group A below, an alkenyl group that may have 1 to 3 substituents selected from Group A below, or an alkynyl group that may have 1 to 3 substituents selected from Group A below and that may be protected with a protecting group;

$R^2$ and $R^3$ each independently represent a hydrogen atom, a halogen atom, or an alkyl group that may have 1 to 3 substituents selected from Group A below;

$R^4$ and $R^5$ each independently represent a hydrogen atom, a halogen atom, or a nitro group;

$R^{6'}$ and $R^{9'}$ each independently represent
- a hydrogen atom,
- an alkyl group, an alkenyl group, or an alkynyl group, each of which may have 1 to 3 substituents selected from Group A below, or
- a cycloalkyl group, an aryl group, a heteroaryl group, a heterocyclic group, a cycloalkylalkyl group, a cycloalkylalkenyl group, a cycloalkylalkynyl group, an arylalkyl group, an arylalkenyl group, an arylalkynyl group, a heteroarylalkyl group, a heteroarylalkenyl group, a heteroarylalkynyl group, a heterocyclic alkyl group, a heterocyclic alkenyl group, or a heterocyclic alkynyl group, each of which may have 1 to 3 substituents selected from Group B below, when $R^{6'}$ and $R^{9'}$ have one or more hydroxyl groups, amino groups, or alkylamino groups, the hydroxyl groups, amino groups, or alkylamino groups may each be protected with a protecting group;

Q is —$NR^aR^b$ or a group represented by $R^7$;

R⁷ represents
a hydrogen atom,
an alkyl group, an alkenyl group, or an alkynyl group, each of which may have 1 to 3 substituents selected from Group A below, or
a cycloalkyl group, a heterocyclic group, an aryl group, a heteroaryl group, an arylalkyl group, or a heterocyclic alkyl group, each of which may have 1 to 3 substituents selected from Group B below;
R⁸ represents a hydrogen atom or an alkyl group that may have 1 to 3 substituents selected from Group A below;
Group A: a halogen atom, a nitro group, —O—$R^a$, -(an alkylene group)-$OR^a$, —[O-(an alkylene group)]$_n$-$OR^a$, —$NR^aR^b$, —$NR^b$-(an alkylene group)-$OR^a$, —$NR^aSO_2R^b$, —C=N—$OR^a$, —$CO_2R^a$, —$CONR^aR^b$, —$NR^aCOR^b$, —$COR^a$, —$SR^a$, —$SO_2R^a$, and —$SO_2NR^aR^b$;
Group B: a halogen atom, a nitro group, —O—$R^a$, -(an alkylene group)-$OR^a$, —[O-(an alkylene group)]$_n$-$OR^a$, —$NR^aR^b$, —$NR^b$-(an alkylene group)-$OR^a$, —$NR^aSO_2R^b$, —C=N—$OR^a$, —$CO_2R^a$, —$CONR^aR^b$, —$NR^aCOR^b$, —$COR^a$, —$SR^a$, —$SO_2R^a$, —$SO_2NR^aR^b$, an oxo group, an alkyl group, an alkenyl group, an alkynyl group, an aryl group, and a heteroaryl group;
wherein $R^a$ and $R^b$ above may be identical or different, and represent
a hydrogen atom,
an alkyl group that may have an OH group,
an aryl group, or
a heteroaryl group,
and n=1 to 4,
or a pharmaceutically acceptable salt thereof, the method comprising reacting the synthetic intermediate (W) of [37] and a hydroxylamine derivative (Z1) represented by formula (7):

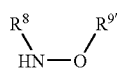

(7)

wherein, R⁸ represents a hydrogen atom or an alkyl group that may have 1 to 3 substituents selected from Group A below,
$R^{9'}$ represents
a hydrogen atom,
an alkyl group, an alkenyl group, or an alkynyl group, each of which may have 1 to 3 substituents selected from Group A below, or
a cycloalkyl group, an aryl group, a heteroaryl group, a heterocyclic group, a cycloalkylalkyl group, a cycloalkylalkenyl group, a cycloalkylalkynyl group, an arylalkyl group, an arylalkenyl group, an arylalkynyl group, a heteroarylalkyl group, a heteroarylalkenyl group, a heteroarylalkynyl group, a heterocyclic alkyl group, a heterocyclic alkenyl group, or a heterocyclic alkynyl group, each of which may have 1 to 3 substituents selected from Group B below,
when $R^{9'}$ has a hydroxyl group, an amino group, or an alkylamino group, the hydroxyl group, amino group, or alkylamino group may be protected with a protecting group;
Group A: a halogen atom, a nitro group, —O—$R^a$, -(an alkylene group)-$OR^a$, —[O-(an alkylene group)]$_n$-$OR^a$, —$NR^aR^b$, —$NR^b$-(an alkylene group)-$OR^a$, —$NR^aSO_2R^b$, —C=N—$OR^a$, —$CO_2R^a$, —$CONR^aR^b$, —$NR^aCOR^b$, —$COR^a$, —$SR^a$, —$SO_2R^a$, and —$SO_2NR^aR^b$;
Group B: a halogen atom, a nitro group, —O—$R^a$, -(an alkylene group)-$OR^a$, —[O-(an alkylene group)]$_n$-$OR^a$, —$NR^aR^b$, —$NR^b$-(an alkylene group)-$OR^a$, —$NR^aSO_2R^b$, —C=N—$OR^a$, —$CO_2R^a$, —$CONR^aR^b$, —$NR^aCOR^b$, —$COR^a$, —$SR^a$, —$SO_2R^a$, —$SO_2NR^aR^b$, an oxo group, an alkyl group, an alkenyl group, an alkynyl group, an aryl group, and a heteroaryl group;
wherein $R^a$ and $R^b$ above may be identical or different, and represent
a hydrogen atom,
an alkyl group that may have an OH group,
an aryl group, or
a heteroaryl group,
and n=1 to 4;

[47] a method for preparing a compound of formula (1):

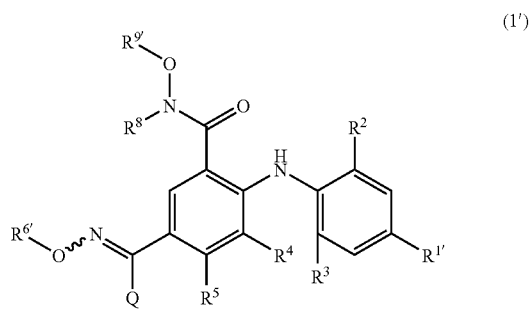

(1')

wherein,
the wavy line ∿
indicates that the compound can be either one of the stereoisomers, E-form or Z-form, depending on the manner of binding of O— to —N,
$R^{1'}$ represents a hydrogen atom, a halogen atom, —S—$R^a$, —SO—$R^a$, —$SO_2$—$R^a$, —$COOR^a$, an alkyl group that may have 1 to 3 substituents selected from Group A below, an alkenyl group that may have 1 to 3 substituents selected from Group A below, or an alkynyl group that may have 1 to 3 substituents selected from Group A below and that may be protected with a protecting group;
R² and R³ each independently represent a hydrogen atom, a halogen atom, or an alkyl group that may have 1 to 3 substituents selected from Group A below;
R⁴ and R⁵ each independently represent a hydrogen atom, a halogen atom, or a nitro group;
$R^{6'}$ and $R^{9'}$ each independently represent
a hydrogen atom,
an alkyl group, an alkenyl group, or an alkynyl group, each of which may have 1 to 3 substituents selected from Group A below, or
a cycloalkyl group, an aryl group, a heteroaryl group, a heterocyclic group, a cycloalkylalkyl group, a cycloalkylalkenyl group, a cycloalkylalkynyl group, an arylalkyl group, an arylalkenyl group, an arylalkynyl group, a heteroarylalkyl group, a heteroarylalkenyl group, a heteroarylalkynyl group, a heterocyclic alkyl group, a heterocyclic alkenyl group, or a heterocyclic alkynyl group, each of which may have 1 to 3 substituents selected from Group B below,
when $R^{6'}$ and $R^{9'}$ have one or more hydroxyl groups, amino groups, or alkylamino groups, the hydroxyl groups, amino groups, or alkylamino groups may each be protected with a protecting group;
Q is —$NR^aR^b$ or a group represented by R⁷;
R⁷ represents
a hydrogen atom,
an alkyl group, an alkenyl group, or an alkynyl group, each of which may have 1 to 3 substituents selected from Group A below, or a cycloalkyl group, a heterocyclic group, an aryl group, a heteroaryl group, an arylalkyl group, or a heterocyclic alkyl group, each of which may have 1 to 3 substituents selected from Group B below;

$R^8$ represents a hydrogen atom or an alkyl group that may have 1 to 3 substituents selected from Group A below;

Group A: a halogen atom, a nitro group, —O—$R^a$, -(an alkylene group)-$OR^a$, —[O-(an alkylene group)]$_n$$OR^a$, —$NR^aR^b$, —$NR^b$-(an alkylene group)-$OR^a$, —$NR^aSO_2R^b$, —C=N—$OR^a$, —$CO_2R^a$, —$CONR^aR^b$, —$NR^aCOR^b$, —$COR^a$, —$SR^a$, —$SO_2R^a$, and —$SO_2NR^aR^b$;

Group B: a halogen atom, a nitro group, —O—$R^a$, -(an alkylene group)-$OR^a$, —[O-(an alkylene group)]$_n$-$OR^a$, —$NR^aR^b$, —$NR^b$-(an alkylene group)-$OR^a$, —$NR^aSO_2R^b$, —C=N—$OR^a$, —$CO_2R^a$, —$CONR^aR^b$, —$NR^aCOR^b$, —$COR^a$, —$SR^a$, —$SO_2R^a$, —$SO_2NR^aR^b$, an oxo group, an alkyl group, an alkenyl group, an alkyl group, an aryl group, and a heteroaryl group;

wherein $R^a$ and $R^b$ above may be identical or different, and represent
a hydrogen atom,
an alkyl group that may have an OH group,
an aryl group, or
a heteroaryl group,
and n=1 to 4, or a pharmaceutically acceptable salt thereof, the method comprising reacting the synthetic intermediate (X) of [40], a hydroxylamine derivative (Z1), and a hydroxylamine derivative (Z2) in the same reaction system simultaneously or sequentially, wherein the hydroxylamine derivative (Z1) is represented by formula (7):

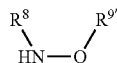
(7)

wherein, $R^8$ represents a hydrogen atom or an alkyl group that may have 1 to 3 substituents selected from Group A below;

$R^{9'}$ represents
a hydrogen atom,
an alkyl group, an alkenyl group, or an alkynyl group, each of which may have 1 to 3 substituents selected from Group A below, or
a cycloalkyl group, an aryl group, a heteroaryl group, a heterocyclic group, a cycloalkylalkyl group, a cycloalkylalkenyl group, a cycloalkylalkynyl group, an arylalkyl group, an arylalkenyl group, an arylalkynyl group, a heteroarylalkyl group, a heteroarylalkenyl group, a heteroarylalkynyl group, a heterocyclic alkyl group, a heterocyclic alkenyl group, or a heterocyclic alkynyl group, each of which may have 1 to 3 substituents selected from Group B below, when $R^{9'}$ has a hydroxyl group, an amino group, or an alkylamino group, the hydroxyl group, amino group, or alkylamino group may be protected with a protecting group;

Group A: a halogen atom, a nitro group, —O—$R^a$, -(an alkylene group)-$OR^a$, —[O-(an alkylene group)]$_n$-$OR^a$, —$NR^aR^b$, —$NR^b$-(an alkylene group)-$OR^a$, —$NR^aSO_2R^b$, —C=N—$OR^a$, —$CO_2R^a$, —$CONR^aR^b$, —$NR^aCOR^b$, —$COR^a$, —$SR^a$, —$SO_2R^{a1}$, and —$SO_2NR^aR^b$;

Group B: a halogen atom, a nitro group, —O—$R^a$, -(an alkylene group)-$OR^a$, —[O-(an alkylene group)]$_n$-$OR^a$, —$NR^aR^b$, —$NR^b$-(an alkylene group)-$OR^a$, —$NR^aSO_2R^b$, —C=N—$OR^a$, —$CO_2R^a$, —$CONR^aR^b$, —$NR^aCOR^b$, —$COR^a$, —$SR^a$, —$SO_2R^a$, —$SO_2NR^aR^b$, an oxo group, an alkyl group, an alkenyl group, an alkyl group, an aryl group, and a heteroaryl group;

wherein $R^a$ and $R^b$ above may be identical to or different, and represent
a hydrogen atom,
an alkyl group that may have an OH group,
an aryl group, or
a heteroaryl group,
and n=1 to 4, and the hydroxylamine derivative (Z2) is represented by formula (8):

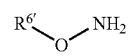
(8)

wherein, $R^{6'}$ represents
a hydrogen atom,
an alkyl group, an alkenyl group, or an alkynyl group, each of which may have 1 to 3 substituents selected from Group A below, or
a cycloalkyl group, an aryl group, a heteroaryl group, a heterocyclic group, a cycloalkylalkyl group, a cycloalkylalkenyl group, a cycloalkylalkynyl group, an arylalkyl group, an arylalkenyl group, an arylalkynyl group, a heteroarylalkyl group, a heteroarylalkenyl group, a heteroarylalkynyl group, a heterocyclic alkyl group, a heterocyclic alkenyl group, or a heterocyclic alkynyl group, each of which may have 1 to 3 substituents selected from Group B below, when $R^{6'}$ has a hydroxyl group, an amino group, or an alkylamino group, the hydroxyl group, amino group, or alkylamino group may be protected with a protecting group;

Group A: a halogen atom, a nitro group, —O—$R^a$, -(an alkylene group)-$OR^a$, —[O-(an alkylene group)]$_n$-$OR^a$, —$NR^aR^b$, —$NR^b$-(an alkylene group)-$OR^a$, —$NR^aSO_2R^b$, —C=N—$OR^a$, —$CO_2R^a$, —$CONR^aR^b$, —$NR^aCOR^b$, —$COR^a$, —$SR^a$, —$SO_2R^a$, and —$SO_2NR^aR^b$;

Group B: a halogen atom, a nitro group, —O—$R^a$, -(an alkylene group)-$OR^a$, —[O-(an alkylene group)]$_n$-$OR^a$, —$NR^aR^b$, —$NR^b$-(an alkylene group)-$OR^a$, —$NR^aSO_2R^b$, —C=N—$OR^a$, —$CO_2R^a$, —$CONR^aR^b$, —$NR^aCOR^b$, —$COR^a$, —$SR^a$, —$SO_2R^a$, —$SO_2NR^aR^b$, an oxo group, an alkyl group, an alkenyl group, an alkynyl group, an aryl group, and a heteroaryl group;

wherein $R^a$ and $R^b$ above may be identical or different, and represent
a hydrogen atom,
an alkyl group that may have an OH group,
an aryl group, or
a heteroaryl group,
and n=1 to 4;

[48] a method for preparing a compound of formula (1):

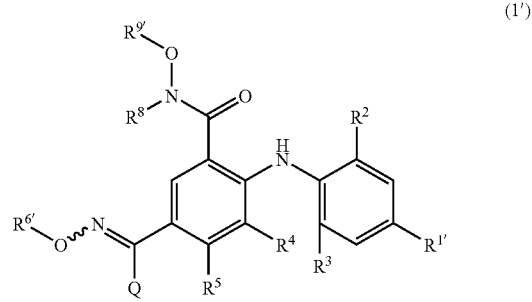
(1')

wherein the wavy line ∼∼∼ indicates that the compound can be either one of the stereoisomers, E-form or Z-form, depending on the manner of binding of O— to —N, $R^{1'}$ represents a hydrogen atom, a halogen atom, —S—$R^a$, —SO—$R^a$, —SO$_2$—$R^a$, —COO$R^a$, an alkyl group that may have 1 to 3 substituents selected from Group A below, an alkenyl group that may have 1 to 3 substituents selected from Group A below, or an alkynyl group that may have 1 to 3 substituents selected from Group A below and that may be protected with a protecting group;

$R^2$ and $R^3$ each independently represent a hydrogen atom, a halogen atom, or an alkyl group that may have 1 to 3 substituents selected from Group A below;

$R^4$ and $R^5$ each independently represent a hydrogen atom, a halogen atom, or a nitro group;

$R^{6'}$ and $R^{9'}$ each independently represent a hydrogen atom, an alkyl group, an alkenyl group, or an alkynyl group, each of which may have 1 to 3 substituents selected from Group A below, or a cycloalkyl group, an aryl group, a heteroaryl group, a heterocyclic group, a cycloalkylalkyl group, a cycloalkylalkenyl group, a cycloalkylalkynyl group, an arylalkyl group, an arylalkenyl group, an arylalkynyl group, a heteroarylalkyl group, a heteroarylalkenyl group, a heteroarylalkynyl group, a heterocyclic alkyl group, a heterocyclic alkenyl group, or a heterocyclic alkynyl group, each of which may have 1 to 3 substituents selected from Group B below, when $R^{6'}$ and $R^{9'}$ have one or more hydroxyl groups, amino groups, or alkylamino groups, the hydroxyl groups, amino groups, or alkylamino groups may each be protected with a protecting group;

Q is —NR$^a$R$^b$ or a group represented by $R^7$;

$R^7$ represents a hydrogen atom, an alkyl group, an alkenyl group, or an alkynyl group, each of which may have 1 to 3 substituents selected from Group A below, or a cycloalkyl group, a heterocyclic group, an aryl group, a heteroaryl group, an arylalkyl group, or a heterocyclic alkyl group, each of which may have 1 to 3 substituents selected from Group B below;

$R^8$ represents a hydrogen atom or an alkyl group that may have 1 to 3 substituents selected from Group A below;

Group A: a halogen atom, a nitro group, —O—$R^a$, -(an alkylene group)-O$R^a$, —[O-(an alkylene group)]$_n$-O$R^6$, —NR$^a$R$^b$, —NR$^b$-(alkylene group)-O$R^a$, —NR$^a$SO$_2$R$^b$, —C≡N—O$R^a$, —CO$_2$R$^a$, —CONR$^a$R$^b$, —NR$^a$COR$^b$, —COR$^a$, —SR$^a$, —SO$_2$R$^a$, and —SO$_2$NR$^a$R$^b$;

Group B: a halogen atom, a nitro group, —O—$R^{a1}$, -(an alkylene group)-O$R^a$, —[O-(an alkylene group)]$_n$-O$R^a$, —NR$^a$R$^b$, —NR$^b$-(an alkylene group)-O$R^a$, —NR$^a$SO$_2$R$^b$, —C≡N—O$R^a$, —CO$_2$R$^a$, —CONR$^a$R$^b$, —NR$^a$COR$^b$, —COR$^a$, —SR$^a$, —SO$_2$R$^a$, —SO$_2$NR$^a$R$^b$, an oxo group, an alkyl group, an alkenyl group, an alkynyl group, an aryl group, and a heteroaryl group;

wherein $R^a$ and $R^b$ above may be identical or different, and represent a hydrogen atom, an alkyl group that may have an OH group, an aryl group, or a heteroaryl group, and n=1 to 4, or a pharmaceutically acceptable salt thereof, the method comprising reacting the synthetic intermediate (Y) of [43] and a hydroxylamine derivative (Z2) represented by formula (8):

(8)

wherein, $R^{6'}$ represents a hydrogen atom, an alkyl group, an alkenyl group, or an alkynyl group, each of which may have 1 to 3 substituents selected from Group A, or a cycloalkyl group, an aryl group, a heteroaryl group, a heterocyclic group, a cycloalkylalkyl group, a cycloalkylalkenyl group, a cycloalkylalkynyl group, an arylalkyl group, an arylalkenyl group, an arylalkynyl group, a heteroarylalkyl group, a heteroarylalkenyl group, a heteroarylalkynyl group, a heterocyclic alkyl group, a heterocyclic alkenyl group, or a heterocyclic alkynyl group, each of which may have 1 to 3 substituents selected from Group B below, when $R^{6'}$ has a hydroxyl group, an amino group, or an alkylamino group, the hydroxyl group, amino group, or alkylamino group may be protected with a protecting group;

Group A: a halogen atom, a nitro group, —O—$R^a$, -(an alkylene group)-O$R^a$, —[O-(an alkylene group)]$_n$-O$R^a$, —NR$^a$R$^b$, —NR$^b$-(an alkylene group)-O$R^a$, —NR$^a$SO$_2$R$^b$, —C≡N—O$R^a$, —CO$_2$R$^a$, —CONR$^a$R$^b$, —NR$^a$COR$^b$, —COR$^a$, —SR$^a$, —SO$_2$R$^a$, and SO$_2$NR$^a$R$^b$;

Group B: a halogen atom, a nitro group, —O—$R^a$, -(an alkylene group)-O$R^a$, —[O-(an alkylene group)]$_n$-O$R^a$, —NR$^a$R$^b$, —NR$^b$-(an alkylene group)-O$R^a$, —NR$^a$SO$_2$R$^b$, —C≡N—O$R^a$, —CO$_2$R$^a$, —CONR$^a$R$^b$, —NR$^a$COR$^b$, —COR$^a$, —SR$^a$, —SO$_2$R$^a$, —SO$_2$NR$^a$R$^b$, an oxo group, an alkyl group, an alkenyl group, an alkynyl group, an aryl group, and a heteroaryl group;

wherein $R^a$ and $R^b$ above may be identical or different, and represent a hydrogen atom, an alkyl group that may have an OH group, an aryl group, or a heteroaryl group, and n=1 to 4;

[49] a synthetic intermediate (Z) of the compound of formula (1) of [1], represented by formula (65):

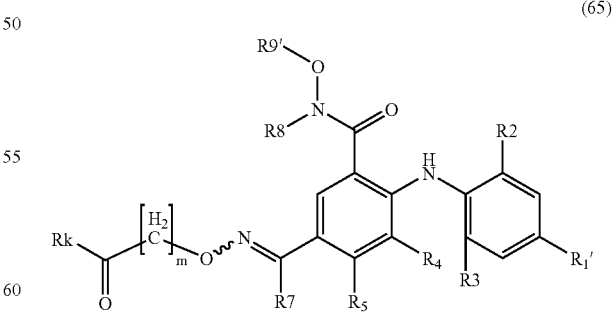

(65)

wherein, the wavy line ∼∼∼ indicates that the compound can be either one of the stereoisomers, E-form or Z-form, depending on the manner of binding of O— to —N, $R^{1'}$ represents a hydrogen atom, a halogen atom, —S—$R^a$, —SO—$R^a$, —SO$_2$—$R^a$, —COO$R^a$, an alkyl group that may have 1 to 3 substituents selected from Group A below, an alkenyl group that may have 1 to 3 substituents selected from Group A below, or an alkynyl group that may have 1 to 3 substituents selected from Group A below and may be protected with a protecting group;

$R^2$ and $R^3$ each independently represent a hydrogen atom, a halogen atom, or an alkyl group that may have 1 to 3 substituents selected from Group A below;

$R^4$ and $R^5$ each independently represent a hydrogen atom, a halogen atom, or a nitro group;

$R^7$ represents
a hydrogen atom,
an alkyl group, an alkenyl group, or an alkynyl group, each of which may have 1 to 3 substituents selected from Group A below, or
a cycloalkyl group, a heterocyclic group, an aryl group, a heteroaryl group, an arylalkyl group, or a heterocyclic alkyl group, each of which may have 1 to 3 substituents selected from Group B below;

$R^8$ represents a hydrogen atom or an alkyl group that may have 1 to 3 substituents selected from Group A below;

$R^{9'}$ represents
a hydrogen atom,
an alkyl group, an alkenyl group, or an alkynyl group, each of which may have 1 to 3 substituents selected from Group A below, or
a cycloalkyl group, an aryl group, a heteroaryl group, a heterocyclic group, a cycloalkylalkyl group, a cycloalkylalkenyl group, a cycloalkylalkynyl group, an arylalkyl group, an arylalkenyl group, an arylalkynyl group, a heteroarylalkyl group, a heteroarylalkenyl group, a heteroarylalkynyl group, a heterocyclic alkyl group, a heterocyclic alkenyl group, or a heterocyclic alkynyl group, each of which may have 1 to 3 substituents selected from Group B below, and when $R^{9'}$ has a hydroxyl group, an amino group, or an alkylamino group, the hydroxyl group, amino group, or alkylamino group may be protected with a protecting group;

Group A: a halogen atom, a nitro group, —O—$R^a$, -(an alkylene group)-O$R^a$, —[O-(an alkylene group)]$_n$-O$R^a$, —N$R^aR^b$, —N$R^b$-(an alkylene group)-O$R^a$, —N$R^a$SO$_2R^b$, —C=N—O$R^a$, —CO$_2R^a$, —CON$R^aR^b$, —N$R^a$CO$R^b$, —CO$R^8$, —S$R^a$, —SO$_2R^a$, and —SO$_2$N$R^aR^b$;

Group B: a halogen atom, a nitro group, —O—$R^a$, -(an alkylene group)-O$R^a$, —[O-(an alkylene group)]$_n$-O$R^a$, —N$R^aR^b$, —N$R^b$-(an alkylene group)-O$R^a$, —N$R^a$SO$_2R^b$, —C=N—O$R^a$, —CO$_2R^8$, —CON$R^aR^b$, —N$R^a$CO$R^b$, —CO$R^a$, —S$R^a$, —SO$_2R^a$, —SO$_2$N$R^aR^b$, an oxo group, an alkyl group, an alkenyl group, an alkynyl group, an aryl group, and a heteroaryl group;

wherein $R^a$ and $R^b$ above may be identical or different, and represent
a hydrogen atom,
an alkyl group that may have an OH group,
an aryl group, or
a heteroaryl group,
and n=1 to 4; and $R^k$ each independently represent a hydrogen atom, a C1-C4 alkyl group, an aryl group, or a heteroaryl group;

an arbitrary hydrogen atom in a repeating unit represented by above —[CH$_2$]m- (m is an integer from 1 to 4) may be replaced with a group represented by $R^c$; $R^c$ represents a C1-C4 alkyl group, an aryl group, or a heteroaryl group, $R^c$ may be substituted with a hydroxyl-group that may be protected with a protecting group, and when two or more hydrogen atoms are each substituted with $R^c$, each $R^c$ may be identical to or different from each other;

[50] a synthetic intermediate (P) of the compound of formula (1) of [1], represented by formula (66):

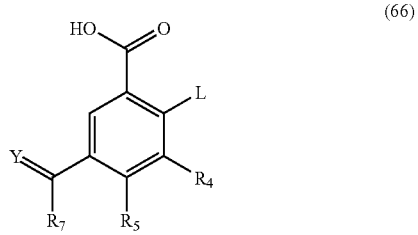

(66)

wherein, Y represents CH$_2$ or an oxygen atom;
L represents a leaving group;
$R^4$ and $R^5$ each independently represent a hydrogen atom, a halogen atom, or a nitro group;

$R^7$ represents
a hydrogen atom,
an alkyl group, an alkenyl group, or an alkynyl group, each of which may have 1 to 3 substituents selected from Group A below, or
a cycloalkyl group, a heterocyclic group, an aryl group, a heteroaryl group, an arylalkyl group, or a heterocyclic alkyl group, each of which may have 1 to 3 substituents selected from Group B below;

Group A: a halogen atom, a nitro group, —O—$R^a$, -(an alkylene group)-O$R^a$, —[O-(an alkylene group)]$_n$-O$R^a$, —N$R^aR^b$, —N$R^b$-(an alkylene group)-O$R^a$, —N$R^a$SO$_2R^b$, —C=N—O$R^a$, —CO$_2R^a$, —CON$R^aR^b$, —N$R^a$CO$R^b$, —CO$R^a$, —S$R^a$, —SO$_2R^a$, and —SO$_2$N$R^aR^b$;

Group B: a halogen atom, a nitro group, —O—$R^a$, -(an alkylene group)-O$R^a$, —[O-(an alkylene group)]$_n$-O$R^a$, —N$R^aR^b$, —N$R^b$-(an alkylene group)-O$R^a$, —N$R^a$SO$_2R^b$, —C=N—O$R^a$, —CO$_2R^a$, —CON$R^aR^b$, —N$R^a$CO$R^b$, —CO$R^a$, —S$R^a$, —SO$_2R^a$, —SO$_2$N$R^aR^b$, an oxo group, an alkyl group, an alkenyl group, an alkynyl group, an aryl group, and a heteroaryl group;

wherein $R^a$ and $R^b$ above may be identical or different, and represent
a hydrogen atom,
an alkyl group that may have an OH group,
an aryl group, or
a heteroaryl group,
and n=1 to 4;
m=1 to 4; and
the leaving group described above represents a halogen atom or an activated hydroxyl group;

[51] the compound according to [50], wherein
L represents a fluorine atom, a chlorine atom, a bromine atom, or an iodine atom,
Y represents CH$_2$ or an oxygen atom,
$R^4$ and $R^5$ each independently represent a hydrogen atom or a fluorine atom, and
$R^7$ represents a hydrogen atom;

[52] a pharmaceutical composition, which comprises as an active ingredient a compound of any one of [1] to [30] or a pharmaceutically acceptable salt thereof;

[53] a mitogen-activated protein kinase kinase (MEK) inhibitor which comprises as an active ingredient the compound of any one of [1] to [30] or a pharmaceutically acceptable salt thereof;

[54] a prophylactic or therapeutic agent for a proliferative disease, which comprises as an active ingredient a compound of any one of [1] to [30] or a pharmaceutically acceptable salt thereof;

[55] the prophylactic or therapeutic agent for a proliferative disease of [54], wherein the proliferative disease is at least one of those selected from psoriasis, restenosis, autoimmune diseases, and atherosclerosis;

[56] the prophylactic or therapeutic agent for a proliferative disease of [54], wherein the proliferative disease is a cancer;

[57] the prophylactic or therapeutic agent for a proliferative disease of [56], wherein the cancer is that in which MEK is overexpressed;

[58] the prophylactic or therapeutic agent for a proliferative disease of [56] or [57], wherein the cancer is a breast, lung, colorectal, prostate, liver, ovarian, uterine, or pancreatic cancer;

[59] a method for preventing or treating a proliferative disease, wherein the method comprises administering a therapeutically effective amount of a composition comprising the compound of any one of [1] to [30], or a pharmaceutically acceptable salt thereof, to a patient in need thereof;

[60] the method of [59], wherein the proliferative disease is at least one of those selected from psoriasis, restenosis, autoimmune diseases, and atherosclerosis; [61] the method of [59], wherein the proliferative disease is a cancer;

[62] the method of [59], wherein the cancer is that in which MEK is overexpressed;

[63] the method of [61] or [62], wherein the cancer is a breast, lung, colorectal, prostate, liver, ovarian, uterine, or pancreatic cancer;

[64] a prophylactic or therapeutic agent for sequelae of cardiac failure, which comprises as an active ingredient a compound of any one of [1] to [30], or a pharmaceutically acceptable salt thereof;

[65] a method for preventing, treating, or reducing a sequelae of stroke, which comprises administering a therapeutically effective amount of a composition comprising the compound of any one of [1] to [30], or a pharmaceutically acceptable salt thereof, to a patient in need thereof;

[66] a prophylactic or therapeutic agent for symptoms of xenograft rejection, which comprises as an active ingredient a compound of any one of [1] to [30] or a pharmaceutically acceptable salt thereof;

[67] a method for preventing, treating, or reducing a symptom of xenograft rejection, wherein the method comprises administering an organ transplant or bone marrow transplant patient with a pharmaceutically effective amount of a composition comprising the compound of any one of [1] to [30], or a pharmaceutically acceptable salt thereof;

[68] a prophylactic or therapeutic agent for osteoarthrosis, which comprises as an active ingredient a compound of any one of [1] to [30], or a pharmaceutically acceptable salt thereof;

[69] a method for preventing or treating osteoarthrosis, which comprises administering a therapeutically effective amount of a composition comprising a compound of any one of [1] to [30] or a pharmaceutically acceptable salt thereof to a patient in need thereof;

[70] a prophylactic or therapeutic agent for rheumatoid arthritis, which comprises as an active ingredient a compound of any one of [1] to [30], or a pharmaceutically acceptable salt thereof;

[71] a method for preventing or treating rheumatoid arthritis, which comprises administering a therapeutically effective amount of a composition comprising the compound of any one of [1] to [30], or a pharmaceutically acceptable salt thereof, to a patient in need thereof;

[72] a prophylactic or therapeutic agent for asthma, which comprises as an active ingredient the compound of any one of [1] to [30], or a pharmaceutically acceptable salt thereof;

[73] a method for preventing or treating asthma, which comprises administering a therapeutically effective amount of a composition comprising a compound of any one of [1] to [30], or a pharmaceutically acceptable salt thereof, to a patient in need thereof;

[74] a prophylactic or therapeutic agent for cystic fibrosis, which comprises as an active ingredient the compound of any one of [1] to [30], or a pharmaceutically acceptable salt thereof;

[75] a method for preventing or treating cystic fibrosis, which comprises administering a therapeutically effective amount of a composition comprising a compound of any one of [1] to [30], or a pharmaceutically acceptable salt thereof, to a patient in need thereof;

[76] a prophylactic or therapeutic agent for hepatomegaly, which comprises as an active ingredient a compound of any one of [1] to [30], or a pharmaceutically acceptable salt thereof;

[77] a method for preventing or treating hepatomegaly, which comprises administering a therapeutically effective amount of a composition comprising a compound of any one of [1] to [30], or a pharmaceutically acceptable salt thereof, to a patient in need thereof;

[78] a prophylactic or therapeutic agent for cardiomegaly, which comprises as an active ingredient the compound of any one of [1] to [30], or a pharmaceutically acceptable salt thereof;

[79] a method for preventing or treating cardiomegaly, which comprises administering a therapeutically effective amount of a composition comprising a compound of any one of [1] to [30], or a pharmaceutically acceptable salt thereof, to a patient in need thereof;

[80] a prophylactic or therapeutic agent for Alzheimer's disease, which comprises as an active ingredient a compound of any one of [1] to [30], or a pharmaceutically acceptable salt thereof;

[81] a method for preventing or treating Alzheimer's disease, which comprises administering a therapeutically effective amount of a composition comprising a compound of any one of [1] to [30], or a pharmaceutically acceptable salt thereof, to a patient in need thereof;

[82] a prophylactic or therapeutic agent for diabetes, which comprises as an active ingredient a compound of any one of [1] to [30], or a pharmaceutically acceptable salt thereof;

[83] a method for preventing or treating diabetes, which comprises administering a therapeutically effective amount of a composition comprising a compound of any one of [1] to [30], or a pharmaceutically acceptable salt thereof, to a patient in need thereof;

[84] a prophylactic or therapeutic agent for septic shock, which comprises as an active ingredient a compound of any one of [1] to [30], or a pharmaceutically acceptable salt thereof;

[85] a method for preventing or treating septic shock, which comprises administering a therapeutically effective amount of a composition comprising a compound of any one of [1] to [30], or a pharmaceutically acceptable salt thereof, to a patient in need thereof;

[86] a prophylactic or therapeutic agent for a viral infection, which comprises as an active ingredient a compound of any one of [1] to [30], or a pharmaceutically acceptable salt thereof;

[87] the prophylactic or therapeutic agent of [86], wherein the virus is an HIV virus;

[88] a method for preventing or treating a viral infection, which comprises administering a therapeutically effective amount of a composition comprising a compound of any one of [1] to [30], or a pharmaceutically acceptable salt thereof, to a patient in need thereof;

[89] the method of [88], wherein the virus is an HIV virus.

[90] a method for preventing or treating a cancer using a combination of a pharmaceutical composition comprising as an active ingredient a compound of any one of [1] to [30], or a pharmaceutically acceptable salt thereof, and radiotherapy, a chemotherapy agent, or an angiogenesis inhibitor; and,

[91] the use of a compound of any one of [1] to [30], or a pharmaceutically acceptable salt thereof, for producing a prophylactic or therapeutic agent for a disease in which MEK inhibition is effective.

As used herein, "an alkyl group" refers to a monovalent group that is derived by removing any one hydrogen atom from an aliphatic hydrocarbon, which does not comprise a heteroatom or an unsaturated carbon-carbon bond in its skeleton, and comprises a subset of a hydrocarbyl or a hydrocarbon structure comprising hydrogen atoms and carbon atoms. An alkyl group comprises a linear or a branched structure. As an alkyl group, an alkyl group that comprises 1 to 8 carbon atoms (C1-C8, hereinafter "C1-C8" means the number of carbon atoms) is preferable, and a C1-C6 alkyl group is more preferable. In the case of an alkyl group in Group A or B, a C1-C4 alkyl group is preferable.

Examples of an alkyl group specifically include a methyl group, an ethyl group, an n-propyl group, an i-propyl group, an n-butyl group, a sec-butyl group, a t-butyl group, an isobutyl group, a pentyl group, an isopentyl group, a 2,3-dimethylpropyl group, a hexyl group, a 2,3-dimethylhexyl group, a 1,1-dimethylpentyl group, a heptyl group, and an octyl group.

When an alkyl group comprises 1 to 3 substituents selected from Group A above, the substituents preferably include:

Group C: $-O-R^a$, $-NR^aR^b$, $-$(C1-C4-alkylene group)-$OR^a$, $-[O-$(C1-C4 alkylene group)$]n$-$OR^a$, $-NR^b-$(C1-C4 alkylene group)-$OR^b$, $-NR^aSO_2$, $-C\equiv N-OR^a$, $-CONR^aR^b$, $-NR^aCOR^b$, $-SR^a$, and $-SO_2R^a$, wherein $R^a$ and $R^b$ are preferably a hydrogen atom, or an alkyl group that may comprise an OH group.

An alkylene group is preferably a C1-C4 alkylene group, and an alkyl group is preferably a C1-C4 alkyl group. Preferably, n is 1 to 4.

As used herein, "an alkenyl group" refers to a monovalent group that comprises at least one double bond (two adjacent $Sp^2$ carbon atoms). Depending on the configuration of the double bond and substituents (if present), the geometrical form of the double bond can be entgegen (E) or zusammen (Z), or cis or trans configuration. An alkenyl group may be linear or branched, and a C2-C8 alkenyl group is preferable, and a C2-C4 alkenyl group is more preferable. In the case of an alkenyl group in Group A or B, a C2-C4 alkenyl group is preferable.

Examples of such an alkenyl group specifically include a vinyl group, an allyl group, a 1-propenyl group, a 2-propenyl group, a 1-butenyl group, a 2-butenyl group (comprising cis and trans forms), a 3-butenyl group, a pentenyl group, and a hexenyl group.

As used herein, "an alkynyl group" refers to a monovalent group that comprises at least one triple bond (two adjacent SP carbon atoms). An alkynyl group may be linear or branched, and a C2-C8 alkynyl group is preferable, and a C2-C4 alkynyl group is more preferable. In the case of an alkynyl group in Group A or B, a C3-C4 alkynyl group is preferable.

Examples of an alkynyl group specifically includes an ethynyl group, a 1-propynyl group, a propargyl group, a 3-butynyl group, a pentynyl group, a hexynyl group, a 3-phenyl-2-propynyl group, a 3-(2'-fluorophenyl)-2-propynyl group, a 2-hydroxy-2-propynyl group, a 3-(3-fluorophenyl)-2-propynyl group, and a 3-methyl-(5-phenyl)-4-pentynyl group.

An alkenyl or alkynyl group may each have one or more double or triple bonds. They may have double bond(s) and triple bond(s) simultaneously.

As used herein, "a cycloalkyl group" refers to a cyclic aliphatic hydrocarbon group, and a C3-C8 cycloalkyl group is preferable. Examples of a cycloalkyl group specifically include a cyclopropyl group, a cyclobutyl group, a cyclopentyl group, a cyclohexyl group, a cycloheptyl group, and a cyclooctyl group.

As used herein, "an alkylene group" refers to a divalent group that is derived by removing any one more hydrogen atom from the "alkyl group" above, and a C1-C4 alkylene group is preferable, and a C1-C2 alkylene group is more preferable. Examples of an alkylene group specifically include a methylene group, a 1,2-ethylene group, a 1,1-ethylene group, a 1,3-propylene group, a tetramethylene group, a pentamethylene group, and a hexamethylene group.

As used herein, "an aryl group" refers to a monovalent aromatic hydrocarbon ring, and a C6-C10 aryl group is preferable. Examples of an aryl group specifically include a phenyl group, a 1-naphthyl group, and a 2-naphthyl group.

As used herein, "a heteroatom" refers to a sulfur, oxygen, or nitrogen atom.

As used herein, "a heteroaryl group" refers to an aromatic ring group comprising one or more heteroatoms among atoms constituting the ring, and may be partially saturated. The ring may be a monocyclic, or a bicyclic heteroaryl group that is condensed with a benzene ring or a monocyclic heteroaryl ring. The number of the atoms constituting the ring is preferably 5 to 10 (a C5-C10 heteroaryl group).

Examples of a heteroaryl group specifically include a furyl group, a thienyl group, a pyrrolyl group, an imidazolyl group, a pyrazolyl group, a thiazolyl group, an isothiazolyl group, an oxazolyl group, an isoxazolyl group, an oxadiazolyl group, a thiadiazolyl group, a triazolyl group, a tetrazolyl group, a pyridyl group, a pyrimidyl group, a pyridazinyl group, a pyrazinyl group, a triazinyl group, a benzofuranyl group, a benzothienyl group, a benzothiadiazolyl group, a benzothiazolyl group, a benzoxazolyl group, a benzoxadiazolyl group, a benzoimidazolyl group, an indolyl group, an isoindolyl group, an indazolyl group, a quinolyl group, an isoquinolyl group, a cinnolinyl group, a quinazolinyl group, a quinoxalinyl group, a benzodioxolyl group, an indolizinyl group, and an imidazopyridyl group.

As used herein, "a heterocyclic group" refers to a monocyclic nonaromatic monovalent ring, which preferably comprises 3 to 8 atoms constituting the ring (a C3-C8 heterocyclic group) among which 1 to 3 heteroatoms are comprised, and may comprise double bonds in the ring.

Examples of a heterocyclic group specifically include a morpholino group, a thiomorpholino group, a piperidin-1-yl group, a 4-substituted-piperidin-1-yl group, a piperazin-1-yl group, a 4-substituted-piperazin-1-yl group, a pyrrolidin-1-yl-group, a pyrrolinyl group, an imidazolidinyl group, an imidazolinyl group, a pyrazolidinyl group, a pyrazolinyl group, a 2-oxo-pyrrolidin-1-yl group, and a 2-oxoimidazolidin-1-yl group. Among these, a morpholino group, a thiomorpholino group, a piperidin-1-yl group, a 4-substituted-piperidin-1-yl group, a piperazin-1-yl group, and a 4-substituted-piperazin-1-yl group can be preferably used.

When the heterocyclic group comprises a substituent selected from Group B above, it is preferably an —O—$R^a$ or an alkyl group, and $R^a$ is preferably a hydrogen atom or an alkyl group. The alkyl group is preferably a C1-C4 alkyl group.

As used herein, "a halogen atom" refers to a fluorine, chlorine, bromine, or iodine atom.

As used herein, "a cycloalkylalkyl group" refers to a group in which any hydrogen atom in the "alkyl group" defined above is substituted with the "cycloalkyl group" defined above, and a C3-C8-cycloalkyl-C1-C4-alkyl group is preferable. Examples of a cycloalkylalkyl group specifically include a cyclopropylmethyl group, a cyclopropylethyl group, a cyclopentylmethyl group, a cyclopentylethyl group, a cyclohexylmethyl group, and a cyclohexylethyl group.

As used herein, "a cycloalkylalkenyl group" refers to a group in which any hydrogen atom in the "alkenyl group" defined above is substituted with the "cycloalkyl group" defined above. As a cycloalkylalkenyl group, a C3-C8-cycloalkyl-C2-C4-alkenyl group is preferable.

As used herein, "a cycloalkylalkynyl group" refers to a group in which any hydrogen atom in the "alkynyl group" defined above is substituted with the "cycloalkyl group" defined above. As a cycloalkylalkynyl group, a C3-C8-cycloalkyl-C2-C4-alkynyl group is preferable.

As used herein, "an arylalkyl group" refers to a group in which any hydrogen atom in the "alkyl group" defined above is substituted with the "aryl group" defined above, and a C6-C10-aryl-C1-C4-alkyl group is preferable.

Examples of an arylalkyl group specifically include a benzyl group, a phenethyl group, and a 3-phenyl-1-propyl group.

As used herein, "an arylalkenyl group" refers to a group in which any hydrogen atom in the "alkenyl group" defined above is substituted with the "aryl group" defined above, and a C6-C-10-aryl-C2-C4-alkenyl group is preferable.

As used herein, "an arylalkynyl group" refers to a group in which any hydrogen atom in the "alkynyl group" defined above is substituted with the "aryl group" defined above, and a C6-C10-aryl-C2-C4-alkynyl group is preferable.

As used herein, "a heteroarylalkyl group" refers to a group in which any hydrogen atom in the "alkyl group" defined above is substituted with the "heteroaryl group" defined above, and a C5-C10-heteroaryl-C1-C4-alkyl group is preferable. Examples of a heteroarylalkyl group specifically include a pyridyl-4-yl-methyl group, an oxazolyl-2-yl-methyl group, a 2-(pyridyl-4-yl)ethyl group, a 2-(oxazolyl-2-yl)ethyl group, a 1H-imidazol-2-ylmethyl group, and a 3H-imidazol-4-ylmethyl group.

As used herein, "a heteroarylalkenyl group" refers to a group in which any hydrogen atom in the "alkenyl group" defined above is substituted with the "heteroaryl group" defined above, and a C5-C10-heteroaryl-C2-C4-alkenyl group is preferable.

As used herein, "a heteroarylalkynyl group" refers to a group in which any hydrogen atom in the "alkynyl group" defined above is substituted with the "heteroaryl group" defined above, and a C5-C10-heteroaryl-C2-C4-alkynyl group is preferable.

As used herein, "a heterocyclic alkyl group" refers to a group in which any hydrogen atom in the "alkyl group" defined above is substituted with the "heterocyclic group" defined above, and a C3-C8-heterocyclic-C1-C4-alkyl group is preferable. Examples of a heterocyclic alkyl group specifically include a morpholin-4-yl-methyl group, a 2-(morpholin-4-yl)ethyl group, a 4-hydroxy-piperidin-1-ylmethyl group, a 2-(4-hydroxy-piperidin-1-yl)ethyl group, a 4-methyl-piperazin-1-yl-methyl group, a 2-(4-methyl-piperazin-1-yl-)ethyl group, a 2-(2-oxo-pyrrolidin-1-yl)ethyl group, and a 2-(2-oxoimidazolidin-1-yl)ethyl group.

As used herein, "a heterocyclic alkenyl group" means a group in which any hydrogen atom in an above-defined "alkenyl group" is replaced with an above-defined "heterocyclic group". Examples of the heterocyclic alkenyl group are preferably C3-C8 heterocyclic C2-C4 alkenyl groups.

As used herein, "a heterocyclic alkynyl group" means a group in which any hydrogen atom in an above-defined "alkynyl group" is replaced with an above-defined "heterocyclic group". Examples of the heterocyclic alkynyl group are preferably C3-C8 heterocyclic C2-C4 alkynyl groups.

As used herein, "a hydroxyalkyl group" means a group in which any hydrogen atom in an above-defined "alkyl group" is replaced with a hydroxyl group. Examples of the hydroxyalkyl group are preferably hydroxy C1-C4 alkyl groups.

As used herein, "dihydroxyalkyl group" means a group in which any two hydrogen atoms in an above-defined "alkyl group" are each replaced with a hydroxyl group. Examples of the dihydroxyalkyl group are preferably dihydroxy C1-C4 alkyl groups.

As used herein, "an alkyloxyalkyl group" used herein means a group in which the hydrogen atom of the hydroxyl group in an above-defined "hydroxyalkyl group" is replaced with an "alkyl group" defined above. Examples of the alkyloxyalkyl group are preferably C1-C8 alkyloxy C1-C4 alkyl groups.

As used herein, "a hydroxyalkyloxyalkyl group" means a group in which any hydrogen atom in the terminal alkyl group of an above-defined "alkyloxyalkyl group" is replaced with a hydroxyl group. Examples of the hydroxyalkyloxyalkyl group are preferably hydroxy C1-C8 alkyloxy C1-C4 alkyl groups.

As used herein, "an aminoalkyl group" means a group in which any hydrogen atom in an above-defined "alkyl group" is replaced with an amino group ($H_2N$—). Examples of the aminoalkyl group are preferably amino C1-C4 alkyl groups.

As used herein, "an alkylaminoalkyl group" means a group in which any one or two hydrogen atoms in the amino group of an above-defined "aminoalkyl group" are replaced with an above-defined "alkyl group". Examples of the alkylaminoalkyl group are preferably C1-C8 alkylamino C1-C4 alkyl groups. When two hydrogen atoms are replaced with alkyl groups, these alkyl groups may be identical to or different from each other.

As used herein, "a hydroxyalkylaminoalkyl group" means a group in which any hydrogen atom in the terminal alkyl group of an above-defined "alkylaminoalkyl group" is replaced with a hydroxyl group. Examples of the hydroxyalkylaminoalkyl group are preferably hydroxy C1-C8 alkylamino C1-C4 alkyl groups.

As used herein, "an iminoalkyl group" means a group in which any hydrogen atom in an "alkyl group" defined above is replaced with an imino group (—NH). Examples of the iminoalkyl group are preferably imino C1-C4 alkyl groups.

As used herein, "a hydroxyiminoalkyl group" means a group in which the hydrogen atom in the imino group of an above-defined "iminoalkyl group" is replaced with a hydroxyl group. Examples of the hydroxyiminoalkyl group are preferably hydroxyimino C1-C4 alkyl groups.

As used herein, "alkoxyiminoalkyl group" means a group in which the hydrogen atom in the hydroxyl group of an above-defined "hydroxyiminoalkyl group" is replaced with an above-defined "alkyl group". Examples of the alkoxyiminoalkyl group are preferably C1-C8 alkyloxyimino C1-C4 alkyl groups.

A free form or a pharmaceutically acceptable salt of Compound I is also included in the present. Such a "salt" is a salt formed with compound I of the present invention. It is not particularly limited as long as it is pharmaceutically acceptable, and includes acid salts formed by a reaction of an acid with compound I, and base salts formed by a reaction of a base with compound I.

Acids used to prepare pharmaceutically acceptable acid salts of compound I of the present invention preferably form non-toxic acid salts by reacting with compound I of the present invention. Examples of acid salts include hydrochloride, hydrobromide, hydroiodide, nitrate, sulfate, bisulfate, phosphate, acidic phosphate, acetate, lactate, citrate, acidic citrate, tartarate, bitartarate, succinate, maleate, fumarate, gluconate, saccharate, benzoate, methanesulfonate, ethanesulfonate, benzenesulfonate, p-toluenesulfonate, and 1,1'-methylene-bis-(2-hydroxy-3-naphthoate).

Bases used to prepare pharmaceutically acceptable base salts of compound I of the present invention, preferably form non-toxic base salts by reacting with compound I of the present invention. Examples of base salts include alkali metal salts such as sodium salt and potassium salt, alkali earth metal salts such as calcium salt and magnesium salt, water-soluble amine addition salts such as ammonium salt, N-methylglucamine salt, lower alkanolammonium salt, and salts derived from bases other than pharmaceutically acceptable organic amines.

When compound I of the present invention is left in the atmosphere, it absorbs moisture so that hygroscopic water attaches thereto, or it becomes a hydrate, and such salts are also encompassed in the present invention.

Furthermore, compound I of the present invention may absorb certain kinds of other solvents to form solvates, and such salts are also encompassed in the present invention.

In the present description, "MEK" (MAPK/ERK/Kinase: MAPK stands for mitogen activated protein kinase, and ERK stands for extracellular stimulus-regulated kinase) means a dual specificity kinase relating to MAP kinase and ERK kinase, and "MEK inhibition" means antagonizing, inhibiting, or counteracting the activity of a protein produced by the MEK cascade or in response to MEK. Therefore, "MEK inhibition" comprises antagonizing, inhibiting, or counteracting the activity of MAP/ERK kinase or genes encoding MAP/ERK kinase.

Herein, "proliferative disease" means diseases caused by a defect in the intracellular signal transduction system, or in the signal transduction mechanism of a certain type of protein, and this phrase encompasses cancers, psoriasis, restenosis, autoimmune diseases, and atherosclerosis.

In the present invention, groups conventionally used as protecting groups for ethynyl groups can be used without particular limitation as the "protecting groups" comprised in $T_1$ or $R^{1'}$. Examples are silyl groups such as trimethylsilyl group, triethylsilyl group, isopropyldimethylsilyl group, t-butyldimethylsilyl group, methyldiisopropylsilyl group, methyldi-t-butylsilyl group, triisopropylsilyl group, diphenylmethylsilyl group, diphenylbutylsilyl group, diphenylisopropylsilyl group, or phenyldiisopropylsilyl group. Among them, trimethylsilyl group and such are preferred.

Groups conventionally used as protecting groups for hydroxyl groups can be used without particular limitation as the "protecting groups" comprised in $T_2$, $T_3$, $R^{6'}$, or $R^{9'}$. Examples include alkylsilyl groups such as trimethylsilyl group, triethylsilyl group, isopropyldimethylsilyl group, t-butyldimethylsilyl group, methyldiisopropylsilyl group, methyldi-t-butylsilyl group, triisopropylsilyl group, diphenylmethylsilyl group, diphenylbutylsilyl group, diphenylisopropylsilyl group, or phenyldiisopropylsilyl group; C1-C6 alkylcarbonyl groups such as acetyl group or propionyl group; phenylcarbonyl group; C1-C6 alkyl-oxycarbonyl group such as methoxycarbonyl group, ethoxycarbonyl group, ort-butoxycarbonyl group; tetrahydrofuranyl group; alkoxymethyl group such as methoxymethyl group or ethoxymethyl group; alkoxylated alkoxymethyl groups such as 2-methoxyethoxymethyl group; alkoxyethyl groups such as 1-ethoxyethyl group; benzyloxymethyl group; substituted benzyl groups such as benzyl group, 4-methylbenzyl group, 4-methoxybenzyl group, or o-nitrobenzyl group; and formyl group. Among them, alkylsilyl groups are preferable, and t-butyldimethylsilyl group is more preferable.

Groups conventionally used as protecting groups for amino groups or alkylamino groups can be used without particular limitation as the "protecting groups" comprised in $R^{6'}$, or $R^{9'}$. Examples include alkoxycarbonyl groups such as methoxycarbonyl group, ethoxycarbonyl group, 2,2,2-trichloroethoxycarbonyl group, 2-trimethylsilylethoxycarbonyl group, 2-chloroethoxycarbonyl group, 2,2-dichloroethoxycarbonyl group, 1-methyl-1-(4-biphenylyl)ethoxycarbonyl group, or t-butoxycarbonyl group; carbonyl groups such as benzylthiocarbonyl group, formyl group, acetyl group, chloroacetyl group, trichloroacetyl group, benzoyl group, o-nitrophenylacetyl group, propionyl group, or pivaloyl group; alkylsilyl group such as trimethylsilyl group, triethylsilyl group, triisopropylsilyl group, t-butyldimethylsilyl group, t-butyldiphenylsilyl group, or i-propyldimethylsilyl group. Among them, alkoxycarbonyl groups are preferable, and t-butoxycarbonyl group is more preferable.

Preferable examples of compound I of the present invention represented by formula (1) are the following compounds:
(1) $R^1$ is preferably, for example, an iodine atom, bromine atom, vinyl group, or ethynyl group, and is more preferably, for example, an iodine atom or ethynyl group.
(2) $R^2$ is preferably, for example, a hydrogen atom, chlorine atom, fluorine atom, methyl group, or hydroxymethyl group, and is more preferably, for example, a fluorine atom or chlorine atom.
(3) $R^3$ is preferably, for example, a hydrogen atom, chlorine atom, or fluorine atom, and is more preferably, for example, a hydrogen atom.
(4) $R^4$ is preferably, for example, a hydrogen atom, or a fluorine atom, and is more preferably, for, example, a fluorine atom.
(5) $R^5$ is preferably, for example, a halogen atom, and is more preferably, for example, a fluorine atom.
(6) Examples of $R^6$ preferably include a hydrogen atom; an alkyl group, an alkenyl group, or an alkynyl group, each of which may comprise 1 to 3 substituents selected from Group C below; or a cycloalkylalkyl group, an arylalkyl group, a heteroarylalkyl group, or a heterocyclic alkyl group, each of which may comprise 1 to 3 substituents selected from Group D below;
Group C: —O—$R^a$, —N$R^a R^b$, —(C1-C4 alkylene group)-O$R^a$, —[O—(C1-C4 alkylene group)]n-O$R^a$, —N$R^b$—(C1-C4 alkylene group)-O$R^a$, —N$R^a$SO$_2$$R^b$, —C=N—O$R^a$, —CON$R^a R^b$, —N$R^a$CO$R^b$, —S$R^a$, and —SO$_2$$R^a$;
Group D: —O—$R^a$, —(C1-C4 alkylene group)-O$R^a$, —[O—(C1-C4 alkylene group)]$_n$-O$R^a$, —N$R^b$—(C1-C4 alkylene group)-O$R^a$, —C=N—O$R^a$, —CON$R^a R^b$, —N$R^a$CO$R^b$, —S$R^a$, —SO$_2$$R^a$, a C1-C4 alkyl group, and an oxo group;
provided that $R^a$ and $R^b$ may be identical to or different, and represent a hydrogen atom; an alkyl group that may comprise an OH group; an aryl group; or a heteroaryl group. In Groups C and D, the alkylene group is preferably a C1-C4 alkylene group, and the alkyl group is preferably a C1-C4 alkyl group. The alkyl group of $R^a$ and $R^b$ is preferably a C1-C4 alkyl group. Preferably, n is 1 to 4.

Examples of $R^6$ more preferably include a hydrogen atom, an alkyl group, an alkenyl group, an alkynyl group, a hydroxyalkyl group, a dihydroxyalkyl group, a hydroxyalkyloxyalkyl group, a hydroxyalkylaminoalkyl group, a hydroxyiminoalkyl group, an alkoxyiminoalkyl group, a cycloalkylalkyl group, an arylalkyl group, a heteroarylalkyl group, a heterocyclic alkyl group, a heterocyclic alkyl group containing a hydroxy group, an alkylcarbamoylalkyl group, a hydroxyalkylcarbamoylalkyl group, a hydroxyalkylcycloalkylalkyl group, an acetylaminoalkyl group, an acetyl(alkyl)aminoalkyl group, a heterocyclic alkyl group containing an oxo group, a heteroarylalkyl group containing an oxo group, an alkylsulfanylalkyl group, an alkylsulfonylalkyl group, an aminoalkyl group, and an alkylaminoalkyl group.

Examples of $R^6$ more preferably include a hydrogen atom, a methyl group, an isopropyl group, a 2-hydroxyethyl group, a 2-hydroxypropyl group, a 3-hydroxypropyl group, a 2,3-dihydroxypropyl group, a 2-hydroxy-1-(hydroxymethyl)ethyl group, a 2-hydroxy-2-methylpropyl group, a 2-hydroxy-1-methylethyl group, a cyclopropylmethyl group, a cyclopentylmethyl group, a 2-(2-hydroxyethoxy)ethyl group, a 2-(2-hydroxyethylamino)ethyl group, a 2-(morpholin-4-yl)ethyl group, a 2-(4-methylpiperazin-1-yl)ethyl group, a 2-(4-hydroxypiperidin-1-yl)ethyl group, a 2-(hydroxyimino)ethyl group, a 2-(methoxyimino)ethyl group, a 2-methylcarbamoyl-ethyl group, a 2-propenyl group, a 2-propynyl group, a benzyl group, a pyridin-4-ylmethyl group, a oxazol-2-ylmethyl group, a 3-hydroxy-3-methylbutyl group, a 3-hydroxy-2,2-dimethylpropyl group, a 1-hydroxymethyl-cyclopropyl-methyl group, a 4-hydroxylbutyl group, a 3-methoxy-3-methylbutyl group, a 2-methoxyethyl group, a 2-methylsulfanylethyl group, a 2-methanesulfonylethyl group, a 2-aminoethyl group, a 2-methylaminoethyl group, a 2-dimethylaminoethyl group, a 2-(piperidin-1-yl)ethyl group, a 2-(pyrrolidin-1-yl)ethyl group, a 2-((S)-2-hydroxymethyl-pyrrolidin-1-yl)ethyl group, a 2-((R)-2-hydroxymethyl-pyrrolidin-1-yl)ethyl group, a methylcarbamoyl-methyl group, a 2-dimethylcarbamoyl-ethyl group, a 3-methylcarbamoyl-propyl group, a (2-hydroxyethylcarbamoyl)methyl group, a 2-acetylaminoethyl group, a 2-acetylmethylaminoethyl group, a 2-(2-oxo-pyrrolidin-1-yl)ethyl group, a 2-(2-oxoimidazolidin-1-yl)ethyl group, a 1H-imidazol-2-ylmethyl group, a 3H-imidazol-4-ylmethyl group, and a 2-methanesulfonylamino-ethyl group.

$R^6$ is yet more preferably a hydrogen atom, a 2-hydroxyethyl group, a 3-hydroxypropyl group, a 3-hydroxy-3-methylbutyl group, a 3-hydroxy-2,2-dimethyl-propyl group, a 1-hydroxymethyl-cyclopropyl-methyl group, a 4-hydroxybutyl group, a 3-methoxy-3-methylbutyl group, a 2-methoxyethyl group, a 2,3-dihydroxupropyl group, a 2-hydroxy-1-(hydroxymethyl)ethyl group, a 2-hydroxypropyl group, a 2-hydroxy-2-methylpropyl group, a 2-hydroxy-1-methylethyl group, or a 2-(2-hydroxyethoxy)ethyl group, a 2-methylsulfanylethyl group, a 2-methanesulfonylethyl group.

$R^6$ may yet more preferably be a 2-aminoethyl group, a 2-methylaminoethyl group, a 2-dimethylaminoethyl group, a 2-(2-hydroxyethylamino)ethyl group, a 2-(morpholin-4-yl)ethyl group, a 2-(piperidin-1-yl)ethyl group, a 2-(4-methylpiperazin-1-yl)ethyl group, a 2-(4-hydroxypiperidin-1-yl)ethyl group, a 2-(pyrrolidin-1-yl)ethyl group, a 2-((S)-2-hydroxymethyl-pyrrolidin-1-yl)ethyl group, a 2-((R)-2-hydroxymethyl-pyrrolidin-1-yl)ethyl group, a 2-(hydroxyimino)ethyl group, a 2-(methoxyimino)ethyl group, a methylcarbamoyl-methyl group, a 2-methylcarbam-oyl-ethyl group, a 2-dimethylcarbamoyl-ethyl group, a 3-methylcarbamoyl-propyl group, a (2-hydroxyethylcarbamoyl)methyl group, a 2-acetylaminoethyl group, a 2-acetylmethylaminoethyl group, a 2-(2-oxopyrrolidin-1-yl)ethyl group, a 2-(2-oxoimidazolidin-1-yl)ethyl group, a 1H-imidazol-2-ylmethyl group, a 3H-imidazol-4-ylmethyl group, a pyridin-4-ylmethyl group, an oxazol-2-ylmethyl group, or a 2-methanesulfonylamino-ethyl group.

$R^6$ may still more preferably be a methyl group, an isopropyl group, a cyclopropylmethyl group, a cyclopentylmethyl group, a 2-propenyl group, a 2-propynyl group, or a benzyl group.

Among these, $R^6$ is particularly preferably a hydrogen atom, a 2-hydroxyethyl group, a 2-hydroxypropyl group, a 2-hydroxy-2-methylpropyl group, a 2,3-dihydroxypropyl group, a 3-hydroxypropyl group, a 2-dimethylaminomethyl group, a 2-aminoethyl group, a 2-methylaminoethyl group, a 2-acetylaminoethyl group, a 2-acetylmethylaminoethyl group, a 2-(2-oxopyrrolidin-1-yl)ethyl group, a 2-(2-oxoimidazolidin-1-yl)ethyl group, a 1H-imidazol-2-ylmethyl group, a pyridin-4-ylmethyl group, a 3-hydroxy-2,2-dimethyl-propyl group, a 2-methylsulfanylethyl group, a 2-methanesulfonylethyl group, a methylcarbamoylmethyl group, a 2-methylcarbamoyl-ethyl group, a 2 dimethylcarbamoyl-ethyl group, a 3-methylcarbamoylpropyl group, or a (2-hydroxyethylcarbamoyl)methyl group.

(7) Examples of Q preferably include a hydrogen atom; $-NR^aR^b$;

an alkyl group, an alkenyl group, or an alkynyl group, each of which may comprise 1 to 3 substituents selected from Group C below; or a cycloalkylalkyl group, an arylalkyl group, a heteroarylalkyl group, or a heterocyclic alkyl group, each of which may comprise 1 to 3 substituents selected from Group D below;

Group C: $-O-R^a$, $-(C1-C4$ alkylene group$)-OR^a$, $-[O-(C1-C4$ alkylene group$)]n-OR^a$, $-NR^b-(C1-C4$ alkylene group$)-OR^a$, $-C=N-OR^a$, $-CONR^aR^b$, $-NR^aCOR^b$, $-SR^a$, and $-SO_2R^a$;

Group D: $-O-R^a$, $-(C1-C4$ alkylene group$)-OR^a$, $-[O-(C1-C4$ alkylene group$)]n-OR^a$, $-NR^b-(C1-C4$ alkylene group$)-OR^a$, $-C=N-OR^a$, $-CONR^aR^b$, $-NR^aCOR^b$, $-SR^a$, $-SO_2R^a$, a C1-C4 alkyl group, and an oxo group;

provided that $R^a$ and $R^b$ may be identical to or different, and represent a hydrogen atom; an alkyl group that may have comprise an OH group; an aryl group; or a heteroaryl group. In Groups C and D, the alkylene group is preferably a C1-C4 alkylene group, and the alkyl group is preferably a C1-C4 alkyl group. The alkyl group of $R^a$ and $R^b$ is preferably a C1-C4 alkyl group. Preferably, n is 1 to 4.

In addition, examples of Q preferably include a hydrogen atom, a methyl group, an isopropyl group, a 2-hydroxyethyl group, a 2,3-dihydroxypropyl group, a 2-(morpholin-4-yl) ethyl group, a 2-propenyl group, a benzyl group, an amino group, or a methylamino group, and more preferably include a hydrogen atom and a methyl group. Q may more preferably be $-NR^aR^b$.

When Q is $R^7$, $R^7$ is more preferably a hydrogen atom or an alkyl group.

(8) Examples of $R^8$ preferably include a hydrogen atom or a methyl group, and more preferably include a hydrogen atom.

(9) Examples of $R^9$ preferably include a hydrogen atom; an alkyl group, an alkenyl group, or an alkynyl group, each of which may comprise 1 to 3 substituents selected from Group C below; or a cycloalkylalkyl group, an arylalkyl group, a heteroarylalkyl group, or a heterocyclic alkyl group, each of which may comprise 1 to 3 substituents selected from Group D below;

Group C: —O—$R^a$, —[O-(alkylene group)]n-O$R^a$, —$NR^b$-(alkylene group)-O$R^a$, and —C=N—O$R^a$, Group D: —O—$R^a$, —[O-(alkylene group)]n-O$R^a$, —$NR^b$-(alkylene group)-O$R^a$, —C=N—O$R^a$, and an alkyl group;

provided that $R^a$ and $R^b$ may be identical to or different, and represent a hydrogen atom, an alkyl group, an aryl group, or a heteroaryl group. In Groups C and D, the alkylene group is preferably a C1-C4 alkylene group, and the alkyl group is preferably a C1-C4 alkyl group. The alkyl group of $R^a$ and $R^b$ is preferably a C1-C4 alkyl group. Preferably, n is 1 to 4.

$R^9$ is more preferably, for example, a hydrogen atom, alkyl group, alkenyl group, alkynyl group, hydroxyalkyl group, dihydroxyalkyl group, hydroxyalkyloxyalkyl group, hydroxyalkylaminoalkyl group, hydroxyiminoalkyl group, alkoxyiminoalkyl group, cycloalkylalkyl group, arylalkyl group, heteroarylalkyl group, heterocyclic alkyl group, or hydroxy group-containing heterocyclic alkyl group.

$R^9$ is even more preferably, for example, a hydrogen atom, methyl group, isopropyl group, 2-hydroxyethyl group, 3-hydroxypropyl group, 2,3-dihydroxypropyl group, 2-hydroxy-1-(hydroxymethyl)ethyl group, 2-hydroxypropyl group, 2-methyl-2-hydroxypropyl group, 1-methyl-2-hydroxyethyl group, cyclopropylmethyl group, cyclopentylmethyl group, 2-(2-hydroxyethoxy)ethyl group, 2-(2-hydroxyethylamino)ethyl group, 2-(morpholin-4-yl)ethyl group, 2-(4-methylpiperazin-1-yl)ethyl group, 2-(4-hydroxypiperidin-1-yl)ethyl group, 2-(hydroxyimino)ethyl group, 2-(methoxyimino)ethyl group, 2-propenyl group, 2-propynyl group, benzyl group, pyridylmethyl group, or oxazol-2-ylmethyl group, and is especially preferably, for example, a 2-hydroxyethyl group, 2,3-dihydroxypropyl group, 2-hydroxy-1-(hydroxymethyl) ethyl group, or 2-(hydroxyimino)ethyl group.

$R^9$ may be a 2-hydroxyethyl group, 3-hydroxypropyl group, 2,3-dihydroxypropyl group, 2-hydroxy-1-(hydroxymethyl)ethyl group, 2-hydroxypropyl group, 2-methyl-2-hydroxypropyl group, or 1-methyl-2-hydroxyethyl group.

Furthermore, $R^9$ may be a 2-(2-hydroxyethylamino)ethyl group, 2-(morpholin-4-yl)ethyl group, 2-(4-methylpiperazin-1-yl)ethyl group, 2-(4-hydroxypiperidin-1-yl)ethyl group, 2-(hydroxyimino)ethyl group, 2-(methoxyimino) ethyl group, pyridylmethyl group, or oxazol-2-ylmethyl group.

$R^9$ may also be a methyl group, isopropyl group, cyclopropylmethyl group, cyclopentylmethyl group, 2-propenyl group, 2-propynyl group, or benzyl group.

Of these, $R^9$ is preferably an alkyl group comprising at least one hydroxy group.

(10) $R^a$ is preferably, for example, a hydrogen atom, methyl group, ethyl group, phenyl group, pyridyl group, oxazolyl group, or 2-hydroxyethyl group, and is more preferably, for example, a hydrogen atom, methyl group, or ethyl group.

(11) Examples of $R^b$ preferably include a hydrogen atom, a methyl group, an ethyl group, a phenyl group, a pyridyl group, an oxazolyl group, and a 2-hydroxyethyl group, and more preferably include a hydrogen atom, a methyl group, and an ethyl group.

(12) Preferably, $R^2$ above is a fluorine atom, $R^3$ above is a hydrogen atom, $R^4$ above is a fluorine atom, and $R^5$ above is a fluorine atom.

(13) In formula (1) above, an oximether group represented by a substituent $R^6$—O—N=C(Q)- may be either E form or Z form.

Specifically, the substituent may be either E-oxime represented by formula (a) below:

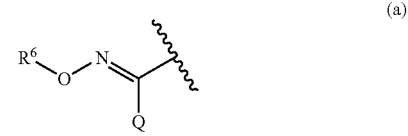

or Z-oxime represented by formula (b) below:

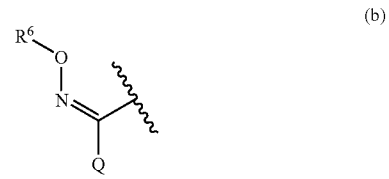

wherein, $R^6$ and Q have the same meanings as $R^6$ and Q in formula (1).

Among these, Z-oxime is preferable.

Any embodiments for $R^1$ to $R^9$, $R^a$, and $R^b$ can be selected from the preferable embodiments (1) to (13) above, and a compound with a combination of these embodiments are comprised in the present invention.

More specifically, examples of the compound I of the present invention represented by formula (1):

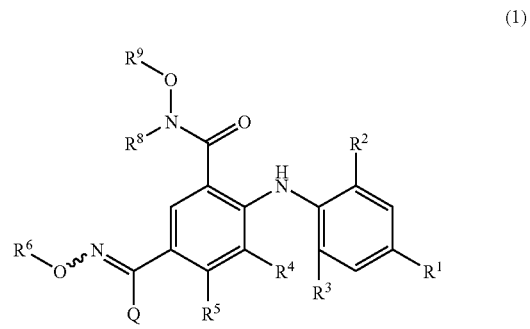

include those described below, but are not limited thereto. The names of the compounds corresponding to the numbers in the table are also described. In the table below, "Me" indicates a methyl group, "i-Pr" indicates a isopropyl group, and "•" indicates a binding site. The wavy line ⁓ indicates that the compound can be either one of the stereoisomers, E-form or Z-form, depending on the manner of binding of O— to —N.

TABLE 1
| | E/Z | R¹ | R² | R³ | R⁴ | R⁵ | R⁶ | Q | R⁸ | R⁹ |
|---|---|---|---|---|---|---|---|---|---|---|
| 1 | E | I | F | H | F | F |  | H | H | 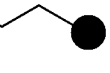 |
| 2 | E |  | F | H | F | F |  | H | H |  |
| 3 | E | 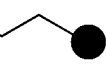 | F | H | F | F |  | H | H | 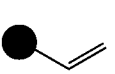 |
| 4 | E | I | H | H | F | F |  | H | H | 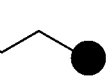 |
| 5 | E | I | Cl | H | F | F |  | H | H |  |
| 6 | E | I | Me | H | F | F |  | H | H |  |
| 7 | E | I | CH₂OH | H | F | F |  | H | H |  |
| 8 | E | I | F | Cl | F | F |  | H | H |  |
| 9 | E | I | F | F | F | F |  | H | H |  |
| 10 | E | I | F | H | H | F |  | H | H | 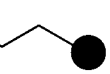 |
| 11 | E | I | F | H | F | F |  | H | H |  |
| 12 | E | I | F | H | F | F |  | H | H |  |
| 13 | E | I | F | H | F | F |  | H | H |  |
| 14 | E | I | F | H | F | F |  | H | H |  |
| 15 | E | I | F | H | F | F | 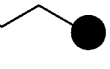 | H | H |  |
| 16 | E | I | F | H | F | F | 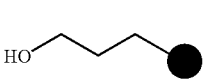 | H | H | 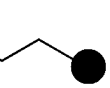 |
| 17 | E | I | F | H | F | F |  | H | H | 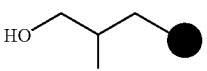 |
| 18 | E | I | F | H | F | F | 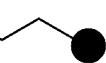 | H | H |  |

TABLE 1-continued
| | E/Z | R¹ | R² | R³ | R⁴ | R⁵ | R⁶ | Q | R⁸ | R⁹ |
|---|---|---|---|---|---|---|---|---|---|---|
| 19 | E | I | F | H | F | F | 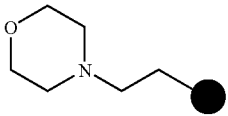 | H | H | 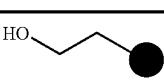 |
| 20 | E | I | F | H | F | F | 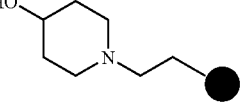 | H | H | 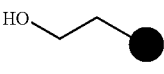 |
| 21 | E | I | F | H | F | F | 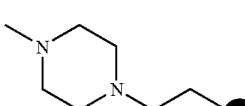 | H | H | 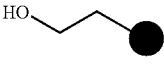 |
| 22 | E | I | F | H | F | F | 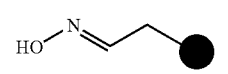 | H | H | 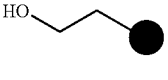 |
| 23 | E | I | F | H | F | F | 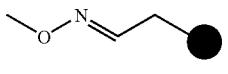 | H | H | 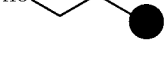 |
| 24 | E | I | F | H | F | F | H | H | H | 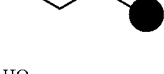 |
| 25 | E | I | F | H | F | F | Me | H | H | 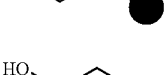 |
| 26 | E | I | F | H | F | F | i-Pr | H | H | 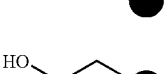 |
| 27 | E | I | F | H | F | F | 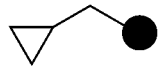 | H | H | 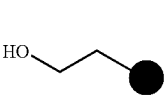 |
| 28 | E | I | F | H | F | F | 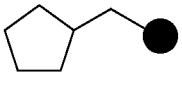 | H | H |  |
| 29 | E | I | F | H | F | F |  | H | H | 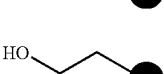 |
| 30 | E | I | F | H | F | F |  | H | H | 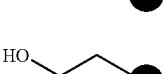 |
| 31 | E | I | F | H | F | F | 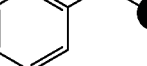 | H | H |  |
| 32 | E | I | F | H | F | F | 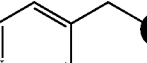 | H | H | 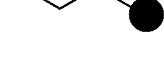 |
| 33 | E | I | F | H | F | F | 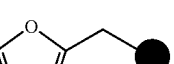 | H | H | 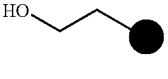 |
| 34 | E | I | F | H | F | F | 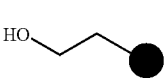 | Me | H | 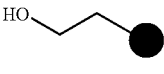 |

TABLE 1-continued
| | E/Z | R¹ | R² | R³ | R⁴ | R⁵ | R⁶ | Q | R⁸ | R⁹ |
|---|---|---|---|---|---|---|---|---|---|---|
| 35 | E | I | F | H | F | F | 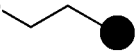 | i-Pr | H | 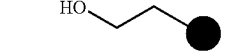 |
| 36 | E | I | F | H | F | F |  | 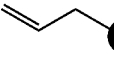 | H |  |
| 37 | E | I | F | H | F | F |  | 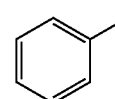 | H |  |
| 38 | E | I | F | H | F | F |  | 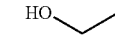 | H |  |
| 39 | E | I | F | H | F | F | 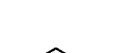 |  | H |  |
| 40 | E | I | F | H | F | F |  | 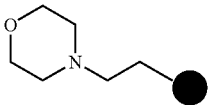 | H |  |
| 41 | E | I | F | H | F | F |  | NH₂ | H |  |
| 42 | E | I | F | H | F | F | 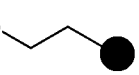 | MeNH | H | 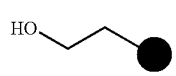 |
| 43 | E | I | F | H | F | F | 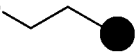 | H | Me | 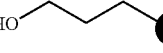 |
| 44 | E | I | F | H | F | F |  | H | H |  |
| 45 | E | I | F | H | F | F |  | H | H | 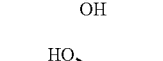 |
| 46 | E | I | F | H | F | F | 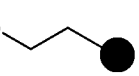 | H | H | 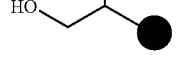 |
| 47 | E | I | F | H | F | F | 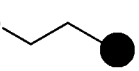 | H | H | 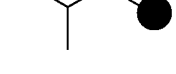 |
| 48 | E | I | F | H | F | F | 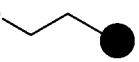 | H | H |  |
| 49 | E | I | F | H | F | F | 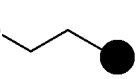 | H | H | 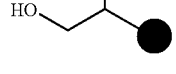 |
| 50 | E | I | F | H | F | F | 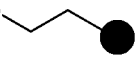 | H | H | 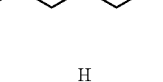 |
| 51 | E | I | F | H | F | F |  | H | H |  |

TABLE 1-continued
| | E/Z | R¹ | R² | R³ | R⁴ | R⁵ | R⁶ | Q | R⁸ | R⁹ |
|---|---|---|---|---|---|---|---|---|---|---|
| 52 | E | I | F | H | F | F | 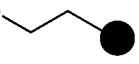 | H | H | 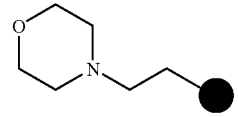 |
| 53 | E | I | F | H | F | F | 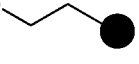 | H | H | 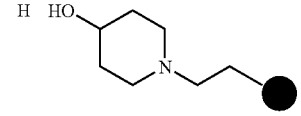 |
| 54 | E | I | F | H | F | F | 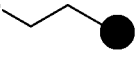 | H | H | 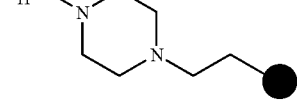 |
| 55 | E | I | F | H | F | F | 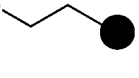 | H | H | 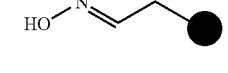 |
| 56 | E | I | F | H | F | F |  | H | H |  |
| 57 | E | I | F | H | F | F | 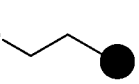 | H | H | H |
| 58 | E | I | F | H | F | F | 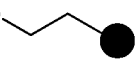 | H | H | Me |
| 59 | E | I | F | H | F | F | 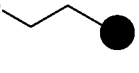 | H | H | i-Pr |
| 60 | E | I | F | H | F | F | 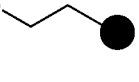 | H | H | 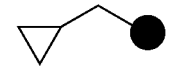 |
| 61 | E | I | F | H | F | F |  | H | H | 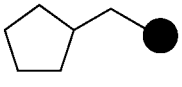 |
| 62 | E | I | F | H | F | F | 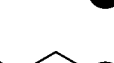 | H | H |  |
| 63 | E | I | F | H | F | F |  | H | H | 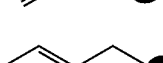 |
| 64 | E | I | F | H | F | F |  | H | H | 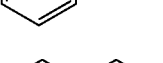 |
| 65 | E | I | F | H | F | F |  | H | H | 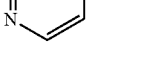 |
| 66 | E | I | F | H | F | F |  | H | H | 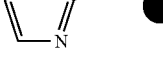 |
| 67 | E |  | F | H | F | F |  | H | H |  |

TABLE 1-continued

| | E/Z | R¹ | R² | R³ | R⁴ | R⁵ | R⁶ | Q | R⁸ | R⁹ |
|---|---|---|---|---|---|---|---|---|---|---|
| 68 | E | ●≡ | | F | H | F | F | HO~~●  | H | H | HO~~CH(OH)~~● |
| 69 | E | ●≡ | | F | H | F | F | HO~~● | H | H | (HOCH₂)₂CH~~● |
| 70 | E | ●≡ | | F | H | F | F | HO~~~● | H | H | HO~~● |
| 71 | E | ●≡ | | F | H | F | F | HO~CH(OH)~● | H | H | HO~~● |
| 72 | E | ●≡ | | F | H | F | F | (HOCH₂)₂CH~● | H | H | HO~~● |
| 73 | E | ●≡ | | F | H | F | F | HOC(CH₃)₂CH₂~● | H | H | HO~~● |
| 74 | E | I | | F | H | F | F | CH₃NHC(O)CH₂CH₂~● | H | H | HO~~● |

TABLE 2

| | E/Z | R¹ | R² | R³ | R⁴ | R⁵ | R⁶ | Q | R⁸ | R⁹ |
|---|---|---|---|---|---|---|---|---|---|---|
| 75 | E | I | F | H | F | F | (CH₃)₂N~CH₂CH₂~● | H | H | HO~~● |
| 76 | E | I | F | H | F | F | piperidinyl-CH₂CH₂~● | H | H | HO~~● |
| 77 | E | I | F | H | F | F | CH₃O-C(CH₃)₂-CH₂CH₂~● | H | H | HO~~● |
| 78 | E | I | F | H | F | F | HO-C(CH₃)₂-CH₂CH₂~● | H | H | HO~~● |
| 79 | E | I | F | H | F | F | HOCH₂-C(CH₃)₂-CH₂~● | H | H | HO~~● |
| 80 | E | I | F | H | F | F | HOCH₂-C(cyclopropyl)-CH₂~● | H | H | HO~~● |

TABLE 2-continued
| | E/Z | R¹ | R² | R³ | R⁴ | R⁵ | R⁶ | Q | R⁸ | R⁹ |
|---|---|---|---|---|---|---|---|---|---|---|
| 81 | E | I | F | H | F | F |  | H | H | 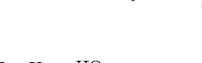 |
| 82 | E | I | F | H | F | F | 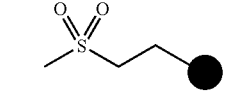 | H | H |  |
| 83 | E | I | F | H | F | F |  | H | H | 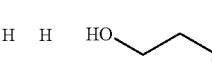 |
| 84 | E | I | F | H | F | F | 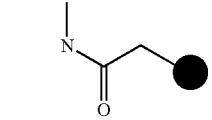 | H | H |  |
| 85 | E | I | F | H | F | F | 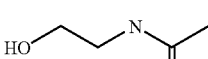 | H | H | 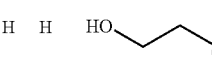 |
| 86 | E | I | F | H | F | F |  | H | H | 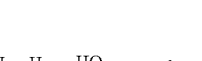 |
| 87 | E | I | F | H | F | F | 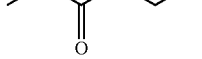 | H | H |  |
| 88 | E | I | F | H | F | F | 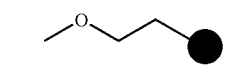 | H | H | 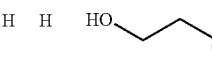 |
| 89 | E | I | F | H | F | F |  | H | H | 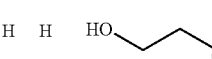 |
| 90 | E | I | F | H | F | F |  | H | H |  |
| 91 | E | I | F | H | F | F | 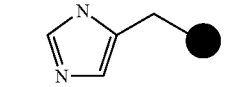 | H | H | 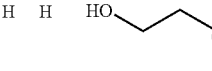 |
| 92 | E | I | F | H | F | F | 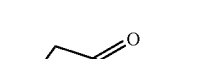 | H | H | 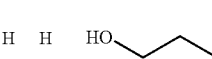 |
| 93 | E | I | F | H | F | F | 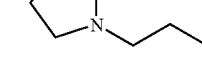 | H | H |  |
| 94 | E | I | F | H | F | F | 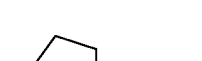 | H | H | 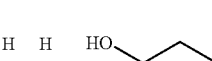 |

TABLE 2-continued

| | E/Z | R¹ | R² | R³ | R⁴ | R⁵ | R⁶ | Q | R⁸ | R⁹ |
|---|---|---|---|---|---|---|---|---|---|---|
| 95 | E | I | F | H | F | F | | H | H | |
| 96 | E | I | F | H | F | F | | H | H | |
| 97 | E | I | F | H | F | F | | H | H | |
| 98 | E | I | F | H | F | F | | H | H | |
| 99 | E | I | F | H | F | F | | H | H | |
| 101 | E | | F | H | F | F | | H | H | |
| 102 | Z | I | F | H | F | F | | H | H | |
| 103 | Z | | F | H | F | F | | H | H | |
| 104 | Z | I | F | H | F | F | | H | H | |
| 105 | Z | I | F | H | F | F | | H | H | |
| 106 | Z | I | F | H | F | F | | H | H | |
| 107 | Z | I | F | H | F | F | | H | H | |
| 108 | Z | I | F | H | F | F | | H | H | |
| 109 | Z | I | F | H | F | F | | H | H | |

TABLE 2-continued

| | E/Z | R¹ | R² | R³ | R⁴ | R⁵ | R⁶ | Q | R⁸ | R⁹ |
|---|---|---|---|---|---|---|---|---|---|---|
| 110 | Z | I | F | H | F | F | HO-CH₂CH₂-N(-)-C(=O)-CH₂-● | H | H | HO-CH₂CH₂-● |
| 111 | Z | I | F | H | F | F | CH₃-N(-)-C(=O)-CH₂CH₂-● | H | H | HO-CH₂CH₂-● |
| 112 | Z | I | F | H | F | F | HO-CH₂CH₂-● | H | H | HO-CH₂-CH(OH)-CH₂-● |
| 113 | Z | I | F | H | F | F | (imidazolidin-2-one-N-yl)-CH₂CH₂-● | H | H | HO-CH₂CH₂-● |
| 114 | Z | I | F | H | F | F | (2-oxopyrrolidin-1-yl)-CH₂CH₂-● | H | H | HO-CH₂CH₂-● |
| 115 | E | I | F | H | F | F | CH₃-S(=O)₂-NH-CH₂CH₂-● | H | H | HO-CH₂CH₂-● |
| 116 | E | I | F | H | F | F | (CH₃)₂N-C(=O)-CH₂CH₂-● | H | H | HO-CH₂CH₂-● |

The names of compounds corresponding to the above-mentioned compound numbers are indicated below:

(1): (E)-3,4-difluoro-2-(2-fluoro-4-iodo-phenylamino)-N-(2-hydroxy-ethoxy)-5-[(2-hydroxy-ethoxyimino)-methyl]-benzamide;
(2): (E)-2-(4-ethynyl-2-fluoro-phenylamino)-3,4-difluoro-N-(2-hydroxy-ethoxy)-5-[(2-hydroxy-ethoxyimino)-methyl]-benzamide;
(3): (E)-3,4-difluoro-2-(2-fluoro-4-vinyl-phenylamino)-N-(2-hydroxy-ethoxy)-5-[(2-hydroxy-ethoxyimino)-methyl]-benzamide;
(4): (E)-3,4-difluoro-N-(2-hydroxy-ethoxy)-5-[(2-hydroxy-ethoxyimino)-methyl]-2-(4-iodo-phenylamino)-benzamide;
(5): (E)-2-(2-chloro-4-iodo-phenylamino)-3,4-difluoro-N-(2-hydroxy-ethoxy)-5-[(2-hydroxy-ethoxyimino)-methyl]-benzamide;
(6): (E)-3,4-difluoro-N-(2-hydroxy-ethoxy)-5-[(2-hydroxy-ethoxyimino)-methyl]-2-(4-iodo-2-methyl-phenylamino)-benzamide;
(7): (E)-3,4-difluoro-N-(2-hydroxy-ethoxy)-5-[(2-hydroxy-ethoxyimino)-methyl]-2-(2-hydroxymethyl-4-iodo-phenylamino)-benzamide;
(8): (E)-2-(2-chloro-6-fluoro-4-iodo-phenylamino)-3,4-difluoro-N-(2-hydroxy-ethoxy)-5-[(2-hydroxy-ethoxyimino)-methyl]-benzamide;
(9): (E)-2-(2,6-difluoro-4-iodo-phenylamino)-3,4-difluoro-N-(2-hydroxy-ethoxy)-5-[(2-hydroxy-ethoxyimino)-methyl]-benzamide;
(10): (E)-4-fluoro-2-(2-fluoro-4-iodo-phenylamino)-N-(2-hydroxy-ethoxy)-5-[(2-hydroxy-ethoxyimino)-methyl]-benzamide;
(11): (E)-3,4-difluoro-2-(2-fluoro-4-iodo-phenylamino)-N-(2-hydroxy-ethoxy)-5-[(3-hydroxy-propoxyimino)-methyl]-benzamide;
(12): (E)-5-[(2,3-dihydroxy-propoxyimino)-methyl]-3,4-difluoro-2-(2-fluoro-4-iodo-phenylamino)-N-(2-hydroxy-ethoxy)-benzamide;
(13): (E)-3,4-difluoro-2-(2-fluoro-4-iodo-phenylamino)-N-(2-hydroxy-ethoxy)-5-[(2-hydroxy-1-hydroxymethyl-ethoxyimino)-methyl]-benzamide;
(14): (E)-3,4-difluoro-2-(2-fluoro-4-iodo-phenylamino)-N-(2-hydroxy-ethoxy)-5-[(2-hydroxy-propoxyimino)-methyl]-benzamide;
(15): (E)-3,4-difluoro-2-(2-fluoro-4-iodo-phenylamino)-N-(2-hydroxy-ethoxy)-5-[(2-hydroxy-2-methyl-propoxyimino)-methyl]-benzamide;
(16): (E)-3,4-difluoro-2-(2-fluoro-4-iodo-phenylamino)-N-(2-hydroxy-ethoxy)-5-[(2-hydroxy-1-methyl-ethoxyimino)-methyl]-benzamide;
(17): (E)-3,4-difluoro-2-(2-fluoro-4-iodo-phenylamino)-N-(2-hydroxy-ethoxy)-5-{[(2-hydroxy-ethoxy)-ethoxyimino]-methyl}-benzamide;
(18): (E)-3,4-difluoro-2-(2-fluoro-4-iodo-phenylamino)-N-(2-hydroxy-ethoxy)-5-{[(2-hydroxy-ethylamino)-ethoxyimino]-methyl}-benzamide;
(19): (E)-3,4-difluoro-2-(2-fluoro-4-iodo-phenylamino)-N-(2-hydroxy-ethoxy)-5-[(2-morpholin-4-yl-ethoxyimino)-methyl]-benzamide;

(20): (E)-3,4-difluoro-2-(2-fluoro-4-iodo phenylamino)-N-(2-hydroxy-ethoxy)-5-{[2-(4-hydroxy-piperidin-1-yl)-ethoxyimino]-methyl}-benzamide;

(21): (E)-3,4-difluoro-2-(2-fluoro-4-iodo-phenylamino)-N-(2-hydroxy-ethoxy)-5 {[2-(4-methyl-piperadin-1-yl)-ethoxyimino]-methyl}-benzamide;

(22): (E)-3,4-difluoro-2-(2-fluoro-4-iodo-phenylamino)-N-(2-hydroxy-ethoxy)-5-[(2-hydroxyimino-ethoxyimino)-methyl]-benzamide;

(23): (E)-3,4-difluoro-2-(2-fluoro-4-iodo-phenylamino)-N-(2-hydroxy-ethoxy)-5-[(2-methoxyimino-ethoxyimino)-methyl]-benzamide;

(24): (E)-3,4-difluoro-2-(2-fluoro-4-iodo-phenylamino)-N-(2-hydroxy-ethoxy)-5-(hydroxyimino-methyl)-benzamide;

(25): (E)-3,4-difluoro-2-(2-fluoro-4-iodo-phenylamino)-N-(2-hydroxy-ethoxy)-5-(methoxyimino-methyl)-benzamide;

(26): (E)-3,4-difluoro-2-(2-fluoro-4-iodo-phenylamino)-N-(2-hydroxy-ethoxy)-5-(isopropoxyimino-methyl-benzamide;

(27): (E)-5-(cyclopropylmethoxyimino-methyl)-3,4-difluoro-2-(2-fluoro-4-iodo-phenylamino)-N-(2-hydroxy-ethoxy)-benzamide;

(28): (E)-5-(cyclopentylmethoxyimino-methyl)-3,4-difluoro-2-(2-fluoro-4-iodo-phenylamino)-N-(2-hydroxy-ethoxy)-benzamide;

(29): (E)-5-(allyloxyimino-methyl)-3,4-difluoro-2-(2-fluoro-4-iodo-phenylamino)-N-(2-hydroxy-ethoxy)-benzamide;

(30): (E)-3,4-difluoro-2-(2-fluoro-4-iodo-phenylamino)-N-(2-hydroxy-ethoxy)-5-(2-propynylimino-methyl)-benzamide;

(31): (E)-5-(benzyloxyimino-methyl)-3,4-difluoro-2-(2-fluoro-4-iodo-phenylamino)-N-(2-hydroxy-ethoxy)-benzamide;

(32): (E)-3,4-difluoro-2-(2-fluoro-4-iodo-phenylamino)-N-(2-hydroxy-ethoxy)-5-[(pyridin-4-ylmethoxyimino)-methyl]-benzamide;

(33): (E)-3,4-difluoro-2-(2-fluoro-4-iodo-phenylamino)-N-(2-hydroxy-ethoxy)-57[(oxazol-2-ylmethoxyimino)-methyl]-benzamide;

(34): (E)-3,4-difluoro-2-(2-fluoro-4-iodo-phenylamino)-N-(2-hydroxy-ethoxy)-5-[1-(2-hydroxy-ethoxyimino)-ethyl]-benzamide;

(35): (E)-3,4-difluoro-2-(2-fluoro-4-iodo-phenylamino)-N-(2-hydroxy-ethoxy)-5-[1-(2-hydroxy-ethoxyimino)-2-methyl-propyl]-benzamide;

(36): (E)-3,4-difluoro-2-(2-fluoro-4-iodo-phenylamino)-N-(2-hydroxy-ethoxy)-5-[1-(2-hydroxy-ethoxyimino)-3-butenyl]-benzamide;

(37): (E)-3,4-difluoro-2-(2-fluoro-4-iodo-phenylamino)-N-(2-hydroxy-ethoxy)-5-[1-(2-hydroxy-ethoxyimino)-2-phenylethyl]-benzamide;

(38) (E)-3,4-difluoro-2-(2-fluoro-4-iodo-phenylamino)-N-(2-hydroxy-ethoxy)-5-[3-hydroxy-1-(2-hydroxy-ethoxyimino)-propyl]-benzamide;

(39) (E)-5-[3,4-dihydroxy-1-(2-hydroxy-ethoxyimino)-butyl]-3,4-difluoro-2-(2-fluoro-4-iodo-phenylamino)-N-(2-hydroxy-ethoxy)-benzamide;

(40): (E)-3,4-difluoro-2-(2-fluoro-4-iodo-phenylamino)-N-(2-hydroxy-ethoxy)-5-[1-(2-hydroxy-ethoxyimino)-3-morpholin-4-yl-propyl]-benzamide;

(41): (E)-3,4-difluoro-2-(2-fluoro-4-iodo-phenylamino)-N-(2-hydroxy-ethoxy)-5-[N-(2-hydroxy-ethoxyimino)-carbamimidoyl]-benzamide;

(42): (E)-3,4-difluoro-2-(2-fluoro-4-iodo-phenylamino)-N-(2-hydroxy-ethoxy)-5-[N-(2-hydroxy-ethoxyimino)-N'-methyl-carbamimidoyl]-benzamide;

(43): (E)-3,4-difluoro-2-(2-fluoro-4-iodo-phenylamino)-N-(2-hydroxy-ethoxy)-5-[(2-hydroxy-ethoxyimino)-methyl]-N-methyl-benzamide;

(44): (E)-3,4-difluoro-2-(2-fluoro-4-iodo-phenylamino)-5-[(2-hydroxy-ethoxyimino)-methyl]-N-(3-hydroxy-propoxy)-benzamide;

(45): (E)-N-(2,3-dihydroxy-propoxy)-3,4-difluoro-2-(2-fluoro-4-iodo-phenylamino)-5-[(2-hydroxy-ethoxyimino)-methyl]-benzamide;

(46): (E)-3,4-difluoro-2-(2-fluoro-4-iodo-phenylamino)-5-[(2-hydroxy-ethoxyimino)-methyl]-N-(2-hydroxy-1-hydroxymethyl-ethoxy)-benzamide;

(47): (E)-3,4-difluoro-2-(2-fluoro-4-iodo-phenylamino)-5-[(2-hydroxy-ethoxyimino)-methyl]-N-(2-hydroxy-propoxy)-benzamide;

(48): (E)-3,4-difluoro-2-(2-fluoro-4-iodo-phenylamino)-5-[(2-hydroxy-ethoxyimino)-methyl]-N-(2-hydroxy-2-methyl-propoxy)-benzamide;

(49): (E)-3,4-difluoro-2-(2-fluoro-4-iodo-phenylamino)-5-[(2-hydroxy-ethoxyimino)-methyl]-N-(2-hydroxy-1-methyl-ethoxy)-benzamide;

(50): (E)-3,4-difluoro-2-(2-fluoro-4-iodo-phenylamino)-N-[(2-hydroxy-ethoxy)-ethoxy]-5-[(2-hydroxy-ethoxyimino)-methyl]-benzamide;

(51): (E)-3,4-difluoro-2-(2-fluoro-4-iodo-phenylamino)-5-[(2-hydroxy-ethylamino)-ethoxy]-benzamide;

(52): (E)-3,4-difluoro-2-(2-fluoro-4-iodo-phenylamino)-5-[(2-hydroxy-ethoxyimino)-methyl]-N-(2-morpholin-4-yl-ethoxy)-benzamide;

(53): (E)-3,4-difluoro-2-(2-fluoro-4-iodo-phenylamino)-5-[(2-hydroxy-ethoxyimino)-methyl]-N-[2-(4-hydroxy-piperidin-1-yl)-ethoxy]]-benzamide;

(54): (E)-3,4-difluoro-2-(2-fluoro-4-iodo-phenylamino)-5-[(2-hydroxy-ethoxyimino)-methyl]-N-[2-(4-methyl-piperadin-1-yl)-ethoxy]]-benzamide;

(55): (E)-3,4-difluoro-2-(2-fluoro-4-iodo-phenylamino)-5-[(2-hydroxy-ethoxyimino)-methyl]-N-(2-hydroxyimino-ethoxy)-benzamide;

(56): (E)-3,4-difluoro-2-(2-fluoro-4-iodo-phenylamino)-5-[(2-hydroxy-ethoxyimino)-methyl]-N-(2-methoxyimino-ethoxy)-benzamide;

(57): (E)-3,4-difluoro-2-(2-fluoro-4-iodo-phenylamino)-N-hydroxy-5-[(2-hydroxy-ethoxyimino)-methyl]-benzamide;

(58): (E)-3,4-difluoro-2-(2-fluoro-4-iodo-phenylamino)-5-[(2-hydroxy-ethoxyimino)-methyl]-N-methoxy-benzamide;

(59): (E)-3,4-difluoro-2-(2-fluoro-4-iodo-phenylamino)-5-[(2-hydroxy-ethoxyimino)-methyl]-N-isopropoxy-benzamide; (60): (E)-N-cyclopropylmethoxy-3,4-difluoro-2-(2-fluoro-4-iodo-phenylamino)-5-[(2-hydroxy-ethoxyimino)-methyl]-benzamide;

(61): (E)-N-cyclopentylmethoxy-3,4-difluoro-2-(2-fluoro-4-iodo-phenylamino)-5-[(2-hydroxy-ethoxyimino)-methyl]-benzamide;

(62): (E)-N-allyloxy-3,4-difluoro-2-(2-fluoro-4-iodo-phenylamino)-5-[(2-hydroxy-ethoxyimino)-methyl]-benzamide;

(63): (E)-3,4-difluoro-2-(2-fluoro-4-iodo-phenylamino)-5-[(2-hydroxy-ethoxyimino)-methyl]-N-(2-propynyloxy)-benzamide;

(64): (E)-N-benzyloxy-3,4-difluoro-2-(2-fluoro-4-iodo-phenylamino)-5-[(2-hydroxy-ethoxyimino)-methyl]-benzamide;

(65): (E)-3,4-difluoro-2-(2-fluoro-4-iodo-phenylamino)-5-[(2-hydroxy-ethoxyimino)-methyl]-N-(pyridin-4-yl-methoxy)-benzamide;
(66): (E)-3,4-difluoro-2-(2-fluoro-4-iodo-phenylamino)-5-[(2-hydroxy-ethoxyimino)-methyl]-N-(oxazol-2-yl-methoxy)-benzamide;
(67): (E)-2-(4-ethynyl-2-fluoro-phenylamino)-3,4-difluoro-5-[(2-hydroxy-ethoxyimino)-methyl]-N-(3-hydroxy-propoxy)-benzamide;
(68): (E)-N-(2,3-dihydroxy-propoxy)-2-(4-ethynyl-2-fluoro-phenylamino)-3,4-difluoro-5-[(2-hydroxy-ethoxyimino)-methyl]-benzamide;
(69): (E)-2-(4-ethynyl-2-fluoro-phenylamino)-3,4-difluoro-5-[(2-hydroxy-ethoxyimino)-methyl]-N-(2-hydroxy-1-hydroxymethyl-ethoxy)-benzamide;
(70): (E)-2-(4-ethynyl-2-fluoro-phenylamino)-3,4-difluoro-N-(2-hydroxy-ethoxy)-5-[(3-hydroxy-propoxyimino)-methyl]-benzamide;
(71): (E)-5-[(2,3-dihydroxy-propoxyimino)-methyl]-2-(4-ethynyl-2-fluoro-phenylamino)-3,4-difluoro-N-(2-hydroxy-ethoxy)-benzamide;
(72): (E)-2-(4-ethynyl-2-fluoro-phenylamino)-3,4-difluoro-N-(2-hydroxy-ethoxy)-5-[(2-hydroxy-1-hydroxymethyl-ethoxyimino)-methyl]-benzamide;
(73): (E)-2-(4-ethynyl-2-fluoro-phenylamino)-3,4-difluoro-N-(2-hydroxyethoxy)-5-[(2-hydroxy-2-methyl-propoxyimino)-methyl]-benzamide; and
(74): (E)-3,4-difluoro-2-(2-fluoro-4-iodo-phenylamino)-N-(2-hydroxy-ethoxy)-5-[(2-methylcarbamoyl-ethoxyimino)-methyl]-benzamide.
(75): (E)-5-[(2-dimethylamino-ethoxyimino)-methyl]-3,4-difluoro-2-(2-fluoro-4-iodo-phenylamino)-N-(2-hydroxy-ethoxy)-benzamide,
(76): (E)-3,4-difluoro-2-(2-fluoro-4-iodo-phenylamino)-N-(2-hydroxy-ethoxy)-5-[(2-piperidin-1-yl-ethoxyimino)-methyl]-benzamide,
(77): (E)-3,4-difluoro-2-(2-fluoro-4-iodo-phenylamino)-N-(2-hydroxy-ethoxy)-5-[(3-methoxy-3-methyl-butoxyimino)-methyl]-benzamide,
(78): (E)-3,4-difluoro-2-(2-fluoro-4-iodo-phenylamino)-N-(2-hydroxy-ethoxy)-5-[(3-hydroxy-3-methy 1-butoxyimino)-methyl]-benzamide,
(79): (E)-3,4-difluoro-2-(2-fluoro-4-iodo-phenylamino)-5-[(E)-(3-hydroxy-2,2-dimethyl-propoxyimino)-methyl]-N-(2-hydroxy-ethoxy)-benzamide,
(80): (E)-3,4-difluoro-2-(2-fluoro-4-iodo-phenylamino)-N-(2-hydroxy-ethoxy)-5-[(1-hydroxymethyl-cyclopropyli-ethoxyimino)-methyl]-benzamide,
(81): (E)-3,4-difluoro-2-(2-fluoro-4-iodo-phenylamino)-5-[(4-hydroxy-butoxyimino)-methyl]-N-(2-hydroxy-ethoxy)-benzamide,
(82): (E)-3,4-difluoro-2-(2-fluoro-4-iodo-phenylamino)-N-(2-hydroxy-ethoxy)-5-[(2-methylsulfanyl-ethoxyimino)-methyl]-benzamide,
(83): (E)-3,4-difluoro-2-(2-fluoro-4-iodo-phenylamino)-N-(2-hydroxy-ethoxy)-5-[(2-methanesulfonyl-thoxyimino)-methyl]-benzamide,
(84): (E)-3,4-difluoro-2-(2-fluoro-4-iodo-phenylamino)-N-(2-hydroxy-ethoxy)-5-[methylcarbamoylmethoxyimino-methyl]-benzamide,
(85): (E)-3,4-difluoro-2-(2-fluoro-4-iodo-phenylamino)-N-(2-hydroxy-ethoxy)-5-{[(2-hydroxyethylcarbamoyl)-methoxyimino]-methyl}-benzamide,
(86): (E)-3,4-difluoro-2-(2-fluoro-4-iodo-phenylamino)-N-(2-hydroxy-ethoxy)-5-{[(3-methylcarbamoyl-propoxyimino)-methyl]-benzamide,
(87): (E)-3,4-difluoro-2-(2-fluoro-4-iodo-phenylamino)-N-(2-hydroxy-ethoxy)-5-[(2-methoxy-ethoxyimino)-methyl]-benzamide,
(88): (E)-3,4-difluoro-2-(2-fluoro-4-iodo-phenylamino)-N-(2-hydroxy-ethoxy)-5-[isopropoxyimino-methyl]-benzamide,
(89): (E)-3,4-difluoro-2-(2-fluoro-4-iodo-phenylamino)-N-(2-hydroxy-ethoxy)-5-[(3H-imidazol-4-ylmethoxyimino)-methyl]-benzamide,
(90): (E)-3,4-difluoro-2-(2-fluoro-4-iodo-phenylamino)-N-(2-hydroxy-ethoxy)-5-{[2-(2-oxo-pyrrolidin-1-yl)-ethoxyimino]-methyl}-benzamide, (91): (E)-3,4-difluoro-2-(2-fluoro-4-iodo-phenylamino)-N-(2-hydroxy-ethoxy)-5-[(2-pyrrolidin-1-yl-ethoxyimino)-methyl]-benzamide,
(92): (E)-3,4-difluoro-2-(2-fluoro-4-iodo-phenylamino)-N-(2-hydroxy-ethoxy)-5-{[2-(2-oxo-imidazolidin-1-yl)-ethoxyimino]-methyl}-benzamide,
(93): (E)-3,4-difluoro-2-(2-fluoro-4-iodo-phenylamino)-N-(2-hydroxy-ethoxy)-5-{[2-((S)-hydroxymethyl-pyrrolidin-1-yl)-ethoxyimino]-methyl}-benzamide,
(94): (E)-5-[(2-amino-ethoxyimino)-methyl]-3,4-difluoro-2-(2-fluoro-4-iodo-phenylamino)-N-(2-hydroxy-ethoxy)-benzamide,
(95): (E)-{2-[2,3-difluoro-4-(2-fluoro-4-iodo-phenylamino)-5-(2-hydroxy-ethoxycarbamoyl)-benzylideneaminooxy]-ethyl}-carbamic acid tert-butyl ester,
(96): (E)-5-[(2-acetylamino-ethoxyimino)-methyl]-3,4-difluoro-2-(2-fluoro-4-iodo-phenylamino)-N-(2-hydroxy-ethoxy)-benzamide,
(97): (E)-3,4-difluoro-2-(2-fluoro-4-iodo-phenylamino)-N-(2-hydroxy-ethoxy)-5-[(1H-imidazol-2-ylmethoxyimino)-methyl]-benzamide,
(98): (E)-3,4-difluoro-2-(2-fluoro-4-iodo-phenylamino)-N-(2-hydroxy-ethoxy)-5-[(2-methylamino-ethoxyimino)-methyl]-benzamide,
(99): (E)-5-{[2-(acetyl-methyl-amino)-ethoxyimino]-methyl}-3,4-difluoro-2-(2-fluoro-4-iodo-phenylamino)-N-(2-hydroxyethoxy)-benzamide,
(101): (E)-2-(4-ethynyl-2-fluoro-phenylamino)-3,4-difluoro-N-(2-hydroxy-ethoxy)-5-[(2-methylcarbamoyl-ethoxyimino)-methyl]-benzamide,
(102): (Z)-3,4-difluoro-2-(2-fluoro-4-iodo-phenylamino)-N-(2-hydroxy-ethoxy)-5-[(2-hydroxy-ethoxyimino)-methyl]-benzamide,
(103): (Z)-2-(4-ethynyl-2-fluoro-phenylamino)-3,4-difluoro-N-(2-hydroxy-ethoxy)-5-[(2-hydroxy-ethoxyimino)-methyl]-benzamide,
(104): (Z)-3,4-difluoro-2-(2-fluoro-4-iodo-phenylamino)-N-(2-hydroxy-ethoxy)-5-[(2-methanesulfonyl-ethoxyimino)-methyl]-benzamide,
(105): (dl)-(Z)-5-[(2,3-dihydroxy-propoxyimino)-methyl]-3,4-difluoro-2-(2-fluoro-4-iodo-phenylamino)-N-(2-hydroxy-ethoxy)-benzamide,
(106): (Z)-5-[(2-acetylamino-ethoxyimino)-methyl]-3,4-difluoro-2-(2-fluoro-4-iodo-phenylamino)-N-(2-hydroxy-ethoxy)-benzamide,
(107): (Z)-3,4-difluoro-2-(2-fluoro-4-iodo-phenylamino)-N-(2-hydroxy-ethoxy)-5-[(2-methylcarbamoyl-ethoxyimino)-methyl]-benzamide,
(108): (Z)-3,4-difluoro-2-(2-fluoro-4-iodo-phenylamino)-N-(2-hydroxy-ethoxy)-5-[(2-hydroxy-2-methyl-propoxyimino)-methyl]-benzamide,
(109): (Z)-3,4-difluoro-2-(2-fluoro-4-iodo-phenylamino)-N-(2-hydroxy-ethoxy)-5-(methylcarbamoylmethoxyimino-methyl]-benzamide, (110): (Z)-3,4-difluoro-2-(2-fluoro-4-iodo-phenylamino)-N-(2-hydroxy-ethoxy)-5-{[(2-hydroxyethylcarbamoyl)-methoxyimino]-methyl}-benzamide, (111): (Z)-3,4-difluoro-2-(2-fluoro-4-iodo-phenylamino)-N-(2-hydroxy-ethoxy)-5-{[(3-methylcarbamoyl-propoxyimino)-methyl]-benzamide, (112): dl-(Z)—N-(2,3-dihydroxy-propoxy)-3,4-difluoro-2-(2-fluoro-4-iodo-phenylamino)-5-[(2-hydroxy-ethoxyimino)-methyl]-benzamide, (113): (Z)-3,4-difluoro-2-(2-fluoro-4-iodo-phenylamino)-N-(2-hydroxy-ethoxy)-5-{[2-(2-oxo-imidazolidin-1-yl)-ethoxyimino]-methyl}-benzamide, (114): (Z)-3,4-difluoro-2-(2-fluoro-4-iodo-phenylamino)-N-(2-hydroxy-ethoxy)-5-{[2-(2-oxo-pyrrolidin-1-yl)-ethoxyimino]-methyl}-benzamide, (115): (E)-3,4-difluoro-2-(2-fluoro-4-iodo-phenylamino)-N-(2-hydroxy-ethoxy)-5-[(2-methanesulfonylamino-ethoxyimino)-methyl]-benzamide, and (116): (E)-3,4-difluoro-2-(2-fluoro-4-iodo-phenylamino)-N-(2-hydroxy-ethoxy)-5-[dimethylcarbamoylethoxyimino-methyl]-benzamide.

Examples of compound I of the present invention preferably include compound Nos. (1), (2), (3), (5), (6), (7), (11), (12), (13), (14), (15), (17), (19), (20), (21), (24), (25), (32), (44), (45), (46), (55), (67), (68), (69), (70), (71), (72), (73), (74), (75), (76), (77), (78), (79), (80), (81), (82), (83), (84), (85), (86), (90), (92), (94), (96), (97), (98), (99), (101), (102), (103), (104), (105), (106), (107), (108), (109), (110), (111), (112), (113), (114), (115), and (116), more preferably include the compound Nos. (1), (2), (11), (12), (14), (15), (17), (24), (25), (32), (44), (45), (46), (67), (68), (70), (71), (73), (74), (78), (79), (80), (81), (83), (84), (85), (86), (90), (92), (94), (96), (97), (98), (99), (101), (102), (103), (104), (105), (106), (107), (108), (109), (110), (11.1), (112), (113), and (114), and particularly preferably include compound Nos. (1), (2), (11), (15), (73), (74), (83), (84), (85), (86), (90), (94), (96), (97), (98), (99), (101), (102), (103), (104), (105), (106), (107), (108), (109), (110), (111), (112), (113), and (114).

The synthetic intermediates U, V, W, X, Y, and P represented by the following formulas (2) to (6) may be preferably used as synthetic intermediates in the production of compound I, but the synthetic intermediates are not limited thereto.

Synthetic Intermediate U

The synthetic intermediate (U) is represented by formula (2) shown below.

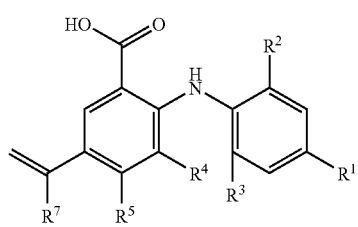

(2)

In formula (2), $R^1$, $R^2$, $R^3$, $R^4$, $R^5$, and $R^7$ have the same meaning as $R^1$, $R^2$, $R^3$, $R^4$, $R^5$, and $R^7$ in the aforementioned formula (1), and their preferred embodiments are also the same.

Herein, when $R^1$ comprises an alkynyl group, the alkynyl group may be protected by a protecting group. In such cases, $R^1$ may be herein denoted as $R^{1'}$.

Preferred embodiments include a compound in which $R^1$ is an iodine atom, bromine atom, ethynyl group, or vinyl group, wherein the ethynyl group may be protected by a protecting group, $R^2$ is a chlorine atom or fluorine atom, $R^3$ is a hydrogen atom, $R^4$ is a hydrogen atom or fluorine atom, $R^5$ is a fluorine atom, and $R^7$ is a hydrogen atom;

an alkyl group, alkenyl group, or alkynyl group, each of which may comprise 1 to 3 substituents selected from Group E; or a cycloalkylalkyl group, arylalkyl group, heteroarylalkyl group, or heterocyclic alkyl group, each of which may comprise 1 to 3 substituents selected from Group F below, Group E: —O—$R^a$, —(C1-C4 alkylene group)-$OR^a$, —[O—(C1-C4-alkylene group)]n-$OR^a$, —$NR^b$—(C1-C4 alkylene group)-$OR^a$, —C=N—$OR^a$, —$CONR^aR^b$, —$NR^aCOR^b$, —$SR^a$, $SO_2R^a$;

Group F: —O—$R^a$, —(C1-C4 alkylene group)-$OR^a$, —[O—(C1-C4 alkylene group)]n-$OR^a$, —$NR^b$—(C1-C4 alkylene group)-$OR^a$, —C=N—$OR^a$, —$CONR^aR^b$, —$NR^aCOR^b$, —$SR^a$, —$SO_2R^a$, C1-C4 alkyl group;

provided that, $R^a$ and $R^b$ are identical to or different from each other, and independently represent a hydrogen atom; C1-C4 alkyl group that may comprise an OH group; aryl group; or heteroaryl group, and n=1 to 4.

Specific examples of synthetic intermediate (U) are compounds represented by the following formulas (21) and (22).

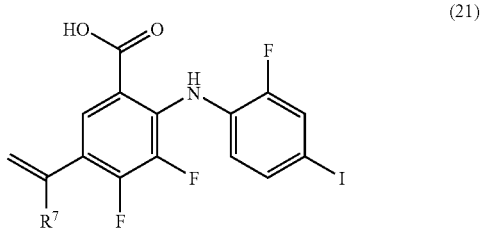

(21)

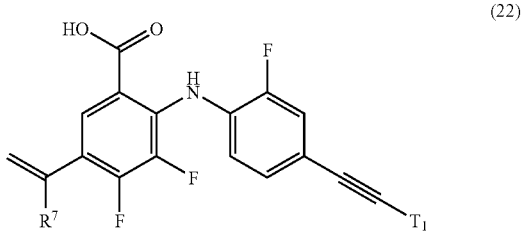

(22)

In formula (22), $T_1$ denotes a hydrogen atom or a protecting group.

An example of a compound of formula (21) includes 3,4-difluoro-2-(2-fluoro-4-iodophenylamino)-5-vinyl-benzoic acid ($R^7$=hydrogen atom).

Examples of a compound of formula (22) include:

2-(4-ethynyl-2-fluorophenylamino)-3,4-difluoro-5-vinyl-benzoic acid ($T_1$=hydrogen atom); and 2-(4-trimethylsilanylethynyl-2-fluorophenylamino)-3,4-difluoro-5-vinyl-benzoic acid ($R^7$=hydrogen atom, $T_1$=trimethylsilyl group).

Synthetic Intermediate V

Synthetic intermediate (V) is represented by formula (3) shown below.

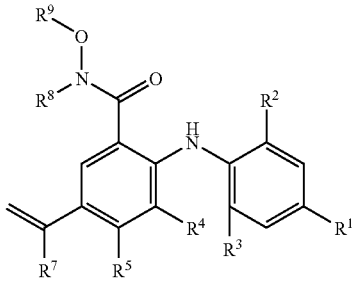

(3)

In formula (3), $R^1$, $R^2$, $R^3$, $R^4$, $R^5$, $R^7$, $R^8$, and $R^9$ have the same meaning as $R^1$, $R^2$, $R^3$, $R^4$, $R^5$, $R^7$, $R^8$, and $R^9$ in the aforementioned formula (1), and their preferred embodiments are also the same.

Wherein, if $R^1$ comprises an alkynyl group, the alkynyl group may be protected by a protecting group. In such cases, $R^1$ may be denoted herein as $R^{1'}$ Furthermore, when $R^9$ comprises a hydroxyl group, an amino group, or an alkylamino group, the hydroxyl group, amino group, or alkylamino group may be protected by a protecting group. In such cases, $R^9$ may be denoted herein as $R^{9'}$.

Preferred embodiments include a compound in which $R^1$ is an iodine atom, bromine atom, ethynyl group, or vinyl group, wherein the ethynyl group may be protected by a protecting group, $R^2$ is a chlorine atom or fluorine atom, $R^3$ is a hydrogen atom, $R^4$ is a hydrogen atom or fluorine atom, $R^5$ is a fluorine atom, $R^8$ is a hydrogen atom or methyl group, and $R^7$ and $R^9$ are hydrogen atoms; an alkyl group, alkenyl group, or alkynyl group, each of which may comprise 1 to 3 substituents selected from Group E shown below; or a cycloalkylalkyl group, arylalkyl group, heteroarylalkyl group, or heterocyclic alkyl group, each of which may comprise 1 to 3 substituents selected from group F shown below, and when $R^9$ comprises a hydroxyl group, an amino group, or an alkylamino group, the hydroxyl group, amino group, or alkylamino group may be protected by a protecting group:

Group E: —O—$R^a$, —(C1-C4 alkylene group)-O$R^a$, —[O—(C1-C4 alkylene group)]n-O$R^a$, —N$R^b$—(C1-C4 alkylene group)-O$R^a$, —C=N—O$R^a$, —CON$R^aR^b$, —N$R^a$CO$R^b$, —S$R^a$, —SO$_2R^a$; and Group F: —O—$R^a$, —(C1-C4 alkylene group)-O$R^a$, —[O—(C1-C4 alkylene group)]n-O$R^a$, —N$R^b$—(C1-C4 alkylene group)-O$R^a$, —C=N—O$R^a$, CON$R^aR^b$, N$R^a$CO$R^b$, —S$R^a$, —SO$_2R^a$, C1-C4 alkyl group;

provided that, $R^a$ and $R^b$ are identical to or different from each other and independently represent a hydrogen atom; C1-C4 alkyl group that may comprise an OH group; aryl group; or heteroaryl group, and n=1 to 4.

Specific examples of synthetic intermediate (V) include compounds represented by formulas (31) and (32).

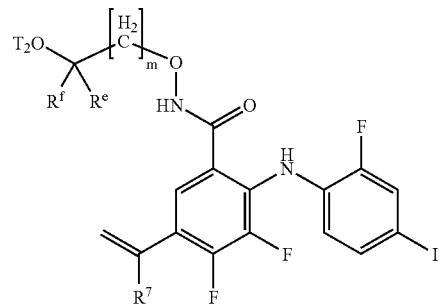

(31)

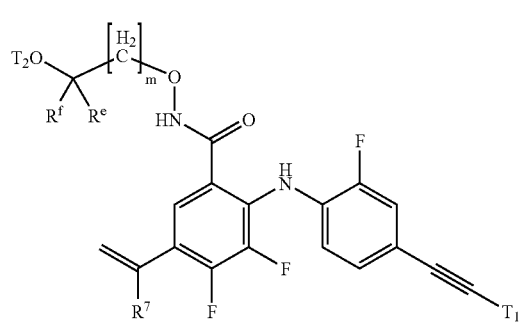

(32)

In formulas (31) and (32) shown above, $T_1$ and $T_2$ independently represent a hydrogen atom or a protecting group. $R^e$ and $R^f$ independently represent a hydrogen atom or a C1-C4 alkyl group, aryl group, or heteroaryl group;

an arbitrary hydrogen atom in a repeating unit represented by above —[CH$_2$]m- (m is an integer from 1 to 4) may be replaced with a group represented by $R^c$; $R^c$ represents a C1-C4 alkyl group, an aryl group, or a heteroaryl group, $R^c$ may be substituted with a hydroxyl group that may be protected with a protecting group, and when two or more hydrogen atoms are each substituted with $R^c$, each $R^c$ may be identical to or different from each other.

Examples of a compound of formula (31) include 3,4-difluoro-2-(2-fluoro-4-iodophenylamino)-N-(2-hydroxy-ethoxy)-5-vinylbenzamide
($R^c=R^d=R^e=R^f=R^7=T_2$=hydrogen atom, m=1), and 3,4-difluoro-2-(2-fluoro-4-iodophenylamino)-N-(t-butyl-2-dimethylsilanyloxy-ethoxy)-5-vinylbenzamide
($R^c=R^d=R^e=R^f=R^7$=hydrogen atom, $T_2$=dimethyl t-butylsilyl group, m=1).

Examples of a compound of formula (32) include 2-(4-ethynyl-2-fluorophenylamino)-3,4-difluoro-N-(2-hydroxy-ethoxy)-5-vinylbenzamide ($T_1=T_2$=hydrogen atom), 2-(4-trimethylsilanylethynyl-2-fluorophenylamino)-3,4-difluoro-N-(t-butyl-2-dimethylsilanyloxy-ethoxy)-5-vinylbenzamide ($R^c=R^d=R^e=R^f=R^7$=hydrogen atom, $T_1$=trimethylsilyl group, $T_2$=dimethyl t-butylsilyl group, m=1).

Synthetic Intermediate W

Synthetic intermediate (W) is represented by formula (4) shown below.

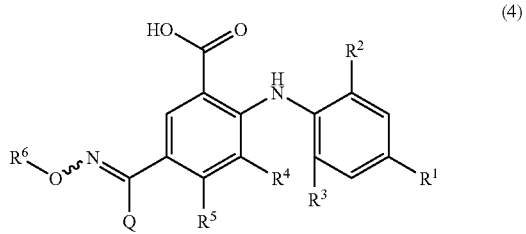

(4)

In formula (4), the wavy line ⁓ indicates that the compound can be either one of the stereoisomers, E-form or Z-form, depending on the manner of binding of O— to —N, $R^1$, $R^2$, $R^3$, $R^4$, $R^5$, $R^6$, and Q have the same meaning as $R^1$, $R^2$, $R^3$, $R^4$, $R^5$, $R^6$, and Q in the aforementioned formula (1), and their preferred embodiments are also the same.

Wherein, if $R^1$ comprises an alkynyl group, the alkynyl group may be protected by a protecting group. In such cases, $R^1$ may be denoted herein as $R^{1'}$.

Furthermore, when $R^6$ comprises a hydroxyl group, an amino group, or an alkylamino group, the hydroxyl group, amino group, or alkylamino group may be protected by a protecting group. In such cases, $R^6$ may be denoted herein as $R^{6'}$.

Preferred embodiments of synthetic intermediate (W) include a compound in which $R^1$ is an iodine atom, bromine atom, ethynyl group, or vinyl group, wherein the ethynyl group may be protected by a protecting group, $R^2$ is a chlorine atom or fluorine atom, $R^3$ is a hydrogen atom, $R^4$ is a hydrogen atom or fluorine atom, $R^5$ is a fluorine atom, $R^6$ is a hydrogen atom; alkyl group, alkenyl group, or alkynyl group, each of which may comprise 1 to 3 substituents selected from Group E shown below; or cycloalkylalkyl group, arylalkyl group, heteroarylalkyl group, or heterocyclic alkyl group, each of which may comprise 1 to 3 substituents selected from Group F shown below, and Q is a hydrogen atom; —$NR^aR^b$; an alkyl group, alkenyl group, or alkynyl group, each of which may comprise 1 to 3 substituents selected from Group E shown below; or a cycloalkylalkyl group, arylalkyl group, heteroarylalkyl group, or heterocyclic alkyl group, each of which may comprise 1 to 3 substituents selected from Group F shown below, and when $R^6$ comprises a hydroxyl group, an amino group, or an alkylamino group, the hydroxyl group, amino group, or alkylamino group may be protected by a protecting group.

Group E: —O—$R^a$, —$NR^aR^b$, —(C1-C4 alkylene group)-$OR^a$, —[O—(C1-C4 alkylene group)]n-$OR^a$, —$NR^b$—(C1-C4 alkylene group)-$OR^a$, —C=N—$OR^8$, —$NR^aSO_2R^b$, —$CONR^aR^b$, —$NR^aCOR^b$, —$SR^a$, —$SO_2R^a$;

Group F: —O—$R^a$, —(C1-C4 alkylene group)-$OR^a$, —[O—(C1-C4 alkylene group)]n-$OR^a$, —$NR^b$—(C1-C4 alkylene group)-$OR^a$, —C=N—$OR^a$, —$CONR^aR^b$, —$NR^aCOR^b$, —$SR^a$, —$SO_2R^a$, oxo group, C1-C4 alkyl group;

provided that, $R^a$ and $R^b$ are identical to or different from each other and independently represent a hydrogen atom; C1-C4 alkyl group that may comprise an OH atom; aryl group; or heteroaryl group, and n=1 to 4.

Specific examples of synthetic intermediate (W) include compounds represented by formulas (41), (42), (63), and (64).

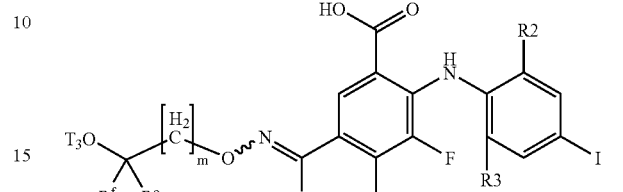

(41)

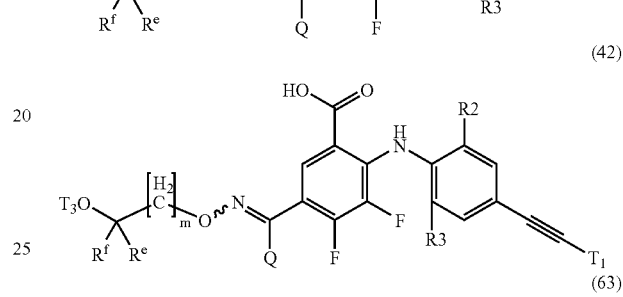

(42)

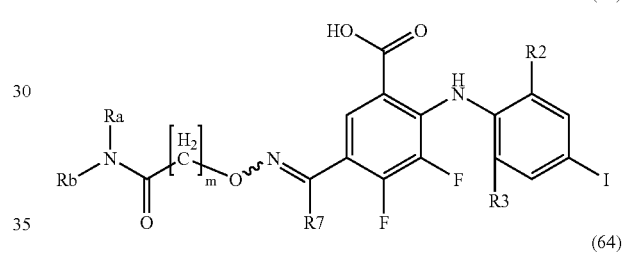

(63)

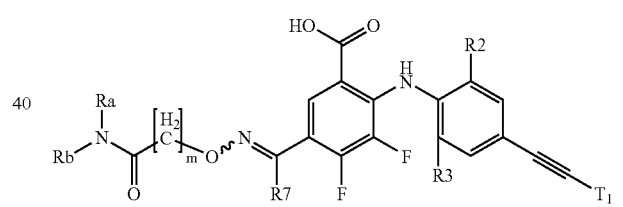

(64)

In the formulas shown above, the wavy line ⁓ indicates that the compound can be either one of the stereoisomers, E-form or Z-form, depending on the manner of binding of O— to —N.

$T_1$ and $T_3$ independently represent a hydrogen atom or a protecting group.

$R^2$ and $R^3$ independently represent a hydrogen atom; halogen atom; or alkyl group which may comprise 1 to 3 substituents selected from Group A shown below, $R^7$ is a hydrogen atom; an alkyl group, alkenyl group, or alkynyl group, each of which may comprise 1 to 3 substituents selected from Group A shown below; or a cycloalkyl group, heterocyclic group, aryl group, heteroaryl group, arylalkyl group, or heterocyclic alkyl group, each of which may comprise 1 to 3 substituents selected from Group B shown below, Group A: a halogen atom, nitro group, —O—$R^a$, -(alkylene group)-$OR^a$, —[O-(alkylene group)]n-$OR^a$, —$NR^aR^b$, —$NR^b$-(alkylene group)-$OR^a$, —$NR^aSO_2R^b$, —C=N—$OR^a$, —$CO_2R^a$, —$CONR^aR^b$, —$NR^aCOR^b$, —$COR^a$, —$SR^a$, —$SO_2R^a$, —$SO_2NR^aR^b$;

Group B: a halogen atom, nitro group, —O—$R^a$, -(alkylene group)-$OR^a$, —[O-(alkylene group)]n-$OR^a$, —$NR^aR^b$, —$NR^b$-(alkylene group)-$OR^a$, —$NR^aSO_2R^b$, —C=N—$OR^a$, —$CO_2R^a$, —$CONR^aR^b$, —$NR^aCOR^b$, —$COR^a$, —$SR^a$, —$SO_2R^a$, —$SO_2NR^aR^b$, oxo group, alkyl group, alkenyl group, alkynyl group, aryl group, heteroaryl group;

Q is a hydrogen atom; —$NR^aR^b$; an alkyl group, alkenyl group, or alkynyl group, each of which may comprise 1 to 3 substituents selected from Group E shown below; or a cycloalkylalkyl group, arylalkyl group, heteroarylalkyl group, or heterocyclic alkyl group, each of which may comprise 1 to 3 substituents selected from Group F shown below, Group E: —O—$R^a$, —(C1-C4 alkylene group)-$OR^a$, —[O—(C1-C4 alkylene group)]n-$OR^a$, —$NR^b$—(C1-C4 alkylene group)-$OR^a$, —C=N—$OR^a$, —$CONR^aR^b$, —$NR^aCOR^b$, —$SR^a$, —$SO_2R^a$;

Group F: —O—$R^a$, —(C1-C4 alkylene group)-$OR^a$, —[O—(C1-C4 alkylene group)]n-$OR^a$, —$NR^b$—(C1-C4 alkylene group)-$OR^a$, —C=N—$OR^a$, —$CONR^aR^b$, —$NR^aCOR^b$, —$SR^a$, —$SO_2R^a$, C1-C4 alkyl group;

$R^a$ and $R^b$ are identical to or different from each other and independently represent a hydrogen atom; C1-C4 alkyl group that may comprise an OH group; aryl group; or heteroaryl group, and n—1 to 4.

$R^e$ and $R^f$ independently represent a hydrogen atom, C1-C4 alkyl group, aryl group, or heteroayl group;

an arbitrary hydrogen atom in a repeating unit represented by above —[$CH_2$]m- (m is an integer from 1 to 4) may be replaced with a group represented by $R^c$; $R^c$ represents a C1-C4 alkyl group, an aryl group, or a heteroaryl group, $R^c$ may be substituted with a hydroxyl group that may be protected with a protecting group, and when two or more hydrogen atoms are each substituted with $R^c$, each $R^c$ may be identical to or different from each other.

Examples of a compound represented by formula (41) include
3,4-difluoro-2-(2-fluoro-4-iodo-phenylamino)-5-[(2-hydroxy-ethoxyimino)-methyl]-benzoic acid ($R^c$=$R^d$=$R^e$=$R^f$=Q=$T_3$=hydrogen atom, m=1), 3,4-difluoro-2-(2-fluoro -4-iodo-phenylamino)-5-[(t-butyl -2-dimethylsilanyloxy-ethoxyimino)-methyl]-benzoic acid ($R^c$=$R^d$=$R^e$=$R^f$=Q=hydrogen atom, $T_3$=dimethyl t-butylsilyl group, m=1), 3,4-difluoro-2-(2-fluoro-4-iodo-phenylamino)-5-[(2-hydroxy-2-methylethoxyimino)-methyl]-benzoic acid, 3,4-difluoro-2-(2-fluoro-4-iodo-phenylamino)-5-[(2-hydroxy-propoxyimino)-methyl]-benzoic acid, and 3,4-difluoro-2-(2-fluoro-4-iodo-phenylamino)-5-[(2-methylcarbamoyl-ethoxyimino)-methyl]-benzoic acid.

Examples of a compound of formula (42) include
2-(4-ethynyl-2-fluoro-phenylamino)-3,4-difluoro-5-[(2-hydroxy-ethoxyimino)-methyl]-benzoic acid ($R^c$=$R^d$=$R^e$=$R^f$=Q=$T_1$=$T_3$=hydrogen atom, m=1), 2-(4-trimethylsilanylethynyl-2-fluoro-phenylamino)-3,4-difluoro-5-[(t-butyl-2-dimethylsilanyloxy-ethoxyimino)-methyl]-benzoic acid ($R^c$=$R^d$=$R^e$=$R^f$=Q=hydrogen atom, $T_1$=trimethylsilyl group, $T_3$=dimethyl t-butylsilyloxy group, m=1), 2-(4-trimethylsilanylethynyl-2-fluoro-phenylamino)-3,4-difluoro-5-[(2-hydroxy-2-methylpropoxyimino)-methyl]-benzoic acid, and 2-(4-trimethylsilanylethynyl-2-fluoro-phenylamino)-3,4-difluoro-5-[(t-butyl-2-dimethylsilanyloxy-2-methylpropoxyimino)-methyl]-benzoic acid.

Synthetic Intermediate X

Synthetic intermediate (X) is represented by formula (5) shown below.

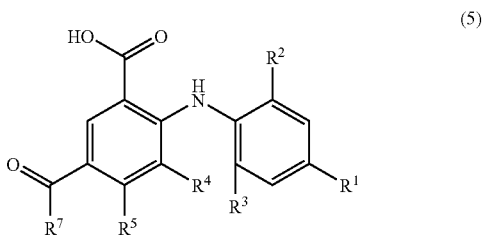

(5)

In formula (5), $R^1$, $R^2$, $R^3$, $R^4$, $R^5$, and $R^7$ have the same meaning as $R^1$, $R^2$, $R^3$, $R^4$, $R^5$, and $R^7$ in the aforementioned formula (1), and their preferred embodiments are also the same.

Wherein, if $R^1$ comprises an alkynyl group, the alkyl group may be protected by a protecting group. In such cases, $R^1$ may be denoted herein as $R^{1'}$.

Preferred embodiments of synthetic intermediate X include a compound in which $R^1$ is an iodine atom, bromine atom, ethynyl group, or vinyl group; wherein the ethynyl group may be protected by a protecting group, $R^2$ is a chlorine atom or fluorine atom, $R^3$ is a hydrogen atom, $R^4$ is a hydrogen atom or fluorine atom, $R^5$ is a fluorine atom, $R^7$ is a hydrogen atom; an alkyl group, alkenyl group, or alkynyl group, each of which may comprise 1 to 3 substituents selected from Group E shown above; or a cycloalkylalkyl group, arylalkyl group, heteroarylalkyl group, or heterocyclic alkyl group, each of which may comprise 1 to 3 substituents selected from group F shown above.

Specific examples of synthetic intermediate (X) are compounds represented by formulas (51) and (52):

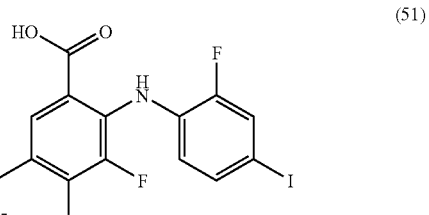

(51)

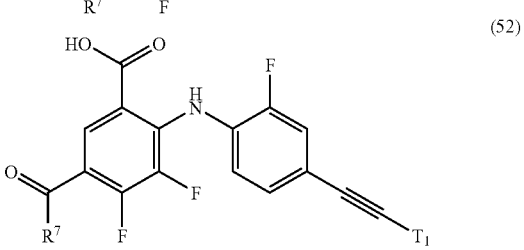

(52)

In formula (52), shown above, $T_1$ denotes a hydrogen atom or a protecting group.

An example of a compound represented by formula (51) includes 3,4-difluoro-2-(2-fluoro-4-iodophenylamino)-5-formyl-benzoic acid ($R^7$=hydrogen atom).

Examples of a compound represented by formula (52) are 2-(4-ethynyl-2-fluoro-phenylamino)-3,4-difluoro-5-formyl-benzoic acid ($R^7$=$T_1$=hydrogen atom), and 2-(4-trimethylsilanylethynyl-2-fluoro-phenylamino)-3,4-difluoro-5-formyl-benzoic acid ((7=hydrogen atom, $T_1$=trimethylsilyl group).

Synthetic Intermediate Y

Synthetic intermediate (Y) is represented by formula (6) shown below.

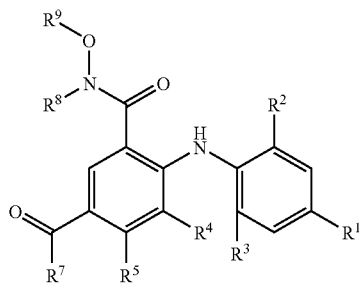

(6)

In formula (6), $R^1$, $R^2$, $R^3$, $R^4$, $R^5$, $R^7$, $R^8$, and $R^9$ have the same meaning as $R^1$, $R^2$, $R^3$, $R^4$, $R^5$, $R^7$, $R^8$, and $R^9$ in the aforementioned formula (1), and their preferred embodiments are also the same.

Wherein, if $R^1$ comprises an alkynyl group, the alkynyl group may be protected by a protecting group. In such cases, $R^1$ may be denoted herein as $R^{1\prime}$.

Furthermore, when $R^9$ comprises a hydroxyl group, an amino group, or an alkylamino group, the hydroxyl group, amino group, or alkylamino group may be protected by a protecting group. In such cases, $R^9$ may be denoted herein as $R^{9\prime}$.

Preferred embodiments of synthetic intermediate Y include a compound in which $R^1$ is an iodine atom, bromine atom, ethynyl group, or vinyl group, and the ethynyl group may be protected by a protecting group, $R^2$ is a chlorine atom or fluorine atom, $R^3$ is a hydrogen atom, $R^4$ is a hydrogen atom or fluorine atom, $R^5$ is a fluorine atom, $R^7$ is a hydrogen atom; an alkyl group, alkenyl group, or alkynyl group, each of which may comprise 1 to 3 substituents selected from Group E shown above; or a cycloalkylalkyl group, arylalkyl group, heteroarylalkyl group, or heterocyclic alkyl group, each of which may comprise 1 to 3 substituents selected from group F shown above, $R^8$ is a hydrogen atom or methyl group, $R^9$ is a hydrogen atom; an alkyl group, alkenyl group, or alkynyl group, each of which may comprise 1 to 3 substituents selected from Group E shown above; or a cycloalkylalkyl group, arylalkyl group, heteroarylalkyl group, or heterocyclic alkyl group, each of which may comprise 1 to 3 substituents selected from group F shown above, and when $R^9$ comprises a hydroxyl group, an amino group, or an alkylamino group, the hydroxyl group, amino group, or alkylamino group may be protected by a protecting group.

Specific examples of synthetic intermediate (Y) are compounds represented by formulas (61) and (62):

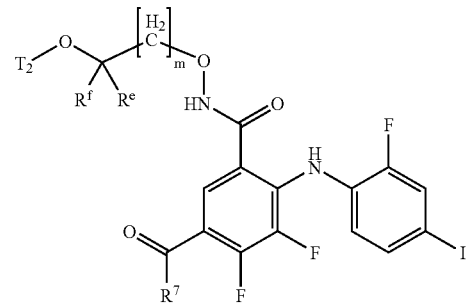

(61)

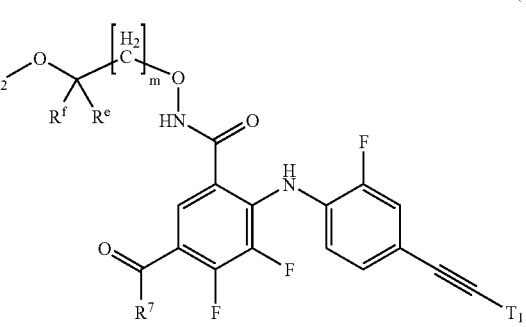

(62)

In formulas (61) and (62), shown above, $T_1$ and $T_2$ independently represent a hydrogen atom or a protecting group. $R^e$ and $R^f$ independently represent a hydrogen atom, C1-C4 alkyl group, aryl group, or heteroaryl group;

an arbitrary hydrogen atom in a repeating unit represented by above —[$CH_2$]m- (m is an integer from 1 to 4) may be replaced with a group represented by $R^c$; $R^c$ represents a C1-C4 alkyl group, an aryl group, or a heteroaryl group, $R^c$ may be substituted with a hydroxyl group that may be protected with a protecting group, and when two or more hydrogen atoms are each substituted with $R^c$, each $R^c$ may be identical to or different from each other.

Examples of a compound represented by formula (61) include 3,4-difluoro-2-(2-fluoro-4-iodo-phenylamino)-5-formyl-N-(2-hydroxyethoxy)-benzamide ($R^c$=$R^d$=$R^e$=$R^f$=$R^7$=$T_2$=hydrogen atom, m=1), and 3,4-difluoro-2-(2-fluoro-4-iodo -phenylamino)-5-formyl-N-(t-butyl-2-dimethylsilanyloxyethoxy)-benzamide ($R^c$=$R^d$=$R^e$=$R^f$=$R^7$=hydrogen atom, $T_2$=dimethyl t-butylsilyl group, m=1).

Examples of a compound represented by formula (62) include 2-(4-ethynyl-2-fluoro-phenylamino)-3,4-difluoro-5-formyl-N-(2-hydroxyethoxy)-benzamide ($R^c$=$R^d$=$R^e$=$R^f$=$R^7$=$T_1$=$T_2$=hydrogen atom, m=1), and 2-(4-trimethylsilanylethynyl-2-fluoro-phenylamino)-3,4-difluoro-5-formyl-N-(t-butyl-2-dimethylsilanyloxyethoxy)-benzamide ($R^c$=$R^d$=$R^e$=$R^f$=$R^7$=hydrogen atom, $T_1$=trimethylsilyl group, $T_2$=dimethyl t-butylsilyl group, m=1).

Furthermore, synthetic intermediate (Z) represented by formula (65), shown below, can be used as a synthetic intermediate of compound (1).

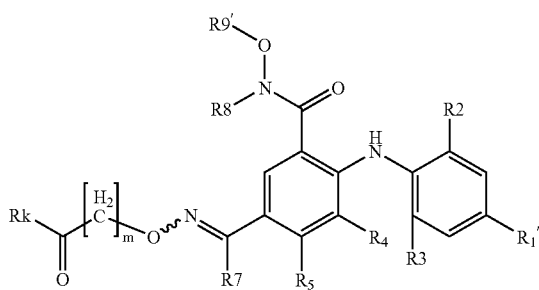

(65)

In formula (65), the wavy line $\sim$ indicates that the compound can be either one of the stereoisomers, E-form or Z-form, depending on the manner of binding of O— to —N.

$R^{1'}$ is a hydrogen atom, halogen atom, —S—$R^a$, —SO—$R^a$, —SO$_2$—$R^a$, —COOR$^a$ or alkyl group that may comprise 1 to 3 substituents selected from Group A shown below, an alkenyl group that may comprise 1 to 3 substituents selected from Group A shown below, or an alkynyl group that may comprise 1 to 3 substituents selected from Group A shown below and may be protected by a protecting group.

$R^2$ and $R^3$ independently represent a hydrogen atom; halogen atom; or an alkyl group that may comprise 1 to 3 substituents selected from Group A mentioned below.

$R^4$ and $R^5$ independently represent a hydrogen atom, halogen atom, or nitro group.

$R^7$ denotes a hydrogen atom; an alkyl group, alkenyl group, or alkynyl group, each of which may comprise 1 to 3 substituents selected from Group A shown below; or a cycloalkyl group, heterocyclic group, aryl group, heteroaryl group, arylalkyl group, or heterocyclic alkyl group, each of which may comprise 1 to 3 substituents selected from Group B shown below.

$R^8$ denotes a hydrogen atom, or an alkyl group that may comprise 1 to 3 substituents selected from Group A shown below.

$R^{9'}$ denotes a hydrogen atom;

an alkyl group, alkenyl group, or alkynyl group, each of which may comprise 1 to 3 substituents selected from Group A shown below; or a cycloalkyl group, aryl group, heteroaryl group, heterocyclic group, cycloalkylalkyl group, cycloalkylalkenyl group, cycloalkylalkynyl group, arylalkyl group, arylalkenyl group, arylalkynyl group, heteroarylalkyl group, heteroarylalkenyl group, heteroarylalkynyl group, heterocyclic alkyl group, heterocyclic alkenyl group, or heterocyclic alkynyl group, each of which may comprise 1 to 3 substituents selected from Group B shown below.

When $R^{9'}$ comprises a hydroxyl group, an amino group, or an alkylamino group, the hydroxyl group, amino group, or alkylamino group may be protected by a protecting group.

Group A: halogen atom, nitro group, —O—$R^a$, -(alkylene group)-OR$^a$, —[O-(alkylene group)]n-OR$^a$, —NR$^a$R$^b$, —NR$^b$-(alkylene group)-OR$^a$, —NR$^a$SO$_2$R$^b$, —C=N—OR$^a$, —CO$_2$R$^a$, —CONR$^a$R$^b$, —NR$^a$COR$^b$, —COR$^a$, —SR$^a$, —SO$_2$R$^a$, and —SO$_2$NR$^a$R$^b$.

Group B: halogen atom, nitro group, —O—$R^a$, -(alkylene group)-OR$^a$, —[O-(alkylene group)]n-OR$^a$, —NR$^a$R$^b$, —NR$^b$-(alkylene group)-OR$^a$, —NR$^a$SO$_2$R$^b$, —C=N—OR$^a$, —CO$_2$R$^a$, —CONR$^a$R$^b$, —NR$^a$COR$^b$, —COR$^a$, —SR$^a$, —SO$_2$R$^a$, —SO$_2$NR$^a$R$^b$, oxo group, alkyl group, alkenyl group, alkynyl group, aryl group, and heteroaryl group.

The aforementioned $R^a$ and $R^b$ are identical to or different from each other, and independently represent a hydrogen atom; alkyl group that may comprise an OH group; aryl group; or heteroaryl group, and n=1 to 4.

$R^k$ independently represent a hydrogen atom, C1-C4 alkyl group, aryl group, or heteroaryl group;

an arbitrary hydrogen atom in a repeating unit represented by above —[CH$_2$]m- (m is an integer from 1 to 4) may be replaced with a group represented by $R^c$; $R^c$ represents a C1-C4 alkyl group, an aryl group, or a heteroaryl group, $R^c$ may be substituted with a hydroxyl group that may be protected with a protecting group, and when two or more hydrogen atoms are each substituted with $R^c$, each $R^c$ may be identical to or different from each other.

Synthetic Intermediate P

Examples of the synthetic intermediate P of the compound of formula (1) include the compound of formula (66):

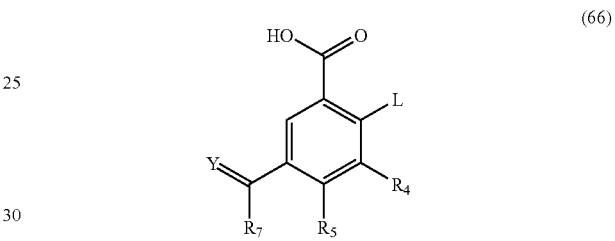

(66)

wherein, Y represents CH$_2$ or an oxygen atom;

L represents a leaving group, $R^4$ and $R^5$ each independently represent a hydrogen atom, a halogen atom, or a nitro group;

$R^7$ represents a hydrogen atom;

an alkyl group, an alkenyl group, or an alkynyl group, each of which may have 1 to 3 substituents selected from Group A below; or a cycloalkyl group, a heterocyclic group, an aryl group, a heteroaryl group, an arylalkyl group, or a heterocyclic alkyl group, each of which may have 1 to 3 substituents selected from Group B below;

Group A: a halogen atom, a nitro group, —O—$R^a$, -(alkylene group)-OR$^a$, —[O-(alkylene group)]n-OR$^a$, —NR$^a$R$^b$, —NR$^b$-(alkylene group)-OR$^a$, —NR$^a$SO$_2$R$^b$, —C=N—OR$^a$, —CO$_2$R$^a$, —CONR$^a$R$^b$, —NR$^a$COR$^b$, —COR$^a$, —SR$^a$, —SO$_2$R$^a$, and —SO$_2$NR$^a$R$^b$;

Group B: a halogen atom, a nitro group, —O—$R^a$, -(alkylene group)-OR$^a$, —[O-(alkylene group)]n-OR$^a$, —NR$^a$R$^b$, —NR$^b$-(alkylene group)-OR$^a$, —NR$^a$SO$_2$R$^b$, —C=N—OR$^a$, —CO$_2$R$^a$, —CONR$^a$R$^b$, —NR$^a$COR$^b$, —COR$^a$, —SR$^a$, —SO$_2$R$^a$, —SO$_2$NR$^a$R$^b$, an oxo group, an alkyl group, an alkenyl group, an alkynyl group, an aryl group, and a heteroaryl group;

provided that $R^a$ and $R^b$ above may be the same or different, and represent a hydrogen atom; an alkyl group that may have an OH group; an aryl group; or a heteroaryl group, and n=1 to 4;

m=1 to 4; and the leaving group described above represents a halogen atom or an activated hydroxyl group.

Examples of the activated hydroxyl group described above include a phosphate ester and a sulfonate ester.

L of the synthetic intermediate (P) described above preferably represents a fluorine atom, a chlorine atom, a bromine atom, or an iodine atom. Y preferably represents CH$_2$ or an oxygen atom. Preferably, R$^4$ and R$^5$ each independently represent a hydrogen atom or a fluorine atom. R$^7$ preferably represents a hydrogen atom.

Compound I of the present invention, which is represented by formula (I), can be prepared, for example, according to the method described below. In reaction processes 1 to 7 and in their descriptions, R$^1$ to R$^9$, R$^a$, R$^b$ and compound I have the same meaning as those of the aforementioned formula (1).

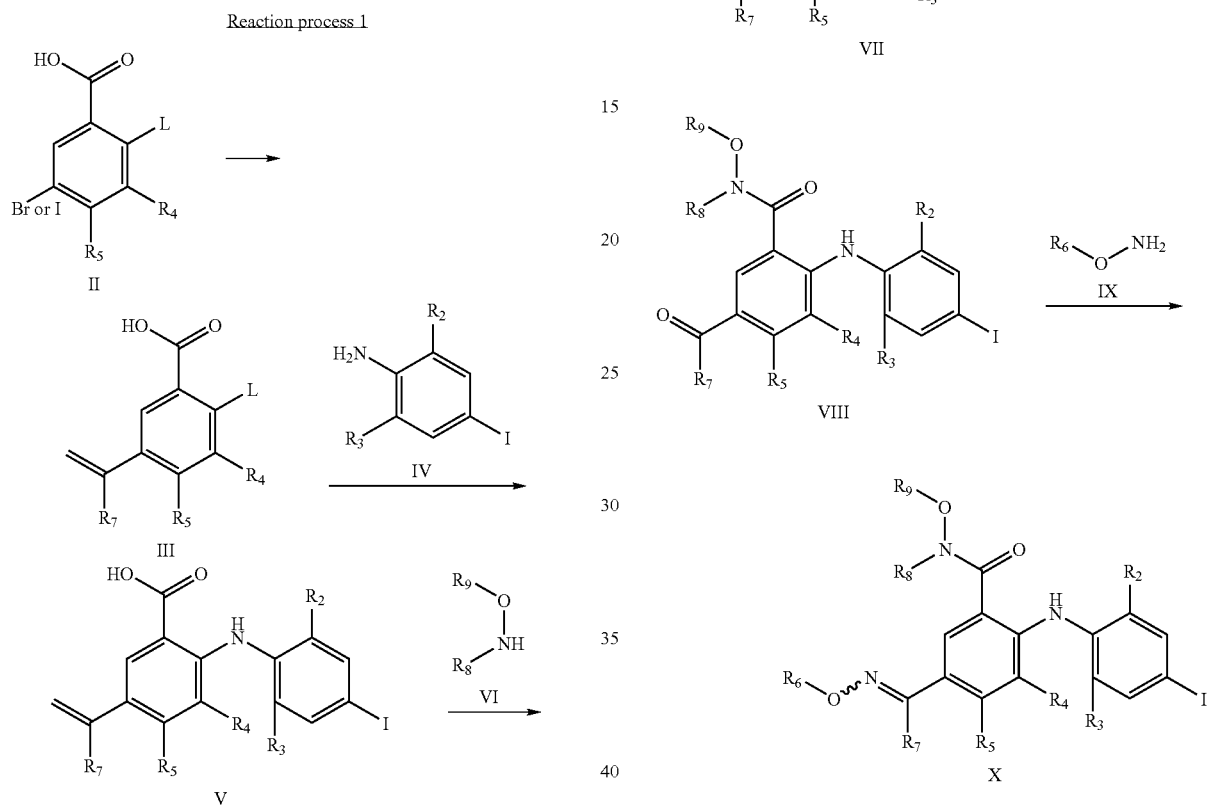

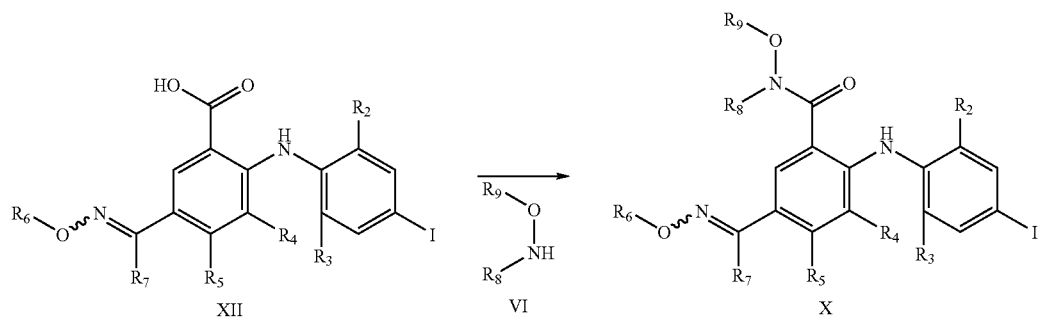
Reaction process 3
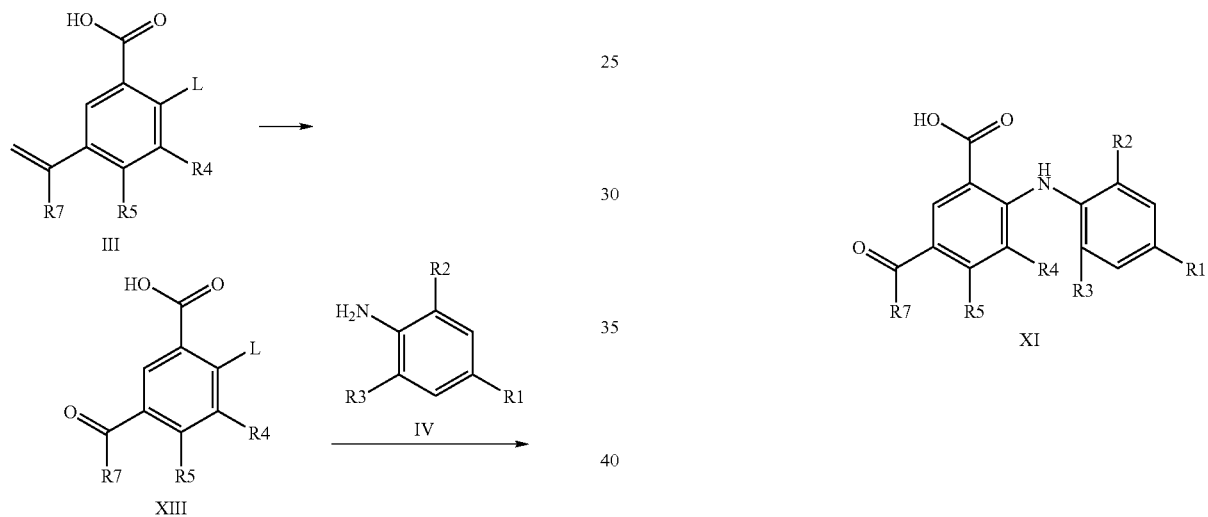
Reaction process 4
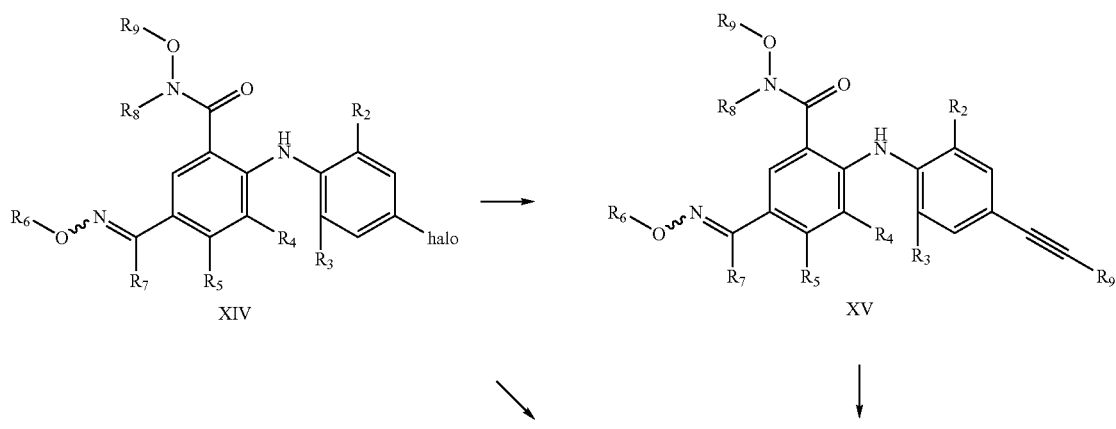

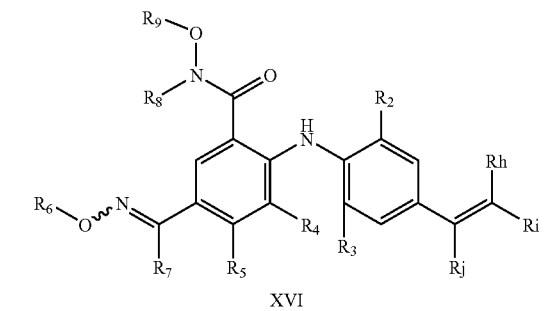
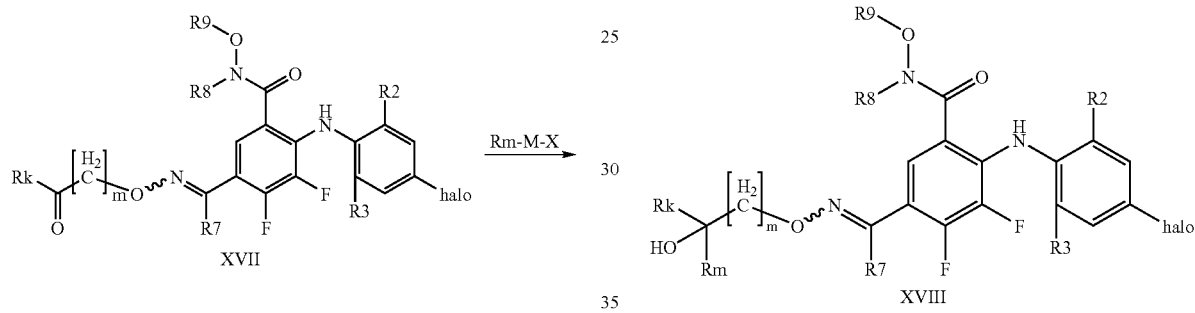
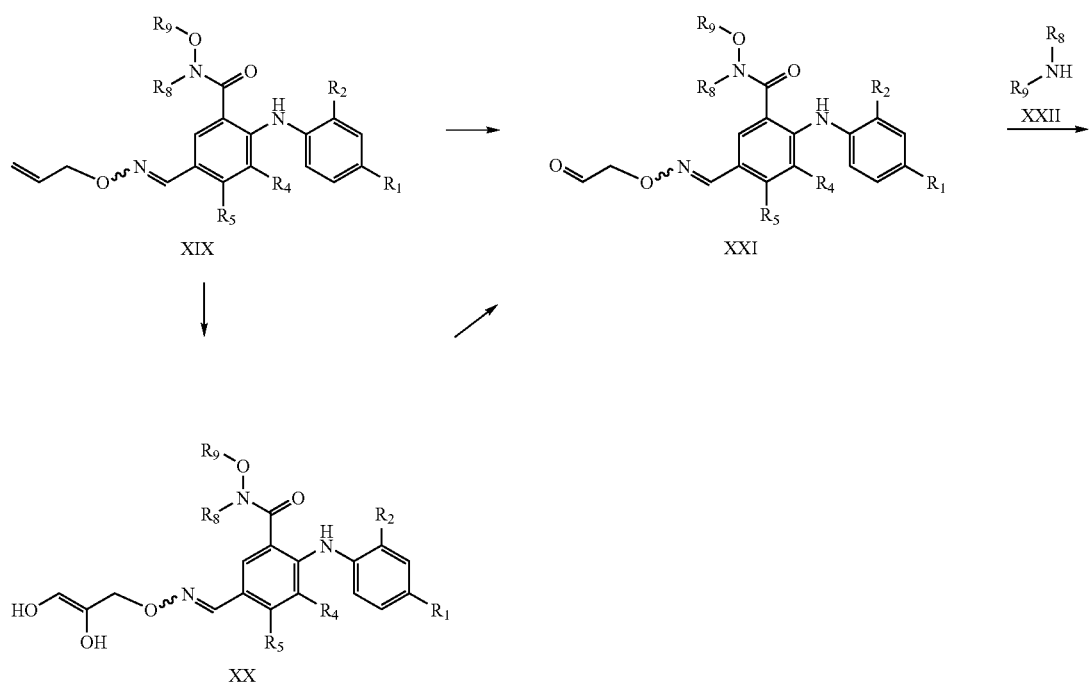

-continued

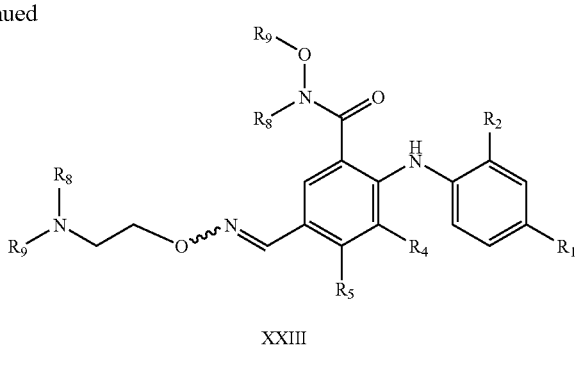

XXIII

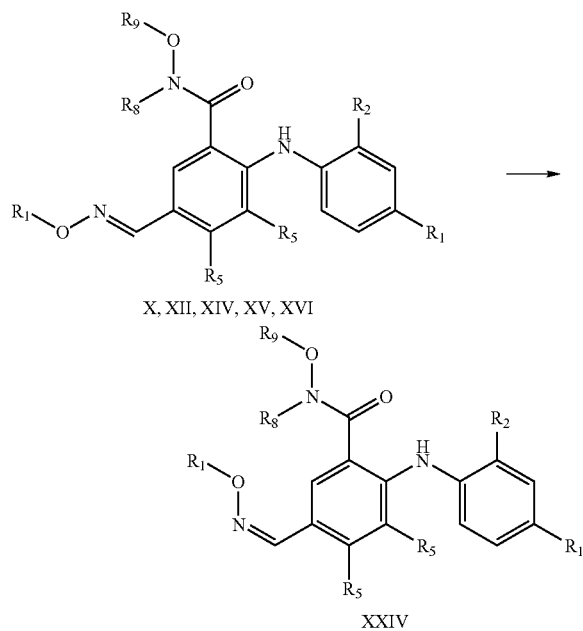

In processes shown above,
the wavy line ∿ indicates that the compound can be either one of the stereoisomers, E-form or Z-form, depending on the manner of binding of O— to —N.

<Reaction Process 1>

Reaction process 1 shows a method for producing compound (X), which belongs to compound I represented by formula (1). In Reaction process 1, L is a leaving group such as a fluorine, chlorine, bromine or iodine, or an activated hydroxyl group such as a phosphate ester or sulfonate ester.

The compound represented by formula (II) (5-iodinated or 5-brominated benzoic acid derivative) can be easily obtained using a method described in known literature (F. Mongin, E. Marzi, and M. Schlosser, European Journal of Organic Chemistry, 2771-2777 (2001), and A. Groweiss, Organic Process Research & Development, 4, 30-33 (2000)), or by a similar method.

Preparation of 5-Vinylbenzoic Acid Derivative (III)

5-vinylbenzoic acid derivative (III) can be obtained, for example, by reacting 5-iodinated or 5-brominated benzoic acid derivative (II) with a vinylated organometallic reagent in an appropriate solvent and in the presence of a transition metal catalyst.

Examples of the solvent include dimethylformamide, tetrahydrofuran (THF), dimethylsulfoxide (DMSO), isopropanol, methanol, and ethanol, and preferably THF or isopropanol is used.

For example, as the transition metal catalyst, a palladium complex may be preferably used. Specifically, $Pd(PPh_3)_4$, $Pd(dppf)Cl_2$, $(PhCN)_2PdCl_2$, $(MeCN)_2PdCl_2$, $(PPh_3)_2PdCl_2$, and such can be used.

Examples of the vinylated-organometallic reagent include vinylated magnesium reagent, vinylated aluminum reagent, vinylated silicon reagent, vinylated boron reagent, vinylated zinc reagent, and vinylated tin reagent. Among them, vinylated tin reagent (Stille method) or vinylated boron reagent (Suzuki method) can be used preferably. An appropriate base such as triethylamine, Hunig's base,
potassium carbonate, cesium carbonate, sodium hydroxide, potassium hydroxide, and sodium ethylate can be added to the reaction system as necessary.

Normally, the reaction can be carried out at approximately 15° C. to approximately 130° C., and preferably at approximately 60° C. to approximately 100° C., for approximately four hours to approximately four days, and preferably for approximately ten hours.

The reaction can be performed easily by referring to the following literature:
a) J. K. Stille, Angew. Chem., Int. Ed. Engl. 1986, 25, 508-524;
b) N. Miyaura, A. Suzuki, Chem. Rev. 1995, 95, 2457-2483;
c) A. Suzuki, J. Organomet. Chem., 1999, 576, 147-168; and
d) Suzuki, A, In Metal-Catalyzed Cross Coupling Reactions; Diederich, F., Stang, P. J., Eds.; VCH: Weinheim, 1998; pp 49-97.

Preparation of 2-(phenylamino)-5-vinylbenzoic Acid Derivative (V)

2-(phenylamino)-5-vinylbenzoic acid derivative (V) can be synthesized by reacting aniline derivative (IV) with 5-vinylbenzoic acid derivative (III). This reaction can be performed using the method described in the patent literature (WO0064856) and the scientific literature (M. H. Chen, V. G Beylin, E. Iakovleva, S. J. Kesten, J. Magano, D. Drieze, Synthetic Communications, 32(3), 411-417 (2002)), or by using a similar method.

Specifically, the reaction can be performed by reacting 5-vinylbenzoic acid derivative (III) with an equivalent amount or an excess amount of the aniline derivative (IV) in a solvent in the presence of a base.

The solvent may be THF, toluene, or such, and a preferable example is THF.

The base is, for example, lithium diisopropylamide, lithium hexamethyldisilazide, n-butyl lithium, sodium hydride, or sodium amide, and is preferably, for example, lithium diisopropylamide or lithium hexamethyldisilazide.

The reaction is normally carried-out at approximately −78° C. to approximately 25° C. for approximately four hours to approximately four days, or preferably for one day.

Preparation of Hydroxamic Acid Derivative (VII)

Conversion to hydroxamic acid derivative (VII) can be accomplished by reacting 2-phenylamino-5-vinylbenzoic acid derivative (V) with a hydroxylamine derivative (VI) represented by $NHR^8OR^9$ in an appropriate solvent and in the presence of a condensing reagent for peptide synthesis and a base.

The solvent may be dichloromethane, THF, dimethylformamide, and such, and is preferably, for example, dichloromethane.

The base is, for example, triethylamine, Hunig's base, or 1,8-diazabicyclo[5.4.0]-7-undecene (DBU), and is preferably, for example, Hunig's base.

The peptide condensing reagent is, for example, 1,3-dicyclohexylcarbodiimide (DCC), 2-ethoxy-1-ethoxycarbonyl-1,2-dihydroquinoline (EEDQ), bromo-tris(pyrrolidino)-phosphonium hexafluorophosphate (PyBrOP), 1-ethyl-3-(3'-dimethylaminopropyl)carbodiimide (EDC), or (benzotriazolyloxy)tripyrrolidino-phosphonium hexafluorophosphate (PyBOP).

Usually, the reaction can be carried out at approximately 10° C. to approximately 30° C., preferably at approximately 22° C. (room temperature) for approximately one hour to approximately two days, preferably for approximately ten hours.

Preparation of Carbonyl Form (VII)

Conversion to carbonyl form (VIII) can be accomplished by reacting the aforementioned hydroxamic acid derivative (VII) in an appropriate solvent with an appropriate oxidizing agent.

The solvent is, for example, THF, diethyl ether, dichloromethane, dimethylformamide, DMSO, chloroform, carbon tetrachloride, or acetonitrile, and is preferably, for example, THF or dichloromethane The oxidizing agent is, for example, ozone, osmium tetroxide-sodium meta-periodic acid, or ruthenium chloride-sodium meta-periodic acid.

Normally, the aforementioned reaction can be carried out at approximately 10° C. to approximately 30° C., preferably at approximately 22° C. (room temperature) for approximately two hours to approximately two days, preferably for approximately ten hours.

Preparation of Compound X

Conversion of carbonyl form (VII) to compound (X) can be accomplished by reacting carbonyl form (VIII) in a solvent with the hydroxylamine derivative (IX) represented by $NH_2OR^6$.

Examples of the solvent include dichloromethane, ethanol, chloroform, THF, dimethylformamide, and diethyl ether, and are preferably dichloromethane and ethanol.

Normally, the reaction can be carried out at approximately 10° C. to approximately 30° C., preferably at approximately 22° C. (room temperature) for approximately one hour to approximately two days, preferably for approximately ten hours.

<Reaction Process 2>

Reaction process 2 shows an example of the preparation of compound (X) from 2-(phenylamino)-5-vinylbenzoic acid derivative (V) of Reaction process 1 through different steps from those of Reaction process 1.

Preparation of Carbonyl Form (XI)

Conversion from 2-(phenylamino)-5-vinylbenzoic acid derivative (V) to carbonyl form (XI) can be performed according to the above-described conversion method of hydroxamic acid derivative (VII) to carbonyl form (VIII).

More specifically, this conversion can be accomplished by reacting 2-(4-iodophenylamino)-5-vinylbenzoic acid derivative (V) in an appropriate solvent with an appropriate oxidizing agent.

The appropriate solvent is, for example, THF, diethyl ether, dichloromethane, dimethylformamide, DMSO, chloroform, carbon tetrachloride, or acetonitrile, and is preferably, for example, THF or dichloromethane. Examples of the oxidizing agent are ozone, osmiumtetroxide-sodium meta-periodic acid, and ruthenium chloride-sodium meta-periodic acid.

Normally, the aforementioned reaction can be carried out at approximately 10° C. to approximately 30° C., preferably at approximately 22° C. (room temperature) for approximately two hours to approximately two days, preferably for approximately ten hours.

Preparation of Compound (XII)

Conversion from carbonyl form (XI) to compound (XII) can be performed according to the conversion method from aldehyde form (VIII) or ketone form (X) to compound I described above.

More specifically, compound (XII) can be obtained by reacting carbonyl form (XI) in a solvent with hydroxylamine derivative (IX) represented by $NH_2OR^6$.

Examples of the solvent are dichloromethane, ethanol, chloroform, THF, dimethylformamide, and diethyl ether, and are preferably dichloromethane and ethanol.

Normally, the aforementioned reaction can be carried out at approximately 10° C. to approximately 30° C., preferably at approximately 22° C. (room temperature) for approximately one hour to approximately two days, preferably for approximately ten hours.

Preparation of Compound X (1)

Conversion from compound (XII) to compound (X) can be performed according to the conversion method of 2-(phenylamino)-5-vinylbenzoic acid derivative (V) to hydroxamic acid derivative (VII) described above.

More specifically, compound I can be obtained by reacting compound (XII) with hydroxylamine derivative (VI), which is represented by $NHR^8OR^9$, in an appropriate solvent and in the presence of a condensing reagent for peptide synthesis and a base.

Examples of the solvent are dichloromethane, THF, and dimethylformamide, and a preferable example is dichloromethane.

The base is, for example, triethylamine, Hunig's base, or DBU, and is preferably, for example, Hunig's base.

The peptide condensing reagent is, for example, 1,3-dicyclohexylcarbodiimide (DCC), 2-ethoxy-1-ethoxycarbonyl-1,2-dihydroquinoline (EEDQ), bromo-tris(pyrrolidino)-phosphonium hexafluorophosphate (PyBrOP), 1-ethyl-3-(3'-dimethylaminopropyl)carbodiimide (EDC), or (benzotriazolyloxy)tripyrrolidino-phosphonium hexafluorophosphate (PyBOP).

Normally, the aforementioned reaction can be carried out at approximately 110° C. to approximately 30° C., preferably at approximately 22° C. (room temperature) for approximately one hour to approximately two days, preferably for approximately ten hours.

Preparation of Compound I (2)

Compound (X) can be obtained, for example, in one step from carbonyl form (XI). In this case, $NHR^8OR^9$ and $NH_2OR^6$ can be reacted with carbonyl form (XI) simultaneously in the same reaction system, or by sequential addition. When performing this reaction, the hydroxylamine derivatives (DC) and (VI) are preferably the same compound.

This conversion can be performed according to the conversion method of carbonyl form (XI) to compound (XII).

More specifically, compound I can be obtained by reacting carbonyl form (XI) with hydroxylamine derivatives (VI) and/or (IX) represented by $NHR^8OR^9$ and/or $NH_2OR^6$ in an appropriate solvent, and in the presence of a condensing reagent for peptide synthesis and a base.

Examples of the solvent are dichloromethane, THF, and dimethylformamide, and a preferable example is dichloromethane.

The base is, for example, triethylamine, Hunig's base, or DBU, and is preferably, for example, Hunig's base.

The peptide condensing reagent is, for example, 1,3-dicyclohexylcarbodiimide (DCC), 2-ethoxy-1-ethoxycarbonyl-1,2-dihydroquinoline (EEDQ), bromo-tris(pyrrolidino)-phosphonium hexafluorophosphate (PyBrOP), 1-ethyl-3-(3'-dimethylaminopropyl)carbodiimide (EDC), or (benzotriazolyloxy)tripyrrolidino-phosphonium hexafluorophosphate (PyBOP).

Normally, the aforementioned reaction can be carried out at approximately 10° C. to approximately 30° C., preferably at approximately 22° C. (room temperature) for approximately one hour to approximately two days, preferably for approximately ten hours.

<Reaction Process 3>

Reaction process 3 shows the preparation of carbonyl form (XI) of reaction process 2 from 5-vinylbenzoic acid derivative (III) through different steps from those of Reaction process 2. Ultimately, compound (I) is yielded from carbonyl form (XI) as in reaction process 2.

Preparation of Compound (XIII)

Compound (XIII) can be prepared from 5-vinylbenzoic acid derivative (III) according to the conversion method of 2-(phenylamino)-5-vinylbenzoic acid derivative (V) to carbonyl form (XI), shown in reaction process 2.

More specifically, compound (XIII) can be obtained by reacting 5-vinylbenzoic acid derivative (III) in an appropriate solvent with an appropriate oxidizing agent.

The solvent is, for example, THF, diethyl ether, dichloromethane, dimethylformamide, DMSO, chloroform, carbon tetrachloride, or acetonitrile, and is preferably, for example, THF or dichloromethane. Examples of the oxidizing agent are ozone, osmium tetroxide-sodium meta-periodic acid, and ruthenium chloride-sodium meta-periodic acid. Normally, the aforementioned reaction can be carried out at approximately 10° C. to approximately 30° C., preferably at approximately 22° C. (room temperature) for approximately two hours to approximately two days, preferably for approximately ten hours.

Preparation of Carbonyl Form (I)

Carbonyl form (XI) can be prepared from compound (XIII) as according to the conversion method of 5-vinylbenzoic acid derivative (III) to 2-(phenylamino)-5-vinylbenzoic acid derivative (V) shown in reaction process 1.

Specifically, the above reaction can be carried out using the method described in the patent literature (WO0064856) or in the scientific literature (M. H. Chen, V. G Beylin, E. Iakovleva, S. J. Kesten, J. Magano, D. Drieze, Synthetic Communications, 32(3), 411-417 (2002)), or using a similar method.

More specifically, carbonyl form (XI) can be obtained by reacting compound (XIII) with an equivalent amount or an excess amount of aniline derivative (IV) in a solvent, and in the presence of a base.

The solvent is, for example, THF or toluene, and is preferably, for example, THF.

The base is, for example, lithiumdiisopropylamide, lithium hexamethyldisilazide, n-butyl lithium, sodium hydride, or sodium amide, and is preferably, for example, lithium diisopropylamide or lithium hexamethyldisilazide.

The reaction is normally carried out at approximately −78° C. to approximately 25° C. for approximately four hours to approximately four days, or preferably for one day.

<Reaction Process 4>

Reaction process 4 particularly shows an example of preparing compound (XV) and compound (XVI), which belong to compound I shown in formula (1), from compound (XIV).

Compound (XIV) is compound I in which $R^1$ is a halogen atom such as an iodine atom, bromine atom, or chlorine atom, and is preferably an iodine atom.

Compounds (XV) and (XVI) refer to compounds in which $R^1$ is an alkynyl group or alkenyl group, and the unsaturated bond is located between the carbon directly bound to the benzene ring carrying $R^2$ and $R^3$ and the carbon adjacent to this carbon. Furthermore, Rg-Rj denote substituents on the unsaturated bond.

Preparation of Compound (XV)

Conversion from compound (XIV) to compound (XV) can be carried out, for example, using the Sonogashira method (K. Sonogashira, Y. Tohda and N. Hagihara, Tetrahedron Lett. 16, 4467-4470 (1975)). Specifically, compound (XV) can be obtained by reacting compound (XIV) with an alkyne in an appropriate solvent such as THF, in the presence of a catalytic amount of palladium complex such as $(PPh_3)_2PdCl_2$, and a catalytic amount of copper reagent such as copper iodide, and further in the presence of an appropriate base such as triethylamine or Hunig's base. Normally, the reaction is carried out at approximately 10° C. to approximately 100° C., and preferably at approximately 40° C. to 60° C., for approximately two hours to approximately two days.

Preparation of Compound (XVI) (1)

The conversion from compound (XIV) to compound (XV) can be performed according to the conversion method of 5-iodinated or 5-brominated benzoic acid derivative (II) to 5-vinylbenzoic acid derivative (III), shown in reaction process 1.

More specifically, compound (XVI) can be obtained by reacting compound (XI) with a vinylated organometallic reagent in an appropriate solvent, in the presence of a transition metal catalyst. Examples of the solvent are dimethylformamide, THF, DMSO, isopropanol, methanol, and ethanol, and preferable examples are THF and isopropanol. The transition metal catalyst is, for example, a palladium complex, and specific examples include $Pd(PPh_3)_4$, $(PhCN)_2PdCl_2$, $(MeCN)_2PdCl_2$, $Pd(dppf)Cl_2$, and $(PPh_3)_2PdCl_2$. The vinylated metallic reagent is, for example, vinylated magnesium reagent, vinylated aluminum reagent, vinylated silicon reagent, vinylated boron reagent, vinylated zinc reagent, or vinylated tin reagent, and is preferably, for example, vinylated tin reagent (Stille method) or vinylated boron reagent (Suzuki method). An appropriate base such as triethylamine, Hunig's base, potassium carbonate, cesium carbonate, sodium hydroxide, potassium hydroxide, and sodium ethylate can be added to the reaction system as necessary.

Normally, the reaction can be carried out at approximately 15° C. to approximately 130° C., and preferably at approximately 60° C., for approximately four hours to approximately four days, and preferably for approximately ten hours.

The reaction can be easily performed on reference to the following literature:

a) J. K. Stille, Angew. Chem., Int. Ed. Engl. 1986, 25, 508-524;
b) N. Miyaura, A. Suzuki, Chem. Rev. 1995, 95, 2457-2483;
c) A. Suzuki, J. Organomet. Chem., 1999, 576, 147-168; and
d) Suzuki, A, In Metal-Catalyzed Cross Coupling Reactions; Diederich, F., Stang, P. J., Eds.; VCH: Weinheim, 1998; pp 49-97.

Preparation of Compound (XVI) (2)

Compound (XVI) can also be obtained by reducing the aforementioned compound (XV).

The reduction method is, for example, a method of performing a hydrogenation in a solvent in the presence of a Lindlar catalyst. The solvent is, for example, ethanol, methanol, or hexane. Normally, the reaction is carried out at approximately 10° C. to approximately 30° C., preferably at approximately 22° C. (room temperature), for approximately ten minutes to approximately two days.

<Reaction Process 5>

Reaction process 5 particularly shows the method of preparing compound (XVIII), which belongs to compound (I) shown in formula (1). When $R^6$ of compound (X) obtained from Reaction processes 1 and 2 is specified as in compound (XVII), compound (XVIII) can be prepared using reaction process 5 (wherein $R^k$ and $R^m$ denote individually a hydrogen atom or a substituted or unsubstituted C1-C4 alkyl group. An arbitrary hydrogen atom in a repeating unit represented by above —[$CH_2$]m- (m is an integer from 1 to 4) may be replaced with a group represented by $R^c$; $R^c$ represents a C1-C4 alkyl group, an aryl group, or a heteroaryl group, $R^c$ may be substituted with a hydroxyl group that may be protected with a protecting group, and when two or more hydrogen atoms are each substituted with $R^c$, each $R^c$ may be identical to or different from each other.

In reaction process 5, Rm-M-X denotes an organometallic reagent, and for example, M is magnesium, zinc, and such, and X denotes a halogen (for example, bromine, iodine, or chlorine, and preferably bromine or iodine) (Grignard method). The organometallic reagent represented by Rm-M-X is, for example, alkyl magnesium bromide or alkyl magnesium iodide, and preferably alkyl magnesium bromide is used.

Preparation of Compound (XVIII)

Conversion of compound (XVII) to compound (XVIII) can be carried out, for example, by using the Grignard method. Specifically, compound (XVIII) can be obtained by dissolving compound (XVII) in an appropriate solvent such as THF or diethyl ether, preferably THF, and by adding an organometallic reagent such as alkyl magnesium bromide or alkyl magnesium iodide, preferably alkyl magnesium bromide, which reacts with the carbonyl. The organometallic reagent is added at a low temperature and is gradually warmed. Normally, the reaction is carried out at approximately −80° C. to 40° C., preferably at approximately −50° C. to 0° C., and for approximately one hour to approximately one day.

<Reaction Process 6>

The reaction process 6 described above indicates a method for manufacturing a compound (I) of formula (1), particularly the compound (XXII). The compound (XIX) can be prepared using the reaction process 1 or 2. $R^n$ and $R^o$ independently represent a hydrogen atom, or a C1-C4 alkyl group which may be substituted.

Preparation of the Compound (XXI)

The compound (XXI) can be prepared from either the compound (XIX) or the compound (CXX).

The compound (XX) can be obtained by reacting the compound (XIX) with a suitable oxidizing agent in a suitable solvent. In some cases, a combination of a catalytic amount of an oxidizing agent and an equimolar amount or more of a reoxidizing agent to the source material can be used.

Examples of the suitable solvent include acetone and tetrahydrofuran. Examples of the oxidizing agent described above include osmium tetroxide. Examples of the suitable reoxidizing agent include N-methylmorpholine-N-oxide and hydrogen peroxide.

The reaction described above can be performed at 0° C. to room temperature, and usually for one hour to ten days, preferably for about one day.

The conversion from the olefin compound (XIX) to the aldehyde compound (XXI) can be achieved by reacting the source compound with a suitable oxidizing agent in a suitable solvent.

Examples of the suitable solvent include methylene chloride and tetrahydrofuran. Examples of the suitable oxidizing agent include ozone (dimethylsulfide, triphenylphosphine, and so on are used for reducing ozonide), osmium tetroxide-sodium metaperiodate, and ruthenium chloride-sodium metaperiodate.

The reaction described above can be done at −78° C. to room temperature, and usually for one hour to ten days, preferably for about one day.

The conversion from the diol compound (XX) to the aldehyde compound (XXI) can be achieved by reacting the compound (XX) with a suitable agent for oxidative cleavage in a suitable solvent. Examples of the suitable solvent include acetone, tetrahydrofuran, benzene, toluene, water, acetic acid, and hydrous methylene chloride. Examples of the suitable agent for oxidative cleavage include sodium metaperiodate, potassium metaperiodate, and lead tetraacetate.

The reaction described above can be performed at 0° C. to room temperature, and usually for one hour to ten days, preferably for about one day.

Preparation of the Compound (XXIII)

The conversion from the aldehyde compound (XXI) to the amino compound (XXIII) can be achieved by reacting the compound XXI) with the amine (XXII) in a suitable solvent in the presence of a suitable reducing agent, and as necessary, a suitable acid.

Examples of the suitable solvent include methanol, ethanol, and tetrahydrofuran. Examples of the suitable reducing agent include sodium cyanoborohydride, sodium triacetoxyborohydride, and borane-pyridine complex. Examples of the suitable acid include hydrochloric acid, acetic acid, and trifluoroacetic acid. The reaction described above can be performed usually at about 0° C. to 80° C., and usually for one hour to ten days, preferably for about one day.

<Reaction Process 7>

The reaction process 7 described above indicates a method for manufacturing a compound (I) of formula (1), particularly the compound (When the oximether moiety of the compound (1) is Z form, the compound (XXI) can be prepared using the reaction process 6.

Preparation of the Compound (XXIV)

The conversion from the compound (X), (XII), (XIV), and (XVI) to the compound (XXIV) can be carried out using a suitable acid.

Examples of the suitable solvent include tetrahydrofuran, methylene chloride, toluene, and ethanol, and preferably include tetrahydrofuran. Examples of the acid described above include PPTS (pyridinium p-toluenesulfonate), p-toluenesulfonic acid, and hydrochloric acid, and preferably include PPTS.

The reaction described above can be performed at room temperature to about 100° C. for about one hour to two days, preferably for about one day.

So far, examples of the methods of producing compound I of the present invention have been shown. The target compounds shown in reaction processes 1 to 7 can be isolated and purified by applying conventional chemical procedures such as extraction, concentration, distillation, crystallization, filtration, recrystallization, and various types of chromatography.

The compounds of the present invention and their pharmaceutically acceptable salts comprise all stereoisomers of compound I represented by formula (1) (for example, enantiomers and diastereomers (comprising cis- and trans- geometric isomers)), racemates of the isomers, and other mixtures. In particular, in the present invention, compound I comprises stereoisomers.

Furthermore, compounds of the present invention and pharmaceutically acceptable salts thereof may exist as tautomers such as keto and enol forms, imine and enamine forms, and respective mixtures thereof. Tautomers exist in solution as a mixture of a tautomeric set. In a solid state, one of the tautomers is usually dominant. Although only one tautomer may be stated, the present invention comprises all tautomers of the compounds of this invention.

In addition, atropisomers of the present invention are also comprised in the present invention. Atropisomers mean isomers of compound I represented by formula (1) which can be separated into those in which rotation is restricted.

These isomers can be isolated by conventional methods that utilize differences in physicochemical properties between the isomers. For example, racemic compounds can be separated into sterically pure isomers by conventional optical resolution methods, such as methods of performing an optical resolution by derivatization to diastereomeric salts with optically active acids such as tartaric acid. Mixture of diastereomers can be separated using fractional crystallization, and various types of chromatography (for example, thin layer chromatography, column chromatography, and gas chromatography).

When compound I of the present invention is obtained in a free form, it can be converted to a salt that can be formed with compound I, or a hydrate or solvate thereof, according to conventional methods.

Furthermore, when compound I of the present invention is obtained as a salt, hydrate, or solvate of compound I, it can be converted to a free form of compound I according to conventional methods.

Compound I of the present invention, or a pharmaceutically acceptable salt thereof, has an excellent MEK inhibitory effect, is extremely stable in vivo and soluble in water, and is useful as a preventive agent or therapeutic agent (and particularly as a therapeutic agent) for proliferative diseases. Furthermore, compound I of the present invention, or a pharmaceutically acceptable salt thereof, is useful as a preventive agent or therapeutic agent (and particularly as a therapeutic agent) for various cancers such as breast cancer, colorectal cancer, ovarian cancer, lung cancer, pancreatic cancer, liver cancer, uterine cancer, brain cancer, prostate cancer, acute leukemia, gastric cancer, and non-small cell lung cancer; psoriasis, restenosis, autoimmune diseases, and atherosclerosis; or diseases such as sequelae of heart failure, xenograft rejection, osteoarthrosis, chronic rheumatoid arthritis, asthma, cystic fibrosis, hepatomegaly, cardiac hypertrophy, Alzheimer's disease, diabetes, septic shock and HIV infection. It is particularly useful as a preventive agent or therapeutic agent (and particularly as a therapeutic agent) against cancers in which MEK is overexpressed.

Furthermore, the present invention relates to methods of preventing or treating proliferative diseases such as cancers.

Another embodiment of the present invention encompasses methods of treating solid or hematopoietic MEK-related (comprising Ras-related) cancers. Examples of cancer are breast cancer, colorectal cancer, ovarian cancer, lung cancer, pancreatic cancer, liver cancer, uterine cancer, brain cancer, prostate cancer, acute leukemia, gastric cancer, and non-small cell lung cancer.

These methods comprise administering a therapeutically effective amount of a pharmaceutical composition comprising the disclosed compound I, or a pharmaceutically acceptable salt thereof, to a patient who needs such treatment, or to a patient suffering from an above-mentioned disease or condition.

When using the pharmaceutical composition of the present invention as a MEK inhibitor, or as a therapeutic or preventive agent against proliferative diseases, the methods of administration include oral, endorectal, parenteral (intravenous, intramuscular, or subcutaneous), intracisternal, vaginal, intraperitoneal, intravesical, local (drip infusion, powder, ointment, gel, or cream) application, and inhalation (intraoral or nasal spray). The dosage forms include tablets, capsules, granules, powders, pills, aqueous and non-aqueous solutions for oral use and suspensions, and pareneteral solutions loaded into containers adapted for packaging into individual doses. Furthermore, the dosage forms can be adapted to various methods of administration comprising a controlled-release formulation such as subcutaneous implants.

The above-mentioned formulations are produced by well known methods, using additives such as excipients, lubricants (coatings), binders, disintegrators, stabilizers, corrigents, and diluents.

Excipients are, for example, starches such as potato starch and cornstarch, lactose, crystalline cellulose, and calcium hydrogen phosphate.

Coatings are, for example, ethylcellulose, hydroxypropylcellulose, hydroxypropylmethylcellulose, shellac, talc, carnauba wax, and paraffin.

Binders are, for example, polyvinylpyrrolidone, macrogol, and the same compounds as the aforementioned excipients.

Disintegrators are, for example, the same compounds as the aforementioned excipients, and croscarmellose sodium, sodium carboxymethylstarch, and chemically-modified starch celluloses such as cross-linked polyvinylpyrrolidone.

Stabilizers are, for example, paraoxybenzoic acid esters such as methylparaben and propylparaben; alcohols such as chlorobutanol, benzylalcohol, and phenylethylalcohol; benzalkonium chloride; phenols such as phenol and cresol; thimerosal; dehydroacetic acid; and sorbic acid.

Corrigents are, for example, sweeteners, sour flavorings and flavorings which are conventionally used.

Furthermore, ethanol, phenol, chlorocresol, purified water, distilled water, and such may be used as solvents for producing liquid agents.

Surfactants or emulsifiers are, for example, polysorbate 80, polyoxyl 40 stearate, and lauromacrogol.

When using the pharmaceutical compositions of the present invention as MEK inhibitors, or as therapeutic or preventive agents against proliferative diseases, the dose of the compounds of the present invention or pharmaceutically acceptable salts thereof differs depending on the symptoms, age, body weight, relative health condition, presence of other medication, method of administration, and such. For example, a generally effective dose for an oral agent as the active ingredient (compound I) for a patient (a warm-blooded animal, especially a human) is a daily dose of preferably 0.1 to 1000 mg per kg body weight, more preferably 1 to 30 mg per kg body weight, and the daily dose for an adult patient with a normal body weight is preferably in the range of 10 to 800 mg. For a parenteral agent, the daily dose is preferably 0.1 to 1000 mg per kg body weight, more preferably 10 to 800 mg per kg body weight. Preferably such a dose is administered at one time or in several portions per day, depending on the symptoms.

BEST MODE FOR CARRYING OUT THE INVENTION

Herein below, the present invention will be more specifically described using Examples, however, it is not to be construed as being limited thereto.

NMR analysis was performed using JNM-EX270 (270 MHz, JEOL) or JNM-GSX400 (400 MHz, JEOL), and NMR data were expressed as chemical shifts in ppm (parts per million) (δ), and the deuteriurm lock signal from the sample solvent was referenced.

Mass spectrum data was obtained using a mass spectrometer JMS-DX303 (JEOL) or JMS-SX/SX102A (JEOL), or a micromass spectrometer (Navigator, Finnigan) equipped with Agilen 1100 gradient high performance liquid chromatography (Agilent Technologies).

Specific rotation was measured using sodium D-line (589 nm) at room temperature.

Commercially available reagents were used without further purification. "Room temperature" means temperatures ranging from about 20° C. to 25° C. All non-aqueous reactions were carried out under a nitrogen atmosphere. Concentration or distillation of solvents under reduced pressure means that a rotary evaporator was used.

In the preparation of compounds, functional groups were protected with protecting groups as required to obtain target molecules, followed by removal of the protecting groups. Selection of protecting groups, as well as protection and removal of protection, were carried out, for example, according to a method described in Greene and Wuts, "Protective groups in Organic Synthesis" (second edition, John Wiley & Sons, 1991).

Example 1

Production of (E)-3,4-difluoro-2-(2-fluoro-4-iodo-phenylamino)-N-(2-hydroxy-ethoxy)-5-[(2-hydroxy-ethoxyimino)-methyl]-benzamide (Compound 1)

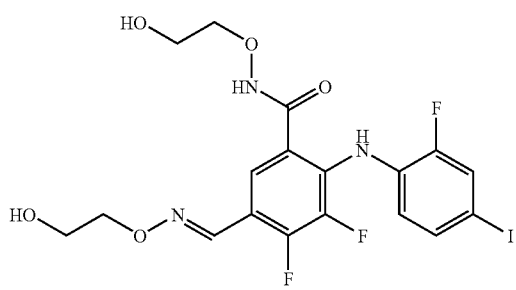

Process A

Preparation of 2,3,4-trifluoro-5-iodo-benzoic Acid

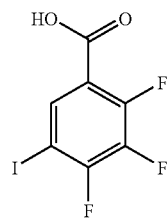

2,3,4-Trifluoro-5-iodo-benzoic acid was prepared according to a method described in the literature (F. Mongin, E. Marzi, and M. Schlosser, European Journal of Organic Chemistry, 2771-2777 (2001), JP-A Hei 11-80075, JP-A Hei 11-80076, WO9,807,682).

Process B

Preparation of 2,3,4-trifluoro-5-vinyl-benzoic Acid

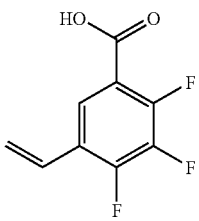

The solution of 2,3,4-Trifluoro-5-iodo-benzoic acid (447 mg, 1.48 mmol) prepared in Process A was dissolved in tetrahydrofuran (10 mL), and tris(dibenzylideneacetone)dipalladium (product number 32877-4, Sigma-Aldrich Inc.) (45 mg, 0.05 mmol), tri-2-furylphosphine (23 mg, 0.01 mmol), and vinyl tributyltin (865 mL, 3.0 mmol) were added thereto. The mixture was stirred at 40° C. for three hours.

After completion of the reaction, insoluble material was removed using a celite column, 1 mol/L solution of sodium hydroxide (30 mL) was added thereto, and methylene chloride was added to separate the phases. A 1 mol/L solution of sodium hydroxide (30 mL) was added to the organic layer, and the phases were separated again. The resultant aqueous layer was acidified with 1 mol/L hydrochloric acid solution (60 mL), and was extracted with methylene chloride (50 mL) twice. The phases were separated, and the resultant organic layer was dried over anhydrous sodium sulfate, and filtered. The product obtained by distillation of the solvent under reduced pressure was then washed with hexane, filtered, and dried to give 2,3,4-trifluoro-5-vinyl-benzoic acid (248.9 mg, 83% yield) as a light yellow solid.

$^1$H-NMR (CDCl$_3$, 270 MHz) δ (PPM): 5.54 (1H, d, J=11.2 Hz), 5.92 (1H, d, J=17.8 Hz), 6.78 (1H, dd, J=17.8, 11.2 Hz), 7.95 (1H, td, J=7.6, 2.6 Hz)

EIMS m/z 202 (M$^+$.)

Process C

Preparation of 3,4-difluoro-2-(2-fluoro-4-iodo-phenylamino)-5-vinyl-benzoic Acid

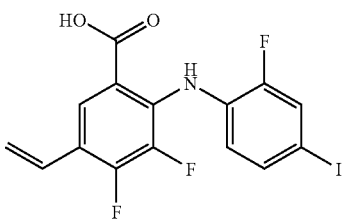

2-Fluoro-4-iodoaniline (5.056 g, 21.336 mmol) was dissolved in anhydrous tetrahydrofuran (30 mL), and 2.0 M lithium diisopropylamide (heptane/tetrahydrofuran/ethylbenzene solution) (13 mL, 26 mmol) was added dropwise thereto at −78° C. under an argon atmosphere whilst stirring.

Five minutes later, a solution of 2,3,4-trifluoro-5-vinyl-benzoic acid (1.724 g, 8.534 mmol) prepared in Process B in anhydrous tetrahydrofuran (20 mL) was added dropwise to the reaction mixture. The reaction temperature was allowed to gradually rise to room temperature. The reaction mixture was then stirred for three days.

One mol/L hydrochloric acid was added until the pH of the reaction mixture reached 3. The solution was then extracted with ethyl acetate. The extract was successively washed with water and saturated brine, and the organic layer was dried over anhydrous sodium sulfate, and then filtered. The solvent was distilled off under reduced pressure, and the resultant dark brown solid was triturated with methylene chloride to give 3,4-difluoro-2-(2-fluoro-4-iodo-phenylamino)-5-vinyl-benzoic acid (2.352 g, 66% yield) as a light yellow solid.

$^1$H-NMR (CD$_3$OD, 270 MHz) δ (PPM): 5.41 (1H, d, J=11.5 Hz), 5.86 (1H, d, J=17.2 Hz), 6.76 (1H, td, J=8.6, 5.6 Hz), 6.79 (1H, dd, J=17.2, 11.5 Hz), 7.41 (1H, m), 7.48 (1H, dd, J=10.6, 2.0 Hz), 8.05 (1H, dd, 7.9, 2.0 Hz)

ESI (LC/MS positive mode) m/z 420 (M+H)

Process D

Preparation of 3,4-difluoro-2-(2-fluoro-4-iodo-phenylamino)-5-formyl-benzoic Acid

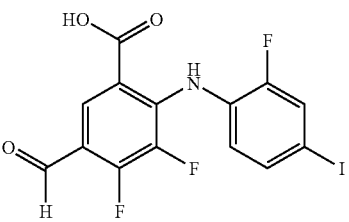

3,4-Difluoro-2-(2-fluoro-4-iodo-phenylamino)-5-vinyl-benzoic acid (200 mg, 0.477 mmol) prepared in Process C was dissolved in tetrahydrofuran (20 mL) and water (1 mL). To this reaction solution, 0.1 M aqueous solution of osmium tetroxide (1.0 mL) and sodium metaperiodate (510 mg, 2.39 mmol) were added at room temperature, and the mixture was stirred for two hours. Insoluble material was removed through a celite column, and the solution was extracted with ethyl acetate.

The extract was washed successively with water and saturated brine, and the organic layer was dried over anhydrous sodium sulfate, and then filtered. The solvent was distilled off under reduced pressure, and the resultant dark brown solid was triturated with methanol to give 3,4-difluoro-2-(2-fluoro-4-iodophenylamino)-5-formyl-benzoic acid (133.6 mg, 66% yield) as a light yellow solid.

$^1$H-NMR (DMSO-d$_6$, 270 MHz) δ (PPM) 7.11 (1H, td, J=8.6, 3.6), 7.53 (1H, m), 7.71 (1H, dd, J=10.2, 1.7 Hz), 8.27 (1H, dd, J=7.3, 1.3 Hz), 10.00 (1H, s), 10.08 (1H, br. s)

ESI (LC/MS positive mode) m/z 422 (M+H)

Process E

Preparation of (E)-N-[2-(t-butyl-dimethyl-silanyloxy)-ethoxy]-5-{[2-(t-butyl-dimethyl-silanyloxy)-ethoxyimino]-methyl}-3,4-difluoro-2-(2-fluoro-4-iodo-phenylamino)-benzimide]

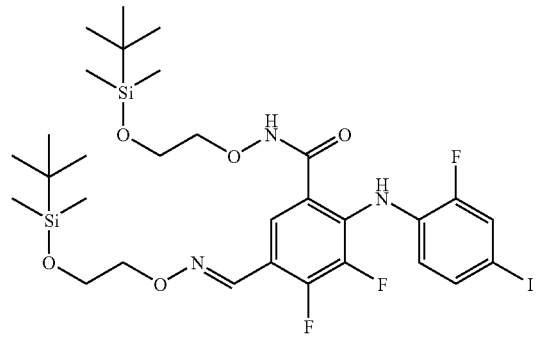

3,4-Difluoro-2-(2-fluoro-4-iodophenylamino)-5-formyl-benzoic acid (130 mg, 0.309 mmol) prepared in Process D was dissolved in anhydrous methylene chloride (5 mL). To this solution, 1-hydroxybenzotriazole (42 mg, 0.309 mmol), 1-ethyl-3-(3-dimethylaminopropyl)-carbodiimide hydrochloride (177 mg, 0.926 mmol), and N,N-diisopropylethylamine (161 μL, 0.926 mmol) were added at room temperature under an argon stream, and the mixture was stirred well. O-[2-(t-butyl-dimethyl-silanyloxy)-ethyl]-hydroxyamine (177 mg, 0.926 mmol) was then added thereto, and the mixture was stirred for 17 hours. After completion of the reaction, the reaction solution was extracted with ethyl acetate.

The extract was washed successively with water and saturated brine, and the organic layer was dried over anhydrous sodium sulfate, and then filtered. The solvent was distilled off under reduced pressure, and the resultant brown oil was purified with Mega Bond Elut silica gel (10 g, Varian, Inc.). From the fractions eluted with 10% ethyl acetate/hexane, N-[2-(t-butyl-dimethyl-silanyloxy)-ethoxy]-5-{[2-(t-butyl-dimethyl-silanyloxy)-ethoxyimino]-m ethyl}-3,4-difluoro-2-(2-fluoro-4-iodo-phenylamino)-benzimide (137.1 mg, 58% yield) was obtained as a light yellow solid.

$^1$H-NMR (CDCl$_3$, 270 MHz) δ (PPM): 0.08 (6H, s), 0.09 (6H, s), 0.87 (9H, s), 0.91 (9H, s), 3.92 (4H, m), 4.12 (2H, m), 4.26 (2H, m), 6.64 (1H, td, J=8.6, 5.3 Hz), 7.35 (1H, m), 7.41 (1H, dd, J=10.3, 1.7 Hz), 7.73 (1H, br. s), 8.22 (1H, s), 8.78 (1H, br. s), 9.43 (1H, br. s)

EIMS m/z 767 (M$^+$)

Process F

Preparation of (E)-3,4-difluoro-2-(2-fluoro-4-iodo-phenylamino)-N-(2-hydroxy-ethoxy)-5-[(2-hydroxy-ethoxyimino)-methyl]-benzamide (Compound 1)

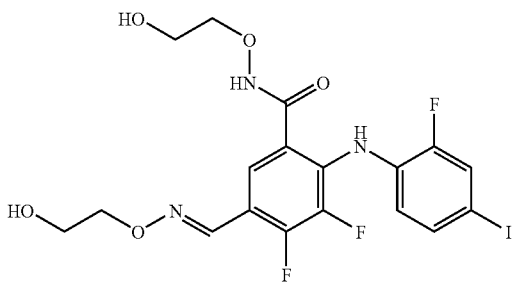

N-[2-(t-butyl-dimethyl-silanyloxy)-ethoxy]-5-{[2-(t-butyl-dimethyl-silanyloxy)-ethoxyimino]-methyl}-3,4-difluoro-2-(2-fluoro-4-iodo-phenylamino)-benzimide (410 mg, 0.534 mmol) prepared in Process E was dissolved in anhydrous tetrahydrofuran (20 mL), tetra-n-butylammonium fluoride (1 mol/L solution in tetrahydrofuran) (1.4 mL, 1.4 mmol) was added dropwise thereto at room temperature, and then the mixture was stirred for 4 hours.

After completion of the reaction, the solvent was distilled off under reduced pressure, and the yellow oil was extracted with ethyl acetate. The extract was washed successively with water and saturated brine, and the organic layer was dried over anhydrous sodium sulfate, and filtered. The solvent was distilled off under reduced pressure, and the resultant brown oil was purified with Mega Bond Elut silica gel (5 g, Varian, Inc.). The light yellow solid obtained from the fractions eluted with 100% ethyl acetate was triturated with ethyl acetate to give 3,4-difluoro-2-(2-fluoro-4-iodo-phenylamino)-N-(2-hydroxy-ethoxy)-5-[(2-hydroxy-ethoxyimino)-methyl]-benzamide (Compound 1) (134 mg, 47% yield) as a white solid.

$^1$H-NMR (CD$_3$OD, 270 MHz) δ (PPM): 3.72 (2H, t, J=4.9 Hz), 3.82 (2H, t, J=4.9 Hz), 3.95 (2H, dd, J=4.9, 4.3 Hz), 4.26 (2H, dd, J=4.9, 4.6), 6.72 (1H, td, J=8.6, 4.3 Hz), 7.39 (1H, m), 7.47 (1H, dd, J=10.6, 1.6 Hz), 7.81 (1H, dd, J=4.9, 1.6 Hz), 8.29 (1H, s)

ESI (LC/MS positive mode) m/z 540 (M+H)

Example 2

Production of (E)-2-(4-ethyl-2-fluoro-phenylamino)-3,4-difluoro-N-(2-hydroxy-ethoxy)-5-[(2-hydroxy-ethoxyimino)-methyl]-benzamide (Compound 2)

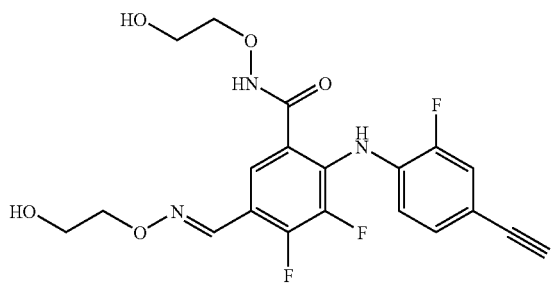

Process A

Preparation of (E)-3,4-difluoro-2-(2-fluoro-4-trimethylsilanylethynyl-phenylamino)-N-(2-hydroxy-ethoxy)-5-[(2-hydroxy-ethoxyimino)-methyl]-benzamide

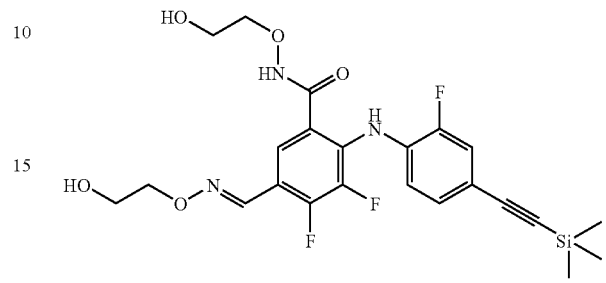

3,4-Difluoro-2-(2-fluoro-4-iodo-phenylamino)-N-(2-hydroxy-ethoxy)-5-[(2-hydroxy-ethoxyimino)-methyl]-benzamide (334 mg, 0.620 mmol) prepared in Example 1 was dissolved in anhydrous tetrahydrofuran (10 mL). (PPh$_3$)$_2$PdCl$_2$ (20,867-1, Sigma-Aldrich Inc.) (21 mg, 0.031 mmol), copper iodide (11 mg, 0.0062 mmol), N,N-diisopropylethylamine (130 μL, 0.774 mmol), and trimethylsilylacetylene (1 mL) were then added thereto at room temperature. The mixture was stirred at 50° C. for two hours.

After completion of the reaction, the solvent was distilled off under reduced pressure, and the brown oil was extracted with ethyl acetate. The extract was washed successively with water and saturated brine, and the organic layer was dried over anhydrous sodium sulfate, and then filtered. The solvent was distilled off under reduced pressure, and the resultant brown oil was purified with Presep silica gel (10 g, Wako Pure Chemical Industries, Ltd.). From the fractions eluted with 10% methanol/methylene chloride, 3,4-difluoro-2-(2-fluoro-4-trimethylsilanylethynyl-phenylamino)-N-(2-hydroxy-ethoxy)-5-[(2-hydroxy-ethoxyimino)-methyl]-benzamide (239.6 mg, 79% yield) was obtained as a yellow solid.

$^1$H-NMR (CDCl$_3$, 270 MHz) δ (PPM): 0.24 (9H, s), 2.58 (1H, br. s), 3.80 (2H, m), 3.95 (2H, m), 4.11 (2H, m), 4.31 (2H, m), 6.77 (1H, td, J=8.2, 5.3 Hz), 7.15 (1H, dd, J=6.6, 2.0 Hz), 7.18 (1H, dd, J=11.5, 1.7 Hz), 7.76 (1H, br. d, J=6.6 Hz), 8.23 (1H, s), 8.77 (1H, br. s), 9.75 (1H, br. s)

ESI (LC/MS positive mode) m/z 510 (M+H)

Process B

Preparation of (E)-2-(4-ethynyl-2-fluoro-phenylamino)-3,4-difluoro-N-(2-hydroxy-ethoxy)-5-[(2-hydroxy-ethoxyimino)-methyl]-benzamide (Compound 2)

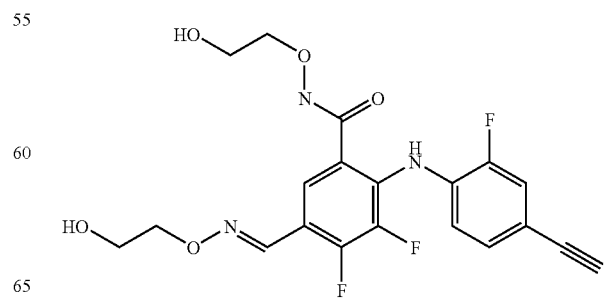

3,4-Difluoro-2-(2-fluoro-4-trimethylsilanylethynyl-phenylamino)-N-(2-hydroxy-ethoxy)-5-[(2-hydroxy-ethoxyimino)-methyl]-benzamide (231.1 mg, 0.454 mmol) prepared in Process A was dissolved in anhydrous tetrahydrofuran (10 mL). Next, tetra-n-butylammonium fluoride (1 mol/L solution in tetrahydrofuran) (0.5 mL, 0.5 mmol) was added dropwise thereto at room temperature, and the mixture was stirred for 30 minutes.

After completion of the reaction, the solvent was distilled off under reduced pressure, and the yellow oil was extracted with ethyl acetate. The extract was washed successively with water and saturated brine, and the organic layer was dried over anhydrous sodium sulfate, and then filtered. The solvent was distilled off under reduced pressure, and the resultant yellow oil was purified with Mega Bond Elut silica gel (10 g, Varian, Inc.). The light yellow solid obtained from the fractions eluted with 5% methanol/methylene chloride was triturated with 20% ethyl acetate/hexane to give 2-(4-ethynyl-2-fluoro-phenylamino)-3,4-difluoro-N-(2-hydroxy-ethoxy)-5-[(2-hydroxy-ethoxyimino)-methyl]-benzamide (Compound 2) (147.3 mg, 74% yield) as a light yellow solid.

$^1$H-NMR (CD$_3$OD, 270 MHz) δ (PPM): 3.45 (1H, s), 3.72 (2H, dd, J=4.9, 4.3 Hz), 3.82 (2H, dd, J=5.3, 4.6 Hz), 3.96 (2H, dd, 4.9, 4.3 Hz), 4.27<(2H, t, J=4.9 Hz), 6.85 (1H, td, J=8.6, 4.6 Hz), 7.18 (2H, m), 7.83 (1H, dd, J=7.0, 2.0 Hz), 8.39 (1H, s)

ESI (LC/MS positive mode) m/z 438 (M+H)

Example 3

Production of (E)-3,4-difluoro-2-(2-fluoro-4-iodo-phenylamino)-N-(2-hydroxy-ethoxy)-5-hydroxyiminomethyl)-benzamide (Compound 3)

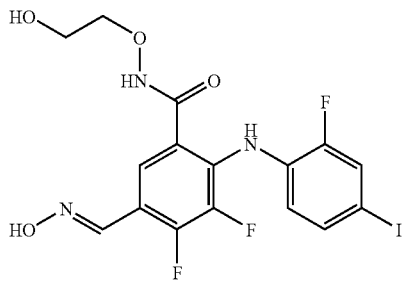

Process A

Preparation of N-[2-(t-butyldimethylsilanyloxy)-ethoxy]-3,4-difluoro-2-(2-fluoro-4-iodophenylamino)-5-vinyl-benzamide

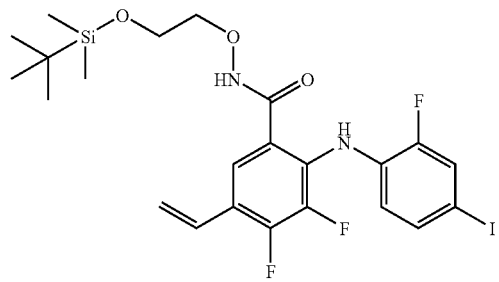

3,4-Difluoro-2-(2-fluoro-4-iodo-phenylamino)-5-vinyl-benzoic acid (6.2 g, 14.8 mmol) prepared in Process C of Example 1 was dissolved in methylene chloride (100 mL). 0-[2-(t-butyldimethylsilanyloxy)-ethyl]-hydroxylamine (3.40 g, 17.8 mmol), 1-ethyl-3-(3-dimethylaminopropyl)-carbodiimide hydrochloride (3.40 g, 17.8 mmol), 1-hydroxybenzotriazole monohydrate (3.0 g, 22.1 mmol), and N,N-diisopropylethylamine (5.1 ml, 29.6 mmol) were added to this solution, and the mixture was stirred at room temperature for 20 hours.

The reaction solution was concentrated under reduced pressure, water (300 ml) was added, and the mixture was extracted with ethyl acetate (500 ml). The organic layer was washed with saturated brine (200 ml), dried over anhydrous sodium sulfate, and then concentrated under reduced pressure. The residue was purified by silica gel column chromatography (500 g, n-hexane/ethyl acetate (20:1)) to give N-[2-(t-butyldimethylsilanyloxy)-ethoxy]-3,4-difluoro-2-(2-fluoro-4-iodophenylamino)-5-vinyl-benzamide (6.36 g, 73%) as a light yellow solid.

$^1$H-NMR (CD$_3$OD, 270 MHz) δ (PPM) 0.07 (6H, s), 0.86 (9H, s), 3.91 (2H, dd, J=5.0, 4.0 Hz), 4.07 (2H, dd, J=5.0, 4.0 Hz), 5.44 (1H, d, J=11.2 Hz), 5.81 (1H, d, J=17.5 Hz), 6.57 (1H, td, J=8.9, 5.0 Hz), 6.74 (1H, dd, J=17.8, 10.9 Hz), 7.32 (1H, br. d, J=7.9 Hz), 7.37-7.42 (2H, m), 8.20 (1H, br. s), 9.38 (1H, br. s)

ESI (LC/MS positive mode) m/z 593 (M+H)

Process B

Preparation of N-[2-(t-butyldimethylsilanyloxy)-ethoxy]-3,4-difluoro-2-(2-fluoro-4-iodophenylamino)-5-formyl-benzamide

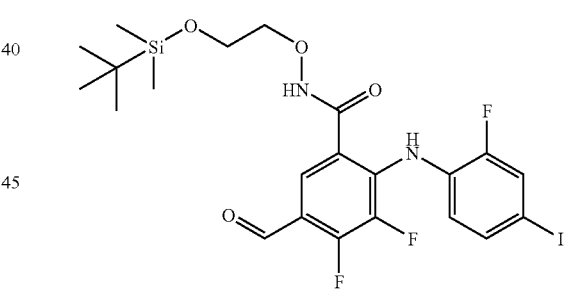

N-[2-(t-Butyldimethylsilanyloxy)-ethoxy]-3,4-difluoro-2-(2-fluoro-4-iodophenylamino)-5-vinyl-benzamide (6.35 g, 10.7 mmol) prepared in Process A was dissolved in a mixed solvent of THF (100 ml) and water (30 ml). Aqueous solution of osmium tetroxide (0.1 mM, 2 ml, 0.2 mmol), and sodium metaperiodate (9.0 g, 42.1 mmol) were added at 10° C., and the mixture was stirred at room temperature for 17 hours. Insoluble material was removed through a celite column, and the solution was extracted with ethyl acetate. The extract was washed successively with water and saturated brine, the organic layer was dried over anhydrous sodium sulfate, and the solvent was distilled off under reduced pressure. The residue was purified by silica gel chromatography (300 g, n-hexane/ethyl acetate (5:1)) to give N-[2-(t-butyldimethylsilanyloxy)-ethoxy]-3,4-difluoro-2-(2-fluoro-4-iodophenylamino)-5-formyl-benzamide (3.24 g, 51%) as a brown solid.

¹H-NMR (CD₃OD, 270 MHz) δ (PPM) 0.11 (6H, s), 0.78 (9H, s), 3.97 (2H, dd, J=5.1, 4.3 Hz), 4.13 (2H, dd, J=4.6, 4.3 Hz), 6.82 (1H, td, J=8.6, 4.1 Hz), 7.30-7.38 (2H, m), 7.78 (1H, dd, J=6.8, 2.2 Hz), 9.64 (2H, br s), 10.15 (1H, s)

ESI (LC/MS positive mode) m/z 595 (M+H)

Also, a byproduct compound, 3,4-difluoro-2-(2-fluoro-4-iodo-phenylamino)-5-formyl-N-(2-hydroxy-ethoxy)-benzamide (formula below) (1.96 g, 38%), in which TBDMS was removed, was obtained as a yellow solid.

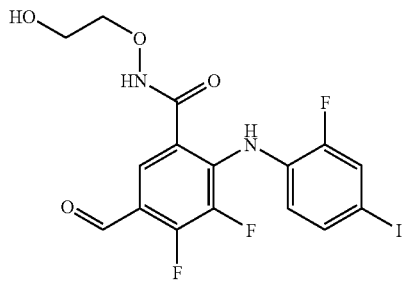

¹H-NMR (DMSOd-₆ 270 MHz) δ (PPM) 3.17 (1H, d, J=4.6 Hz), 3.59 (2H, t, J=4.6 Hz), 3.85 (2H, t, J=4.6 Hz), 6.99 (1H, td, J=8.9, 3.0), 7.48 (1H, d=8.3 Hz), 7.67 (1H, d, J=10.9 Hz), 7.86 (1H, d, J=6.9 Hz), 9.64 (1H, br. s), 10.02 (1H, s)

ESI (LC/MS positive mode) m/z 481 (M+H)

Process C

Preparation of (E)-N-[2-(t-butyldimethylsilanyloxy)-ethoxy]-3,4-difluoro-2-(2-fluoro-4-iodophenylamino)-5-(hydroxyiminomethyl)-benzamide

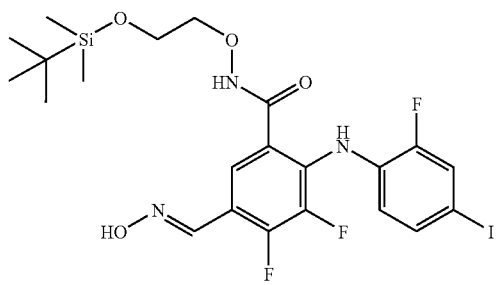

N-[2-(t-butyldimethylsilanyloxy)-ethoxy]-3,4-difluoro-2-(2-fluoro-4-iodophenylamino)-5-formyl-benzamide (10.5 mg, 17.7 μmol) prepared in Process B was dissolved in ethanol (1.5 ml). Hydroxylamine hydrochloride (40 mg, 0.57 mmol) and saturated aqueous solution of sodium bicarbonate (0.3 ml) were added thereto, and the mixture was stirred at room temperature for two hours. Water (5 ml) was added to the reaction solution, which was extracted with ethyl acetate (6 ml×3). The organic layers were combined, washed with saturated brine (8 ml), dried over anhydrous sodium sulfate, and concentrated under reduced pressure. The residue was purified with silica gel-column chromatography (Presep (r) silica gel, 10 g, Wako Pure Chemical Industries, Ltd., n-hexane/ethyl acetate (4:1)) to give N-[2-(t-butyldimethylsilanyloxy)-ethoxy]-3,4-difluoro-2-(2-fluoro-4-iodophenylamino)-5-(hydroxyiminomethyl)-benzamide (5.0 mg, 46%).

¹H-NMR (CD₃OD, 270 MHz) δ (PPM) 0.05 (6H×½, s), 0.09 (6H×½, s), 0.85 (9H×½, s), 0.87 (9H×½, s), 3.87-3.95 (2H, m), 4.09 (2H×½, dd, J=4.6, 4.3 Hz), 4.31 (2H×½, t, J=4.3), 6.59 (1H×½, td, J=8.6, 7.3 Hz), 6.66 (1H×½, td, J=8.6, 5.0 Hz), 7.35 (1H×½, br. d, J=9.2 Hz), 7.41 (1H×½, dt, J=10.2, 1.7 Hz), 7.60 (1H×½, br. s), 7.67 (1H×½, dd, J=6.6, 2.0 Hz), 8.25 (1H×½, s), 8.38 (1H×½, s), 8.55 (1H×½, dd, J=7.6, 1.7 Hz), 8.78 (1H×½, br. s), 9.27 (1H×½, br. s), 9.36 (1H×½, br. s), 9.46 (1H×½, br. s), 10.85 (1H×½, br. s)

ESI (LC/MS positive mode) m/z 610 (M+H)

Process D

Preparation of (E)-3,4-difluoro-2-(2-fluoro-4-iodo-phenylamino)-N-(2-hydroxy-ethoxy)-5-(hydroxyiminomethyl)-benzamide (Compound 3)

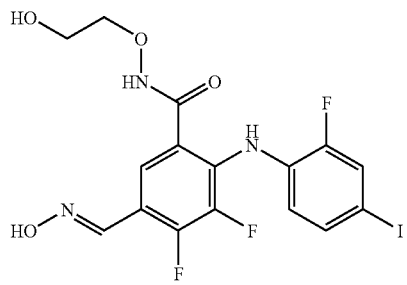

N-[2-(t-butyldimethylsilanyloxy)-ethoxy]-3,4-difluoro-2-(2-fluoro-4-iodophenylamino)-5-(hydroxyiminomethyl)-benzamide (a mixture of two geometric or atropisomers) (5.0 mg, 46%) prepared in Process C was dissolved in THF (1 ml), tetrabutylammonium fluoride (1 M solution in THF, 30 μl, 30 μmol) was added thereto, and the mixture was stirred at room temperature for five hours. Water (8 ml) was added to the reaction solution, which was extracted with ethyl acetate (8 ml×3). The organic layers were combined, washed with 0.1 N hydrochloric acid (8 ml) and saturated brine (8 ml), dried over anhydrous sodium sulfate, and concentrated under reduced pressure. The residue was purified with preparative thin layer chromatography (Silicagel 60 F254, 0.5 mm thickness, Merck & Co., Inc., CH₂Cl₂/MeOH (10:1)) to give 3,4-difluoro-2-(2-fluoro-4-iodo-phenylamino)-N-(2-hydroxy-ethoxy)-5-(hydroxyiminomethyl)-benzamide (Compound 3) (3.9 mg, 96%) as a white solid.

¹H-NMR (CD₃OD, 270 MHz) δ (PPM) 3.71 (2H, dd, J=4.9, 4.3 Hz), 3.93 (2H, dd, J=4.6, 4.3 Hz), 6.70 (1H, td, J=8.6, 4.3 Hz), 7.38 (1H, dt, J=8.3, 1.3 Hz), 7.46 (1H, dd, J=10.9, 2.0 Hz), 7.80 (1H, br. d, J=5.9 Hz), 8.21 (1H, s)

ESI (LC/MS positive mode) m/z 496 (M+H)

Example 4

(E)-3,4-Difluoro-2-(2-fluoro-4-iodo-phenylamino)-N-(2-hydroxy-ethoxy)-5-[(3-hydroxy-propoxy-imino)-methyl]-benzamide (Compound 4)

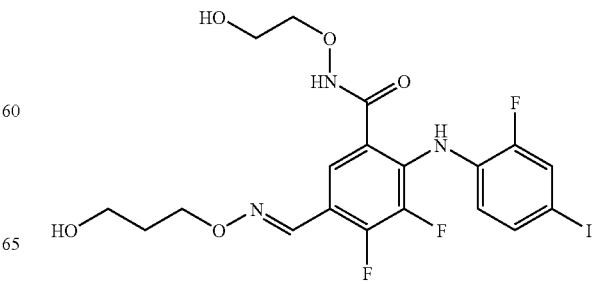

¹H-NMR (CD₃OD, 270 MHz) δ (PPM) 1.94 (2H, quin. J=6.3 Hz), 3.68 (2H, t, J=6.3 Hz), 3.72 (2H, dd, J=4.9, 4.3 Hz), 3.95 (2H, dd, J=4.9, 4.3 Hz), 4.29 (2H, t, J=6.3 Hz), 6.72 (1H, td, =8.6, 4.6 Hz), 7.39 (1H, dt, J=8.3, 1.7 Hz), 7.47 (1H, dd, J=10.6, 2.0 Hz), 7.81 (1H, dd, J=7.3, 2.0 Hz), 8.24 (1H, s)

ESI (LC/MS positive mode) m/z 554 (M+H)

Example 5

(E)-2-(4-Ethynyl-2-fluoro-phenylamino)-3,4-Difluoro-N-(2-hydroxy-ethoxy)-5-[(3-hydroxy-propoxyimino)-methyl]-benzamide (Compound 5)

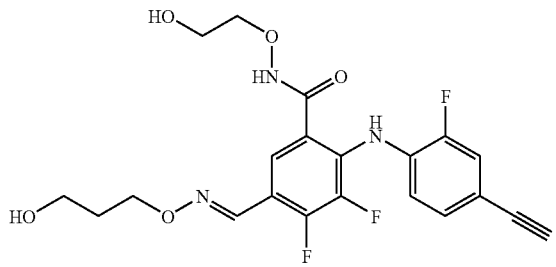

¹H-NMR (CD₃OD, 270 MHz) δ (PPM) 1.94 (2H, quin., J=6.3 Hz), 3.46 (1H, s), 3.68 (2H, dd, J=6.6, 6.3 Hz), 3.72 (2H, dd, J=4.6, 4.3 Hz), 3.96 (2H, dd, J=4.6, 4.3 Hz), 4.29 (2H, dd, J=6.6, 6.3 Hz), 6.84 (1H, td, J=8.2, 4.9 Hz), 7.17 (1H, br. d, J=8.9 Hz), 7.21 (1H, dd, J=13.9, 2.0 Hz), 7.84 (1H, br. d, J=5.6 Hz), 8.25 (1H, s)

ESI (LC/MS positive mode) m/z 452 (M+H)

Example 6

(E)-5-(Allyloxyimino-methyl)-3,4-difluoro-2-(2-fluoro-4-iodo-phenylamino)-N-(2-hydroxy-ethoxy)-benzamide

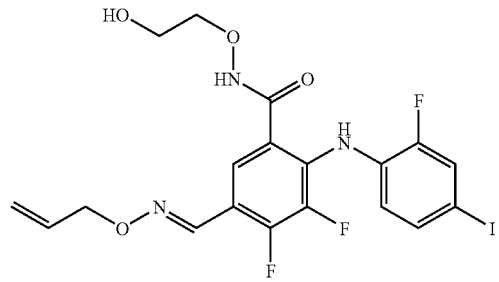

¹H-NMR (CD₃OD, 270 MHz) δ (PPM) 3.71 (2H, dd, J=4.9, 4.3 Hz), 3.94 (2H, dd, 3=4.9, 4.3 Hz), 4.69 (2H, dt, J=5.6, 1.3 Hz), 5.23 (1H, dd, J=10.6, 1.3 Hz), 5.33 (1H, dd, J=17.2, 1.7 Hz), 6.01 (1H, quadruple of triplet J=17.2, 10.6, 5.6 Hz), 6.71 (1H, td, J=8.6, 4.3 Hz), 7.38 (1H, d, J=8.2 Hz), 7.47 (1H, dd, J=10.6, 2.0 Hz), 7.80 (1H, dd, J=6.9, 2.0 Hz), 8.27 (1H, s)

ESI (LC/MS positive mode) m/z 536 (M+H)

Example 7

(E)-dl-5-[(2,3-Dihydroxy-propoxyimino)-methyl]-3,4-difluoro-2-(2-fluoro-4-iodo-phenylamino)-N-(2-hydroxy-ethoxy)-benzamide (Compound 7)

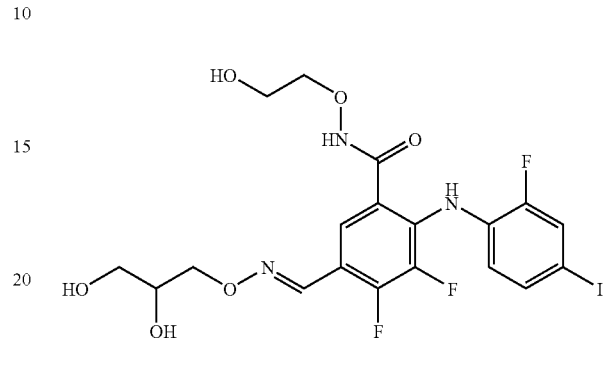

¹H-NMR (CD₃OD, 400 MHz) δ (PPM) 3.58 (1H, dd, J=11.2, 5.9 Hz), 3.63 (1H, dd, J=11.2, 54.9 Hz), 3.77 (2H, m), 3.95 (1H, m), 4.00 (2H, m), 4.16 (1H, dd, J=11.2, 6.3 Hz), 4.26 (1H, dd, J=11.2, 4.4 Hz), 6.67 (1H, td, J=8.8, 4.9 Hz), 7.36 (1H, d, J=8.3 Hz), 7.44 (1H, dd, J=10.7, 1.5 Hz), 7.89 (1H, br. d, J=6.3 Hz), 8.27 (1H, s)

ESI (LC/MS positive mode) m/z 684 (M+H)

Example 8

(E)-dl-5-[(2,3-Dihydroxy-propoxyimino)-methyl]-2-(4-ethynyl-2-fluoro-phenylamino)-3,4-difluoro-N-(2-hydroxy-ethoxy)-benzamide (Compound 8)

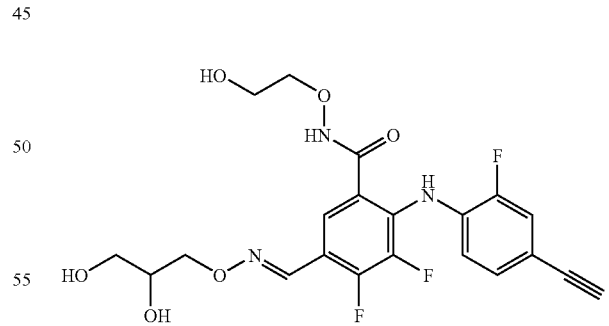

¹H-NMR (CD₃OD, 400 MHz) δ (PPM) 3.46 (1H, s), 3.60 (2H, m), 3.72 (2H, t, J=4.4 Hz), 3.95 (2H, t, J=4.4 Hz), 3.96 (1H, m), 4.18 (1H, dd, J=11.2, 6.3 Hz), 4.29 (1H, dd, J=11.2, 4.9 Hz), 6.85 (1H, td, J=8.3, 4.9 Hz), 7.17 (1H, d, J=8.8 Hz), 7.21 (1H, d, J=13.2 Hz), 7.84 (1H, d, J=5.4 Hz), 8.30 (1H, s)

ESI (LC/MS positive mode) m/z 468 (M+H)

Example 9

(E)-3,4-Difluoro-2-(2-fluoro-4-iodophenylamino)-5-[(2-hydroxyethoxyimino)-methyl]-N-(3-hydroxypropoxy)benzamide

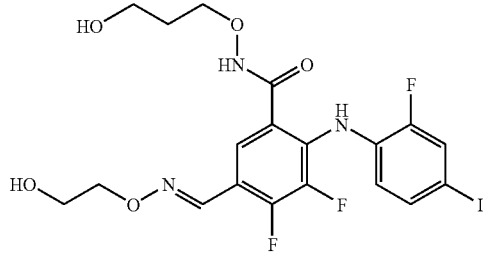

Process A

Preparation of 5-{[2-(tert-butyl-dimethyl-silanyloxy)-ethoxyimino]-methyl}-3,4-difluoro-2-(2-fluoro-4-iodo-phenylamino)-benzoic Acid

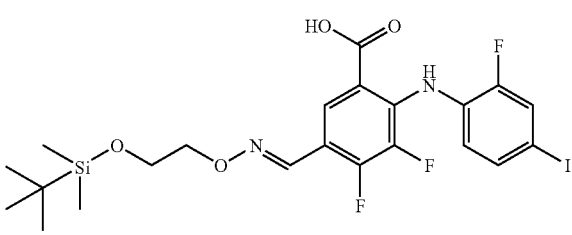

The aldehyde, 3,4-difluoro-2-(2-fluoro-4-iodo-phenylamino)-5-formyl-benzoic acid obtained in Process D of Example 1 is suspended in methylene chloride, an equimolar amount of O-[2-(t-butyl-dimethyl-silanyloxy)-ethyl]-hydroxyamine is added thereto, and the mixture is stirred at room temperature. The reaction solution is concentrated, and the solvent is removed to give 5-{[2-(tert-butyl-dimethyl-silanyloxy)-ethoxyimino]-methyl}-3,4-difluoro-2-(2-fluoro-4-iodo-phenylamino)-benzoic acid as a crude compound. The obtained crude compound was used as it was in the next reaction.

ESI (LC/MS positive mode) m/z 595 (M+H).

Process B

Preparation of 5-{[2-(tert-butyl-dimethyl-silanyloxy)-ethoxyimino]-methyl}-N-[3-(tert-butyl-dimethyl-silanyloxy)-propoxy]-3,4-difluoro-2-(2-fluoro-4-iodo-phenylamino)-benzamide

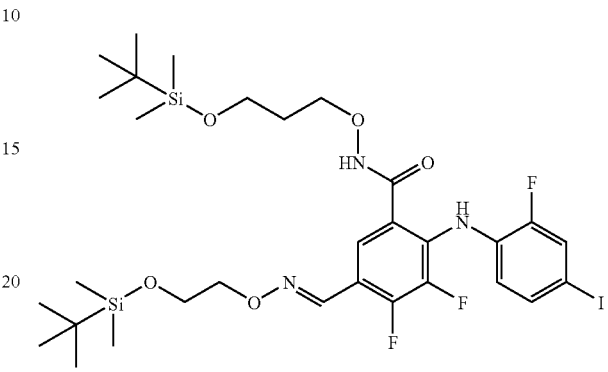

To a solution of 5-{[2-(tert-butyl-dimethyl-silanyloxy)-ethoxyimino]-methyl}-3,4-difluoro-2-(2-fluoro-4-iodo-phenylamino)-benzoic acid (166.4 mg, 0.280 mmol) obtained in Process A in methylene chloride (4 ml), O-[3-(tert-butyl-dimethyl-silanyloxy)-propyl]-hydroxylamine (92.3 mg, 0.449 mmol), 1-hydroxybenzotriazole (49.2 mg, 0.321 mmol), 1-ethyl-3-(3-dimethylaminopropyl)-carbodiimide hydrochloride (131 mg, 0.683 mmol), and N,N-diisopropylethylamine (0.4 ml) were added, and the mixture was stirred at room temperature over night. Water (20 ml) was added to the reaction solution, and the mixture was extracted with methylene chloride. The organic layer was washed with saturated brine, dried over anhydrous sodium sulfate, and concentrated under reduced pressure. The residue was purified by silica gel chromatography (n-hexane:AcOEt 5:1) to give 5-{[2-(tert-butyl-dimethyl-silanyloxy)-ethoxyimino]-methyl}-N-[3-(tert-butyl-dimethyl-silanyloxy)-propoxy]-3,4-difluoro-2-(2-fluoro-4-iodo-phenylamino)-benzamide (101.5 mg, 36%).

$^1$H-NMR (CD$_3$OD, 270 MHz) δ (PPM) 0.06 (6H, s), 0.09 (6H, s), 0.90 (9H, s), 0.91 (9H, s), 1.92 (2H, quin, J=5.9 Hz), 3.79 (2H, t, J=5.9 Hz), 3.91 (2H, t, J=5.0 Hz), 4.13 (2H, t, J=6.3 Hz), 4.26 (2H, dd, J=5.6, 4.6 Hz), 6.65 (1H, td, J=8.6, 5.3 Hz), 7.35 (1H, br. d, J=8.6 Hz), 7.41 (1H, dd, J=10.3, 2.0 Hz), 7.71 (1H, dd, J=7.3, 2.3 Hz), 8.23 (1H, s), 8.71 (1H, br. s), 9.27 (1H, br. s).

O-[3-(tert-butyl-dimethyl-silanyloxy)-propyl]-hydroxylamine used in the condensation reaction above was prepared according to the method described in the literature below.

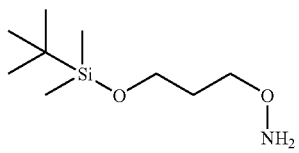

Harnden, Michael; Wyatt, Paul G; Boyd, Malcolm R.; Sutton, David, J. Med. Chem., 33, 1990, 187-196.

Process C

Preparation of (E)-3,4-difluoro-2-(2-fluoro-4-iodo-phenylamino)-5-[(2-hydroxyethoxyimino)-methyl]-N-(3-hydroxypropoxy)-benzamide

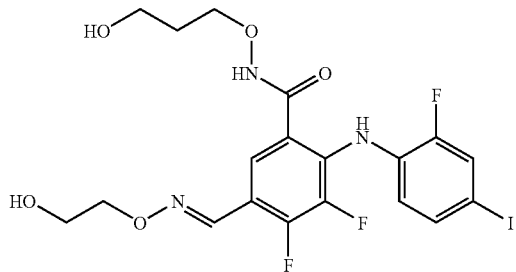

To a solution of 5-{[2-(tert-butyl-dimethyl-silanyloxy)-ethoxyimino]-methyl}-N-[3-(tert-butyl-dimethyl-silanyloxy)-propoxy]-3,4-difluoro-2-(2-fluoro-4-iodo-phenylamino)-benzamide (101.5 mg, 0.139 mmol) obtained in Process B in tetrahydrofuran (5 ml), tetra-n-butylammonium fluoride (1 M solution in tetrahydrofuran, 0.5 ml, 0.5 mmol) was added, and the mixture was stirred at room temperature over night. Water (8 ml) and saturated brine (2 ml) was added to the reaction solution, and the mixture was extracted with ethyl acetate (15 ml×2). The organic layer was combined, washed with saturated brine (15 ml×2), dried over anhydrous sodium sulfate, and concentrated under reduced pressure. The residue was purified by preparative TLC to give (E)-3,4-difluoro-2-(2-fluoro-4-iodophenylamino)-5-[(2-hydroxyethoxyimino)-methyl]-N-(3-hydroxypropoxy)-benzamide (29.5 mg, 38%).

$^1$H-NMR (CD$_3$OD, 270 MHz) δ (PPM) 1.85 (2H, quin, J=6.3 Hz), 3.69 (2H, t, J=6.3 Hz), 3.82 (2H, dd, J=5.0, 4.0 Hz), 3.96 (2H, t, J=6.6 Hz), 4.26 (2H, dd, J=5.3, 4.6 Hz), 6.71 (1H, td, J=8.9, 4.6 Hz), 7.38 (1H, dt, J=8.6, 1.3 Hz), 7.46 (1H, dd, J=10.6, 2.0 Hz), 7.80 (1H, dd, J=7.3, 2.3 Hz), 8.28 (1H, s).

ESI (LC/MS positive mode) m/z 554 (M+H)

Example 10

(E)-N-Allyloxy-3,4-difluoro-2-(2-fluoro-4-iodophenylamino)-5-[(2-hydroxyethoxyimino)-methyl]benzamide

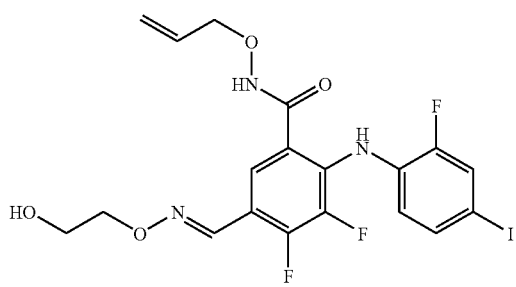

Process A

Preparation of N-allyloxy-5-{[2-(tert-butyl-dimethyl-silanyloxy)-ethoxyimino]-methyl}-3,4-difluoro-2-(2-fluoro-4-iodo-phenylamino)-benzamide

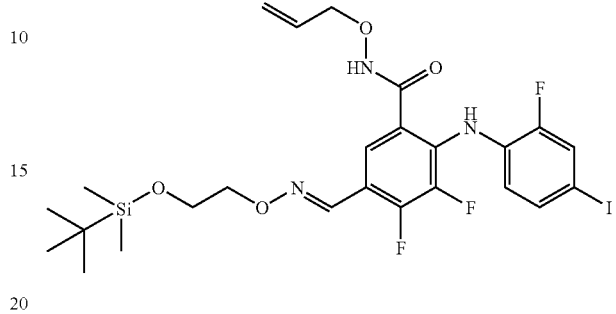

This compound can be obtained by condensing 5-{[2-(tert-butyl-dimethyl-silanyloxy)-ethoxyimino]-methyl}-3,4-difluoro-2-(2-fluoro-4-iodo-phenylamino)-benzoic acid obtained in Process A of Example 9 as a source compound with O-allylhydroxylamine, under the same reaction conditions as for Process B of Example 9.

$^1$H-NMR (CD$_3$OD, 270 MHz) δ (PPM) 0.09 (6H, s), 0.91 (9H, s), 3.91 (2H, t, J=5.0 Hz), 4.26 (2H, t, J=5.0 Hz), 4.50 (2H, d, J=6.6 Hz), 5.36 (1H, d, J=9.9 Hz), 5.38 (1H, d, J=17.2 Hz), 6.06 (1H, ddt, J=17.2, 10.6, 6.6 Hz), 6.64 (1H, td, J=8.6, 4.6 Hz), 7.35 (br. d, J=8.9 Hz), 7.41 (1H, dd, J=9.9, 1.7 Hz), 7.71 (br. d, J=5.0 Hz), 8.14 (1H, s), 8.60 (1H, br, s), 8.80 (1H, br. s).

ESI (LC/MS positive mode) m/z 650 (M+H)

The O-Allylhydroxylamine used in the above condensation reaction is commercially available (Fluka, Inc.).

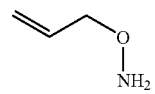

Process B

Preparation of (E)-N-allyloxy-3,4-difluoro-2-(2-fluoro-4-iodophenylamino)-5-[(2-hydroxyethoxyimino)-methyl]benzamide

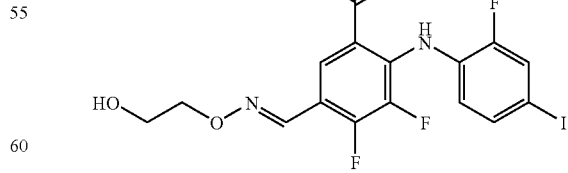

This compound can be obtained by desilylating the compound obtained in the above Process A, under the same conditions as for Process C of Example 9.

$^1$H-NMR (CD$_3$OD, 270 MHz) δ (PPM) 3.82 (2H, dd, J=5.0, 3.6 Hz), 4.26 (2H, dd, J=6.3, 5.0 Hz), 4.36 (2H, d,

J=6.3 Hz), 5.25 (1H, ddd, J=10.2, 1.0, 0.7 Hz), 5.33 (1H, dq, J=17.5, 1.3 Hz), 6.00 (1H, ddt, J=16.8, 10.6, 6.6 Hz), 6.71 (1H, td, J=8.9, 4.6 Hz), 7.39 (1H, ddd, J=8.3, 2.0, 1.3 Hz), 7.48 (1H, dd, J=10.9, 2.0 Hz), 7.62 (1H, dd, J=7.3, 2.0 Hz), 8.29 (1H, s).

ESI (LC/MS positive mode) m/z 536 (M+H)

Example 11

(E)-dl-N-(2,3-Dihydroxy-propoxy)-3,4-difluoro-2-(2-fluoro-4-iodophenylamino)-5-[(2-hydroxyethoxy-imino)-methyl]benzamide

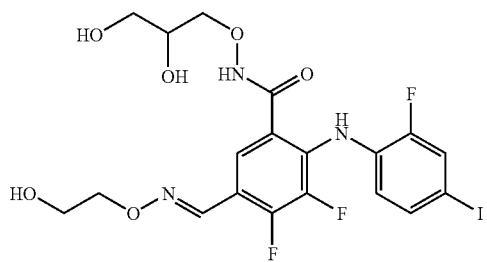

To a solution of N-allyloxy-5-{[2-(tert-butyl-dimethyl-silanyloxy)-ethoxyimino]-methyl}-3,4-difluoro-2-(2-fluoro-4-iodo-phenylamino)-benzamide (73.2 mg, 0.113 mmol) obtained in Process A of Example 10 in tetrahydrofuran (4 ml), osmium tetroxide (0.1 M aqueous solution, 0.113 ml, 0.011 mmol) and hydrogen peroxide solution (30% aqueous solution, 0.1 ml) were added, and the mixture was stirred at room temperature for five hours, and at 4° C. for three days. An aqueous sodium sulfite solution was added to the reaction solution. 1N hydrochloric acid was then added until the pH was about 6. This mixture was extracted with ethyl acetate (8 ml×3), and the combined organic layer was washed with saturated brine, dried over anhydrous sodium sulfate, and concentrated under reduced pressure. The resulting crude compound (77.5 mg) was desilylated under the same conditions as in Process C of Example 9, yielding (E)-dl-N-(2,3-dihydroxy-propoxy)-3,4-difluoro-2-(2-fluoro-4-iodophenylamino)-5-[(2-hydroxyethoxyimino)-methyl]benzamide (41.5 mg, 65%).

$^1$H-NMR (CD$_3$OD, 270 MHz) δ (PPM) 3.55 (1H, dd, J=11.2, 5.3 Hz), 3.60 (1H, dd, J=11.2, 4.3 Hz), 3.80-3.90 (4H, m), 3.94-4.00 (1H, m), 4.26 (2H, dd, J=4.6, 3.6 Hz), 6.72 (1H, td, J=8.6, 4.3 Hz), 7.39 (1H, br d, J=8.6 Hz), 7.47 (1H, dd, J=10.6, 1.7 Hz), 7.82 (1H, dd, J=6.9, 2.0 Hz), 8.29 (1H, s).

ESI (LC/MS positive mode) m/z 570 (M+H)

Example 12

Production of (E)-3,4-difluoro-2-(2-fluoro-4-iodophenylamino)-N-(2-hydroxy-ethoxy)-5-[(2-hydroxy-2-methyl-propoxyimino)-methyl]-benzamide (Compound 12)

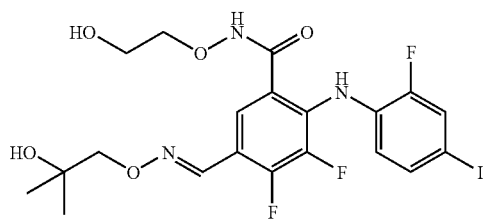

Process A

Preparation of 1-aminooxy-2-methyl-propan-2-ol Hydrochloride

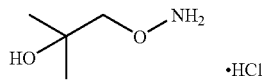

Preparation of 1-aminooxy-2-methyl-propan-2-ol hydrochloride was carried out as described in the following literature:

Monatsh Chem Verw Teile Andere Wiss (1961) 92 p. 725-739.

Process B

Preparation of (E)-3,4-difluoro-2-(2-fluoro-4-iodophenylamino)-N-(2-hydroxy-ethoxy)-5-[(2-hydroxy-2-methyl-propoxyimino)-methyl]-benzamide (Compound 12)

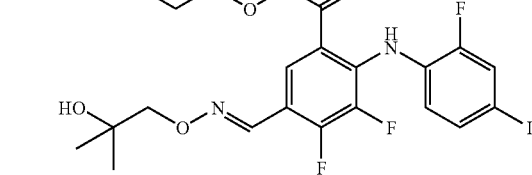

3,4-Difluoro-2-(2-fluoro-4-iodophenylamino-5-formyl-N-(2-hydroxy-ethoxy)-benzamide (32 mg, 0.067 mmol), which was obtained as a byproduct during the preparation of N-[2-(t-butyldimethylsilanyloxy)-ethoxy]-3,4-difluoro-2-(2-fluoro-4-iodophenylamino)-5-formyl benzamide in Process B of Example 3, was dissolved in methylene chloride (3.0 mL) and N,N-diisopropylethylamine (1 mL). 1-Aminooxy-2-methyl-propan-2-ol hydrochloride prepared in Process A above was added thereto at room temperature. This mixture was stirred for 16 hours.

After completion of the reaction, the solvent was distilled off under reduced pressure, and the brown oil was extracted with ethyl acetate. The extract was washed successively with 0.1 N hydrochloric acid, water, and saturated brine, and the organic layer was dried over anhydrous sodium sulfate, and filtered. The solvent was distilled off under reduced pressure, and the resultant brown oil was purified with Mega Bond Elut silica gel (5 g, Varian, Inc.: 5% methylene chloride/methanol as an eluent) to give 3,4-difluoro-2-(2-fluoro-4-iodophenylamino)-N-(2-hydroxy-ethoxy)-5-[(2-hydroxy-2-methyl-propoxyimino)-methyl]-benzamide (Compound 12) (24.4 mg, 65%) as a light brown solid.

$^1$H-NMR (CD$_3$OD, 270 MHz) δ (PPM) 3.30 (6H, s), 3.72 (2H, m), 3.94 (2H, m), 4.08 (2H, s), 6.72 (1H, m), 7.38 (1H, d 8.6 z), 7.47 (1H, d, J=10.9 Hz), 7.80 (1H, br. d, J=5.3 Hz), 8.30 (1H, s)

ESI (LC/MS positive mode) m/z 568 (M+H)

Example 13

Production of (E)-2-(4-ethynyl-2-fluoro-phenylamino)-3,4-difluoro-N-(2-hydroxy-ethoxy)-5-[(2-hydroxy-2-methyl-propoxyimino)-methyl]-benzamide

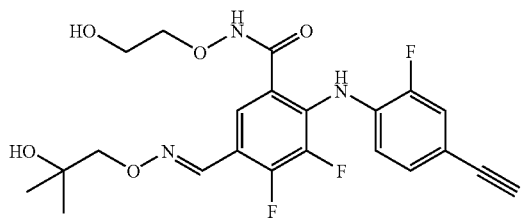

Process A

Preparation of (E)-3,4-difluoro-2-(2-fluoro-4-trimethylsilanylethynyl-phenylamino)-N-(2-hydroxy-ethoxy)-5-[(2-hydroxy-2-methylpropoxyimino)-methyl]-benzamide

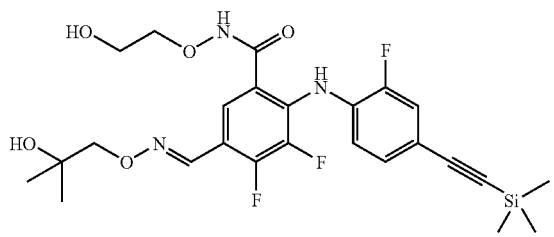

3,4-Difluoro-2-(2-fluoro-4-iodophenylamino)-N-(2-hydroxy-ethoxy)-5-[(2-hydroxy-2-methyl-propoxyimino)-methyl]-benzamide (14.6 mg, 0.025 mmol) prepared in Example 12 was dissolved in anhydrous tetrahydrofuran (2.0 ml). Next, $(PPh_3)_2PdCl_2$ (20,867-1, Sigma-Aldrich, Inc.) (1.0 mg, 0.00127 mmol), copper iodide (2.0 mg, 0.0094 mmol), N,N-diisopropylethylamine (10 μL, 0.057 mmol), and trimethylsilylacetylene (35 μL, 0.25 mmol) were added thereto at room temperature, and the mixture was stirred at 50° C. overnight.

After completion of the reaction, the solvent was distilled off under reduced pressure, and the yellow oil was extracted with ethyl acetate. The extract was washed successively with water and saturated brine, and the organic layer was dried over anhydrous sodium sulfate, and filtered. The solvent was distilled off under reduced pressure, and the resultant yellow oil was purified with Mega Bond Elut silica gel (5 g, Varian, Inc.). From the fractions eluted with 50% ethyl acetate/hexane to 100% ethyl acetate, 3,4-difluoro-2-(2-fluoro-4-trimethylsilanylethynyl-phenylamino)-N-(2-hydroxy-ethoxy)-5-[(2-hydroxy-2-methylpropoxyimino)-methyl]-benzamide (12.2 mg, 88%) was obtained as a yellow solid.

$^1$H-NMR (CD$_3$OD, 270 MHz) δ (PPM) 0.21 (9H, s), 1.26 (6H, s), 3.72 (2H, m), 3.94 (2H, m), 4.08 (2H, s), 6.83 (1H, m), 7.13 (1H, d, J=9.6 Hz), 7.17 (1H, dd, J=13.5, 2.0 Hz), 7.83 (1H, br. d, J=7.6 Hz), 8.31 (1H, s)

ESI (LC/MS positive mode) m/z 538 (M+H)

Process B

Preparation of (E)-2-(4-ethynyl-2-fluoro-phenylamino)-3,4-difluoro-N-(2-hydroxy-ethoxy)-5-[(2-hydroxy-2-methyl-propoxyimino)-methyl]-benzamide

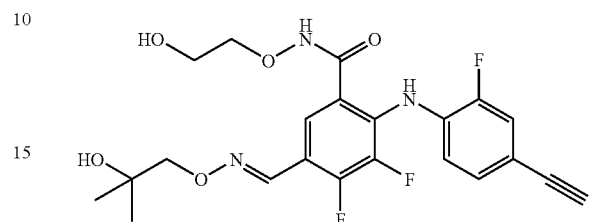

3,4-Difluoro-2-(2-fluoro-4-trimethylsilanylethynyl-phenylamino)-N-(2-hydroxy-ethoxy)-5-[(2-hydroxy-2-methyl-propoxyimino)-methyl]-benzamide (12.2 mg, 0.027 mmol) obtained in Process A above was dissolved in anhydrous tetrahydrofuran (2.0 ml). Next, tetra-n-butylammonium fluoride (1 mol/L solution in tetrahydrofuran) (50 μL, 0.05 mmol) was added dropwise at room temperature, and the mixture was stirred for one hour.

After completion of the reaction, the solvent was distilled off under reduced pressure, and the yellow oil was extracted with ethyl acetate. The extract was washed successively with water and saturated brine, and the organic layer was dried over anhydrous sodium sulfate, and filtered. The solvent was distilled off under reduced pressure, and the resultant yellow oil was purified with Mega Bond Elut silica gel (5 g, Varian, Inc.: 100% methylene chloride to 5% methylene chloride/methanol as an eluent), followed by preparative TLC (100% ethyl acetate as a developing solvent) to give 2-(4-ethynyl-2-fluoro-phenylamino)-3,4-difluoro-N-(2-hydroxy-ethoxy)-5-[(2-hydroxy-2-methyl-propoxyimino)-methyl]-benzamide (8.2 mg, 68%) as a off-white solid.

$^1$H-NMR (CD$_3$OD, 270 MHz) δ (PPM) 1.26 (6H, s), 3.46 (1H, s), 3.71 (2H, m), 3.95 (2H, m), 4.08 (2H, s), 6.85 (1H, m), 7.16 (d, J=8.9 Hz), 7.21 (1H, dd, J=13.9, 1.6 Hz), 7.82 (1H, br. d, J=5.3 Hz), 8.31 (1H, s)

ESI (LC/MS positive mode) m/z 466 (M+H)

Example 14

Production of (E)-3,4-difluoro-2-(2-fluoro-4-iodophenylamino)-N-(2-hydroxy-ethoxy)-5-[(2-methyl-carbamoyl-ethoxyimino)-methyl]-benzamide (Compound 14)

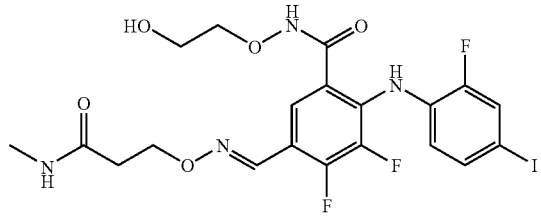

Production of 3-aminooxy-N-methyl-propionamide

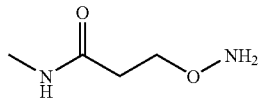

Process A

Preparation of 3-(1,3-dioxo-1,3-dihydro-isoindol-2-yloxy)-propionic Acid Methyl Ester

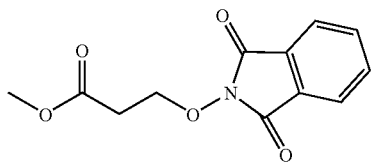

3-Hydroxy-propionic acid methyl ester (5 g, 48.27 mmol) was dissolved in anhydrous tetrahydrofuran (150 ml) under an argon stream. To this solution, triphenylphosphine (12.6 g, 48.027 mmol) and N-hydroxyphthalimide (7.83 g, 48.027 mmol) were added and dissolved while being stirred. Next, the reaction solution was cooled in an ice bath, and diisopropyl azocarboxylate (11 mL, 52.83 mmol) was added dropwise thereto. The reaction solution was then stirred at room temperature for four hours.

After completion of the reaction, the reaction solution was concentrated under reduced pressure. To the resultant yellow oily residue, diethyl ether/hexane (1:1) was added, and the mixture was stirred thoroughly at room temperature. After a while, a white precipitate appeared. This precipitate was filtered off, and the filtrate was concentrated under reduced pressure. The resultant yellow oily residue was left stand at room temperature for ten hours to precipitate a white solid. This solid was washed thoroughly with 20% ethyl acetate/hexane to give 3-(1,3-dioxo-1,3-dihydro-isoindol-2-yloxy)-propionic acid methyl ester (1.5 g, 12%).

$^1$H-NMR (CDCl$_3$, 270 MHz) δ (PPM) 2.86 (2H, t, J=6.6 Hz), 3.73 (3H, s), 4.52 (2H, t, J=6.6 Hz), 7.66-7.89-4H, m).
ESI (LC/MS positive mode) m/z 250 (M+H)
Process B Preparation of 3-aminooxy-N-methyl-propionamide

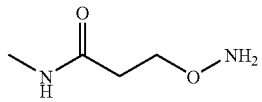

3-(1,3-Dioxo-1,3-dihydro-isoindol-2-yloxy)-propionic acid methyl ester (1.5 g, 6.019 mmol) was dissolved in methylene chloride (50 mL), 40% solution of methylamine in methanol was added at room temperature, and the mixture was stirred at 40° C. for 17 hours.

After completion of the reaction, insoluble precipitate was filtered off, and the filtrate was concentrated under reduced pressure. The resultant light-yellow oily residue was purified with Mega Bond Elut silica gel (5 g, Varian, Inc.: 10% methylene chloride/methanol as an eluent) to give 3-aminooxy-N-methyl-propionamide (233 mg, 33%) as a colorless oil.

$^1$H-NMR (CDCl$_3$, 270 MHz) δ (PPM) 2.50 (2H, t, J=5.9 Hz), 2.81 (3H, d, J=4.6 Hz), 3.94 (2H, t, 3=5.9 Hz), 5.40 (2H, br. s), 6.10 (1H, br. s)
EIMS m/z 118 (M+)
Process C Preparation of (E)-3,4-difluoro-2-(2-fluoro-4-iodophenylamino)-N-(2-hydroxy-ethoxy)-5-[(2-methylcarbamoyl-ethoxyimino)-methyl]-benzamide

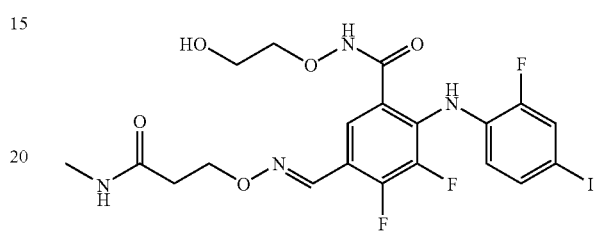

3,4-Difluoro-2-(2-fluoro-4-iodophenylamino-5-formyl-N-(2-hydroxy-ethoxy)-benzamide (25 mg, 0.052 mmol), which was obtained as a byproduct during the preparation of N-[2-(t-butyldimethylsilanyloxy)-ethoxy]-3,4-difluoro-2-(2-fluoro-4-iodophenylamino)-5-formyl-benzamide in Process B of Example 3 above, was dissolved in a mixed solvent of methylene chloride (3.0 mL) and anhydrous tetrahydrofuran (1.0 ml). 3-Aminooxy-N-methyl-propionamide was added thereto at room temperature, and the mixture was stirred for 17 hours.

After completion of the reaction, the solvent was distilled off under reduced pressure, and the light-yellow solid was triturated with 20% ethyl acetate/hexane solution, and filtered to give 3,4-difluoro-2-(2-fluoro-4-iodo-phenylamino)-N-(2-hydroxy-ethoxy)-5-[(2-methylcarbamoyl-ethoxyimino)-methyl]-benzamide (Compound 14) (17 mg, 56%) as a white solid.

$^1$H-NMR (CD$_3$OD, 270 MHz) δ (PPM) 2.59 (2H, t, J=5.9 Hz), 2.72 (3H, s), 3.72 (2H, m), 3.95 (2H, m), 4.43 (2H, t, J=5.9 Hz), 6.72 (1H, dt, J=8.9, 4.3 Hz), 7.39 (1H, m), 7.47 (1H, dd, J=10.9, 2.0 Hz), 7.80 (1H, dd, J=6.9, 2.0 Hz), 8.23 (1H, s)
ESI (LC/MS positive mode) m/z 581 (M+H)

Example 15

Production of (E)-3,4-difluoro-2-(2-fluoro-4-iodophenylamino)-N-(2-hydroxy-ethoxy)-5-[(2-hydroxy-propoxyimino)-methyl]-benzamide (Compound 15)

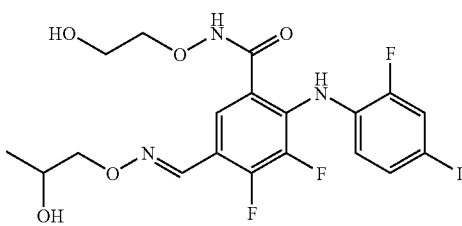

Process A

Preparation of (E)-N-[2-(t-butyldimethylsilanyloxy)-ethoxy]-3,4-difluoro-2-(2-fluoro-4-iodo-phenylamino)-5-[(2-oxo-ethoxyimino)-methyl]-benzamide

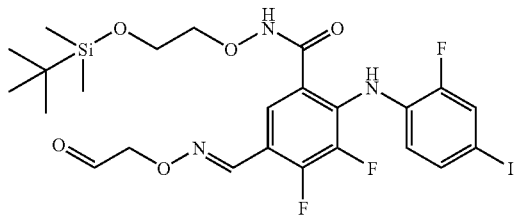

Similarly to Process B of Example 12, 5-(allyloxyimino-methyl)-N-[2-(t-butyldimethylsilanyloxy)-ethoxy]-3,4-difluoro-2-(2-fluoro-4-iodo-phenylamino)-benzamide (formula below) (100 mg, 0.154 mmol), which was prepared using N-[2-(t-butyldimethylsilanyloxy)-ethoxy]-3,4-difluoro-2-(2-fluoro-4-iodophenylamino)-5-formyl-benzamide obtained in Process B of Example 3 and O-allylhydroxylamine as starting materials, was dissolved in tetrahydrofuran (10 mL) and water (3 mL). 0.1 M aqueous solution of osmium tetroxide (0.05 mL) and sodium metaperiodate (131 mg, 0.616 mmol) were added to this reaction solution at room temperature, and the mixture was stirred for 19 hours. Insoluble material was removed through a celite column, and the solution was extracted with ethyl acetate.

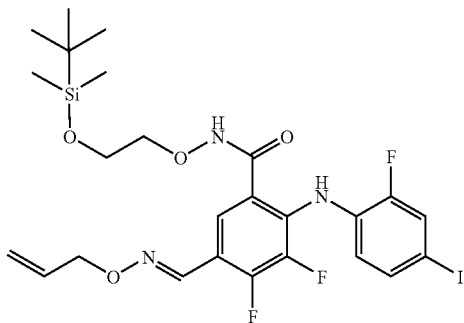

The extract was washed successively with water and saturated brine, and the organic layer was dried over anhydrous sodium sulfate, and filtered. The solvent was distilled off under reduced pressure, and the resultant dark-brown solid was purified with Mega Bond Elut silica gel (5 g, Varian, Inc.). From the fractions eluted with 60% ethyl acetate/hexane, N-[2-(t-butyldimethylsilanyloxy)-ethoxy]-3,4-difluoro-2-(2-fluoro-4-iodo-phenylamino)-5-[(2-oxo-ethoxyimino)-methyl]-benzamide (83.1 mg, 83%) was obtained as a light-brown solid.

$^1$H-NMR (CDCl$_3$, 270 MHz) δ (PPM) 0.08 (6H, s), 0.86 (9H, s), 3.94 (2H, m), 4.11 (2H, m), 4.70 (2H, s), 6.87 (1H, m), 7.38 (1H, m), 7.43 (1H, m), 7.53 (1H, m), 7.64 (1H, s), 8.86 (0.5H, br. s), 9.42 (0.5H, br. s), 9.87 (1H, br. s)

ESI (LC/MS positive mode) m/z 652 (M+H)

Process B

Preparation of (E)-N-[2-(t-butyldimethylsilanyloxy)-ethoxy]-3,4-difluoro-2-(2-fluoro-4-iodo-phenylamino)-5-[(2-hydroxy-propoxyimino)-methyl]-benzamide

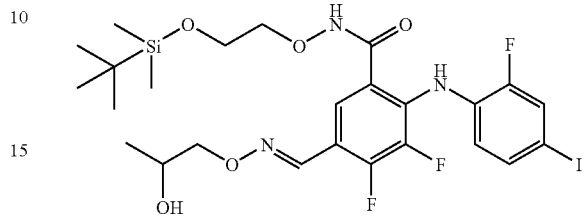

N-[2-(t-butyldimethylsilanyloxy)-ethoxy]-3,4-difluoro-2-(2-fluoro-4-iodo-phenylamino)-5-[(2-oxo-ethoxyimino)-methyl]-benzamide (60 mg, 0.092 mmol) prepared in Process A was dissolved in anhydrous tetrahydrofuran (2.0 mL) under an argon atmosphere. This reaction solution was cooled to −78° C., and then 0.93 M methyl magnesium bromide (0.25 mL) was added thereto. The reaction solution was allowed to gradually warm to room temperature, and stirred for eight hours. The reaction was quenched with saturated aqueous solution of ammonium chloride, and the solution was extracted with ethyl acetate.

The extract was washed successively with water and saturated brine, and the organic layer was dried over anhydrous sodium sulfate, and filtered. The solvent was distil led off under reduced pressure, and the resultant oily residue was purified with Mega Bond Elut silica gel (5 g; Varian, Inc.). From the fractions eluted with 60% ethyl acetate/hexane, N-[2-(t-butyldimethylsilanyloxy)-ethoxy]-3,4-difluoro-2-(2-fluoro-4-iodo-phenylamino)-5-[(2-hydroxy-propoxyimino)-methyl]-benzamide (21.5 mg, 35%) was obtained as a white solid.

$^1$H-NMR (CDCl$_3$, 270 MHz) δ (PPM) 0.08 (6H, s), 0.87 (9H, s), 1.24 (3H, d, J=6.3 Hz), 3.93-4.20 (7H, m), 6.64 (1H, m), 7.35 (1H, d, J=8.6 Hz), 7.41 (1H, dd, J=10.2, 1.6 Hz), 7.66 (1H, m), 8.25 (1H, s), 8.83 (0.5H, br. s), 9.64 (0.5H, br. s)

ESI (LC/MS positive mode) m/z 668 (M+H)

Process C

Preparation of (E)-3,4-difluoro-2-(2-fluoro-4-iodo-phenylamino)-N-(2-hydroxy-ethoxy)-5-[(2-hydroxy-propoxyimino)-methyl]-benzamide (Compound 15)

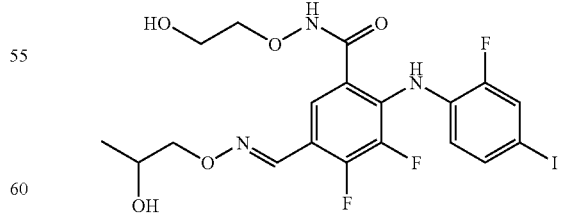

N-[2-(t-butyldimethylsilanyloxy)-ethoxy]-3,4-difluoro-2-(2-fluoro-4-iodo-phenylamino)-5-[(2-hydroxy-propoxy-imino)-methyl]-benzamide (20 mg, 0.029 mmol) prepared in Process B was dissolved in anhydrous tetrahydrofuran (2 mL). Tetra-n-butylammonium fluoride (1 mol/L solution in tetrahydrofuran) (30 μL, 0.03 mmol) was added dropwise at room temperature, and the mixture was stirred for 1.5 hours.

After completion of the reaction, the solvent was distilled off under reduced pressure, and the yellow oil was extracted with ethyl acetate. The extract was washed successively with water and saturated brine, and the organic layer was dried over anhydrous sodium sulfate, and filtered. The solvent was distilled off under reduced pressure, and the resultant brown oil was purified with preparative TLC (TLC plate, silica gel 60F254, Merck & Co., Inc.) using 5% methanol/dichloromethane as a developing solvent. Fractionation was carried out with a mixed solvent of methanol and ethyl acetate, and the fraction was concentrated to give 3,4-difluoro-2-(2-fluoro-4-iodo-phenylamino)-N-(2-hydroxy-ethoxy)-5-[(2-hydroxy-propoxyimino)-methyl]-benzamide (Compound 15) (6.7 mg, 40%) as a white solid.

$^1$H-NMR (CD$_3$OD, 270 MHz) δ (PPM) 1.20 (3H, d, J=6.2 Hz), 3.72 (2H, m), 3.94 (2H, m), 4.08 (3H, m), 6.71 (1H, dt, J=8.6, 4.3 Hz), 7.38 (1H, m), 7.47 (1H, dd, J=10.9, 2.0 Hz), 7.81 (1H, dd, J=6.9, 2.0 Hz), 8.28 (1H, s)

ESI (LC/MS positive mode) m/z 554 (M+H)

Example 16

Production of (E)-5-[(2-dimethylamino-ethoxyimino)-methyl]-3,4-difluoro-2-(2-fluoro-4-iodo-phenylamino)-N-(2-hydroxy-ethoxy)-benzamide (Compound 16)

Compound 16 was produced according to the same method as in Example 3.

$^1$H-NMR (CD$_3$OD, 270 MHz) δ (PPM) 2.49 (6H, s), 2.93 (2H, t, J=5.3 Hz), 3.72 (2H, m), 3.96

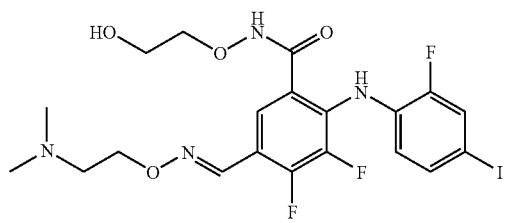

(2H, m), 4.36 (2H, t, J=5.3 Hz), 6.70 (1H, m), 7.38 (1H, d, J=8.2 Hz), 7.46 (1H, d, J=10.6 Hz), 7.85 (1H, br. d, J=6.3 Hz), 8.27 (1H, s)

ESI (LC/MS positive mode) m/z 567 (M+H).

In the production of compound 16, the coupling item, O-(2-dimethylamino-ethyl)-hydroxylamine hydrochloride shown below was prepared according to methods described in the following literature:
Villani, F. J. et al.; J. Pharm. Sci.; 1969; 138-141

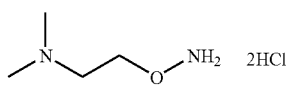

Example 17

Production of (E)-3,4-difluoro-2-(2-fluoro-4-iodo-phenylamino)-N-(2-hydroxy-ethoxy)-5-[(2-piperidin-1-yl-ethoxyimino)-methyl]-benzamide (Compound 17)

The compound 17 was produced according to the same method as in Example 3.

$^1$H-NMR (DMSO-d$_6$, 270 MHz) δ (PPM) 1.38 (2H, m), 1.50 (4H, m), 2.45 (4H, m), 2.64 (2H,

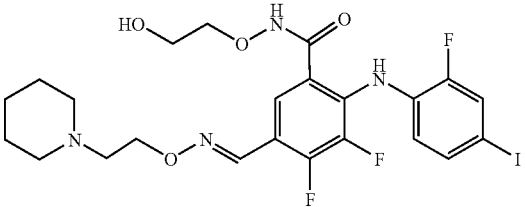

m), 3.56 (2H, m), 3.83 (2H, m), 4.26 (2H, t, J=5.3 Hz), 6.79 (1H, m), 7.46 (1H, d, J=8.2 Hz), 7.61 (1H, d, J=10.2 Hz), 7.73 (1H, d, J=5.6 Hz), 8.26 (1H, s)

ESI (LC/MS positive mode) m/z 607 (M+H)

In the production of compound 17, the coupling item shown below, O-[2-(1-piperidinyl)ethyl]hydroxylamine hydrochloride, was prepared according to the method described in the following literature:

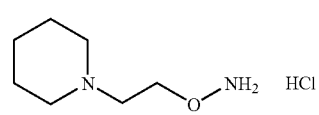

Favara, D.; Nicola, M.; Pappalardo, M.; Bonardi, G; Luca, C.; et al.; Farmaco Ed. Sci.; 10; 1987; 697-708.

Example 18

Production of (E)-3,4-difluoro-2-(2-fluoro-4-iodo-phenylamino)-N-(2-hydroxy-ethoxy)-5-[(2-morpholin-4-yl-ethoxyimino)-methyl]-benzamide (Compound 18)

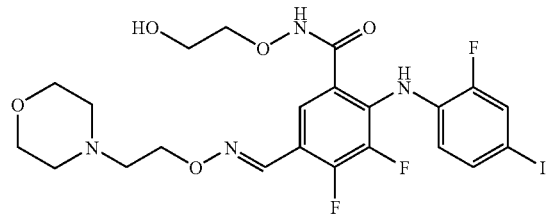

Compound 18 was produced according to method as in Example 3.

$^1$H-NMR (CD$_3$OD, 270 MHz) δ (PPM) 2.59 (4H, m), 2.77 (2H, t, J=5.6 Hz), 3.72 (6H, m), 3.95 (2H, dd, J=4.9, 4.3 Hz), 4.36 (2H, t, J=5.6 Hz), 6.72 (1H, td, J=8.6, 4.3 Hz), 7.38 (1H, d, J=8.6 Hz), 7.47 (1H, dd, J=10.9, 2.0 Hz), 7.80 (1H, dd, J=6.9, 2.0 Hz), 8.25 (1H, s)

ESI (LC/MS positive mode) m/z 609 (M+H)

In the production of compound 18, the coupling item shown below, O-(2-morpholin-4-yl-ethyl)-hydroxylamine hydrochloride, was prepared according to the method described in the following literature:

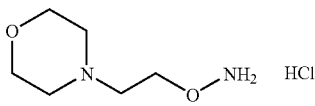

Favara, D.; Nicola, M.; Pappalardo, M.; Bonardi, G; Luca, C.; et al.; Farmaco Ed. Sci.; 10; 1987; 697-708.

Example 19

Production of (E)-3,4-difluoro-2-(2-fluoro-4-iodo-phenylamino)-N-(2-hydroxy-ethoxy)-5-{[2-(4-hydroxy-piperidin-1-yl)-ethoxyimino]-methyl}-benzamide (Compound 19)

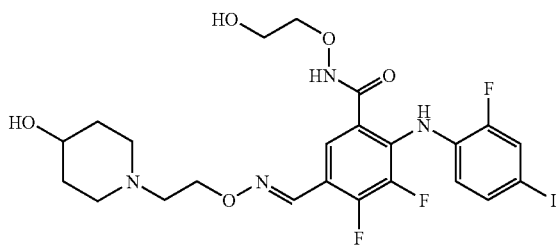

To (R,S)$_5$-[(2,3-dihydroxy-propoxyimino)-methyl]-3,4-difluoro-2-(2-fluoro-4-iodo-phenylamino)-N-(2-hydroxy-ethoxy)-benzamide (Example 7) (20.4 mg, 0.036 mmol) described herein, anhydrous tetrahydrofuran (2.0 ml) and distilled water (1.0 ml) were added, and the mixture was cooled to −15° C. and stirred for ten minutes. Then, sodium periodate (9.2 mg, 0.108 mmol, 3.0 eq.) was added, and the mixture was warmed to room temperature, and stirred for eight hours. Reaction completion was monitored using LC-MS. After confirming the disappearance of the source material, distilled water (10 ml) was added to the reaction mixture, and the mixture was extracted with ethyl acetate (60 ml) and dried over sodium sulfate. The solvent was distilled off to give a crude aldehyde product (19.3 mg, 100% yield).

MS4A (30 mg), 4-hydroxy-piperidine (3.8 mg, 0.037 mmol, 1.05 eq.), and borane-pyridine complex (11.1 μl, 0.111 mmol, 3.2 eq.) were sequentially added to a solution of the resulting aldehyde in methanol (1.0 ml). The mixture was stirred at room temperature for 14 hours. Reaction completion was monitored by LC-MS. After confirming the disappearance of the source material, a 6N aqueous solution of hydrochloric acid (3 ml) was added to the reaction mixture, and the mixture was stirred at room temperature for two hours. The mixture was then adjusted to pH 7 by adding an aqueous sodium hydroxide solution, and extracted with ethyl acetate (60 ml). The extract was twice washed with 20 ml of saturated aqueous sodium bicarbonate solution, and dried over sodium sulfate. The solvent was evaporated off to give a pale yellow solid (14 mg). The solid was purified by preparative thin layer chromatography (Rf: 0.5, developing solvent: CH$_2$Cl$_2$MeOH=2:1) to give (E)-3,4-difluoro-2-(2-fluoro-4-iodo-phenylamino)-N-(2-hydroxy-ethoxy)-5-{[2-(4-hydroxy-piperidin-1-yl)-ethoxyimino]-methyl}-benzamide (Compound 19) (4.2 mg, 18.9% yield).

$^1$H-NMR (CD$_3$OD, 270 MHz) δ (PPM) 1.50-1.68 (2H, m), 1.75-1.90 (3H, m), 2.40-2.55 (2H, m), 2.87 (2H, t, =5.3 Hz), 2.95-3.05 (2H, m), 3.62 (4H, t, J=4.6 Hz), 3.85 (2H, t, J=4.6 Hz), 4.31 (2H, t, J=5.3 Hz), 6.72 (1H, td, J=8.6, 4.3 Hz), 7.29 (1H, d, J=8.6 Hz), 7.47 (1H, dd, J=10.6, 2.0 Hz), 7.74 (1H, dd, J=6.9, 2.0 Hz), 8.19 (1H, s)

ESI (LC/MS positive mode) m/z 623 (M+H)

Example 20

Production of (E)-3,4-difluoro-2-(2-fluoro-4-iodo-phenylamino)-N-(2-hydroxy-ethoxy)-5-{[2-((S)-hydroxymethyl-pyrrolidin-1-yl)-ethoxyimino]-methyl}-benzamide (Compound 20)

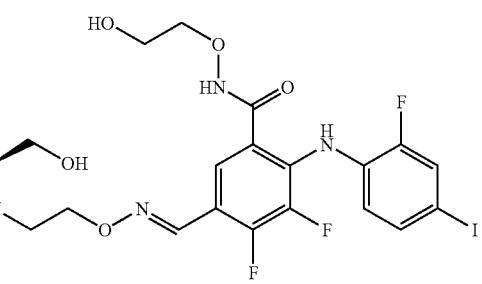

The compound 20 was prepared using the same method as in Example 19.

$^1$H-NMR (CD$_3$OD, 270 MHz) δ (PPM) 1.55-1.70 (1H, m), 1.70-1.78 (1H, m), 1.85-1.95 (1H, m), 2.40-2.50 (1H, m), 2.70-2.80 (2H, m), 3.20-3.35 (2H, m), 3.45-3.55 (3H, m), 3.67 (2H, t, J=4.6 Hz), 3.90 (2H, t, J=4.6 Hz), 4.25 (2H, t, J=5.6 Hz), 6.72 (1H, td, J=8.6, 5.3 Hz), 7.25 (1H, d, J=8.6 Hz), 7.33 (1H, dd, J=10.9, 2.0 Hz), 7.85 (1H, d, J=6.6 Hz), 8.17 (1H, s)

ESI (LC/MS positive mode) m/z 623 (M+H)

Example 21

Production of (E)-3,4-difluoro-2-(2-fluoro-4-iodo-phenylamino)-N-(2-hydroxy-ethoxy)-5-[(2-pyrrolidin-1-yl-ethoxyimino)-methyl]-benzamide (Compound 21)

The compound 21 was prepared using the same method as in Example 3.

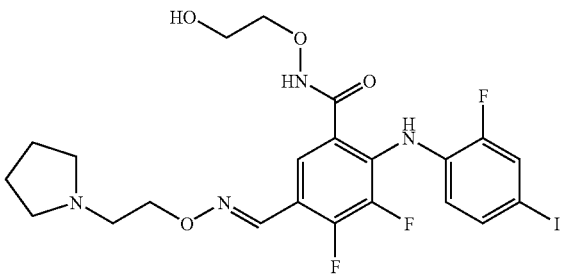

$^1$H-NMR (CDCl$_3$, 270 MHz) δ (PPM) 1.92 (4H, br, s), 2.85 (4H, br, s), 3.04 (2H, t, J=5.6 Hz), 3.78 (2H, br-t, J=4.6 Hz), 4.10 (2H, br-t, J=4.6 Hz), 4.37 (2H, t, J=5.6 Hz), 6.58 (1H, td, J=8.3, 5.6 Hz), 7.32 (1H, d, J=8.6 Hz), 7.38 (1H, dd, J=10.2, 2.0 Hz), 7.85 (1H, d, J=6.9 Hz), 8.14 (1H, s)

ESI (LC/MS positive mode) m/z 593 (M+H)

In the production of the compound 21, the coupling item shown below, O-(2-pyrrolidin-1-yl-ethyl)-hydroxylamine, was prepared according to the method described in WO02/06213A2.

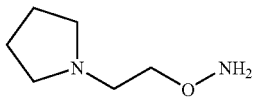

$^1$H-NMR (CDCl$_3$, 270 MHz) δ (PPM) 1.80-1.95 (4H, m), 2.75-2.85 (4H, m), 2.92 (2H, t, J=5.6 Hz), 3.90 (2H, t, J=5.6 Hz), 5.95 (2H, br, s)
ESI (LC/MS positive mode) m/z 131 (M+H)

Example 22

Production of (E)-5-[(2-amino-ethoxyimino)-methyl]-3,4-difluoro-2-(2-fluoro-4-iodo-phenylamino)-N-(2-hydroxy-ethoxy)-benzamide (Compound 22)

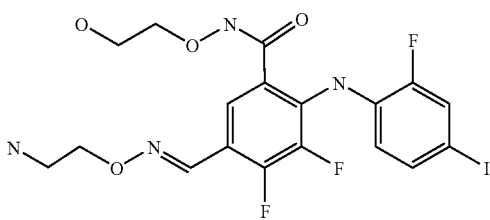

Process A

Preparation of (E)-{2-[2,3-difluoro-4-(2-fluoro-4-iodo-phenylamino)-5-(2-hydroxy-ethoxycarbamoyl)-benzylideneaminooxy]-ethyl}-carbamic Acid Tert-butyl Ester

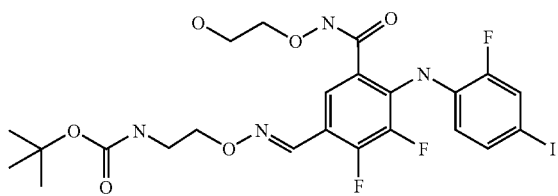

First, a known compound (CAS75051-55-7) synthesized according to the method described in J. Med. Chem., 1999, 42, 2007 and WO02/06213

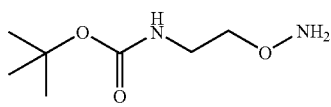

was used to prepare the above intermediate, (E)-{2-[2,3-difluoro-4-(2-fluoro-4-iodo-phenylamino)-5-(2-hydroxy-ethoxycarbamoyl)-benzylideneaminooxy]-ethyl}-carbamic acid tert-butyl ester, according to the method described in Example 3.

$^1$H-NMR (DMSO-d$_6$, 270 MHz) δ (PPM) 1.38 (9H, s), 3.26 (2H, t, J=5.9 Hz), 3.56 (2H, t, J=4.3 Hz), 3.83 (2H, t, J=4.3 Hz), 4.36 (2H, t, J=5.9 Hz), 4.72 (1H, s), 6.79 (1H, m), 6.95 (1H, m), 7.38 (1H, d, J=8.9 Hz), 7.60 (1H, d, J=10.6 Hz), 7.69 (1H, d, J=6.3 Hz), 8.27 (1H, s), 8.86 (0.5H, br. s), 11.98 (0.5H, br. s)
ESI (LC/MS positive mode) m/z 639 (M+H)

Process B

Preparation of 5-[(2-amino-ethoxyimino)-methyl]-3,4-difluoro-2-(2-fluoro-4-iodo-phenylamino)-N-(2-hydroxy-ethoxy)-benzamide

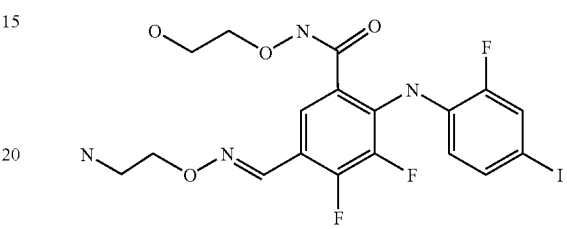

1 N HCl solution in ethyl acetate (1 ml) was added to a solution of {2-[2,3-difluoro-4-(2-fluoro-4-iodo-phenylamino)-5-(2-hydroxy-ethoxycarbamoyl)-benzylideneaminooxy]-ethyl}-carbamic acid tert-butyl ester (55 mg, 0.31 mmol) prepared in Process A in ethyl acetate (5 ml). This mixture was then stirred at room temperature for 1.5 hours. After the completion of the reaction, the reaction solution was neutralized with saturated sodium bicarbonate solution (50 ml) and extracted with ethyl acetate (100 ml×3). The extract was washed with saturated brine, and the organic layer was dried over anhydrous sodium sulfate and filtered. The solvent was evaporated off under reduced pressure, and the resulting residue was washed with diethyl ether (10 ml) and then recrystallized from methanol to give 5-[(2-amino-ethoxyimino)-methyl]-3,4-difluoro-2-(2-fluoro-4-iodo-phenylamino)-N-(2-hydroxy-ethoxy)-benzamide (17.31 mg, 37% yield) as a pale yellow solid.

$^1$H-NMR (DMSO-d$_6$, 270 MHz) δ (PPM) 3.05 (2H, t, J=5.6), 3.56 (2H, t, J=4.6), 3.80 (2H, t, J=4.6), 4.28 (2H, t, J=5.3 Hz), 6.79 (1H, m), 7.38 (1H, d, J=9.0 Hz), 7.61 (1H, d, J=10.9 Hz), 8.08 (1H, d, J=7.3 Hz), 8.26 (1H, s)
ESI (LC/MS positive mode) m/z 539 (M+H)

Example 23

Production of (E)-3,4-difluoro-2-(2-fluoro-4-iodo-phenylamino)-N-(2-hydroxy-ethoxy)-5-[(2-methylamino-ethoxyimino)-methyl]-benzamide (Compound 23)

The compound 23 was prepared using the same method as in Example 3.

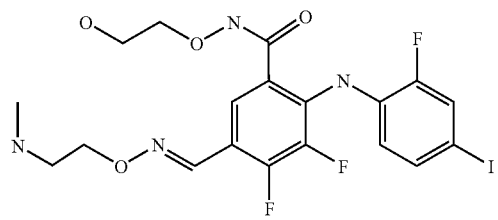

¹H-NMR (DMSO-d₆, 270 MHz) δ (PPM) 3.05 (2H, t, J=5.6), 3.54 (2H, t, J=4.6), 3.80 (2H, t, J=4.6), 4.29 (2H, t, J=5.3 Hz), 6.79 (1H, m), 7.38 (1H, d, J=9.0 Hz), 7.61 (1H, d, J=10.9 Hz), 7.98 (1H, d, J=7.3 Hz), 8.27 (1H, s)

ESI (LC/MS positive mode) m/z 553 (M+H)

The known compound (2-methylamino-ethyl)-hydroxylamine hydrochloride (CAS 187617-82-9), shown below, was used as a coupling item in the production of the compound 23.

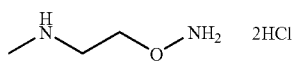

Example 24

Production of (E)-5-[(2-acetylamino-ethoxyimino)-methyl]-3,4-difluoro-2-(2-fluoro-4-iodo-phenylamino)-N-(2-hydroxy-ethoxy)-benzamide (Compound 24)

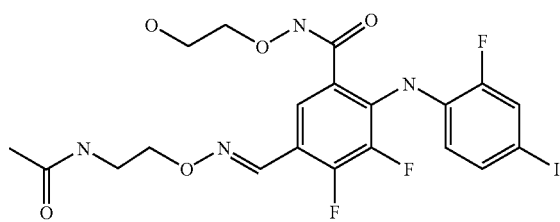

To a solution of 5-[(2-amino-ethoxyimino)-methyl]-3,4-difluoro-2-(2-fluoro-4-iodo-phenylamino)-N-(2-hydroxy-ethoxy)-benzamide (8.14 mg, 0.02 mmol) described in Example 22 in a mixture of dimethylformamide (1 ml) and methanol (5 ml), N-methoxy-diacetamide (100 mg, 0.76 mmol) was added, and the mixture was stirred at room temperature for 14 hours. After completion of the reaction, the solvent was distilled off under reduced pressure, and the resulting residue was purified with Mega Bond Elut silica gel (5 g, Varian, Inc.). From the fractions eluted with 6% methanol/methylene chloride, 5-[(2-acetylamino-ethoxyimino)-methyl]-3,4-difluoro-2-(2-fluoro-4-iodo-phenylamino)-N-(2-hydroxy-ethoxy)-benzamide (8.10 mg, 92% yield) was obtained as a pale yellow solid.

¹H-NMR (DMSO-d₆, 400 MHz) δ (PPM) 1.82 (3H, s), 3.36 (2H, t, J=5.6), 3.57 (2H, br. s), 3.84 (2H, br. s), 4.15 (2H, t, J=5.6 Hz), 4.73 (1H, s), 6.81 (1H, m), 7.40 (1H, d, J=7.6 Hz), 7.61 (1H, d, J=10.8 Hz), 7.71 (1H, br. s), 8.00 (1H, s), 8.28 (1H, s), 8.90 (0.5H, br. s), 11.98 (0.5H, br. s)

ESI (LC/MS positive mode) m/z 581 (M+H)

Example 25

Production of (E)-5-{[2-(acetyl-methyl-amino)-ethoxyimino]-methyl}-3,4-difluoro-2-(2-fluoro-4-iodo-phenylamino)-N-(2-hydroxyethoxy)-benzamide (Compound 25)

This compound was synthesized according to the synthesis method in Example 24, using the compound described in Example 23.

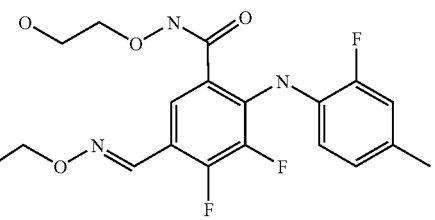

¹H-NMR (DMSO-d₆, 270 MHz) δ (PPM) 1.98 and 1.99 (3H, each s), 2.84 and 3.01 (3H, each s), 3.50-3.70 (4H, m), 3.84 (2H, br. s), 4.23 and 4.29 (2H, each t, J=5.3 Hz), 4.73 (1H, s), 6.81 (1H, m), 7.40 (1H, d, J=7.9 Hz), 7.61 (1H, d, J=10.8 Hz), 7.71 (1H, br. d), 8.00 (1H, s), 8.29 (1H, d, J=9.2), 8.89 (0.5H, br. s), 11.96 (0.5H, br. s)

ESI (LC/MS positive mode) m/z 595 (M+H)

Example 26

Production of (E)-3,4-difluoro-2-(2-fluoro-4-iodo-phenylamino)-N-(2-hydroxy-ethoxy)-5-{[2-(2-oxo-pyrrolidin-1-yl)-ethoxyimino]-methyl}-benzamide (Compound 26)

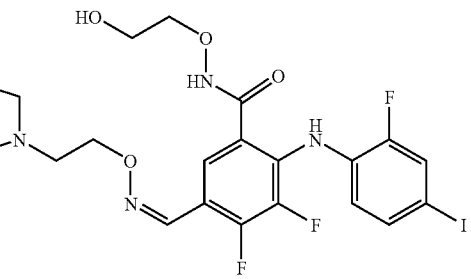

The compound 26 was prepared according to the same method as in Example 3.

¹H-NMR (DMSO-d₆, 270 MHz) δ (PPM) 1.95 (2H, m), 2.20 (2H, t, J=6.2 Hz), 3.42 (2H, t, J=7.2 Hz), 3.50 (2H, t, J=5.2 Hz), 3.56 (2H, br), 3.33 (2H, br), 4.29 (2H, t, J=5.2 Hz), 6.81 (1H, m), 7.40 (1H, d, J=8.2 Hz), 7.59 (1H, d, 3=10.9 Hz), 7.70 (1H, br), 8.28 (1H, s)

ESI (LC/MS positive mode) In/Z 607 (M+H)

In the Production of the compound 26, the coupling item, 1-(2-aminooxy-ethyl)-pyrrolidin-2-one shown below was prepared according to the method described below.

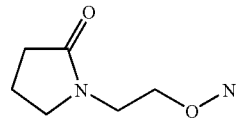

Process 1

1-(2-Hydroxy-ethyl)-pyrrolidin-2-one (1.00 g, 7.74 mmol, commercial product), PPh₃ (2.07 g, 7.90 mmol), N-hydroxyphthalimide (1.29 g, 7.90 mmol), and diisopropyl azodicarboxylate (1.60 g, 7.90 mmol) were added to anhydrous THF at 0° C. under a nitrogen atmosphere, and the mixture was stirred. After 4 hours, the reaction mixture was purified by silica gel chromatography to give 2-(2-(2-oxo-pyrrolidin-1-yl)-ethoxy)-isoindol-1,3-dione (1.21 g).

¹H-NMR (CDCl₃, 270 MHz) δ (PPM) 2.13 (2H, m), 2.45 (2H, t, J=8.0 Hz), 3.70 (4H, m), 4.39 (2H, t, J=8.6 Hz) 7.52 (2H, m), 7.83 (2H, m)

Process 2

2-(2-(2-Oxo-pyrrolidin-1-yl)-ethoxy)-isoindol-1,3-dione (590 mg, 2.15 mmol) and methylhydrazine (119 mg, 2.58 mmol) were mixed in methylene chloride, and the mixture was stirred at room temperature for 3 hours. The reaction mixture was purified by silica gel chromatography to give 1-(2-aminooxy-ethyl)-pyrrolidin-2-one (the title compound, 298 mg).

¹H-NMR (CDCl₃, 270 MHz) δ (PPM) 2.05 (2H, m, 72.41 (2H, t, c=8.0 Hz), 3.43 (2H, t, 3=8.0 Hz), 3.54 (2H, t, J=5.2 Hz), 3.77 (2H, t, J=5.2 Hz)

Example 27

Production of (E)-3,4-difluoro-2-(2-fluoro-4-iodo-phenylamino)-N-(2-hydroxy-ethoxy)-5-{[2-(2-oxo-imidazolidin-1-yl)-ethoxyimino]-methyl}-benzamide (Compound 27)

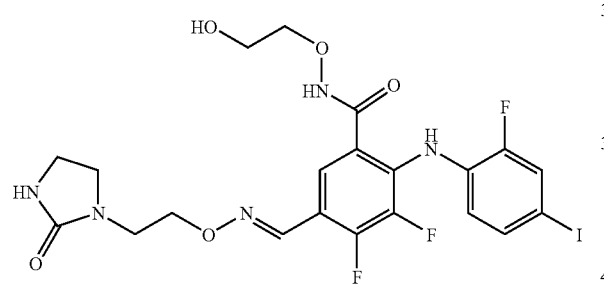

The compound 27 was prepared according to the same method as in Example 3.

¹H-NMR (CDCl₃, 270 MHz) δ (PPM) 3.35-3.43 (2H, m), 3.49 (2H, t, J=5.3 Hz), 3.55-3.63 (2H, m), 3.72 (2H, t, J=4.6 Hz), 3.95 (2H, t, J=4.6 Hz), 4.30 (2H, t, J=5.3 Hz), 4.37 (2H, t, J=5.6 Hz), 6.71 (1H, td, J=8.6, 4.6 Hz), 7.38 (1H, d, J=7.4 Hz), 7.47 (1H, dd, J=10.6, 2.0 Hz), 7.82 (1H, d, J=7.3 Hz), 8.26 (1H, s)

ESI (LC/MS positive mode) m/z 608 (M+H)

In the Production of the compound 27, the coupling item, O-[2-(2-oxo-imidazolidin-1-yl)-ethyl]-hydroxylamine shown below was prepared according to the method described in WO02/06213A2.

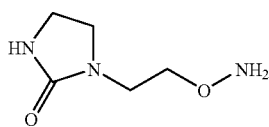

¹H-NMR (CDCl₃, 270 MHz) δ (PPM), 3.45 (2H, t, J=5.3 Hz), 3.45-3.60 (4H, m), 3.79 (2H, t, J=5.3 Hz), 4.65 (2H, br, s)

Example 28

Production of (E)-3,4-difluoro-2-(2-fluoro-4-iodo-phenylamino)-N-(2-hydroxy-ethoxy)-5-[(1H-imidazol-2-ylmethoxyimino)-methyl]-benzamide (Compound 28)

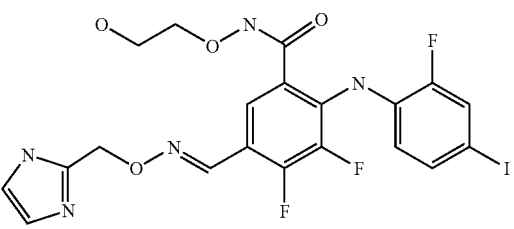

The compound 28 was prepared according to the method in Example 3.

¹H-NMR (DMSO-d₆, 270 MHz) δ (PPM) 3.56 (2H, m), 3.82 (2H, m), 5.25 (2H, s), 6.79 (1H, m), 7.25 (2H, br. s), 7.39 (H, d, J=7.6 Hz), 7.60 (1H, d, J=10.5 Hz), 7.70 (1H, m), 7.74 (1H, m), 8.35 (1H, s)

ESI (LC/MS positive mode) m/z 576 (M+H)

In the Production of the compound 28, O-(1H-imidazol-2-ylmethyl)-hydroxylamine (CAS 372105-57-2) was used as the coupling item. This compound can be prepared according to the method described in the patent DE3040257.

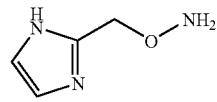

Example 29

Production of (E)-3,4-difluoro-2-(2-fluoro-4-iodo-phenylamino)-N-(2-hydroxy-ethoxy)-5-[(3H-imidazol-4-ylmethoxyimino)-methyl]-benzamide (Compound 29)

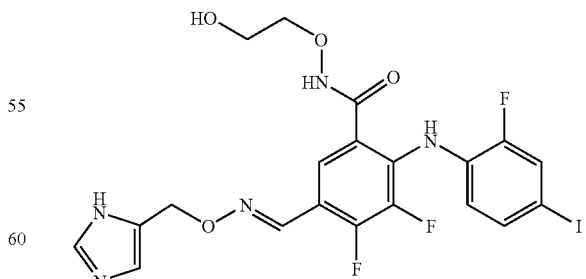

The compound 29 was prepared according to the method in Example 3.

¹H-NMR (CD₃OD, 270 MHz) δ (PPM) 3.73 (2H, t, J=4.6 Hz), 3.96 (2H, t, J=4.6 Hz), 5.16 (2H, s), 6.71 (1H, m), 7.16

(1H, s), 7.38 (1H, dd, J=6.5, 1.0 Hz), 7.47 (1H, dd, J=10.5, 2.0 Hz), 7.69 (1H, s), 7.85 (1H, dd, J=7.2, 2.0 Hz), 8.24 (1H, s)

ESI (LC/MS positive mode) m/z 576 (M+H)

In the Production of the compound 29, the coupling item, O-(3H-imidazol-4-ylmethyl)-hydroxylamine shown below was prepared according to the method described below.

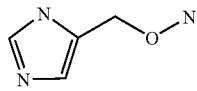

Process 1

(3H-Imidazol-4-yl)-methanol (90 mg, 0.92 mmol) obtained by reducing 3H-imidazole-4-carboaldehyde (commercial product) with lithium aluminum hydride in THF was mixed with $PPh_3$ (245 mg, 0.94 mmol), N-hydroxy-phthalimide (153 mg, 0.94 mmol), and diisopropyl azodicarboxylate (189 mg, 0.94 mmol) in anhydrous THF at 0° C. under a nitrogen atmosphere, and the mixture was stirred. After 4 hours, the reaction mixture was purified by silica gel chromatography to give 2-(3H-imidazol-4-ylmethoxy)-isoindol-1,3-dione (30 mg).

$^1$H-NMR (CDCl$_3$, 270 MHz) δ (PPM) 5.26 (2H, s), 7.21 (1H, s), 7.66 (1H, s), 7.75 (2H, m), 7.83 (2H, m)

Process 2

2-(3H-Imidazol-4-ylmethoxy)-isoindol-1,3-dione (30 mg, 0.12 mmol) and methylhydrazine (6.8 mg, 0.15 mmol) were mixed in methylene chloride, and the mixture was stirred at room temperature for 3 hours. The reaction mixture was used as it was in the next reaction (synthesis of CH4926623).

Example 30

Production of (E)-3,4-difluoro-2-(2-fluoro-4-iodo-phenylamino)-N-(2-hydroxy-ethoxy)-5-[(pyridin-4-ylmethoxyimino)-methyl]-benzamide (Compound 30)

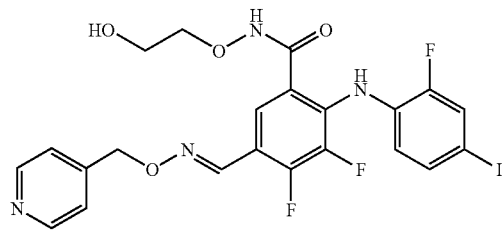

The compound 30 was prepared according to the method in Example 3.

$^1$H-NMR (DMSO-d$_6$, 270 MHz) δ (PPM) 3.53 (2H, m), 3.80 (2H, m), 5.28 (2H, s), 6.77 (1H, m), 7.39 (2H, d, J=5.9 Hz), 7.60 (1H, d, J=8.9 Hz), 7.60 (1H, partially hidden) 7.74 (1H, m), 8.43 (1H, s), 8.57 (2H, d, J=5.9 Hz)

ESI (LC/MS positive mode) m/z 587 (M+H)

In the Production of the compound 30, the coupling item, O-pyridin-4-ylmethyl-hydroxylamine shown below was prepared according to the method described in the literature below.

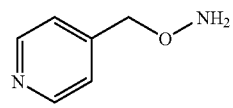

Patent; Giogyszerkutato Intezet; CH 566961; 1972; DE 2241035

Example 31

Production of (E)-3,4-difluoro-2-(2-fluoro-4-iodo-phenylamino)-N-(2-hydroxy-ethoxy)-5-[methoxy-imino-methyl]-benzamide (Compound 31)

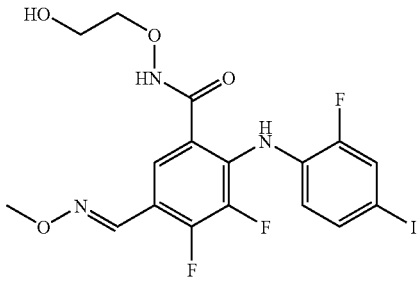

The compound 31 was prepared according to the method in Example 3.

$^1$H-NMR (DMSO-d6, 270 MHz) δ (PPM) 3.57 (2H, br. q, J=5.3 Hz), 3.83 (2H, t, J=4.3 Hz), 3.94 (3H, s), 4.73 (1H, br. t, J=5.3 Hz), 6.81 (1H, td, J=8.6, 4.0 Hz), 7.41 (1H, br. d, J=7.6 Hz), 7.61 (1H, dd, J=10.9, 2.0 Hz), 7.68 (1H, br. d, J=7.0 Hz), 8.27 (1H, s), 8.88 (1H, br. s, NH), 11.98 (1H, br. s, NH).

ESI (LC/MS positive mode) m/z 510 (M+H)

In the Production of the compound 31, the coupling item, O-methyl-hydroxylamine shown below was a commercially available reagent (Kanto Kagaku Co.).

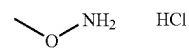

Example 32

Production of (E)-3,4-difluoro-2-(2-fluoro-4-iodo-phenylamino)-N-(2-hydroxy-ethoxy)-5-[isopropoxy-imino-methyl]-benzamide (Compound 32)

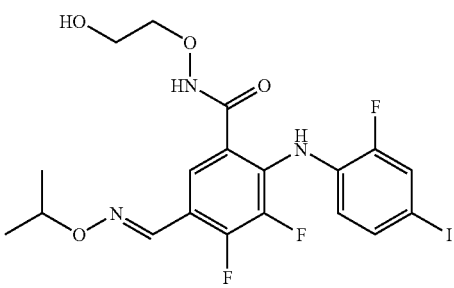

The compound 32 was prepared according to the method in Example 3.

¹H-NMR (DMSO-d6, 270 MHz) δ (PPM) 1.27 (6H, d, J=6.3 Hz), 3.57 (2H, br. q, J=4.3 Hz), 3.84 (2H, t, J=4.6 Hz), 4.44 (1H, qui, J=6.3 Hz) 4.73 (1H, br. t, J=5.6 Hz), 6.80 (1H, td, J=9.2, 4.3 Hz), 7.40 (1H, br. d, J=7.9 Hz), 7.61 (1H, dd, J=10.9, 2.0 Hz), 7.69 (1H, br. d, J=6.9 Hz), 8.22 (1H, s), 8.84 (1H, br. s, NH), 11.98 (1H, br. s, NH).

ESI (LC/MS positive mode) m/z 538 (M+H)

In the Production of the compound 32, the coupling item, 2-(ammoniooxy)propane chloride shown below was a commercially available reagent (Interchim S.A.).

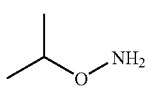

Example 33

Production of (E)-3,4-difluoro-2-(2-fluoro-4-iodo-phenylamino)-N-(2-hydroxy-ethoxy)-5-[(3-hydroxy-3-methyl-butoxyimino)-methyl]-benzamide (Compound 33

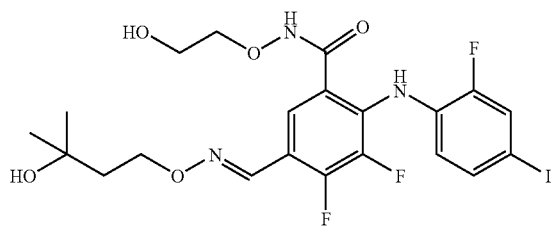

The compound 33 was prepared according to the method in Example 3.

¹H-NMR (CD₃OD, 270 MHz) δ (PPM) 1.25 (6H, s), 1.91 (2H, t, J=6.9 Hz), 3.72 (2H, dd, J=5.0, 4.3 Hz), 3.95 (2H, dd, J=5.0, 4.3 Hz), 4.87 (2H, t, J=6.9 Hz), 6.71 (1H, t, J=8.6, 4.3 Hz), 7.39 (1H, br. d, J=8.6 Hz), 7.47 (1H, dd, J=10.6, 2.0 Hz), 7.81 (1H, br. d, J=5.3 Hz), 8.22 (1H, s)

ESI (LC/MS positive mode) m/z 582 (M+H)

In the Production of the compound 33, the coupling item, 4-aminooxy-2-methyl-butan-2-ol shown below was prepared according to the method described in WO02/06213.

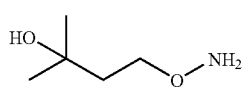

¹H-NMR (CDCl₃, 270 MHz) δ (PPM) 1.25 (3H, s), 1.26 (3H, s), 1.80 (2H, t, J=5.9 Hz), 3.90 (2H, dt, J=6.3. 1.3 Hz), 5.30 (2H, br. s)

ESI (LC/MS positive mode) m/z 120 (M+H)

Example 34

Production of (E)-3,4-difluoro-2-(2-fluoro-4-iodo-phenylamino)-5-[(E)-(3-hydroxy-2,2-dimethyl-propoxyimino)-methyl]-N-(2-hydroxy-ethoxy)-benzamide (Compound 34)

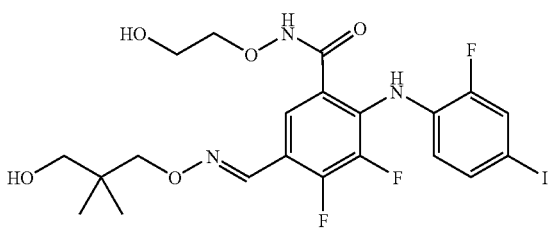

The compound 34 was prepared according to the method in Example 3.

¹H-NMR (CD₃OD, 270 MHz) δ (PPM) 0.96 (6H, s), 3.52 (2H, s), 3.72 (2H, t, J=4.6 Hz), 3.95 (2H, t, J=4.6 Hz), 4.05 (2H, s), 6.71 (1H, dt, J=8.6, 4.6 Hz), 7.39 (1H, br. d, J=8.6 Hz), 7.47 (1H, dd, J=10.9, 2.0 Hz), 7.80 (1H, br. d, J=4.9 Hz), 8.25 (1H, s)

ESI (LC/MS positive mode) m/z 582 (M+H)

In the Production of the compound 34, the coupling item, 3-aminooxy-2,2-dimethyl-propan-1-ol shown below was prepared according to the method described in WO02/06213.

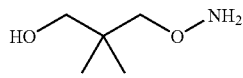

Example 35

Production of (E)-3,4-difluoro-2-(2-fluoro-4-iodo-phenylamino)-N-(2-hydroxy-ethoxy)-5-[(1-hydroxymethyl-cyclopropylmethoxyimino)-methyl]-benzamide (Compound 35)

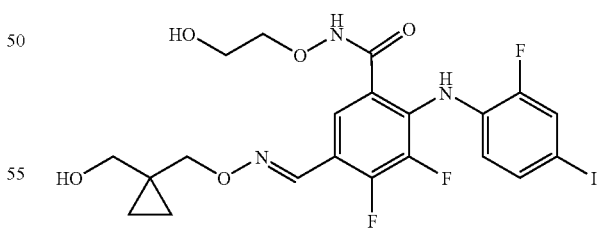

The compound 35 was prepared according to the method in Example 3.

¹H-NMR (CD₃OD, 270 MHz) δ (PPM) 0.53 (2H, m), 0.60 (2H, m), 3.50 (2H, s), 3.71 (2H, m), 3.94 (2H, m), 4.16 (2H, s), 6.71 (1H, td, J=8.6, 4.6 Hz), 7.38 (1H, br. d, J=8.9 Hz), 7.47 (1H, dd, J=10.6, 1.6 Hz), 7.79 (1H, br. d, J=6.3 Hz), 8.26 (1H, s)

ESI (LC/MS positive mode) m/z 580(M+H)

In the Production of the compound 35, the coupling item, (1-aminooxymethyl-cyclopropyl)-methanol shown below was prepared according to the method described in WO02/06213.

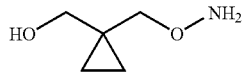

Example 36

Production of (E)-3,4-difluoro-2-(2-fluoro-4-iodo-phenylamino)-5-[(4-hydroxy-butoxyimino)-methyl]-N-(2-hydroxy-ethoxy)-benzamide (Compound 36)

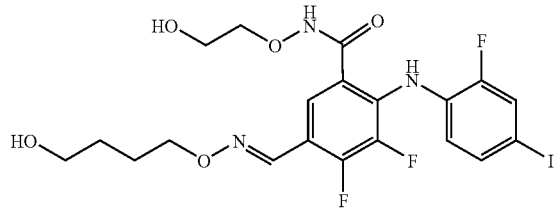

The compound 36 was obtained by coupling the source compound with O-[4-(tert-butyl-dimethyl-silanyloxy)-butyl]-hydroxylamine shown below according to the method in Example 3 followed by desilylation.

$^1$H-NMR (CD$_3$OD, 270 MHz) δ (PPM) 1.64 (2H, m), 1.79 (2H, m), 3.60 (2H, t, J=6.3 Hz), 3.72 (2H, dd, J=4.9, 4.3 Hz), 3.95 (2H, dd, J=4.9, 4.3 Hz), 4.22 (2H, t, J=6.3 Hz), 6.71 (1H, td, J=8.6, 4.3 Hz), 7.39 (1H, m), 7.47 (1H, dd, J=10.6, 2.0 Hz), 7.80 (1H, br. d, J=5.3 Hz), 8.23 (1H, s)

ESI (LC/MS positive mode) m/z 568 (M+H)

O-[4-(Tert-butyl-dimethyl-silanyloxy)-butyl]-hydroxylamine shown below, which was used in Example 36, was prepared according to the method described in WO02/06213.

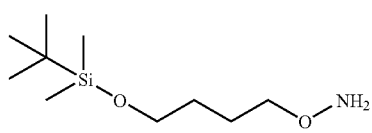

Example 37

Production of (E)-3,4-difluoro-2-(2-fluoro-4-iodo-phenylamino)-N-(2-hydroxy-ethoxy)-5-[(3-methoxy-3-methyl-butoxyimino)-methyl]-benzamide (Compound 37)

The compound 37 was prepared according to the method in Example 3.

$^1$H-NMR (CD$_3$OD, 270 MHz) δ (PPM) 1.22 (6H, s), 1.99 (2H, t, J=7.3 Hz), 3.23 (3H, s), 3.71

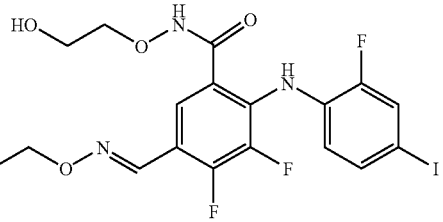

(2H, m), 3.95 (2H, m), 4.28 (2H, t, J=7.3 Hz), 6.71 (1H, td, J=8.9, 4.6 Hz), 7.38 (1H, m), 7.47 (1H, dd, J=10.6, 2.0 Hz), 7.80 (1H, m), 8.21 (1H, s)

ESI (LC/MS positive mode) m/z 596 (M+H)

In the Production of the compound 37, the coupling item, 4-aminooxy-2-methyl-buthan-2-ol shown below was prepared according to the method described in WO02/06213.

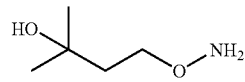

$^1$H-NMR (CDCl$_3$, 270 MHz) δ (PPM) 1.25 (3H, s), 1.26 (3H, s), 1.80 (2H, t, J=5.9 Hz), 3.90 (2H, dt, J=6.3. 1.3 Hz), 5.30 (2H, br. s)

ESI (LC/MS positive mode) m/z 120 (M+H)

Example 38

Production of (E)-3,4-difluoro-2-(2-fluoro-4-iodo-phenylamino)-N-(2-hydroxy-ethoxy)-5-[(2-methoxy-ethoxyimino)-methyl]-benzamide (Compound 38D

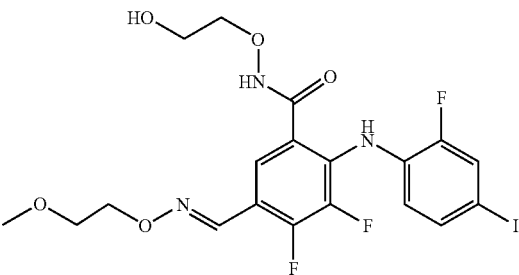

The compound 38 was prepared according to the method in Example 3.

$^1$H-NMR (DMSO-d6, 270 MHz) δ (PPM) 3.29 (3H, s, Me), 3.56 (2H, t, J=4.9 Hz), 3.61 (2H, t, J=4.6 Hz), 3.82 (2H, t, J=5.0 Hz), 4.27 (2H, t, J=4.3 Hz), 6.80 (1H, td, J=8.9, 4.3 Hz), 7.40 (1H, d, J=8.6 Hz), 7.61 (1H, dd, J=10.9, 2.0 Hz), 7.73 (1H, d, J=7.3 Hz), 8.29 (1H, s), 8.84 (1H, br. s, NH), 11.98 (1H, br. s, NH).

ESI (LC/MS positive mode) m/z 554 (M+H)

In the Production of the compound 38, O-(2-methoxy-ethyl)-hydroxylamine shown below, which is used for the coupling, was prepared according to the method described in WO0206213.

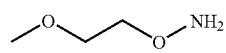

Example 39

Production of (E)-3,4-difluoro-2-(2-fluoro-4-iodo-phenylamino)-N-(2-hydroxy-ethoxy)-5-[(2-methyl-sulfanyl-ethoxyimino)-methyl]-benzamide (Compound 39)

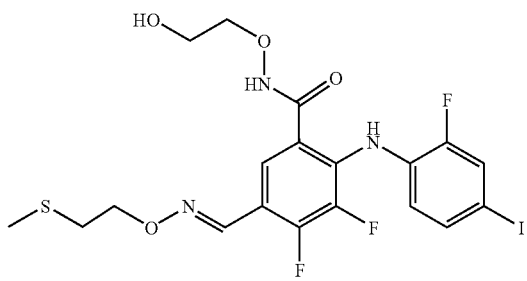

The compound 39 was prepared according to the method in Example 3.

$^1$H-NMR (CD$_3$OD, 270 MHz) δ (PPM) 2.15 (3H, s), 2.82 (2H, dd, J=6.9, 6.6 Hz), 3.72 (2H, dd, J=4.9, 4.3 Hz), 3.95 (2H, dd, J=4.9, 4.3 Hz), 4.34 (2H, dd, J=6.9, 6.6 Hz), 6.72 (1H, td, J=8.6, 4.3 Hz), 7.39 (1H, m), 7.47 (1H, dd, J=10.6, 2.0 Hz), 7.81 (1H, dd, J=7.3, 2.0 Hz), 8.25 (1H, s)

ESI (LC/MS positive mode) m/z 570 (M+H)

In the Production of the compound 39, O-(2-methylsulfanyl-ethyl)-hydroxylamine shown below, which is used for the coupling, was prepared according to the method described in WO03077855A2.

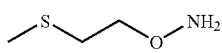

Example 40

Production of (E)-3,4-difluoro-2-(2-fluoro-4-iodo-phenylamino)-N-(2-hydroxy-ethoxy)-5-[(2-methane-sulfonyl-ethoxyimino)-methyl]-benzamide (Compound 40)

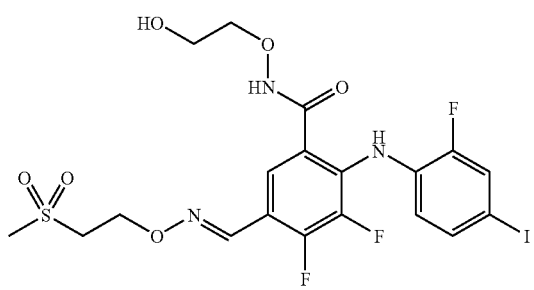

The compound 40 was prepared according to the method in Example 3.

$^1$H-NMR (CD$_3$OD, 270 MHz) δ (PPM) 3.02 (3H, s), 3.57 (2H, dd, J=5.9, 5.6 Hz), 3.72 (2H, dd, J=4.9, 4.3 Hz), 3.95 (2H, dd, J=4.9, 4.3 Hz), 4.61 (2H, dd, J=5.9, 5.6 Hz), 6.88 (1H, td, J=8.6, 4.3 Hz), 7.39 (1H, m), 7.48 (1H, dd, J=10.6, 2.0 Hz), 7.84 (1H, dd, J=6.9, 2.0 Hz), 8.33 (1H, s)

ESI (LC/MS positive mode) m/z 602 (M+H)

O-(2-Methanesulfonyl-ethyl)-hydroxylamine shown below, which was used in the coupling reaction for the compound 40, was prepared according to the method described in WO03077855A2.

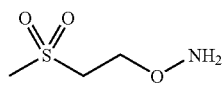

Example 41

Production of (E)-2-(4-ethynyl-2-fluoro-phenylamino)-3,4-difluoro-N-(2-hydroxy-ethoxy)-5-[(2-methylcarbamoyl-ethoxyimino)-methyl]-benzamide (Compound 41)

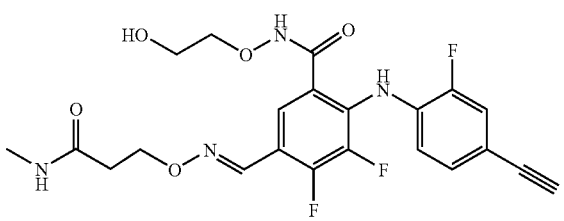

This compound was synthesized from 3,4-difluoro-2-(2-fluoro-4-iodo-phenylamino)-N-(2-hydroxy-ethoxy)-5-[(2-methylcarbamoyl-ethoxyimino)-methyl]-benzamide (Example 14, Compound 14), and the actual reaction was carried out according to the method for manufacturing 2-(4-ethynyl-2-fluoro-phenylamino)-3,4-difluoro-N-(2-hydroxy-ethoxy)-5-[(2-hydroxy-ethoxyimino)-methyl]-benzamide (Example 2, Compound 2).

$^1$H-NMR (CD$_3$OD, 270 MHz) δ (PPM) 2.59 (2H, t, J=6.3 Hz), 2.73 (3H, s), 3.45 (1H, s), 3.76 (2H, m), 3.79 (2H, m), 4.43 (2H, t, J=6.3 Hz), 6.83 (1H, td, J=8.3, 5.3 Hz), 7.16 (1H, br. d, J=8.6 Hz), 7.20 (1H, dd, J=13.6, 2.0 Hz), 7.90 (1H, m), 8.23 (1H, s)

ESI (LC/MS positive mode) m/z 479 (M+H)

Example 42

Production of (E)-3,4-difluoro-2-(2-fluoro-4-iodo-phenylamino)-N-(2-hydroxy-ethoxy)-5-[dimethyl-carbamoylethoxyimino-methyl]-benzamide (Compound 42)

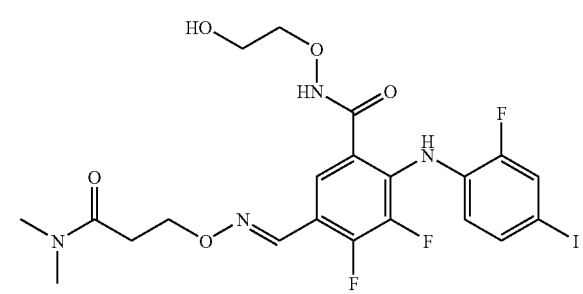

Process A

Preparation of (E)-3-[1-[2,3-difluoro-4-(2-fluoro-4-iodo-phenylamino)-5-(2-hydroxy-ethoxycarbamoyl)-phenyl]-meth-(E)-ylideneaminooxy]-propionic acid methyl ester

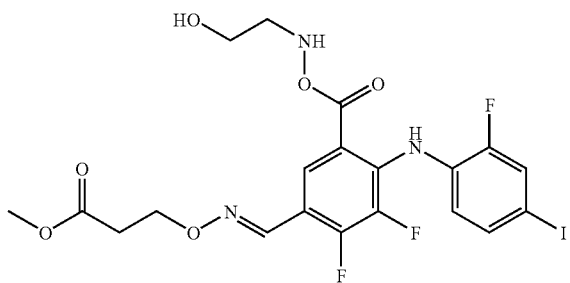

The compound XX was prepared according to the method in Example 3. The crude compound obtained by treating the reaction mixture was used in the next reaction without further purification.

$^1$H-NMR (CD$_3$OD, 270 MHz) δ (PPM) 2.76 (2H, t, J=5.9 Hz), 3.70 (3H, s), 3.72 (2H, t, J=5.0 Hz), 3.95 (2H, t, J=5.0 Hz), 4.44 (2H, t, J=5.9 Hz), 6.72 (1H, td, J=8.6, 4.3 Hz), 7.39 (1H, ddd, J=8.6, 2.0, 1.0 Hz), 7.48 (1H, dd, J=10.6, 2.0 Hz), 7.79 (1H, d, J=5.3 Hz), 8.22 (1H, s).

ESI (LC/MS positive mode) m/z 582 (M+H)

3-Aminooxy-propionic acid methyl ester used in the coupling reaction for the compound xx was prepared according to the method described in J. Gen. Chem. USSR (Engl. Transl.), 31, 1961, 1863-1865; Zh. Obshch. Khim., 31, 1961, 1992-1995.

Process B

Preparation of (E)-3-[1-[2,3-difluoro-4-(2-fluoro-4-iodo-phenylamino)-5-(2-hydroxy-ethoxycarbamoyl)-phenyl]-meth-(E)-ylideneaminooxy]-propionic acid

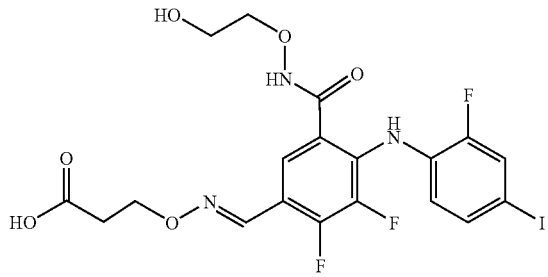

To a solution of (E)-3-[1-[2,3-difluoro-4-(2-fluoro-4-iodo-phenylamino)-5-(2-hydroxy-ethoxycarbamoyl)-phenyl]-meth-(E)-ylideneaminooxy]-propionic acid methyl ester (159 mg) obtained in Process A in tetrahydrofuran (4 ml), 1N aqueous solution of sodium hydroxide (2.5 ml) was added while being cooled with ice, and the mixture was stirred at room temperature for 1 hour. To the reaction solution, 1N hydrochloric acid (2.5 ml) was added, and the mixture was extracted with ethyl acetate. The organic layer was washed with saturated brine, dried over magnesium sulfate, and concentrated under reduced pressure. The residue was purified by silica gel column chromatography (CH$_2$Cl$_2$:MeOH:AcOH=100:10:1) to give (E)-3-[1-[2,3-difluoro-4-(2-fluoro-4-iodo-phenylamino)-5-(2-hydroxy-ethoxycarbamoyl)-phenyl]-meth-(E)-ylideneaminooxy]-propionic acid (124 mg) as a pale yellow solid.

$^1$H-NMR (CD$_3$OD, 270 MHz) δ (PPM) 2.72 (2H, t, J=6.3 Hz), 3.72 (2H, t, J=4.3 Hz), 3.96 (2H, t, J=4.3 Hz), 4.43 (2H, t, J=6.3 Hz), 6.72 (1H, td, J=8.9, 4.6 Hz), 7.38 (1H, d, J=9.2 Hz), 7.46 (1H, dd, J=10.6, 1.7 Hz), 7.80 (1H, dd, J=6.9, 2.0 Hz), 8.23 (1H, s).

Process C

Production of (E)-3,4-difluoro-2-(2-fluoro-4-iodo-phenylamino)-N-(2-hydroxy-ethoxy)-5-[dimethylcarbamoylethoxyimino-methyl]-benzamide (Compound 42)

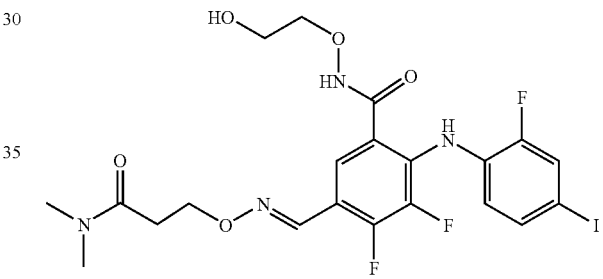

To a solution of (E)-3-[1-[2,3-difluoro-4-(2-fluoro-4-iodo-phenylamino)-5-(2-hydroxy-ethoxycarbamoyl)-phenyl]-meth-(E)-ylideneaminooxy]-propionic acid (19.9 mg, 0.035 mmol) obtained in Process B in methylene chloride (2 ml), 1-hydroxybenzotriazole (9.7 mg, 0.071 mmol), 1-ethyl-3-(3-dimethylaminopropyl)-carbodiimide hydrochloride (14.3 mg, 0.074 mmol), dimethylamine (2N solution in tetrahydrofuran, 100 μl), and N,N-diisopropylethylamine (18.5 A1) were added, and the mixture was stirred for 6 hours. 0.2 N Hydrochloric acid was added to the reaction solution, and the mixture was extracted with ethyl acetate. The organic layer was washed with saturated aqueous solution of sodium bicarbonate, dried over magnesium sulfate, and concentrated under reduced pressure. The resulting residue was purified by silica gel column chromatography (CH$_2$Cl$_2$:MeOH=20:1) to give (E)-3,4-difluoro-2-(2-fluoro-4-iodo-phenylamino)-N-(2-hydroxy-ethoxy)-5-[dimethylcarbamoylethoxyimino-methyl]-benzamide (Compound 42) (12.6 mg, 61%) as a colorless solid.

$^1$H-NMR (CD$_3$OD, 270 MHz) δ (PPM) 2.80 (2H, t, J=6.6 Hz), 2.94 (3H, s), 3.09 (3H, s), 3.72 (2H, t, J=4.3 Hz), 3.95 (2H, t, J=4.3 Hz), 4.46 (2H, t, J=6.6 Hz), 6.72 (1H, td, J=8.9, 4.3 Hz), 7.39 (1H, ddd, J=8.3, 2.0, 1.0 Hz), 7.47 (1H, dd, J=10.6, 2.0 Hz), 7.80 (dd, J=6.9, 2.0 Hz), 8.23 (1H, s)

ESI (LC/MS positive mode) m/z 595 (M+H)

Example 43

Production of (E)-3,4-difluoro-2-(2-fluoro-4-iodo-phenylamino)-N-(2-hydroxy-ethoxy)-5-[methylcarbamoylmethoxyimino-methyl]-benzamide (Compound 43)

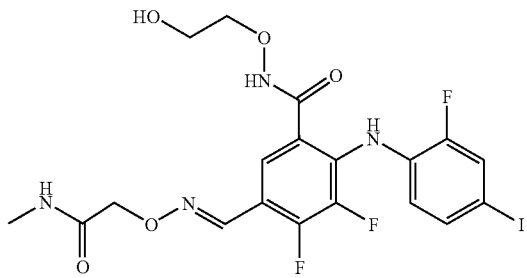

The compound 43 was prepared according to the method in Example 3.

¹H-NMR (DMSO-d6, 270 MHz) δ (PPM) 2.63 (3H, d, J=4.6 Hz), 3.56 (2H, t, J=4.6 Hz), 3.83 (2H, t, J=4.3 Hz), 4.57 (2H, s), 4.73 (1H, br. s, OH), 6.82 (1H, td, J=8.9, 4.0 Hz), 7.41 (1H, br. d, J=8.6 Hz), 7.61 (1H, dd, J=10.9, 2.0 Hz), 7.69 (1H, br. d, J=6.3 Hz), 7.87 (1H, br q, J=4.6 Hz, NH), 8.40 (1H, s), 8.92 (1H, br. s, NH), 12.01 (1H, br. s, NH).

ESI (LC/MS positive mode) m/z 567 (M+H)

In the synthesis of the compound 43, 2-aminooxy-N-methyl-acetamide shown below was used in the coupling reaction. The method for preparing 2-aminooxy-N-methyl-acetamide is described below.

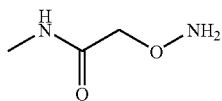

Process A

Synthesis of (1,3-dioxo-1,3-dihydro-isoindol-2-yloxy)-acetic Acid Ethyl Ester

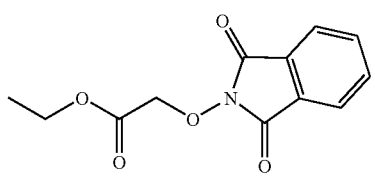

To a solution of ethyl bromoacetate (2.05 g, 12.3 mmol) in dimethylformamide (15 ml), N-hydroxyphthalimide (3.04 g, 18.4 mmol) and Hunig base (N,N-diisopropylethylamine, 4.24 mL) were added at room temperature, and the mixture was stirred at 80° C. overnight. The reaction solution was poured into saturated aqueous solution of ammonium chloride, and the resulting mixture was extracted with ethyl acetate (3×40 ml). The combined organic layer was washed with saturated brine (2×30 ml), dried over $Na_2SO_4$, and concentrated under reduced pressure. The resulting residue was purified by silica gel column chromatography (100 g, n-hexane/ethyl acetate=2:1) to give (1,3-dioxo-1,3-dihydro-isoindol-2-yloxy)-acetic acid ethyl ester (1.83 g, 60%) as a pale yellow solid.

¹H-NMR (CDCl3, 270 MHz) δ (PPM) 1.31 (3H, t, J=6.9 Hz), 4.27 (2H, q, J=6.9 Hz), 4.82 (2H, s), 7.75-7.80 (2H, m), 7.83-7.88 (2H, m).

Process B

Synthesis of 2-aminooxy-N-methyl-acetamide

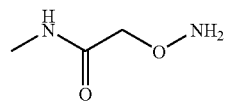

(1,3-Dioxo-1,3-dihydro-isoindol-2-yloxy)-acetic acid ethyl ester (922.5 mg, 3.70 mmol) prepared according to the method described above was dissolved in methanol (4 mL), methylamine (40% solution in methanol, 10 ml) was added thereto at room temperature, and the mixture was stirred at 60° C. overnight. The reaction solution was concentrated under reduced pressure, and methylene chloride was added to the resulting residue. The precipitated solid was filtered, and washed with methylene chloride. The filtrate and the washing were combined and concentrated under reduced pressure. The residue was purified by silica gel column chromatography (30 g, $CH_2Cl_2$/MeOH 8:1) to give 2-aminooxy-N-methyl-acetamide (329.6 mg, 86%) as a colorless syrup.

¹H-NMR (CDCl3, 270 MHz) δ (PPM) 2.88 (3H, d, J=5.0 Hz), 4.17 (2H, s), 5.69 (2H, br. s).

Example 44

Production of (E)-3,4-difluoro-2-(2-fluoro-4-iodo-phenylamino)-N-(2-hydroxy-ethoxy)-5-{[(3-methyl-carbamoyl-propoxyimino)-methyl]-benzamide (Compound 44)

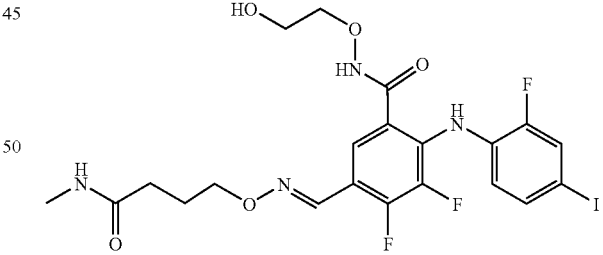

The compound 44 was prepared according to the method in Example 3.

¹H-NMR (DMSO-d6, 270 MHz) δ (PPM) 1.88 (2H, qui, J=7.6 Hz), 2.17 (2H, t, J=6.9 Hz), 2.56 (3H, d, J=4.6 Hz), 3.57 (2H, br. q, J=4.6 Hz), 3.83 (2H, t, J=4.6 Hz), 4.14 (2H, t, J=6.3 Hz), 4.73 (1H, t, J=5.6 Hz, OH), 6.80 (H, td, J=8.9, 4.0 Hz), 7.40 (1H, br. d, J=8.6 Hz), 7.61 (1H, dd, J=10.9, 2.0 Hz), 7.68 (1H, br. d, J=5.6 Hz), 7.77 (1H, br q, J=4.6 Hz, NH), 8.26 (1H, s), 8.87 (1H, br. s, NH), 11.99 (1H, br. s, NH).

ESI (LC/MS positive mode) m/z 595 (M+H)

In the preparation of the compound 44, 4-aminooxy-N-methyl-butylamide shown below was used in the coupling reaction. The method for preparing this compound is described below.

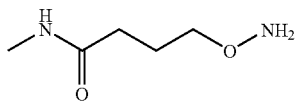

Process A

Synthesis of 4-(1,3-dioxo-1,3-dihydro-isoindol-2-yloxy)-butyric Acid Ethyl Ester

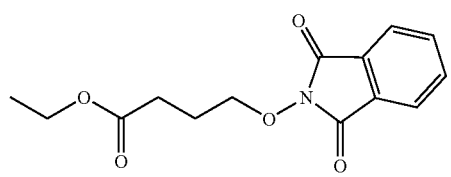

To a solution of ethyl 4-bromo-n-butyrate (1.2 g, 6.13 mmol) in dimethylformamide (9 ml), N-hydroxyphthalimide (1.5 g, 9.19 mmol) and Hunig base (N,N-diisopropylethylamine, 2.13 mL) were added at room temperature, and the mixture was stirred at 80° C. overnight. The reaction solution was poured into saturated aqueous solution of ammonium chloride, and the resulting mixture was extracted with ethyl acetate (3×40 ml). The combined organic layer was washed with saturated brine (2×30 ml), dried over $Na_2SO_4$, and concentrated under reduced pressure. The resulting residue was purified by silica gel column chromatography (100 g, n-hexane/ethyl acetate=2:1) to give 4-(1,3-dioxo-1,3-dihydro-isoindol-2-yloxy)-butyric acid ethyl ester (1.47 g, 100%).

$^1$H-NMR ($CDCl_3$, 270 MHz) δ (PPM) 1.28 (3H, t, J=6.9 Hz), 2.11 (2H, q, J=6.9 Hz), 2.64 (2H, t, J=7.3 Hz), 4.17 (2H, q, J=7.3 Hz), 4.27 (2H, t, J=6.3 Hz), 7.72-7.79 (2H, m), 7.81-7.89 (2H, m).

Process B

Synthesis of 4-aminooxy-N-methyl-butylamide

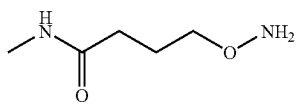

4-(1,3-Dioxo-1,3-dihydro-isoindol-2-yloxy)-butyric acid ethyl ester (997.5 mg, 4.59 mmol) prepared according to the method described above was dissolved in methanol (4 mL), methylamine (40% solution in methanol, 10 ml, 98.0 mmol) was added thereto at room temperature, and the mixture was stirred at 60° C. overnight. The reaction solution was concentrated under reduced pressure, and methylene chloride was added to the resulting residue. The precipitated solid was filtered, and washed with methylene chloride. The filtrate and the washing were combined and concentrated under reduced pressure. The residue was purified by silica gel column chromatography (30 g, $CH_2Cl_2$/MeOH=8:1) to give 4-aminooxy-N-methyl-butylamide (467.3 mg, 77%) as a colorless syrup.

$^1$H-NMR($CDCl_3$, 270 MHz) δ (PPM) 1.94 (2H, q, J=6.3 Hz), 2.25 (2H, t, J=6.9 Hz), 2.81 (3H, d, J=4.6 Hz), 3.70 (t, J=5.9 Hz).

Example 45

Production of (E)-3,4-difluoro-2-(2-fluoro-4-iodo-phenylamino)-N-(2-hydroxy-ethoxy)-5-{[(2-hydroxyethylcarbamoyl)-methoxyimino]-methyl}-benzamide (Compound 45)

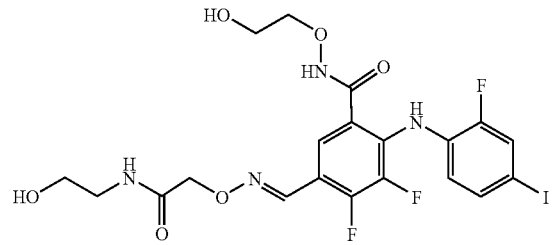

The compound 45 was prepared according to the method in Example 3.

$^1$H-NMR (DMSO-d6, 270 MHz) δ (PPM) 3.19 (2H, q, J=5.9 Hz), 3.42 (2H, q, J=6.3 Hz), 3.56 (2H, br. q, J=4.6 Hz), 3.83 (2H, bt. t, J=ca 5.7 Hz), 4.59 (2H, s), 4.71 (1H, t, J=4.7 Hz, OH), 4.73 (1H, t, J=4.7 Hz, OH), 6.80 (1H, td, J=8.9, 3.6 Hz), 7.41 (1H, br. d, J=8.3 Hz), 7.61 (1H, br. d, J=10.9 Hz), 7.67 (1H, d, J=7.5 Hz), 7.87 (br. t, J=5.6 Hz, NH), 8.41 (1H, s), 8.91 (1H, br. s, NH), 12.00 (1H, br. s, NH).

ESI (LC/MS positive mode) m/z 597 (M+H)

The method for preparing 2-aminooxy-N-(2-hydroxyethyl)-acetamide, which is used in the coupling reaction for preparing the compound 45, is described below.

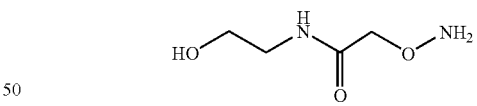

(1,3-Dioxo-1,3-dihydro-isoindol-2-yloxy)-acetic acid ethyl ester (276.3 mg, 1.11 mmol), which is an intermediate used for synthesizing 2-aminooxy-N-methyl-acetamide used as a coupling item in the preparation of the compound 43, was dissolved in methanol (2 mL), ethanolamine (293 mg, 4.79 mmol) was added thereto at room temperature, and the mixture was stirred at 60° C. overnight. The reaction solution was concentrated under reduced pressure, and the resulting residue was purified by silica gel column chromatography (30 g, $CH_2Cl_2$/MeOH 8:1) to give 2-aminooxy-N-methyl-acetamide (107.4 mg, 72%) as a colorless syrup.

$^1$H-NMR (CD3OD, 270 MHz) δ (PPM) 3.37 (2H, t, J=5.6 Hz), 3.63 (2H, t, J=5.6 Hz), 4.10 (2H, s).

Example 46

Production of (E)-3,4-difluoro-2-(2-fluoro-4-iodo-phenylamino)-N-(2-hydroxy-ethoxy)-5-{[2-(2-hydroxy-ethoxy)-ethoxyimino]-methyl}-benzamide (Compound 46)

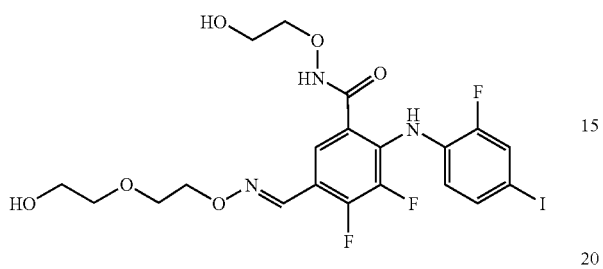

The compound 46 was prepared according to the method in Example 3.

$^1$H-NMR (DMSO-d6, 270 MHz) δ (PPM) 3.59 (2H, td, J=5.6, 1.0 Hz), 3.68 (2H, td, J=5.6, 0.7 Hz), 3.72 (2H, t, J=4.6 Hz), 3.79 (2H, t, J=4.6 Hz), 3.95 (2H, t, J=5.0 Hz), 4.34 (2H, t, J=5.0 Hz), 6.72 (1H, td, J=8.6, 4.3 Hz), 7.39 (1H, br. d, J=8.6 Hz), 7.47 (1H, dd, J=10.6, 2.0 Hz), 7.81 (1H, dd, J=6.9, 2.0 Hz), 8.26 (1H, s).

ESI (LC/MS positive mode) m/z 584 (M+H)

In the preparation of the compound 46, 2-(2-aminooxy-ethoxy)-ethanol, which is used in the coupling reaction, was prepared according to the method described in the literature below. Sebesta, David P.; O'Rourke, Sarah S.; Martinez, Rogelio L.; Pieken, Wolfgang A.; McGee, Danny P. C., Tetrahedron, 52, 1996, 14385-14402.

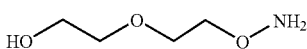

Example 47

Production of (E)-3,4-difluoro-2-(2-fluoro-4-iodo-phenylamino)-N-(2-hydroxy-ethoxy)-5-[(2-methanesulfonylamino-ethoxyimino)-methyl]-benzamide (Compound 47)

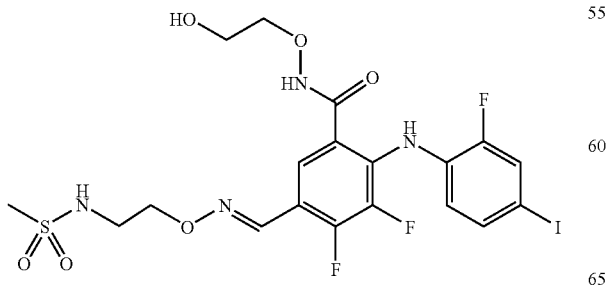

The compound 47 was prepared according to the method in Example 3.

$^1$H-NMR (CD$_3$OD, 270 MHz) δ (PPM) 2.96 (3H, s), 3.43 (2H, m), 3.73 (2H, m), 3.95 (2H, m), 4.28 (2H, m), 6.73 (1H, m), 7.40 (1H, m), 7.49 (1H, m), 7.82 (1H, m), 8.31 (1H, s)

ESI (LC/MS positive mode) m/z 617 (M+H)

In the preparation of the compound 47, N-(2-aminooxy-ethyl)-methanesulfonamide used in the coupling reaction was prepared according to the method described below.

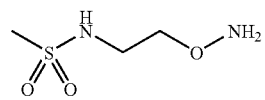

Process A

Preparation of 2-(2-amino-ethoxy)-isoindol-1,3-dione Hydrochloride

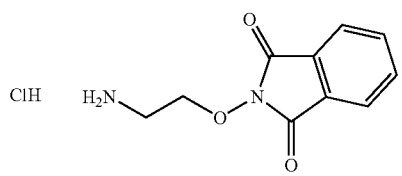

[2-(1,3-Dioxo-1,3-dihydro-isoindol-2-yloxy)-ethyl]-carbamic acid tert-butyl ester (shown below, 500 mg, 1.63 mmol), which can be obtained by the method described in the literature (Takasugi, H; Kochi, H; Masugi, T; Nakano, H; Takaya, T. Journal of Antibiotics (1983), 36(7), 846-54), was dissolved in methanol (10 mL), 5% solution of hydrochloric acid in methanol (1 mL) was added thereto, and the mixture was stirred thoroughly at room temperature for about 24 hours. The reaction solution was concentrated under reduced pressure, and the resulting waxy solid was dissolved in water. This aqueous solution was washed with diethyl ether, and the aqueous layer was lyophilized to give 2-(2-amino-ethoxy)-isoindol-1,3-dione hydrochloride (322 mg, 84% yield) as a white solid.

$^1$H-NMR (CD$_3$OD, 270 MHz) δ (PPM) 3.40 (2H, m), 4.43 (2H, dd, J=5.9, 4.9 Hz), 7.87 (4H, m)

ESI (LC/MS positive mode) m/z 207 (M+H)

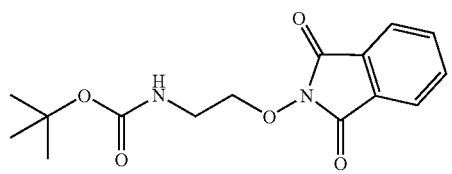

Process B

Preparation of N-[2-(1,3-dioxo-1,3-dihydro-isoindol-2-yloxy)-ethyl]-methanesulfonamide

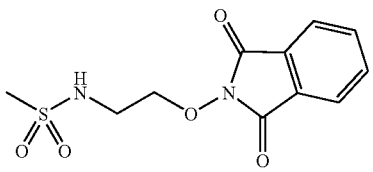

2-(2-Amino-ethoxy)-isoindol-1,3-dione hydrochloride (322 mg, 1.36 mmol) obtained in Process A was dissolved in anhydrous methylene chloride (50 mL) at room temperature, methanesulfonyl chloride (106 μL, 1.36 mmol) and pyridine (1 mL) were added thereto in this order, and the mixture was stirred for 4 hours. After completion of the reaction, the reaction solution was extracted with methylene chloride.

The extract was washed successively with water and saturated brine, and the organic layer was dried over anhydrous sodium sulfate, and filtered. The solvent was distilled off under reduced pressure, and the resulting yellow oil was purified with Mega Bond Elut silica gel (5 g, Varian, Inc.). From the fractions eluted with 100% ethyl acetate, N-[2-(1,3-dioxo-1,3-dihydro-isoindol-2-yloxy)-ethyl]-methanesulfonamide (108.7 mg, 24% yield) was obtained.

$^1$H-NMR (CDCL$_3$, 270 MHz) δ (PPM) 3.05 (3H, s), 3.45 (2H, m), 4.36 (2H, dd, J=4.9, 4.6 Hz), 5.69 (1H, m), 7.84 (4H, m)

ESI (LC/MS positive mode) m/z 285 (M+H)

Process C

Preparation of N-(2-aminooxy-ethyl)-methanesulfonamide

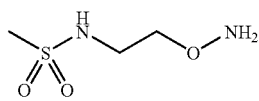

N-[2-(1,3-dioxo-1,3-dihydro-isoindol-2-yloxy)-ethyl]-methanesulfonamide (33.2 mg, 0.116 mmol) obtained in Process B was dissolved in anhydrous methylene chloride (10 mL), methylhydrazine (100 μL) was added thereto at room temperature, and the mixture was stirred for 3 hours. As the reaction proceeds, a white precipitate appeared. After completion of the reaction, the solvent was distilled off. To this residue, a mixture of diethyl ether and ethyl acetate (9:1) was added, and the mixture was stirred thoroughly, and filtered to remove a white insoluble matter. The resulting filtrate was concentrated under reduced pressure to give N-(2-aminooxy-ethyl)-methanesulfonamide (16.7 mg, 93% yield) as a waxy oil.

$^1$H-NMR (CDCL$_3$, 270 MHz) δ (PPM) 3.00 (3H, s), 3.38 (2H, dd, J=5.3, 4.6 Hz), 3.80 (2H, dd, J=4.9, 4.6 Hz), 4.82 (2H, br. s)

ESI (LC/MS positive mode) m/z 155 (M+H)

Example 48

Production of (Z)-2-(4-ethynyl-2-fluoro-phenylamino)-3,4-difluoro-N-(2-hydroxy-ethoxy)-5-[(2-hydroxy-ethoxyimino)-methyl]-benzamide (Compound 48)

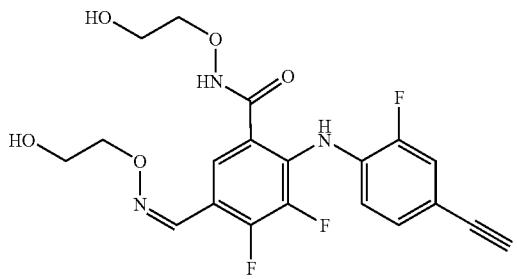

This compound was synthesized as described below from the corresponding E-isomer, (5-[Z-(2-hydroxy-ethoxyimino)-methyl]-3,4-difluoro-2-(2-fluoro-4-ethynyl-phenylamino)-N-(2-hydroxy-ethoxy)-benzamide (Compound 2) described herein.

The E-isomer (14.2 g, 32.5 mmol) and pyridinium paratoluene sulfonate (16.3 g, 65.0 mmol) were dissolved in EtOH (400 mL) and THF (100 mL). The mixture was stirred at room temperature under nitrogen atmosphere for 12 hours, and the completion of the reaction was confirmed by LC-Mass (E:Z=93:7). After the solvent was distilled off, water (300 mL) was added to the resulting solid. This mixture was extracted 3 times with EtOAc (200 mL)/THF (200 mL). The combined organic layer was washed with aqueous solution of NaCl, and dried over Na$_2$SO$_4$, and the solvent was distilled off. The residue was purified by SiO$_2$ chromatography to give (Z)-2-(4-ethynyl-2-fluoro-phenylamino)-3,4-difluoro-N-(2-hydroxy-ethoxy)-5-[(2-hydroxy-ethoxyimino)-methyl]-benzamide (730 mg, 5.1% yield).

$^1$H-NMR (DMSO-d$_6$, 400 MHz) δ (PPM) 3.37 (2H, br), 3.49 (2H, br), 3.63 (2H, br), 3.95 (1H, s), 4.00 (2H, t, J=5.1 Hz), 4.55 (2H, br), 6.76 (1H, ddd, J=8.3, 8.3, 3.9 Hz), 6.99 (1H, d, J=8.3 Hz), 7.15 (1H, d, J=11.7 Hz), 1.41 (1H, s), 8.07 (1H, d, J=5.9), 8.75 (1H, br), 11.90 (1H, br)

ESI (LC/MS positive mode) m/z 438 (M+H)

The Z-oxime forms shown below were prepared from the corresponding E-forms described herein according to the synthetic method in Example 48 described above.

Example 49

Production of (Z)-3,4-difluoro-2-(2-fluoro-4-iodo-phenylamino)-N-(2-hydroxy-ethoxy)-5-[(2-hydroxy-ethoxyimino)-methyl]-benzamide (Compound 49)

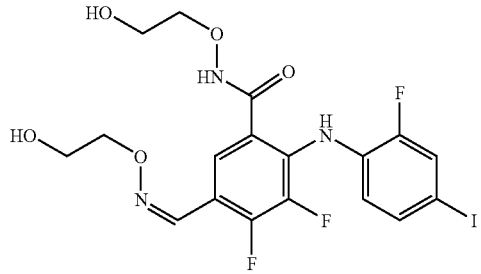

$^1$H-NMR (DMSO-d$_6$, 270 MHz) δ (PPM) 3.57 (2H, br), 3.68 (2H, br), 3.80 (2H, br), 4.19 (2H, t, J=5.0 Hz), 4.75 (2H, br), 6.83 (1H, m), 7.41 (1H, d, J=8.3 Hz), 7.59 (1H, s), 7.61 (1H, d, J=9.6 Hz), 8.26 (1H, d, J=6.9), 8.86 (1H, br), 11.85 (1H, br)

ESI (LC/MS positive mode) m/z 540 (M+H)

Example 50

(Z)-3,4-Difluoro-2-(2-fluoro-4-iodo-phenylamino)-N-(2-hydroxy-ethoxy)-5-[(2-hydroxy-ethoxyimino)-methyl]-benzamide (Compound 50)

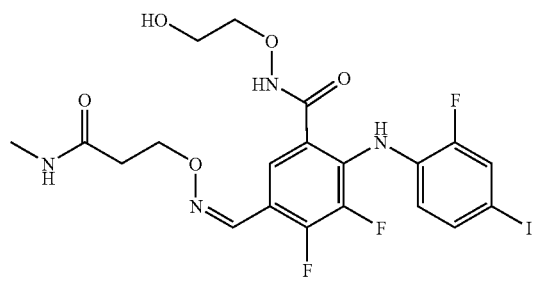

$^1$H-NMR (CD3OD, 270 MHz) δ (PPM) 2.63 (2H, t, J=5.9 Hz), 2.70 (3H, s, Me), 3.74 (2H, t, J=5.0 Hz), 3.97 (2H, t, J=4.6 Hz), 4.47 (2H, t, J=5.9 Hz), 6.77 (1H, td, J=8.6, 4.3 Hz), 7.40 (1H, ddd, J=8.6, 1.9, 1.1 Hz), 7.48 (1H, dd, J=10.6, 2.0 Hz), 7.54 (1H, s), 8.40 (1H, dd, J=7.3, 2.0 Hz).

ESI (LC/MS positive mode) m/z 581 (M+H)

Example 51

(Z)-3,4-Difluoro-2-(2-fluoro-4-iodo-phenylamino)-N-(2-hydroxy-ethoxy)-5-[(2-hydroxy-2-methyl-propoxyimino)-methyl]-benzamide (Compound 51)

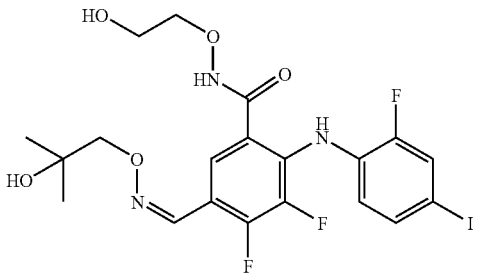

$^1$H-NMR (CD3OD, 270 MHz) δ (PPM) 1.29 (6H, s, 2Me), 3.72 (2H, t, J=5.0 Hz), 3.94 (2H, t, J=4.3 Hz), 4.13 (2H, s), 6.78 (1H, td, J=8.6, 4.3 Hz), 7.40 (1H, br. d, J=8.3 Hz), 7.49 (1H, dd, J=10.2, 1.6 Hz), 7.52 (1H, s), 8.56 (1H, dd, J=7.3, 2.0 Hz).

ESI (LC/MS positive mode) m/z 568 (M+H)

Example 52

(dl)-(Z)-5-[(2,3-Dihydroxy-propoxyimino)-methyl]-3,4-difluoro-2-(2-fluoro-4-iodo-phenylamino)-N-(2-hydroxy-ethoxy)-benzamide (Compound 52)

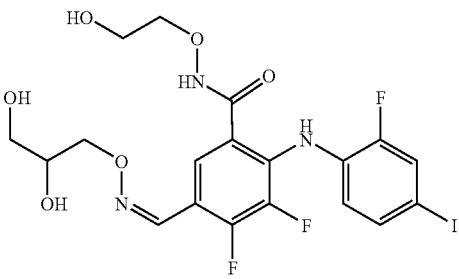

$^1$H-NMR (CD$_3$OD, 270 MHz) δ (PPM) 3.62 (2H, dd, J=5.9, 4.9 Hz), 3.73 (2H, dd, J=5.6, 4.9 Hz), 3.96 (2H, dd, J=5.6, 4.9 Hz), 4.00 (1H, m), 4.25 (1H, dd, J=11.2, 5.9 Hz), 4.33 (1H, dd, J=11.2, 4.6 Hz), 6.76 (1H, td, J=8.6, 4.3 Hz), 7.40 (1H, m), 7.48 (1H, dd, J=10.6, 2.0 Hz), 7.54 (1H, s), 8.53 (1H, dd, J=7.2, 2.0 Hz)

ESI (LC/MS positive mode) m/z 570 (M+H)

Example 53

(Z)-3,4-Difluoro-2-(2-fluoro-4-iodo-phenylamino)-N-(2-hydroxy-ethoxy)-5-[(2-methanesulfonyl-ethoxyimino)-methyl]-benzamide (Compound 53)

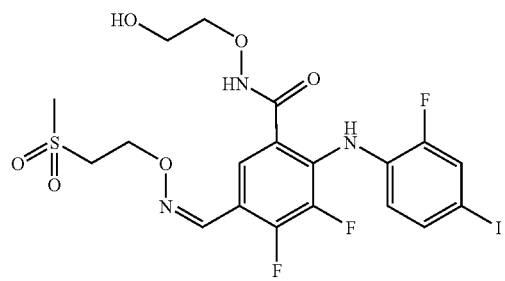

¹H-NMR (CD₃OD, 270 MHz) δ (PPM) 3.01 (3H, s), 3.63 (2H, dd, J=5.6, 5.3 Hz), 3.74 (2H, dd, J=4.9, 4.3 Hz), 3.98 (2H, dd, J=4.9, 4.3 Hz), 4.68 (2H, dd, J=5.6, 5.3 Hz), 6.78 (1H, td, J=8.6, 4.3 Hz), 7.41 (1H, m), 7.49 (1H, dd, J=10.2, 1.6 Hz), 7.61 (1H, s), 8.45 (1H, dd, 3=6.9, 2.0 Hz)

ESI (LC/MS positive mode) m/z 602 (M+H)

Example 54

(Z)-5-[(2-Acetylamino-ethoxyimino)-methyl]-3,4-difluoro-2-(2-fluoro-4-iodo-phenylamino)-N-(2-hydroxy-ethoxy)-benzamide (Compound 54)

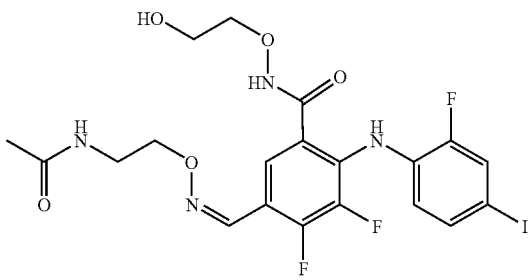

¹H-NMR (CD₃OD, 270 MHz) δ (PPM) 1.93 (3H, s), 3.55 (2H, t, J=5.3 Hz), 3.73 (2H, dd, J=4.9, 4.3 Hz), 3.95 (2H, dd, J=4.9, 4.3 Hz), 4.28 (2H, t, J=5.3 Hz), 6.77 (1H, td, J=8.6, 4.0 Hz), 7.41 (1H, br. d, J=8.6 Hz), 7.48 (1H, dd, J=10.0, 2.0 Hz), 7.53 (1H, s), 8.41 (1H, br. d, J=5.9 Hz)

ESI (LC/MS positive mode) m/z 581 (M+H)

Example 55

(Z)-3,4-Difluoro-2-(2-fluoro-4-iodo-phenylamino)-N-(2-hydroxy-ethoxy)-5-(2-methylcarbamoylpropoxyimino-methyl)-benzamide (Compound 55)

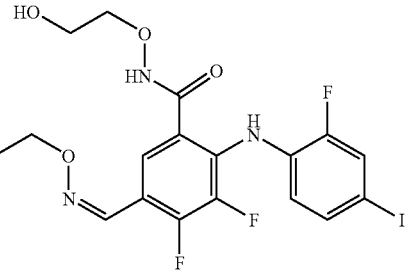

¹H-NMR (DMSO-d6, 270 MHz) δ (PPM) 1.95 (2H, qui, J=6.6 Hz), 2.18 (2H, t, J=7.3 Hz), 2.50 (3H, d, J=4.6 Hz), 3.58 (2H, br. q, J=4.9 Hz), 3.82 (2H, br. t, J=4.6 Hz), 4.18 (2H, t, J=6.6 Hz), 4.74 (1H, br. t, J=5.6 Hz, OH), 6.84 (1H, td, J=8.9, 4.0 Hz), 7.42 (1H, br. d, J=7.6 Hz), 7.59 (1H, s), 7.62 (1H, dd, J=10.6, 2.0 Hz), 7.79 (1H, br q, J=4.6 Hz, NH), 8.21 (br. d, J=6.3 Hz), 8.93 (1H, br. s, NH), 11.98 (1H, br. s, NH).

ESI (LC/MS positive mode) m/z 595 (M+H)

Example 56

(Z)-3,4-Difluoro-2-(2-fluoro-4-iodo-phenylamino)-N-(2-hydroxy-ethoxy)-5-(methylcarbamoylmethoxyimino-methyl)-benzamide (Compound 56)

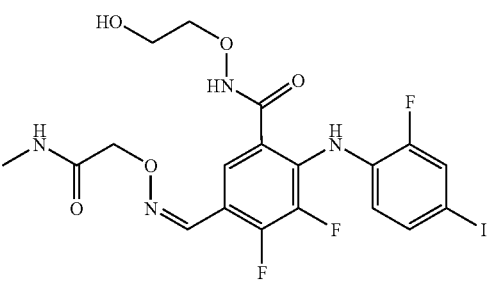

¹H-NMR (CD3OD, 270 MHz) δ (PPM) 2.80 (3H, s), 3.73 (2H, t, J=4.3 Hz), 3.96 (2H, t, J=4.3 Hz), 4.67 (2H, s), 6.79 (1H, td, J=8.6, 4.3 Hz), 7.42 (1H, br. d, J=8.6 Hz), 7.48 (1H, dd, J=10.6, 2.0 Hz), 7.61 (1H, s), 8.49 (1H, dd, J=7.3, 2.3 Hz).

ESI (LC/MS positive mode) m/z 567 (M+H)

Example 57

(Z)-3,4-Difluoro-2-(2-fluoro-4-iodo-phenylamino)-N-(2-hydroxy-ethoxy)-5-{[(2-hydroxyethylcarbamoyl)-methoxyimino]-methyl}-benzamide (Compound 57)

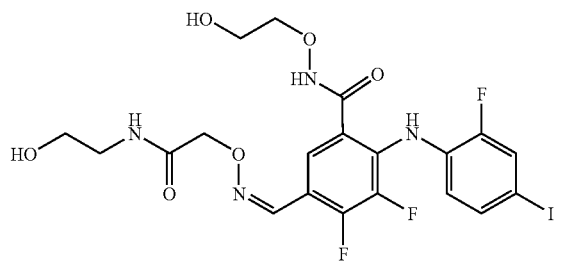

$^1$H-NMR (CD$_3$OD, 270 MHz) δ (PPM) 3.38 (2H, t, J=5.9 Hz), 3.62 (2H, t, J=5.9 Hz), 3.73 (2H, t, J=4.6 Hz), 3.96 (2H, t, J=4.6 Hz), 4.78 (2H, s), 6.79 (1H, td, J=8.6, 4.3 Hz), 7.42 (1H, br. d, J=8.6 Hz), 7.49 (1H, dd, J=10.6, 2.0 Hz), 7.62 (1H, s), 8.48 (1H, dd, J=7.3, 2.3 Hz).

ESI (LC/MS positive mode) m/z 597 (M+H)

Example 58

Production of dl-(Z)—N-(2,3-dihydroxy-propoxy)-3,4-difluoro-2-(2-fluoro-4-iodo-phenylamino)-5-[(2-hydroxy-ethoxyimino)-methyl]-benzamide (Compound 58)

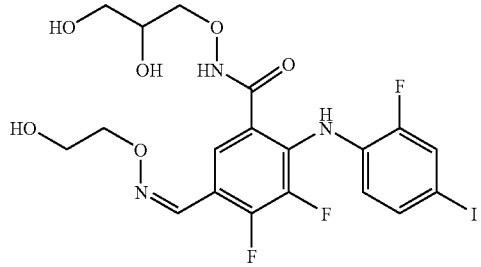

$^1$H-NMR (CD$_3$OD, 270 MHz) δ (PPM) 3.57 (2H, m), 3.85-4.03 (5H, m), 4.31 (2H, dd, J=6.3, 4.6 Hz), 6.78 (1H, td, J=8.6, 4.3 Hz), 7.41 (1H, br. d, J=8.3 Hz), 7.49 (1H, dd, J=10.6, 2.0 Hz), 7.54 (1H, s), 8.54 (1H, dd, J=7.3, 2.3 Hz).

ESI (LC/MS positive mode) m/z 570 (M+H)

Example 59

Production of (Z)-3,4-difluoro-2-(2-fluoro-4-iodo-phenylamino)-N-(2-hydroxy-ethoxy)-5-{[2-(2-oxo-imidazolidin-1-yl)-ethoxyimino]-methyl}-benzamide (Compound 59D

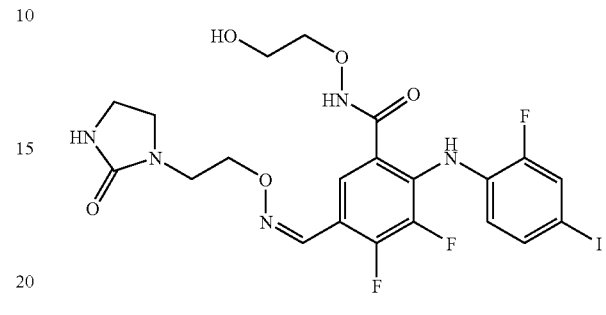

$^1$H-NMR (CDCl$_3$, 270 MHz) δ (PPM) 3.34-3.40 (2H, m), 3.44 (2H, brt, J=5.9 Hz), 3.54-3.58 (2H, m), 3.74 (2H, t, J=4.6 Hz), 3.97 (2H, t, J=4.6 Hz), 4.37 (2H, t, J=5.9 Hz), 6.77 (1H, td, J=8.8, 4.4 Hz), 7.41 (1H, ddd, J=8.3, 2.0, 1.0 Hz), 7.48 (1H, dd, J=10.3, 2.0 Hz), 7.52 (1H, s), 8.39 (1H, d, J=6.4 Hz)

ESI (LC/MS positive mode) m/z 608 (M+H)

Example 60

Production of (Z)-3,4-difluoro-2-(2-fluoro-4-iodo-phenylamino)-N-(2-hydroxy-ethoxy)-5-{[2-(2-oxo-pyrrolidin-1-yl)-ethoxyimino]-methyl}-benzamide (Compound 60)

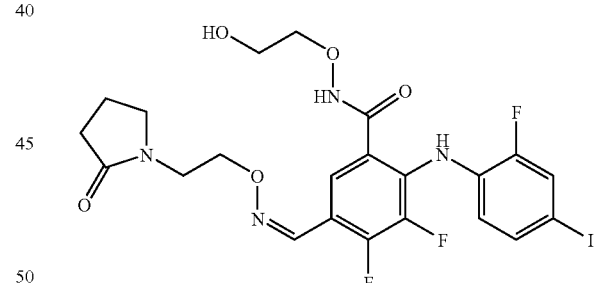

$^1$H-NMR (CD$_3$OD, 270 MHz) δ (PPM) 1.93 (2H, m), 2.25 (2H, t, J=7.9 Hz), 3.44 (2H, t, 3=7.1 Hz), 3.57 (3H, t, J=5.1 Hz), 3.64 (2H, t, 3=4.5 Hz), 3.86 (2H, t, 3=4.5 Hz), 4.28 (2H, t, 3=5.1 Hz), 6.70 (1H, m), 7.30 (1H, m), 7.42 (1H, m), 7.47 (1H, s), 8.28 (1H, m).

ESI (LC/MS positive mode) m/z 607 (M+H)<

Test Example 1

Determination of MEK Inhibitory Activities

The MEK inhibitory activities of Compounds 1 to 5, 7 to 8, 12, and 14 to 60, obtained in Examples 1 to 5, 7 to 8, 12, and 14 to 60, and the known compound below (CI-1040), were determined.

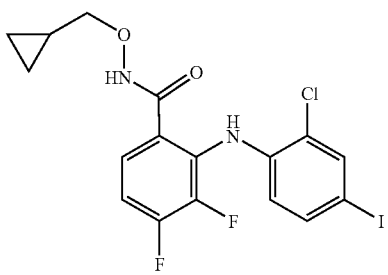

Compound CI-1040 was prepared as described in WO 99/01426 (Example 95).

MEK inhibitory activities were determined by constructing an assay system in which Myelin Basic Protein (MBP) was phosphorylated in proportion to the kinase activity of MEK, according to the method of Raf-1 Kinase Cascade Assay Kit (cat. 17-172, Upstate Biotechnology Inc., NY, USA), with some adjustments of the amount of the enzyme, etc.

The radioisotope used was [$\gamma^{33}$P]-ATP (Amersham Biosciences, K.K.).

The amount of MBP labeled with $^{33}$P was determined using Microbeta 1450 (PerkinElmer, Inc., MA, USA), and the concentration that inhibits activity by 50% (IC50) was calculated.

The results are shown in Table 3.

Test Example 2

Determination of the Activity of Inhibiting Cell Proliferation

The activities of inhibiting cell proliferation by the MEK inhibitory activity were determined for the compound CI-1040, Compounds 1 to 5, 7 to 8, 12, and 14 to 60.

The activities of inhibiting cell proliferation were determined using Cell Counting Kit-78 (Dojindo Laboratories).

Human colon cancer cell line HT-29, obtained from American Type Culture Collection (VA, USA), and human non-small cell lung cancer cell line QG56, obtained from Immuno-Biological Laboratories Co., Ltd., were plated at 2,000 cells/well in a 96-well culture plate, and incubated for four days after addition of a MEK inhibitor of a given concentration.

On the fourth day of incubation, a Cell Counting Kit-8 solution was added, and absorbance (measured wavelength: 450 nm, reference wavelength: 615 nm) was measured according to the protocol attached to the kit, to calculate the concentration that inhibits cell proliferation by 50% (IC50).

These results are shown in Table 3.

Test Example 3

Determination of Stability Against Mouse Liver Microsomes

Compound CI-1040, Compounds 1 to 5, 7 to 8, 12, and 14 to 60 were incubated with mouse liver microsomes (1 mg protein/mL) in 50 mM phosphate buffer (pH 7.4) containing 5 mM $MgCl_2$ and 2 mM NADPH at 37° C. for one hour. The enzyme reaction was quenched with three volumes of acetonitrile, and the reaction mixture was centrifuged at 1,500 rpm for ten minutes to provide a supernatant as a sample to be measured. Stability against mouse liver microsomes was measured using HPLC/MS to determine the compounds in the sample.

These results are shown in Table 3.

Test Example 4

Determination of Stability Against Human Liver Microsomes

Compound CI-1040, Compounds 1 to 5, 7 to 8, 12, and 14 to 60 were incubated with human liver microsomes (1 mg protein/mL) in 50 mM phosphate buffer (pH 7.4) containing 5 mM $MgCl_2$ and 2 mM NADPH at 37° C. for one hour. The enzyme reaction was quenched with three volumes of acetonitrile, and the reaction mixture was centrifuged at 1,500 rpm for ten minutes to provide a supernatant as a sample to be measured. Stability against human liver microsomes was measured using HPLC/MS to determine the compounds in the sample.

These results are shown in Table 3.

Test Example 5

Determination of Water Solubility

Excess amounts of each of Compound CI-1040, Compounds 1 to 5, 7 to 8, 12, and 14 to 60 were placed in a glass vessel, and 50 mM phosphate buffer (pH 6.5) was added thereto. The vessels were sealed, and the contents were sonicated at room temperature (20° C.) for ten minutes, and then stirred with a stirrer for two hours. After reaching solution equilibrium, the solution was separated with a membrane filter, and the solute concentration was determined using HPLC.

These results are shown in Table 3.

The above test Examples 1 to 4 were performed according to "The development of pharmaceuticals, Vol. 15, "Physicochemical properties of formulations", Miyajima K. (Professor of Kyoto University), ed., p. 45-48", and the above Test Example 5 was performed according to "2.2 Method for measuring solubility, 2.2.1 Equilibrium method, a" ("Stirring method", Tokyo Hirokawa publishing Co.).

TABLE 3

| Compound | MEK inhibitory activity IC50 (uM) | Cell proliferation inhibitory activity (HT29) IC50 (uM) | Stability against mouse liver microsome NADPH+ T½ (min) | Stability against human liver microsome NADPH+ T½ (min) | Water solubility (LySA PH 6.5) (uM) |
|---|---|---|---|---|---|
| Compound 1 | 0.10 | 0.08 | 236.7 | 64.6 | 8.3 |
| Compound 2 | 0.24 | 0.15 | 134.9 | 80.3 | 415 |
| Compound 3 | 0.078 | 0.065 | 58.2 | 93.0 | 6.4 |
| Compound 4 | 0.069 | 0.045 | >360 | >360 | 3.8(at pH 6.08) |

TABLE 3-continued

| Compound | MEK inhibitory activity IC50 (uM) | Cell proliferation inhibitory activity (HT29) IC50 (uM) | Stability against mouse liver microsome NADPH+ T½ (min) | Stability against human liver microsome NADPH+ T½ (min) | Water solubility (LySA PH 6.5) (uM) |
|---|---|---|---|---|---|
| Compound 5 | 0.15 | 0.17 | >360 | 246.9 | 426(at pH 6.87) |
| Compound 7 | 0.033 | 0.037 | >360 | 90.6 | 162(at pH 6.67) |
| Compound 8 | 0.15 | 0.185 | >360 | 74.4 | 1469(at pH 6.06) |
| Compound 12 | 0.037 | <0.0195 | >360 | ND | 15 |
| Compound 14 | 0.0097 | 0.038 | 46 | ND | 14 |
| Compound 15 | 0.11 | 0.137 | 58.7 | 159.9 | 8 |
| Compound 16 | 0.244 | 0.21 | 184.9 | >360 | 2395 |
| Compound 17 | 0.287 | 0.92 | >360 | ND* | 462 |
| Compound 18 | 0.262 | 0.14 | >360 | >360 | 164 |
| Compound 19 | 0.693 | 0.750 | >360 | >360 | 2908 |
| Compound 20 | 0.696 | 0.643 | >360 | >360 | 1827 |
| Compound 21 | 0.802 | 0.651 | >360 | >360 | 1484 |
| Compound 22 | 0.075 | 0.036 | >360 | >360 | 146 |
| Compound 23 | 0.085 | 0.088 | ND | ND | ND |
| Compound 24 | 0.048 | 0.086 | >360 | >360 | 16 |
| Compound 25 | 0.030 | 0.044 | 198.0 | 48.8 | 54 |
| Compound 26 | 0.057 | 0.035 | ND | ND | ND |
| Compound 27 | 0.203 | 0.069 | >360 | 144.5 | 10 |
| Compound 28 | 0.020 | 0.050 | >360 | >360 | <31.3 |
| Compound 29 | 0.576 | 0.165 | ND | ND | ND |
| Compound 30 | 0.088 | 0.79 | >360 | ND | <31.3 |
| Compound 31 | 0.335 | 0.463 | ND | ND | ND |
| Compound 32 | 1.251 | 0.084 | ND | ND | ND |
| Compound 33 | 0.0375 | 0.275 | ND | ND | <7.8 |
| Compound 34 | 0.069 | 0.143 | ND | ND | <7.8 |
| Compound 35 | 0.0304 | 0.203 | ND | ND | <7.8 |
| Compound 36 | 0.0450 | 0.365 | ND | ND | <7.8 |
| Compound 37 | 0.287 | 0.60 | ND | ND | ND |
| Compound 38 | 0.395 | 0.476 | ND | ND | ND |
| Compound 39 | 0.232 | 0.114 | ND | ND | <7.8 |
| Compound 40 | 0.067 | 0.027 | >360 | 89.5 | ND |
| Compound 41 | 0.0647 | 0.186 | 212.4 | >360 | 347 |
| Compound 42 | 0.056 | 0.091 | >360 | 104.2 | 29 |
| Compound 43 | 0.119 | 0.077 | >360 | >360 | 57 |
| Compound 44 | 0.025 | 0.328 | >360 | >360 | 6.0 |
| Compound 45 | 0.267 | 0.196 | 128.8 | >360 | 73 |
| Compound 46 | 0.107 | 0.103 | ND | ND | ND |
| Compound 47 | 0.209 | 0.138 | >360 | >360 | 11 |
| Compound 48 | 0.051 | 0.013 | 121.6 | 36.2 | 301 |
| Compound 49 | 0.031 | 0.0048 | >360 | >360 | 75 |
| Compound 50 | 0.011 | 0.0014 | 86.6 | 44.1 | 52 |
| Compound 51 | 0.021 | 0.0060 | ND | ND | <7.8 |
| Compound 52 | 0.015 | 0.0058 | >360 | >360 | 175 |
| Compound 53 | 0.017 | 0.0019 | ND | ND | <7.8 |
| Compound 54 | 0.021 | 0.0065 | >360 | >360 | 20 |
| Compound 55 | 0.037 | 0.0046 | >360 | 97.5 | 12 |
| Compound 56 | 0.049 | 0.0034 | 38.7 | >360 | 85 |
| Compound 57 | 0.019 | 0.027 | >360 | >360 | 224 |
| Compound 58 | 0.027 | 0.037 | 47.4 | 54.6 | 127 |
| Compound 59 | 0.050 | 0.017 | ND | ND | 69 |
| Compound 60 | 0.078 | 0.020 | ND | ND | ND |
| CI-1040 | 0.13 | 0.10 | 10.8 | 28.9 | <<2 |

*ND = not determined

INDUSTRIAL APPLICABILITY

The compounds involved in this invention, and their pharmaceutically acceptable salts, have MEK inhibitory effect and cell proliferation inhibitory effect, and have excellent stability, safety, and water solubility in vivo. Therefore, they are useful for preventing or treating proliferative diseases, for example, cancers, psoriasis, restenosis, autoimmune diseases, and atherosclerosis, and for preventing or treating diseases such as sequelae of cardiac failure, xenograft rejection, osteoarthritis, rheumatoid arthritis, asthma, cystic fibrosis, hepatomegaly, cardiac hypertrophy, Alzheimer's disease, diabetes mellitus, septic shock, and HIV infection.

The invention claimed is:
1. A compound represented by formula (I), or a pharmaceutically acceptable salt thereof:

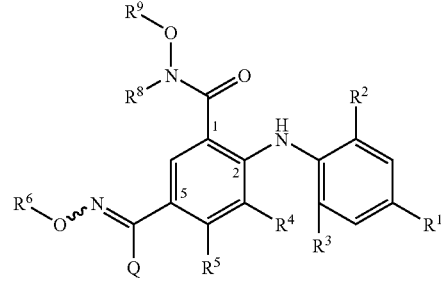

wherein,
the wavy line ～ indicates that the compound can be either one of the stereoisomers, E-form or Z-form, depending on the manner of binding of $R^6O$— to —N, $R^1$ represents a hydrogen atom, a halogen atom, —S—$R^a$, —SO—$R^a$, —SO$_2$—$R^a$, —COO$R^a$, an alkyl group which may have 1 to 3 substituents selected from Group A indicated below, an alkenyl group which may have 1 to 3 substituents selected from Group A indicated below, or an alkynyl group which may have 1 to 3 substituents selected from Group A indicated below, $R^2$ and $R^3$ independently represent a hydrogen atom, a halogen atom, or an alkyl group which may have 1 to 3 substituents selected from Group A indicated below, $R^4$ and $R^5$ independently represent a hydrogen atom, a halogen atom, or a nitro group, $R^6$ and $R^9$ independently represent
a hydrogen atom;
an alkyl group, an alkenyl group, or an alkynyl group, each of which may have 1 to 3 substituents selected from Group A indicated below; or
a cycloalkyl group, an aryl group, a heteroaryl group, a heterocyclic group, a cycloalkylalkyl group, a cycloalkylalkenyl group, a cycloalkylalkynyl group, an arylalkyl group, an arylalkenyl group, an arylalkynyl group, a heteroarylalkyl group, a heteroarylalkenyl group, a heteroarylalkynyl group, a heterocyclic alkyl group, a heterocyclic alkenyl group, or a heterocyclic alkynyl group, each of which may have 1 to 3 substituents selected from Group B indicated below, Q represents —N$R^aR^b$ or a group represented by $R^7$, $R^7$ represents
a hydrogen atom;
an alkyl group, an alkenyl group, or an alkynyl group, each of which may have 1 to 3 substituents selected from Group A indicated below; or
a cycloalkyl group, a heterocyclic group, an aryl group, a heteroaryl group, an arylalkyl group, or a heterocyclic alkyl group, each of which may have 1 to 3 substituents selected from Group B indicated below, $R^8$ represents a hydrogen atom, or an alkyl group which may have 1 to 3 substituents selected from Group A indicated below, Group A: a halogen atom, a nitro group, —O—$R^a$, -(an alkylene group)-O$R^a$, —[O-(an alkylene group)]$_n$-O$R^a$, —N$R^aR^b$, —N$R^b$—(an alkylene group)-O$R^a$, —N$R^a$SO$_2R^b$, —C=N—O$R^a$, —CO$_2R^a$, —CON$R^aR^b$, —N$R^a$CO$R^b$, —CO$R^a$, —S$R^a$, —SO$_2R^a$, and —SO$_2$N$R^aR^b$, Group B: a halogen atom, a nitro group, —O—$R^a$, -(an alkylene group)-O$R^a$, —[O-(an alkylene group)]$_n$-O$R^a$, —N$R^aR^b$, —N$R^b$—(an alkylene group)-O$R^a$, —N$R^a$SO$_2R^b$, —C=N—O$R^a$, —CO$_2R^a$, —CON$R^aR^b$, —N$R^a$CO$R^b$, —CO$R^a$, —S$R^a$, —SO$_2R^a$, —SO$_2$N$R^aR^b$, an oxo group, an alkyl group, an alkenyl group, an alkynyl group, an aryl group, and a heteroaryl group, and the above-mentioned $R^a$ and $R^b$ are identical to or different from each other and independently represent a hydrogen atom; an alkyl group that may be substituted with an OH group; an aryl group; or a heteroaryl group, and n=1 to 4.

2. The compound of claim 1, or a pharmaceutically acceptable salt thereof, wherein $R^1$ is an iodine atom, a bromine atom, a vinyl group, or an ethynyl group.

3. The compound of claim 1, or a pharmaceutically acceptable salt thereof, wherein $R^2$ is a hydrogen atom, a chlorine atom, a fluorine atom, a methyl group, or a hydroxymethyl group.

4. The compound of claim 1, or a pharmaceutically acceptable salt thereof, wherein $R^2$ is a chlorine atom or a fluorine atom.

5. The compound of claim 1, or a pharmaceutically acceptable salt thereof, wherein $R^3$ is a hydrogen atom, a chlorine atom, or a fluorine atom.

6. The compound of claim 1, or a pharmaceutically acceptable salt thereof, wherein $R^3$ is a hydrogen atom.

7. The compound of claim 1, or a pharmaceutically acceptable salt thereof, wherein $R^4$ is a hydrogen atom or a fluorine atom.

8. The compound of claim 1, or a pharmaceutically acceptable salt thereof, wherein $R^5$ is a fluorine atom.

9. The compound of claim 1, or a pharmaceutically acceptable salt thereof,
wherein $R^6$ and $R^9$ independently represent
a hydrogen atom;
an alkyl group, an alkenyl group, or an alkynyl group, each of which may have 1 to 3 substituents selected from Group C indicated below; or
a cycloalkylalkyl group, an arylalkyl group, a heteroarylalkyl group, or a heterocyclic alkyl group, each of which may have 1 to 3 substituents selected from Group D indicated below, Group C: —O—$R^a$, —N$R^aR^b$, -(a C1-C4 alkylene group)-O$R^a$, —[O-(a C1-C4 alkylene group)]$_n$-O$R^a$, —N$R^b$—(a C1-C4 alkylene group)-O$R^a$, —N$R^a$SO$_2R^b$, —C=N—O$R^a$, —CON$R^aR^b$, —N$R^a$CO$R^b$, —S$R^a$, and —SO$_2R^a$, Group D: —O—$R^a$, -(a C1-C4 alkylene group)-O$R^a$, —[O-(a C1-C4 alkylene group)]$_n$-O$R^a$, —N$R^b$-(a C1-C4 alkylene group)-O$R^a$, —C=N—O$R^a$, —CON$R^aR^b$, —N$R^a$CO$R^b$, —S$R^a$, —SO$_2R^a$, an oxo group, and a C1-C4 alkyl group, provided that $R^a$ and $R^b$ are identical to or different from each other and independently represent a hydrogen atom; a C1-C4 alkyl group that may be substituted with an OH group; an aryl group; or a heteroaryl group, and n=1 to 4.

10. The compound of claim 1, or a pharmaceutically acceptable salt thereof, wherein $R^6$ is a hydrogen atom, a methyl group, an isopropyl group, a 2-hydroxyethyl group, a 2-hydroxypropyl group, a 3-hydroxypropyl group, a 2,3-dihydroxypropyl group, a 2-hydroxy-1-(hydroxymethyl)ethyl group, a 2-hydroxypropyl group, a 2-hydroxy-2-methylpropyl group, a 2-hydroxy-1-methylethyl group, a cyclopropylmethyl group, a cyclopentylmethyl group, a 2-(2-hydroxyethoxy)ethyl group, a 2-(2-hydroxyethylamino)ethyl group, a 2-(morpholin-4-yl)ethyl group, a 2-(4-methylpiperazin-1-yl) ethyl group, a 2-(4-hydroxypiperidin-1-yl)ethyl group, a 2-(hydroxyimino)ethyl group, a 2-(methoxyimino)ethyl group, a 2-methylcarbamoyl-ethyl group, a 2-propenyl group, a 2-propynyl group, a benzyl group, a pyridin-4-ylmethyl group, an oxazol-2-ylmethyl group, a 3-hydroxy-3-methylbutyl group, a 3-hydroxy-2,2-dimethyl-propyl group, a 1-hydroxymethyl-cyclopropyl-methyl group, a 4-hydroxylbutyl group, a 3-methoxy-3-methylbutyl group, a 2-methoxyethyl group, a 2-methylsulfanylethyl group, a 2-methanesulfonylethyl group, a 2-aminoethyl group, a 2-methylaminoethyl group, a 2-dimethylaminoethyl group, a 2-(piperidin-1-yl)ethyl group, a 2-(pyrrolidin-1-yl)ethyl group, a 2-((S)-2-hydroxymethyl-pyrrolidin-1-yl)ethyl group, a 2-((R)-2-hydroxymethyl-pyrrolidin-1-yl)ethyl group, a methylcarbamoyl-methyl group, a 2-dimethylcarbamoyl-ethyl group, a 3-methylcarbamoyl-propyl group, a (2-hydroxyethylcarbamoyl)methyl group, a 2-acetylaminoethyl group, a 2-acetylmethylaminoethyl group, a 2-(2-oxopyrrolidin-1-yl)ethyl group, a 2-(2-oxoimidazolidin-1-yl) ethyl group, a 1H-imidazol-2-ylmethyl group, a 3H-imidazol-4-ylmethyl group, or a 2-methanesulfonylamino-ethyl group.

11. The compound of claim 1, or a pharmaceutically acceptable salt thereof, wherein $R^6$ is a hydrogen atom, a 2-hydroxyethyl group, a 3-hydroxypropyl group, a 3-hydroxy-3-methylbutyl group, a 3-hydroxy-2,2-dimethyl-propyl group, a 1-hydroxymethyl-cyclopropyl-methyl group, a 4-hydroxylbutyl group, a 3-methoxy-3-methylbutyl group, a 2-methoxyethyl group, a 2,3-dihydroxypropyl group, a 2-hydroxy-1-(hydroxymethyl)ethyl group, a 2-hydroxypropyl group, a 2-hydroxy-2-methylpropyl group, a 2-hydroxy-1-methylethyl group, a 2-(2-hydroxyethoxy)ethyl group, a 2-methylsulfanylethyl group, or a 2-methanesulfonylethyl group.

12. The compound of claim 1, or a pharmaceutically acceptable salt thereof, wherein $R^6$ is a 2-aminoethyl group, a 2-methylaminoethyl group, a 2-dimethylaminoethyl group, a 2-(2-hydroxyethylamino)ethyl group, a 2-(morpholin-4-yl) ethyl group, a 2-(piperidin-1-yl)ethyl group, a 2-(4-methylpiperazin-1-yl)ethyl group, a 2-(4-hydroxypiperidin-1-yl) ethyl group, a 2-(pyrrolidin-1-yl)ethyl group, a 2-((S)-2-hydroxymethyl-pyrrolidin-1-yl)ethyl group, a 2-((R)-2-hydroxymethyl-pyrrolidin-1-yl)ethyl group, a 2-(hydroxyimino)ethyl group, a 2-(methoxyimino)ethyl group, a methylcarbamoyl-methyl group, a 2-methylcarbamoyl-ethyl group, a 2-dimethylcarbamoyl-ethyl group, a 3-methylcarbamoyl-propyl group, a (2-hydroxyethylcarbamoyl) methyl group, a 2-acetylaminoethyl group, a 2-acetylmethylaminoethyl group, a 2-(2-oxo-pyrrolidin-1-yl)ethyl group, a 2-(2-oxoimidazolidin-1-yl)ethyl group, a 1H-imidazol-2-ylmethyl group, a 3H-imidazol-4-ylmethyl group, a pyridin-4-ylmethyl group, an oxazol-2-ylmethyl group, or a 2-methanesulfonylamino-ethyl group.

13. The compound of claim 1, or a pharmaceutically acceptable salt thereof, wherein $R^6$ is a methyl group, an isopropyl group, a cyclopropylmethyl group, a cyclopentylmethyl group, a 2-propenyl group, a 2-propynyl group, or a benzyl group.

14. The compound of claim 1, or a pharmaceutically acceptable salt thereof, wherein $R^6$ is a hydrogen atom, a 2-hydroxyethyl group, a 2-hydroxypropyl group, a 2-hydroxy-2-methylpropyl group, a 2,3-dihydroxypropyl group, a 3-hydroxypropyl group, a 2-dimethylaminoethyl group, a 2-aminoethyl group, a 2-methylaminoethyl group, a 2-acetylaminoethyl group, a 2-acetylmethylaminoethyl group, a 2-(2-oxo-pyrrolidin-1-yl)ethyl group, a 2-(2-oxoimidazolidin-1-yl)ethyl group, a 1H-imidazol-2-ylmethyl group, a pyridin-4-ylmethyl group, a 3-hydroxy-2,2-dimethyl-propyl group, a 2-methylsulfanylethyl group, a 2-methanesulfonylethyl group, a methylcarbamoylmethyl group, a 2-methylcarbamoyl-ethyl group, a 2-dimethylcarbamoyl-ethyl group, a 3-methylcarbamoylpropyl group, a (2-hydroxyethylcarbamoyl)methyl group, or a 2-methanesulfonylamino-ethyl group.

15. The compound of claim 1,
wherein Q is
a hydrogen atom;
—$NR^aR^b$;
an alkyl group, an alkenyl group, or an alkynyl group, each of which may have 1 to 3 substituents selected from Group C indicated below; or
a cycloalkylalkyl group, an arylalkyl group, a heteroarylalkyl group, or a heterocyclic alkyl group, each of which may have 1 to 3 substituents selected from Group D indicated below;
Group C: —O—$R^a$, —[O-(an alkylene group)]$_n$-O$R^a$, —N$R^b$—(an alkylene group)-O$R^a$, and —C=N—O$R^a$;
Group D: —[O-(an alkylene group)]$_n$-O$R^a$, —N$R^b$—(an alkylene group)-O$R^a$, —C=N—O$R^a$, and an alkyl group;
provided that $R^a$ and $R^b$ are identical to or different from each other and independently represent a hydrogen atom, an alkyl group, an aryl group, or a heteroaryl group, and n=1 to 4.

16. The compound of claim 1, or a pharmaceutically acceptable salt thereof, wherein Q is a hydrogen atom, a methyl group, an isopropyl group, a 2-hydroxyethyl group, a 2,3-dihydroxypropyl group, a 2-(morpholin-4-yl)ethyl group, a 2-propenyl group, a benzyl group, an amino group, or a methylamino group.

17. The compound of claim 1, or a pharmaceutically acceptable salt thereof, wherein Q is —$NR^aR^b$.

18. The compound of claim 1, or a pharmaceutically acceptable salt thereof, wherein Q is an alkyl group.

19. The compound of claim 1, or a pharmaceutically acceptable salt thereof, wherein Q is a hydrogen atom.

20. The compound of claim 1, or a pharmaceutically acceptable salt thereof, wherein $R^8$ is a hydrogen atom or a methyl group.

21. The compound of claim 1, or a pharmaceutically acceptable salt thereof, wherein $R^8$ is a hydrogen atom.

22. The compound of claim 1, or a pharmaceutically acceptable salt thereof, wherein $R^9$ is a hydrogen atom, a methyl group, an isopropyl group, a 2-hydroxyethyl group, a 3-hydroxypropyl group, a 2,3-dihydroxypropyl group, a 2-hydroxy-1-(hydroxymethyl)ethyl group, a 2-hydroxypropyl group, a 2-hydroxy-2-methylpropyl group, a 2-hydroxy-1-methylethyl group, a cyclopropylmethyl group, a cyclopentylmethyl group, a 2-(2-hydroxyethoxy)ethyl group, a 2-(2-hydroxyethylamino)ethyl group, a 2-(morpholin-4-yl) ethyl group, a 2-(4-methylpiperazin-1-yl)ethyl group, a 2-(4-hydroxypiperidin-1-yl)ethyl group, a 2-(hydroxyimino)ethyl group, a 2-(methoxyimino)ethyl group, a 2-propenyl group, a 2-propynyl group, a benzyl group, a pyridylmethyl group, or an oxazol-2-ylmethyl group.

23. The compound of claim 1, or a pharmaceutically acceptable salt thereof, wherein $R^9$ is an alkyl group substituted with at least one hydroxyl group.

24. The compound of claim 1, or a pharmaceutically acceptable salt thereof, wherein $R^9$ is a 2-hydroxyethyl group, a 3-hydroxypropyl group, a 2,3-dihydroxypropyl group, a 2-hydroxy-1-(hydroxymethyl)ethyl group, a 2-hydroxypropyl group, a 2-hydroxy-2-methylpropyl group, or a 2-hydroxy-1-methyl-ethyl group.

25. The compound of claim 1, or a pharmaceutically acceptable salt thereof, wherein $R^9$ is a 2-(2-hydroxyethylamino)ethyl group, a 2-(morpholin-4-yl)ethyl group, a 2-(4-methylpiperazin-1-yl)ethyl group, a 2-(4-hydroxypiperidin-1-yl)ethyl group, a 2-(hydroxyimino)ethyl group, a 2-(methoxyimino)ethyl group, a pyridylmethyl group, or an oxazol-2-ylmethyl group.

26. The compound of claim 1, or a pharmaceutically acceptable salt thereof, wherein $R^9$ is a methyl group, an isopropyl group, a cyclopropylmethyl group, a cyclopentylmethyl group, a 2-propenyl group, a 2-propynyl group, or a benzyl group.

27. The compound of claim 1 or a pharmaceutically acceptable salt thereof, wherein $R^2$ is a fluorine atom, $R^3$ is a hydrogen atom, $R^4$ is a fluorine atom, and $R^5$ is a fluorine atom.

28. The compound of claim 1, or a pharmaceutically acceptable salt thereof, wherein in formula (I), $R^6$—O—N=C(O)— is an E-form oxime represented by formula (a):

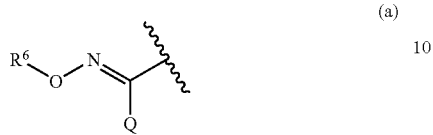

(a)

wherein, $R^6$ and Q have the same meaning as $R^6$ and Q of formula (1).

29. The compound of claim 1, or a pharmaceutically acceptable salt thereof, wherein in formula (1), $R^6$—O—N=C(W)- is a Z-form oxime represented by formula (b):

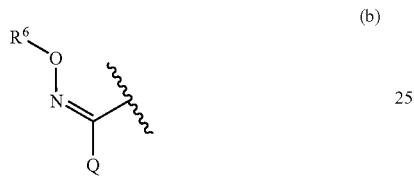

(b)

wherein, $R^6$ and Q have the same meaning as $R^6$ and Q of formula (1).

30. The compound of claim 1 or a pharmaceutically acceptable salt thereof, wherein the compound of formula (I) is selected from the group consisting of:

(1): (E)-3,4-difluoro-2-(2-fluoro-4-iodo-phenylamino)-N-(2-hydroxy-ethoxy)-5-[(2-hydroxy-ethoxyimino)-methyl]-benzamide, (2): (E)-2-(4-ethynyl-2-fluorophenylamino)-3,4-difluoro-N-(2-hydroxy-ethoxy)-5-[(2-hydroxy-ethoxyimino)-methyl]-benzamide, (3): (E)-3,4-difluoro-2-(2-fluoro-4-vinyl-phenylamino)-N-(2-hydroxy-ethoxy)-5-[(2-hydroxy-ethoxyimino)-methyl]-benzamide, (4): (E)-3,4-difluoro-N-(2-hydroxy-ethoxy)-5-[(2-hydroxy-ethoxyimino)-methyl]-2-(4-iodo-phenylamino)-benzamide, (5): (E)-2-(2-chloro-4-iodo-phenylamino)-3,4-difluoro-N-(2-hydroxy-ethoxy)-5-[(2-hydroxy-ethoxyimino)-methyl]-benzamide, (6): (E)-3,4-difluoro-N-(2-hydroxy-ethoxy)-5-[(2-hydroxy-ethoxyimino)-methyl]-2-(4-iodo-2-methyl-phenylamino)-benzamide, (7): (E)-3,4-difluoro-N-(2-hydroxy-ethoxy)-5-[(2-hydroxy-ethoxyimino)-methyl]-2-(2-hydroxymethyl-4-iodo-phenylamino)-benzamide, (8): (E)-2-(2-chloro-6-fluoro-4-iodo-phenylamino)-3,4-difluoro-N-(2-hydroxy-ethoxy)-5-[(2-hydroxy-ethoxyimino)-methyl]-benzamide, (9): (E)-2-(2,6-difluoro-4-iodo-phenylamino)-3,4-difluoro-N-(2-hydroxy-ethoxy)-5-[(2-hydroxy-ethoxyimino)-methyl]-benzamide, (10): (E)-4-fluoro-2-(2-fluoro-4-iodo-phenylamino)-N-(2-hydroxy-ethoxy)-5-[(2-hydroxy-ethoxyimino)-methyl]-benzamide, (11): (E)-3,4-difluoro-2-(2-fluoro-4-iodo-phenylamino)-N-(2-hydroxy-ethoxy)-5-[(3-hydroxy-propoxyimino)-methyl]-benzamide, (12): (E)-5-[(2,3-dihydroxy-propoxyimino)-methyl]-3,4-difluoro-2-(2-fluoro-4-iodo-phenylamino)-N-(2-hydroxy-ethoxy)-benzamide, (13): (E)-3,4-difluoro-2-(2-fluoro-4-iodo-phenylamino)-N-(2-hydroxy-ethoxy)-5-[(2-hydroxy-1-hydroxymethyl-ethoxyimino)-methyl]-benzamide, (14): (E)-3,4-difluoro-2-(2-fluoro-4-iodo-phenylamino)-N-(2-hydroxy-ethoxy)-5-[(2-hydroxy-propoxyimino)-methyl]-benzamide, (15): (E)-3,4-difluoro-2-(2-fluoro-4-iodo-phenylamino)-N-(2-hydroxy-ethoxy)-5-[(2-hydroxy-2-methyl-propoxyimino)-methyl]-benzamide, (16): (E)-3,4-difluoro-2-(2-fluoro-4-iodo-phenylamino)-N-(2-hydroxy-ethoxy-5-[(2-hydroxy-1-methyl-ethoxyimino)-methyl]-benzamide, (17): (E)-3,4-difluoro-2-(2-fluoro-4-iodo-phenylamino)-N-(2-hydroxy-ethoxy)-5-{[(2-hydroxy-ethoxy)-ethoxyimino]-methyl}-benzamide, (18): (E)-3,4-difluoro-2-(2-fluoro-4-iodo-phenylamino)-N-(2-hydroxy-ethoxy)-5-{[(2-hydroxy-ethylamino)-ethoxyimino]-methyl}-benzamide, (19): (E)-3,4-difluoro-2-(2-fluoro-4-iodo-phenylamino)-N-(2-hydroxy-ethoxy)-5-[(2-morpholin-4-yl-ethoxyimino)-methyl]-benzamide, (20): (E)-3,4-difluoro-2-(2-fluoro-4-iodo-phenylamino)-N-(2-hydroxy-ethoxy)-5-{[2-(4-hydroxy-piperidin-1-yl)-ethoxyimino]-methyl}-benzamide, (21): (E)-3,4-difluoro-2-(2-fluoro-4-iodo-phenylamino)-N-(2-hydroxy-ethoxy)-5-{[2-(4-methyl-piperazin-1-yl)-ethoxyimino]-methyl}-benzamide, (22): (E)-3,4-difluoro-2-(2-fluoro-4-iodo-phenylamino)-N-(2-hydroxy-ethoxy)-5-[(2-hydroxyimino-ethoxyimino)-methyl]-benzamide, (23): (E)-3,4-difluoro-2-(2-fluoro-4-iodo-phenylamino)-N-(2-hydroxy-ethoxy)-5-[(2-methoxyimino-ethoxyimino)-methyl]-benzamide, (24): (E)-3,4-difluoro-2-(2-fluoro-4-iodo-phenylamino)-N-(2-hydroxy-ethoxy)-5-(hydroxyimino-methyl)-benzamide, (25): (E)-3,4-difluoro-2-(2-fluoro-4-iodo-phenylamino)-N-(2-hydroxy-ethoxy)-5-(methoxyimino-methyl)-benzamide, (26): (E)-3,4-difluoro-2-(2-fluoro-4-iodo-phenylamino)-N-(2-hydroxy-ethoxy)-5-(isopropoxyimino-methyl)-benzamide, (27): (E)-5-(cyclopropylmethoxyimino-methyl)-3,4-difluoro-2-(2-fluoro-4-iodo-phenylamino)-N-(2-hydroxy-ethoxy)-benzamide, (28): (E)-5-(cyclopentylmethoxyimino-methyl)-3,4-difluoro-2-(2-fluoro-4-iodo-phenylamino)-N-(2-hydroxy-ethoxy)-benzamide, (29): (E)-5-(allyloxyimino-methyl)-3,4-difluoro-2-(2-fluoro-4-iodo-phenylamino)-N-(2-hydroxy-ethoxy)-benzamide, (30): (E)-3,4-difluoro-2-(2-fluoro-4-iodo-phenylamino)-N-(2-hydroxy-ethoxy)-5-(2-propynyloxyimino-methyl)-benzamide, (31): (E)-5-(benzyloxyimino-methyl)-3,4-difluoro-2-(2-fluoro-4-iodo-phenylamino)-N-(2-hydroxy-ethoxy)-benzamide, (32): (E)-3,4-difluoro-2-(2-fluoro-4-iodo-phenylamino)-N-(2-hydroxy-ethoxy)-5-[(pyridin-4-ylmethoxyimino)-methyl]-benzamide, (33): (E)-3,4-difluoro-2-(2-fluoro-4-iodo-phenylamino)-N-(2-hydroxy-ethoxy)-5-[(oxazol-2-ylmethoxyimino)-methyl]-benzamide, (34): (E)-3,4-difluoro-2-(2-fluoro-4-iodo-phenylamino)-N-(2-hydroxy-ethoxy)-5-[1-(2-hydroxy-ethoxyimino)-ethyl]-benzamide, (35): (E)-3,4-difluoro-2-(2-fluoro-4-iodo-phenylamino)-N-(2-hydroxy-ethoxy)-5-[1-(2-hydroxy-ethoxyimino)-2-methyl-propyl]-benzamide, (36): (E)-3,4-difluoro-2-(2-fluoro-4-iodo-phenylamino)-N-(2-hydroxy-ethoxy)-5-[1-(2-hydroxy-ethoxyimino)-3-butenyl]-benzamide, (37): (E)-3,4-difluoro-2-(2-fluoro-4-iodo-phenylamino)-N-(2-hydroxy-ethoxy)-5-[1-(2-hydroxy-ethoxyimino)-2-phenylethyl]-benzamide, (38): (E)-3,4-difluoro-2-(2-fluoro-4-iodo-phenylamino)-N-(2-hydroxy-ethoxy)-5-[3-hydroxy-1-(2-hydroxy-ethoxyimino)-propyl]-benzamide, (39): (E)-5-[3,4-dihydroxy-1-(2-hydroxy-ethoxyimino)-butyl]-3,4-difluoro-2-(2-fluoro-4-iodo-phenylamino)-N-(2-hydroxy-ethoxy)-benzamide, (40): (E)-3,4-difluoro-2-(2-fluoro-4-iodo-phenylamino)-N-(2-hydroxy-ethoxy)-5-[1-(2-hydroxy-ethoxyimino)-3-morpholin-4-yl-propyl]-benzamide, (41): (E)-3,4-difluoro-2-(2-fluoro-4-iodo-phenylamino)-N-(2-hydroxy-ethoxy)-5-[N-(2-hydroxy-ethoxyimino)-carbamimidoyl]-benzamide, (42): (E)-3,4-difluoro-2-(2-fluoro-4-iodo-phenylamino)-N-(2-hydroxy-ethoxy)-5-[N-(2-hydroxy-ethoxyimino)-N'-methyl-carbamimidoyl]-benzamide, (43): (E)-3,4-difluoro-2-(2-fluoro-4-iodo-phenylamino)-N-(2-hydroxy-ethoxy)-5-[(2-hydroxy-ethoxyimino)-methyl]-N-methyl-benzamide, (44): (E)-3,4-difluoro-2-(2-fluoro-4-iodo-phenylamino)-5-[(2-hydroxy-ethoxyimino)-methyl]-N-(3-hydroxy-propoxy)-benzamide, (45): (E)-N-(2,3-dihydroxy-propoxy)-3,4-difluoro-2-(2-fluoro-4-iodo-phenylamino)-5-[(2-hydroxy-ethoxyimino)-methyl]-benzamide, (46): (E)-3,4-difluoro-2-(2-fluoro-4-iodo-phenylamino)-5-[(2-hydroxy-ethoxyimino)-methyl]-N-(2-hydroxy-1-hydroxymethyl-ethoxy)-benzamide, (47): (E)-3,4-difluoro-2-(2-fluoro-4-iodo-phenylamino)-5-[(2-hydroxy-ethoxyimino)-methyl]-N-(2-hydroxy-propoxy)-benzamide, (48): (E)-3,4-difluoro-2-(2-fluoro-4-iodo-phenylamino)-5-[(2-hydroxy-ethoxyimino)-methyl]-N-(2-hydroxy-2-methyl-propoxy)-benzamide, (49): (E)-3,4-difluoro-2-(2-fluoro-4-iodo-phenylamino)-5-[(2-hydroxy-ethoxyimino)-methyl]-N-(2-hydroxy-1-methyl-ethoxy)-benzamide, (50): (E)-3,4-difluoro-2-(2-fluoro-4-iodo-phenylamino)-N-[(2-hydroxy-ethoxy)-ethoxy]-5-[(2-hydroxy-ethoxyimino)-methyl]-benzamide, (51): (E)-3,4-difluoro-2-(2-fluoro-4-iodo-phenylamino)-5-[(2-hydroxy-ethoxyimino)-methyl]-N-[(2-hydroxy-ethylamino)-ethoxy]-benzamide, (52): (E)-3,4-difluoro-2-(2-fluoro-4-iodo-phenylamino)-5-[(2-hydroxy-ethoxyimino)-methyl]-N-(2-morpholin-4-yl-ethoxy)-benzamide, (53): (E)-3,4-difluoro-2-(2-fluoro-4-iodo-phenylamino)-5-[(2-hydroxy-ethoxyimino)-methyl]-N-[2-(4-hydroxy-piperidin-1-yl)-ethoxy]-benzamide, (54): (E)-3,4-difluoro-2-(2-fluoro-4-iodo-phenylamino)-5-[(2-hydroxy-ethoxyimino)-methyl]-N-[2-(4-methyl-piperazin-1-yl)-ethoxy]-benzamide, (55): (E)-3,4-difluoro-2-(2-fluoro-4-iodo-phenylamino)-5-[(2-hydroxy-ethoxyimino)-methyl]-N-(2-hydroxy-imino-ethoxy)-benzamide, (56): (E)-3,4-difluoro-2-(2-fluoro-4-iodo-phenylamino)-5-[(2-hydroxy-ethoxyimino)-methyl]-N-(2-methoxy-imino-ethoxy)-benzamide, (57): (E)-3,4-difluoro-2-(2-fluoro-4-iodo-phenylamino)-N-hydroxy-5-[(2-hydroxy-ethoxyimino)-methyl]-benzylamide, (58): (E)-3,4-difluoro-2-(2-fluoro-4-iodo-phenylamino)-5-[(2-hydroxy-ethoxyimino)-methyl]-N-methoxy-benzamide, (59): (E)-3,4-difluoro-2-(2-fluoro-4-iodo-phenylamino)-5-[(2-hydroxy-ethoxyimino)-methyl]-N-isopropoxy-benzamide, (60): (E)-N-cyclopropylmethoxy-3,4-difluoro-2-(2-fluoro-4-iodo-phenylamino)-5-[(2-hydroxy-ethoxyimino)-methyl]-benzamide, (61): (E)-N-cyclopentylmethoxy-3,4-difluoro-2-(2-fluoro-4-iodo-phenylamino)-5-[(2-hydroxy-ethoxyimino)-methyl]-benzamide, (62): (E)-N-allyloxy-3,4-difluoro-2-(2-fluoro-4-iodo-phenylamino)-5-[(2-hydroxy-ethoxyimino)-methyl]-benzamide, (63): (E)-3,4-difluoro-2-(2-fluoro-4-iodo-phenylamino)-5-[(2-hydroxy-ethoxyimino)-methyl]-N-(2-propynyloxy)-benzamide, (64): (E)-N-benzyloxy-3,4-difluoro-2-(2-fluoro-4-iodo-phenylamino)-5-[(2-hydroxy-ethoxyimino)-methyl]-benzamide, (65): (E)-3,4-difluoro-2-(2-fluoro-4-iodo-phenylamino)-5-[(2-hydroxy-ethoxyimino)-methyl]-N-(pyridin-4-yl-methoxy)-benzamide, (66): (E)-3,4-difluoro-2-(2-fluoro-4-iodo-phenylamino)-5-[(2-hydroxy-ethoxyimino)-methyl]-N-(oxazol-2-yl-methoxy)-benzamide, (67): (E)-2-(4-ethynyl-2-fluoro-phenylamino)-3,4-difluoro-5-[(2-hydroxy-ethoxyimino)-methyl]-N-(3-hydroxy-propoxy)-benzamide, (68): (E)-N-(2,3-dihydroxy-propoxy)-2-(4-ethynyl-2-fluoro-phenylamino)-3,4-difluoro-5-[(2-hydroxy-ethoxyimino)-methyl]-benzamide, (69): (E)-2-(4-ethynyl-2-fluoro-phenylamino)-3,4-difluoro-5-[(2-hydroxy-ethoxyimino)-methyl]-N-(2-hydroxy-1-hydroxymethyl-ethoxy)-benzamide, (70): (E)-2-(4-ethynyl-2-fluoro-phenylamino)-3,4-difluoro-N-(2-hydroxy-ethoxy)-5-[(3-hydroxy-propoxyimino)-methyl]-benzamide, (71): (E)-5-[(2,3-dihydroxy-propoxyimino)-methyl]-2-(4-ethynyl-2-fluoro-phenylamino)-3,4-difluoro-N-(2-hydroxy-ethoxy)benzamide, (72): (E)-2-(4-ethynyl-2-fluoro-phenylamino)-3,4-difluoro-N-(2-hydroxy-ethoxy)-5-[(2-hydroxy-1-hydroxymethyl-ethoxyimino)-methyl]-benzamide, (73): (E)-2-(4-ethynyl-2-fluoro-phenylamino)-3,4-difluoro-N-(2-hydroxyethoxy)-5-[(2-hydroxy-2-methyl-propoxyimino)-methyl]-benzamide, (74): (E)-3,4-difluoro-2-(2-fluoro-4-iodo-phenylamino)-N-(2-hydroxy-ethoxy)-5-[(2-methylcarbamoyl-ethoxyimino)-methyl]-benzamide, (75): (E)-5-[(2-dimethylamino-ethoxyimino)-methyl]-3,4-difluoro-2-(2-fluoro-4-iodo-phenylamino)-N-(2-hydroxy-ethoxy)-benzamide, (76): (E)-3,4-difluoro-2-(2-fluoro-4-iodo-phenylamino)-N-(2-hydroxy-ethoxy)-5-[(2-piperidin-1-yl-ethoxyimino)-methyl]-benzamide, (77): (E)-3,4-difluoro-2-(2-fluoro-4-iodo-phenylamino)-N-(2-hydroxy-ethoxy)-5-[(3-methoxy-3-methyl-butoxyimino)-methyl]-benzamide, (78): (E)-3,4-difluoro-2-(2-fluoro-4-iodo-phenylamino)-N-(2-hydroxy-ethoxy)-5-[(3-hydroxy-3-methyl-butoxyimino)-methyl]-benzamide,
(79): (E)-3,4-difluoro-2-(2-fluoro-4-iodo-phenylamino)-5-[(3-hydroxy-2,2-dimethyl-propoxyimino)-methyl]-N-(2-hydroxy-ethoxy)-benzamide,
(80): (E)-3,4-difluoro-2-(2-fluoro-4-iodo-phenylamino)-N-(2-hydroxy-ethoxy)-5-[(1-hydroxymethyl-cyclopropylmethoxyimino)-methyl]-benzamide,
(81): (E)-3,4-difluoro-2-(2-fluoro-4-iodo-phenylamino)-5-[(4-hydroxy-butoxyimino)-methyl]-N-(2-hydroxy-ethoxy)-benzamide,
(82): (E)-3,4-difluoro-2-(2-fluoro-4-iodo-phenylamino)-N-(2-hydroxy-ethoxy)-5-[(2-methylsulfanyl-ethoxyimino)-methyl]benzamide,
(83): (E)-3,4-difluoro-2-(2-fluoro-4-iodo-phenylamino)-N-(2-hydroxy-ethoxy)-5-[(2-methanesulfonyl-ethoxyimino)-methyl]-benzamide,
(84): (E)-3,4-difluoro-2-(2-fluoro-4-iodo-phenylamino)-N-(2-hydroxy-ethoxy)-5-[methylcarbamoylmethoxyimino-methyl]-benzamide,
(85): (E)-3,4-difluoro-2-(2-fluoro-4-iodo-phenylamino)-N-(2-hydroxy-ethoxy)-5-{[(2-hydroxyethylcarbamoyl)-methoxyimino]-methyl}-benzamide,
(86): (E)-3,4-difluoro-2-(2-fluoro-4-iodo-phenylamino)-N-(2-hydroxy-ethoxy)-5-[(3-methylcarbamoyl-propoxyimino)-methyl]-benzamide,
(87): (E)-3,4-difluoro-2-(2-fluoro-4-iodo-phenylamino)-N-(2-hydroxy-ethoxy)-5-[(2-methoxy-ethoxyimino)-methyl]-benzamide,
(88): (E)-3,4-difluoro-2-(2-fluoro-4-iodo-phenylamino)-N-(2-hydroxy-ethoxy)-5-[isopropoxyimino-methyl]-benzamide,
(89): (E)-3,4-difluoro-2-(2-fluoro-4-iodo-phenylamino)-N-(2-hydroxy-ethoxy)-5-[(3H-imidazol-4-ylmethoxyimino)-methyl]-benzamide,
(90): (E)-3,4-difluoro-2-(2-fluoro-4-iodo-phenylamino)-N-(2-hydroxy-ethoxy)-5-{[2-(2-oxo-pyrrolidin-1-yl)-ethoxyimino]-methyl}-benzamide,
(91): (E)-3,4-difluoro-2-(2-fluoro-4-iodo-phenylamino)-N-(2-hydroxy-ethoxy)-5-[(2-pyrrolidin-1-yl-ethoxyimino)-methyl]-benzamide,
(92): (E)-3,4-difluoro-2-(2-fluoro-4-iodo-phenylamino)-N-(2-hydroxy-ethoxy)-5-{[2-(2-oxo-imidazolidin-1-yl)-ethoxyimino]-methyl}-benzamide,
(93): (E)-3,4-difluoro-2-(2-fluoro-4-iodo-phenylamino)-N-(2-hydroxy-ethoxy)-5-[2-((S)-hydroxymethyl-pyrrolidin-1-yl)ethoxyimino]-methyl-benzamide,
(94): (E)-5-[(2-amino-ethoxyimino)-methyl]-3,4-difluoro-2-(2-fluoro-4-iodo-phenylamino)-N-(2-hydroxyethoxy)-benzamide,
(95): (E)-{2-[2,3-difluoro-4-(2-fluoro-4-iodo-phenylamino)-5-(2-hydroxy-ethoxycarbamoyl)-benzylideneaminooxy]-ethyl}-carbamic acid tert-butyl ester,
(96): (E)-5-[(2-acetylamino-ethoxyimino)-methyl]-3,4-difluoro-2-(2-fluoro-4-iodo-phenylamino)-N-(2-hydroxy-ethoxy)-benzamide,
(97): (E)-3,4-difluoro-2-(2-fluoro-4-iodo-phenylamino)-N-(2-hydroxy-ethoxy)-5-[(1H-imidazol-2-ylmethoxyimino)-methyl]-benzamide,
(98): (E)-3,4-difluoro-2-(2-fluoro-4-iodo-phenylamino)-N-(2-hydroxy-ethoxy)-5-[(2-methylamino-ethoxyimino)-methyl]-benzamide,
(99): (E)-5-{[2-(acetyl-methyl-amino)-ethoxyimino]-methyl}-3,4-difluoro-2-(2-fluoro-4-iodo-phenylamino)-N-(2-hydroxyethoxy)-benzamide,
(101): (E)-2-(4-ethynyl-2-fluoro-phenylamino)-3,4-difluoro-N-(2-hydroxy-ethoxy)-5-[(2-methylcarbamoylethoxyimino)-methyl]-benzamide,
(102): (Z)-3,4-difluoro-2-(2-fluoro-4-iodo-phenylamino)-N-(2-hydroxy-ethoxy)-5-[(2-hydroxy-ethoxyimino)-methyl]-benzamide,
(103): (Z)-2-(4-ethynyl-2-fluoro-phenylamino)-3,4-difluoro-N-(2-hydroxy-ethoxy)-5-[(2-hydroxy-ethoxyimino)-methyl]-benzamide,
(104): (Z)-3,4-difluoro-2-(2-fluoro-4-iodo-phenylamino)-N-(2-hydroxy-ethoxy)-5-[(2-methanesulfonyl-ethoxyimino)-methyl]-benzamide,
(105): (dl)-(Z)-5-[(2,3-dihydroxy-propoxyimino)-methyl]-3,4-difluoro-2-(2-fluoro-4-iodo-phenylamino)-N-(2-hydroxy-ethoxy)-benzamide,
(106): (Z)-5-[(2-acetylamino-ethoxyimino)-methyl]-3,4-difluoro-2-(2-fluoro-4-iodo-phenylamino)-N-(2-hydroxy-ethoxy)-benzamide,
(107): (Z)-3,4-difluoro-2-(2-fluoro-4-iodo-phenylamino)-N-(2-hydroxy-ethoxy)-5-[(2-methylcarbamoyl-ethoxyimino)-methyl]-benzamide,
(108): (Z)-3,4-difluoro-2-(2-fluoro-4-iodo-phenylamino)-N-(2-hydroxy-ethoxy)-5-[(2-hydroxy-2-methyl-propoxyimino)-methyl]-benzamide,
(109): (Z)-3,4-difluoro-2-(2-fluoro-4-iodo-phenylamino)-N-(2-hydroxy-ethoxy)-5-(methylcarbamoylmethoxyimino-methyl)benzamide,
(110): (Z)-3,4-difluoro-2-(2-fluoro-4-iodo-phenylamino)-N-(2-hydroxy-ethoxy)-5-[(2-hydroxyethylcarbamoyl)-methoxyimino]-methyl -benzamide,
(111): (Z)-3,4-difluoro-2-(2-fluoro-4-iodo-phenylamino)-N-(2-hydroxy-ethoxy)-5-{[(3-methylcarbamoyl-propoxyimino)-methyl]-benzamide,
(112): dl-(Z)—N-(2,3-dihydroxy-propoxy)-3,4-difluoro-2-(2-fluoro-4-iodo-phenylamino)-5-[(2-hydroxy-ethoxyimino)-methyl]-benzamide,
(113): (Z)-3,4-difluoro-2-(2-fluoro-4-iodo-phenylamino)-N-(2-hydroxy-ethoxy)-5-{[2-(2-oxo-imidazolidin-1-yl)-ethoxyimino]-methyl}-benzamide,
(114): (Z)-3,4-difluoro-2-(2-fluoro-4-iodo-phenylamino)-N-(2-hydroxy-ethoxy)-5-{[2-(2-oxo-pyrrolidin-1-yl)-ethoxyimino]-methyl}-benzamide,
(115): (E)-3,4-difluoro-2-(2-fluoro-4-iodo-phenylamino)-N-(2-hydroxy-ethoxy)-5-[(2-methanesulfonylaminoethoxyimino)-methyl]-benzamide, and
(116): (E)-3,4-difluoro-2-(2-fluoro-4-iodo-phenylamino)-N-(2-hydroxy-ethoxy)-5-[dimethylcarbamoylethoxyimino-methyl]-benzamide.

31. A pharmaceutical composition, which comprises as an active ingredient a compound of claim 1 or a pharmaceutically acceptable salt thereof.

32. A mitogen-activated protein kinase kinase (MEK) inhibitor which comprises as an active ingredient the compound of claim 1 or a pharmaceutically acceptable salt thereof.

33. A therapeutic agent for a proliferative disease, comprising the compound or pharmaceutically acceptable salt of claim 1 as an active ingredient, wherein the proliferative disease is a cancer in which MEK is overexpressed.

34. A therapeutic agent for a proliferative disease, comprising the compound or pharmaceutically acceptable salt of claim 1 as an active ingredient, wherein the proliferative disease is a breast, lung, colorectal, prostate, liver, gastric, or pancreatic cancer, or leukemia.

* * * * *